(12) United States Patent
Hatakeyama et al.

(10) Patent No.: US 11,160,480 B2
(45) Date of Patent: *Nov. 2, 2021

(54) BIO-ELECTRODE COMPOSITION, BIO-ELECTRODE, AND METHOD FOR MANUFACTURING A BIO-ELECTRODE

(71) Applicant: SHIN-ETSU CHEMICAL CO., LTD., Tokyo (JP)

(72) Inventors: Jun Hatakeyama, Joetsu (JP); Koji Hasegawa, Joetsu (JP); Motoaki Iwabuchi, Joetsu (JP); Yasuyoshi Kuroda, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/428,309

(22) Filed: May 31, 2019

(65) Prior Publication Data

US 2020/0113464 A1 Apr. 16, 2020

(30) Foreign Application Priority Data

Jun. 25, 2018 (JP) .............................. JP2018-119502

(51) Int. Cl.
*A61B 5/25* (2021.01)
*G01N 27/327* (2006.01)
(Continued)

(52) U.S. Cl.
CPC ................ *A61B 5/25* (2021.01); *C08L 41/00* (2013.01); *C08L 83/04* (2013.01); *G01N 27/327* (2013.01);
(Continued)

(58) Field of Classification Search
CPC ................................ A61B 5/0408; A61B 5/25
See application file for complete search history.

(56) References Cited

U.S. PATENT DOCUMENTS 5,981,680 A 11/1999 Petroff et al.
10,695,554 B2 * 6/2020 Hatakeyama ........ A61B 5/0492
(Continued)

FOREIGN PATENT DOCUMENTS

JP H05-095924 A 4/1993
JP 2002-094201 A 3/2002
(Continued)

OTHER PUBLICATIONS

Long, Lizhen et at. "Polymer Electrolytes for Lithium Polymer Batteries". Journal of Materials Chemistry A., vol. 4, pp. 10038-10069, 2016.
(Continued)

*Primary Examiner* — William D Young
(74) *Attorney, Agent, or Firm* — Oliff PLC

(57) ABSTRACT

The present invention provides a bio-electrode composition including (A) an ionic material and (C) a metal powder, wherein the component (A) is a polymer compound containing a repeating unit-a having a structure selected from the group consisting of an ammonium salt, a sodium salt, a potassium salt, and a silver salt of any of fluorosulfonic acid, fluorosulfonimide, and fluorosulfonamide. This can form a living body contact layer for a bio-electrode that is excellent in electric conductivity and biocompatibility, light-weight, manufacturable at low cost, and free from large lowering of the electric conductivity even though it is wetted with water or dried.

21 Claims, 2 Drawing Sheets

(51) Int. Cl.
*C08L 41/00* (2006.01)
*C08L 83/04* (2006.01)
*C08K 3/04* (2006.01)
*C08K 5/19* (2006.01)

(52) U.S. Cl.
CPC ........ *A61B 2562/0209* (2013.01); *C08K 3/04* (2013.01); *C08K 5/19* (2013.01); *C08K 2201/001* (2013.01); *C08L 2203/02* (2013.01); *C08L 2203/20* (2013.01)

(56) References Cited

U.S. PATENT DOCUMENTS

| | | | |
|---|---|---|---|
| 10,792,489 B2 * | 10/2020 | Hatakeyama | C08L 33/26 |
| 2002/0009650 A1 * | 1/2002 | Michot | C07D 285/125 |
| | | | 429/314 |
| 2002/0177039 A1 | 11/2002 | Lu et al. | |
| 2002/0188069 A1 | 12/2002 | Sugo et al. | |
| 2008/0118860 A1 | 5/2008 | Harada et al. | |
| 2009/0012218 A1 * | 1/2009 | Kuroda | C08K 3/24 |
| | | | 524/165 |
| 2009/0061358 A1 | 3/2009 | Ohashi et al. | |
| 2011/0175036 A1 * | 7/2011 | Masahiro | C08K 5/1525 |
| | | | 252/500 |
| 2015/0275060 A1 | 10/2015 | Kuroda et al. | |
| 2016/0155530 A1 | 6/2016 | Someya et al. | |
| 2016/0260518 A1 * | 9/2016 | Hatakeyama | C08L 65/00 |
| 2017/0275510 A1 | 9/2017 | Quan et al. | |

FOREIGN PATENT DOCUMENTS

| | | |
|---|---|---|
| JP | 2002-332305 A | 11/2002 |
| JP | 2003-225217 A | 8/2003 |
| JP | 2004-033468 A | 2/2004 |
| JP | 2004-527902 A | 9/2004 |
| JP | 2005-320418 A | 11/2005 |
| JP | 2008-111103 A | 5/2008 |
| JP | 2009-080474 A | 4/2009 |
| JP | 2011-079946 A | 4/2011 |
| JP | 2015-019806 A | 2/2015 |
| JP | 2015-100673 A | 6/2015 |
| JP | 2015-193803 A | 11/2015 |
| JP | 2016-011338 A | 1/2016 |
| JP | 2016-065238 A | 4/2016 |
| WO | 2013/039151 A1 | 3/2013 |

OTHER PUBLICATIONS

Araki, Teppei, et al. "Printable and Stretchable Conductive Wirings Comprising Silver Flakes and Elastomers". IEE Electron Device Letters, vol. 32, No. 10 32,1424-1426, 2011.

Araki, Teppei, et al. "Effect of Void Volume and Silver Loading on Strain Response of Electrical Resistance in Silver Flakes/ Polyuerethane Composite for Stretchable Conductors". Japanese Journal of Applied Physics 51, 11PD01-1 to 11PD01-5, 2012.

* cited by examiner

[FIG. 1]
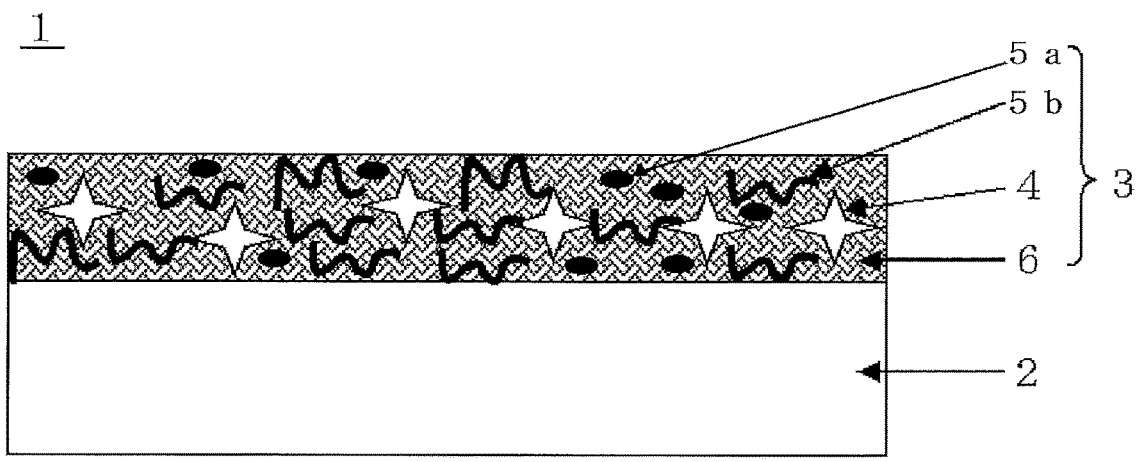
[FIG. 2]
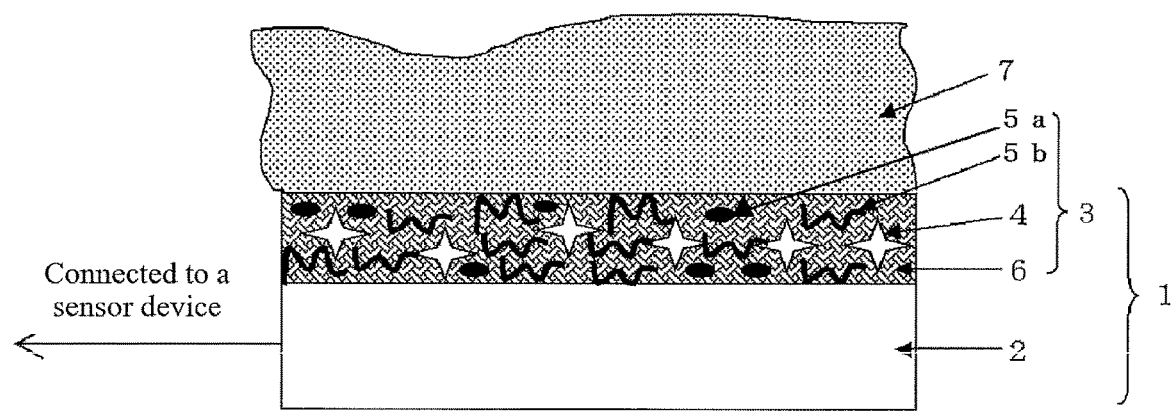
[FIG. 3A]
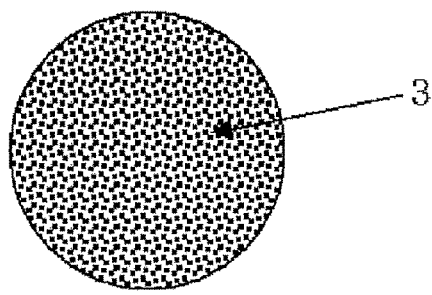

[FIG. 3B]
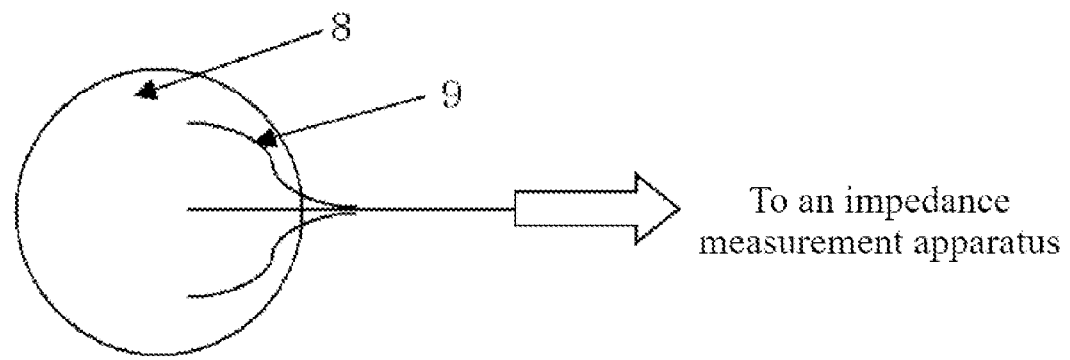
[FIG. 4]
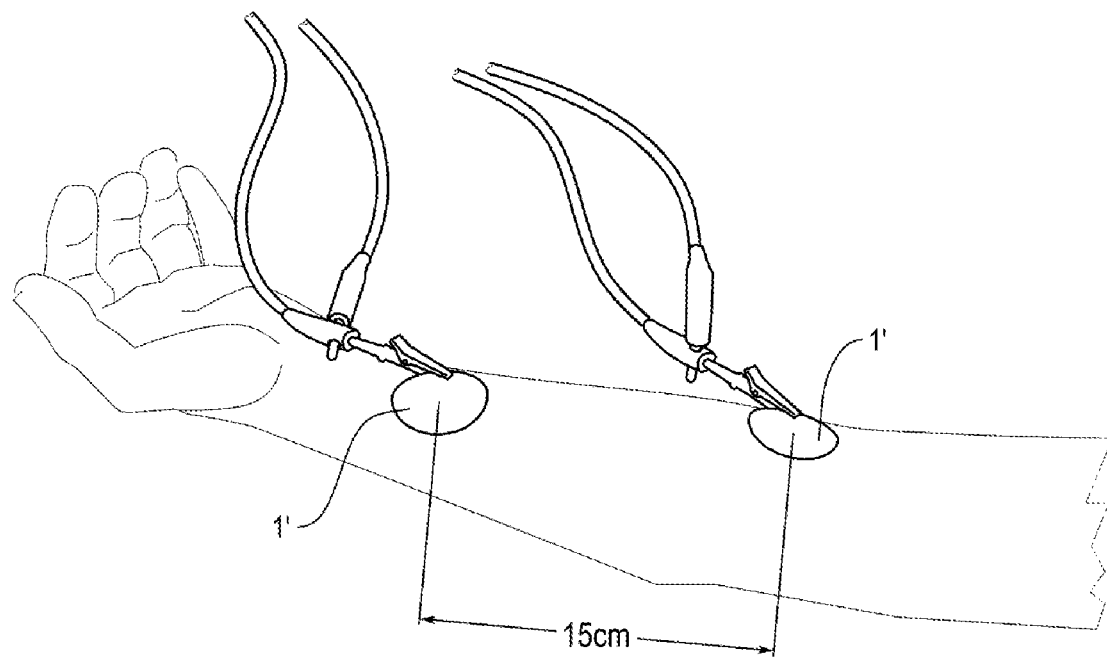

BIO-ELECTRODE COMPOSITION, BIO-ELECTRODE, AND METHOD FOR MANUFACTURING A BIO-ELECTRODE

TECHNICAL FIELD

The present invention relates to a bio-electrode that is used in contact with the skin of a living body capable of detecting physical conditions such as heart rate by an electric signal transmitted from the skin, a method for manufacturing the bio-electrode, and a bio-electrode composition desirably used for a bio-electrode.

BACKGROUND ART

A recent growing popularity of Internet of Things (IoT) has accelerated the development of such major wearable devices as watches and glasses that allow for Internet access. Even in the fields of medicine and sports, wearable devices for constantly monitoring the user's physical state are increasingly demanded, and such technological development is expected to be further encouraged.

In the field of medicine, including an electrocardiogram for detecting an electric signal to measure the motion of the heart, use of wearable devices for monitoring the state of human organs by detecting extremely weak current has been examined. The electrocardiogram measurement is conducted by attaching an electrode coated with an electro-conductive paste to a body, but this is a single (not continuous), short-time measurement. On the other hand, the above medical wearable device is aimed at continuously monitoring the state of physical conditions for a few weeks. Accordingly, a bio-electrode used in a medical wearable device is required to make no changes in electric conductivity even in long-time use and cause no skin allergy. In addition to these, bio-electrodes must be light-weight and produced at low cost.

Medical wearable devices are classified into two types: direct body attachment and clothing attachment. One typical body attachment device is a bio-electrode formed of a hydrophilic gel containing water and electrolytes as ingredients of the above electro-conductive paste (Patent Document 1). The hydrophilic gel, containing sodium, potassium, and calcium electrolytes in a hydrophilic polymer containing water, detects changes in ion concentration from the skin to convert the data into electricity. Meanwhile, one typical clothing attachment device is characterized by a method for using as an electrode a fabric including an electro-conductive polymer, such as PEDOT-PSS (Poly-3,4-ethylenedioxythiophene-polystyrenesulfonate), and a silver paste incorporated into the fiber (Patent Document 2).

However, the use of the hydrophilic gel containing water and electrolytes unfortunately brings about loss of electric conductivity due to water evaporation in drying process. Meanwhile, the use of a higher ionization tendency metal such as copper can cause some users to suffer from skin allergy. The use of an electro-conductive polymer such as PEDOT-PSS can also cause skin allergy due to the strong acidity of the electro-conductive polymer, as well as peeling of the electro-conductive polymer from fibers during washing.

By taking advantage of excellent electric conductivity, the use of electrode materials formed of metal nanowire, carbon black, or carbon nanotube has been examined (Patent Document 3, 4, and 5). With higher contact probability, metal nanowires can conduct electricity in small quantities to be added. Nevertheless, metal nanowires, formed of a pointed thin material, may cause skin allergy. Likewise, carbon nanotubes can stimulate (irritate) a living body. Although the carbon black is not as poisonous as carbon nanotube, it also stimulates the skin. Accordingly, even though these electrode materials themselves cause no allergic reaction, the biocompatibility can be degraded depending on the shape of a material and its inherent stimulation, thereby failing to satisfy both electric conductivity and biocompatibility.

Although metal films seem to function as an excellent bio-electrode thanks to extremely high electric conductivity, this is not always the case. Upon heartbeat, the human skin releases a sodium ion, a potassium ion, or a calcium ion, instead of extremely weak current. It is thus necessary to convert changes in ion concentration into current, which is what less ionized precious metals unfortunately fail to do efficiently. The resulting bio-electrode including the precious metal is characterized by high impedance and high resistance to the skin during electrical conduction.

Meanwhile, the use of a battery containing an ionic liquid has been examined (Patent Document 6). Advantageously, the ionic liquid is thermally and chemically stable, and the electric conductivity is excellent, providing more various battery applications. However, an ionic liquid having smaller molecular weight shown in Patent Document 6 unfortunately dissolves into water. A bio-electrode containing such an ionic liquid in use allows the ionic liquid to be extracted from the electrode by sweating, which not only lowers the electric conductivity, but also causes rough skin by the liquid soaking into the skin.

Batteries using a lithium salt of polymer type sulfonimide have been investigated (Non-Patent Document 1). Lithium has been applied to batteries because of their high ionic mobility, however, this is not a material with biocompatibility.

The bio-electrode fails to give biological information when it is apart from the skin. The detection of even changes in contact area can vary quantities of electricity traveling through the electrode, allowing the baseline of an electrocardiogram (electric signal) to fluctuate. Accordingly, in order to stably detect electric signals from the body, the bio-electrode is required to be in constant contact with the skin and make no changes in contact area. This requirement is satisfied, preferably by use of adhesive biomedical electrodes. Moreover, elastic and flexible biomedical electrodes are needed to follow changes in skin expansion and flexion.

In view of this point, a stretchable electro-conductive ink has been investigated, for example, to be applied to electro-conductive part connecting a biological sensor and a device. Additionally, materials have been proposed in which silver flakes are added to a stretchable polymer such as polyester, polyurethane, and silicone (Patent Document 7, Non-Patent Documents 2 and 3). The addition of silver flakes makes it possible to improve the electroconductivity.

CITATION LIST

Patent Literature

Patent Document 1: International Patent Laid-Open Publication No. WO 2013/039151
Patent Document 2: Japanese Unexamined Patent Application Publication No. 2015-100673
Patent Document 3: Japanese Unexamined Patent Application Publication No. H5-095924
Patent Document 4: Japanese Unexamined Patent Application Publication No. 2003-225217

Patent Document 5: Japanese Unexamined Patent Application Publication No. 2015-019806
Patent Document 6: Japanese Unexamined Patent Application Publication No. 2004-527902
Patent Document 7: Japanese Unexamined Patent Application Publication No. 2002-94201

Non Patent Literature

Non Patent Document 1: J. Mater. Chem. A, 2016, 4, p 10038-10069
Non Patent Document 2: IEEE Electron Device letters, 32, 1424-1426 (2011)
Non Patent Document 3: Jpn. J. Appl. Phys., 51(11), 11PD01 (2012)

SUMMARY OF INVENTION

Technical Problem

The present invention was made in view of the situation to solve the problems, and has an object to provide a bio-electrode composition capable of forming a living body contact layer for a bio-electrode that is excellent in electric conductivity and biocompatibility, is light-weight, can be manufactured at low cost, and can control significant reduction in electric conductivity even though the bio-electrode is wetted with water or dried, a bio-electrode including a living body contact layer formed of the bio-electrode composition, and a method for manufacturing the bio-electrode.

Solution to Problem

To solve the above problems, the present invention provides a bio-electrode composition comprising:
(A) an ionic material; and
(C) a metal powder;
the component (A) being a polymer compound comprising a repeating unit-a having a structure selected from the group consisting of an ammonium salt, a sodium salt, a potassium salt, and a silver salt of any of fluorosulfonic acid, fluorosulfonimide, and fluorosulfonamide.

The bio-electrode composition like this is capable of forming a living body contact layer for a bio-electrode that is excellent in electric conductivity and biocompatibility, light-weight, manufacturable at low cost, and free from large lowering of the electric conductivity even though it is wetted with water or dried.

It is preferable that the repeating unit-a be a repeating unit having at least one structure selected from the group consisting of structures shown by the following general formulae (1)-1 to (1)-4,

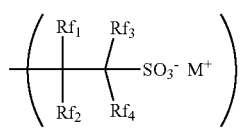

(1)-1

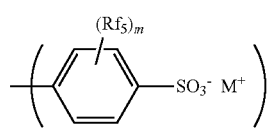

(1)-2

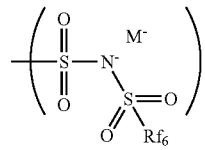

(1)-3

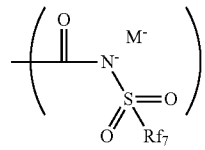

(1)-4 wherein $Rf_1$ and $Rf_2$ each represent a hydrogen atom, a fluorine atom, an oxygen atom, a methyl group, or a trifluoromethyl group, provided that when $Rf_1$ represents an oxygen atom, $Rf_2$ also represents the oxygen atom to form a carbonyl group together with a carbon atom bonded therewith; $Rf_3$ and $Rf_4$ each represent a hydrogen atom, a fluorine atom, or a trifluoromethyl group, provided that one or more of $Rf_1$ to $Rf_4$ is a fluorine atom or a trifluoromethyl group; $Rf_5$, $Rf_6$, and $Rf_7$ each represent a fluorine atom, or a linear or branched alkyl group having 1 to 4 carbon atoms, provided that one or more fluorine atoms are contained; "m" is an integer of 1 to 4; and $M^+$ is an ion selected from an ammonium ion, a sodium ion, a potassium ion, and a silver ion.

The repeating unit-a having such a structure enables the bio-electrode composition to form a living body contact layer for a bio-electrode that is particularly excellent in electric conductivity and biocompatibility, light-weight, manufacturable at low cost, and free from large lowering of the electric conductivity even though it is wetted with water or dried.

It is preferable that the repeating unit-a be at least one repeating unit selected from repeating units-a1 to -a7 shown by the following general formulae (2),

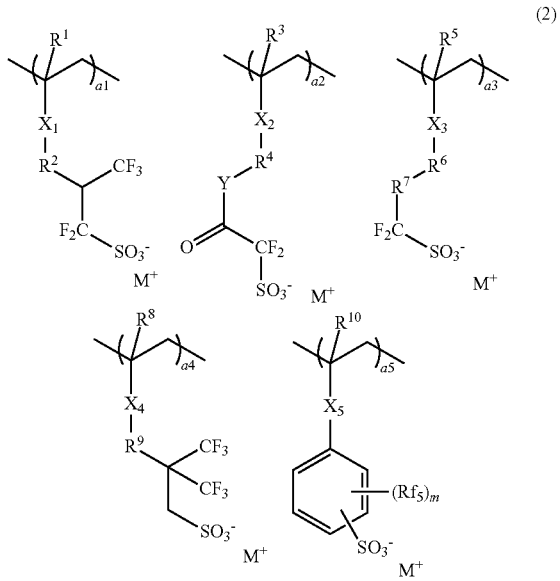

(2)

-continued

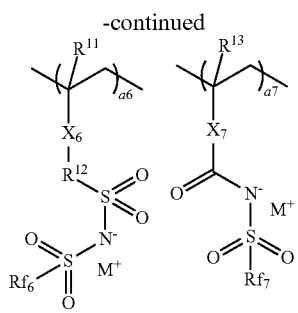

wherein $R^1$, $R^3$, $R^5$, $R^8$, $R^{10}$, $R^{11}$, and $R^{13}$ each independently represent a hydrogen atom or a methyl group; $R^2$, $R^4$, $R^6$, $R^9$, and $R^{12}$ each independently represent any of a single bond, an ester group, or a linear, branched, or cyclic hydrocarbon group having 1 to 13 carbon atoms, optionally having either or both of an ether group and an ester group; $R^7$ represents a linear or branched alkylene group having 1 to 4 carbon atoms, and one or two of the hydrogen atoms in $R^7$ are optionally replaced with a fluorine atom; $X_1$, $X_2$, $X_3$, $X_4$, and $X_6$ each independently represent any of a single bond, a phenylene group, a naphthylene group, an ether group, an ester group, or an amide group; $X_5$ represents any of a single bond, an ether group, or an ester group; $X_7$ represents a single bond, an arylene group having 6 to 12 carbon atoms, or $-C(=O)-O-X_{10}-$; $X_{10}$ represents a linear, branched, or cyclic alkylene group having 1 to 12 carbon atoms, or a divalent aromatic hydrocarbon group having 6 to 10 carbon atoms, optionally having an ether group, a carbonyl group, or an ester group in $X_{10}$; Y represents an oxygen atom or an $-NR^{19}-$ group, optionally bonded to $R^4$ to form a ring; $R^{19}$ represents a hydrogen atom, or a linear or branched alkyl group having 1 to 4 carbon atoms; "i" is an integer of 1 to 4; a1, a2, a3, a4, a5, a6, and a7 are numbers satisfying $0 \leq a1<1.0$, $0 \leq a2<1.0$, $0 \leq a3<1.0$, $0 \leq a4<1.0$, $0 \leq a5<1.0$, $0 \leq a6<1.0$, $0 \leq a7<1.0$, and $0<a1+a2+a3+a4+a5+a6+a7<1.0$; and $M^+$ is an ion selected from an ammonium ion, a sodium ion, a potassium ion, and a silver ion.

With such a component (A), the effect of the present invention can be further improved.

In the bio-electrode composition of the present invention, the component (A) may have a repeating unit-b having silicon, together with the repeating unit-a. In this case, the repeating unit-b is preferably shown by the following general formula (2'),

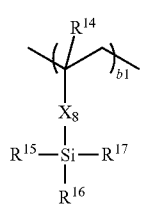 (2')

wherein $R^{14}$ represents a hydrogen atom or a methyl group; $X_8$ represents any of an arylene group having 6 to 12 carbon atoms, a $-C(=O)-O-R^{18}-$ group, or a $-C(=O)-NH-R^{18}-$ group; $R^{18}$ represents any of a single bond, a linear, branched, or cyclic alkylene group having 2 to 12 carbon atoms, or a phenylene group, optionally having one or more groups selected from an ether group, a carbonyl group, an ester group, and an amide group; $R^{15}$, $R^{16}$, and $R^{17}$ each represent a linear, branched, or cyclic alkyl group having 1 to 6 carbon atoms or an aryl group having 6 to 10 carbon atoms, with the alkyl group optionally having one or more species selected from a siloxane bond and a silicon atom in the chain, and the alkyl group and/or the aryl group optionally having a halogen atom; $R^{15}$ and $R^{16}$ or $R^{15}$, $R^{16}$, and $R^{17}$ are optionally bonded to each other to form a ring or a three dimensional structure; and b1 is a number satisfying $0<b1<1.0$ and $0<a1+a2+a3+a4+a5+a6+a7+b1<1.0$.

With such a component (A), the effect of the present invention can be further improved.

It is also preferable that the component (A) have the repeating unit-a that has an ammonium salt structure with the ammonium salt containing an ammonium ion shown by the following general formula (3),

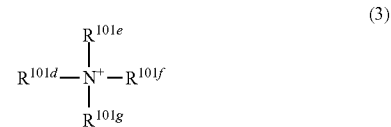 (3)

wherein $R^{101d}$, $R^{101e}$, $R^{101f}$, and $R^{101g}$ each represent a hydrogen atom, a linear, branched, or cyclic alkyl group having 1 to 12 carbon atoms, a linear, branched, or cyclic alkenyl group or alkynyl group having 2 to 12 carbon atoms, or an aromatic group having 4 to 20 carbon atoms, optionally having one or more species selected from an ether group, a carbonyl group, an ester group, a hydroxy group, an amino group, a nitro group, a sulfonyl group, a sulfinyl group, a halogen atom, and a sulfur atom; $R^{101d}$ and $R^{101e}$, or $R^{101d}$, $R^{101e}$, and $R^{101f}$ are optionally bonded to each other together with the nitrogen atom bonded therewith to form a ring in which $R^{101d}$ and $R^{101e}$, or $R^{101d}$, $R^{101e}$, and $R^{101f}$ are each an alkylene group having 3 to 10 carbon atoms, or to form a heteroaromatic ring having the nitrogen atom in the formula within the ring.

The component (A) having such an ammonium ion allows the present invention to achieve more improved effects.

The inventive bio-electrode composition may further comprises (B) a resin other than the component (A). In this case, it is preferable that the component (B) contain a silicone resin having an $R_xSiO_{(4-x)/2}$ unit (wherein, R represents a substituted or unsubstituted monovalent hydrocarbon group having 1 to 10 carbon atoms, and "x" is a number in a range of 2.5 to 3.5) and an $SiO_2$ unit, diorganosiloxane having an alkenyl group, and organohydrogenpolysiloxane having an SiH group.

In case of having the component (B) like this, (A) the ionic material (salt) is compatibilized, thereby making it possible to prevent elution of the salt, and to hold an electric conductivity improver such as metal powders and to achieve adhesion.

It is preferable that the bio-electrode composition further comprise an organic solvent.

The bio-electrode composition like this is further improved in the coating properties.

It is preferable that the component (C) be a powder of a metal selected from gold, silver, platinum, copper, tin, titanium, nickel, aluminum, tungsten, molybdenum, ruthenium, chromium, and indium. It is more preferable that the component (C) be a silver powder, a copper powder, a tin powder, or a titanium powder.

The component (C) like this makes it possible to improve the electronic conductivity of the inventive bio-electrode composition. Particularly, a silver particle is preferable in view of electric conductivity, cost, and biocompatibility.

It is preferable that the bio-electrode composition further comprise a carbon material in addition to the component (C).

The electric conductivity can be more improved by adding a carbon material in addition to the metal powder.

It is preferable that the carbon material be either or both of carbon black and carbon nanotube.

In the bio-electrode composition of the present invention, these carbon materials can be used particularly favorably.

The present invention also provides a bio-electrode comprising an electro-conductive base material and a living body contact layer formed on the electro-conductive base material;

wherein the living body contact layer is a cured material of the inventive bio-electrode composition described above.

The ionic material described above allows the inventive bio-electrode to achieve both of electric conductivity and biocompatibility. The inventive bio-electrode also has adhesion and can keep the contact area with skin constant to obtain electric signals from skin stably in high sensitivity.

It is preferable that the electro-conductive base material comprise one or more species selected from gold, silver, silver chloride, platinum, aluminum, magnesium, tin, tungsten, iron, copper, nickel, stainless steel, chromium, titanium, and carbon.

In the bio-electrode of the present invention, these electro-conductive base materials can be used particularly favorably.

The present invention also provides a method for manufacturing a bio-electrode having an electro-conductive base material and a living body contact layer formed on the electro-conductive base material, comprising: applying the bio-electrode composition described above onto the electro-conductive base material; and curing the bio-electrode composition; thereby forming the living body contact layer.

The inventive method for manufacturing a bio-electrode makes it possible to manufacture the inventive bio-electrode, which is excellent in electric conductivity and biocompatibility, light-weight, and free from large lowering of the electric conductivity even though it is wetted with water or dried, easily and at low cost.

It is preferable that the electro-conductive base material comprise one or more species selected from gold, silver, silver chloride, platinum, aluminum, magnesium, tin, tungsten, iron, copper, nickel, stainless steel, chromium, titanium, and carbon.

In the inventive method for manufacturing a bio-electrode, these electro-conductive base materials can be used particularly favorably.

Advantageous Effects of Invention

As described above, the inventive bio-electrode composition makes it possible to form a living body contact layer for a bio-electrode that is capable of conducting electric signals from skin efficiently to a device (i.e., excellent in electric conductivity), free from the risk of causing allergies even when it is worn on skin for a long time (i.e., excellent in biocompatibility), light-weight, manufacturable at low cost, and free from large lowering of the electric conductivity even though it is wetted with water or dried.

The inventive bio-electrode, with the living body contact layer being formed of a cured material of the inventive bio-electrode composition described above, is excellent in electric conductivity and biocompatibility, light-weight, manufacturable at low cost, and free from large lowering of the electric conductivity even though it is wetted with water or dried as described above.

Additionally, the inventive method for manufacturing a bio-electrode makes it possible to manufacture the inventive bio-electrode, which is excellent in electric conductivity and biocompatibility, light-weight, and free from large lowering of the electric conductivity even though it is wetted with water or dried, easily at low cost.

BRIEF DESCRIPTION OF DRAWINGS

FIG. 1 is a schematic sectional view showing an example of a bio-electrode having a living body contact layer composed of a cured product of the inventive bio-electrode composition;

FIG. 2 is a schematic sectional view showing an example of the inventive bio-electrode worn on a living body;

FIG. 3A is a schematic view of the bio-electrode produced in Examples of the present invention viewed from the living body contact layer side;

FIG. 3B is a schematic view of the bio-electrode produced in Examples of the present invention viewed from the electro-conductive base material side; and FIG. 4 is a schematic of a scene of measuring impedance on the surface of skin by using the bio-electrode produced in Examples of the present invention.

DESCRIPTION OF EMBODIMENTS

As described above, it has been desired to develop a bio-electrode composition capable of forming a living body contact layer for a bio-electrode that is excellent in electric conductivity and biocompatibility, light-weight, manufacturable at low cost, and free from large lowering of the electric conductivity even though it is wetted with water or dried; a bio-electrode in which the living body contact layer is formed from the bio-electrode composition; and a method for manufacturing the same.

The surface of skin releases ions of sodium, potassium, and calcium in accordance with heartbeat. The bio-electrode have to convert the increase and decrease of these ions released from skin to electric signals. Accordingly, the bio-electrode have to be composed of a material that is excellent in ionic conductivity to transmit the increase and decrease of ions.

The present inventors have noticed ionic liquids as a material that is highly ionic conductive. Ionic liquids are characterized by high thermal and chemical stability as well as excellent electric conductivity, thereby having been widely used for battery uses. Illustrative examples of known ionic liquid include hydrochloric acid salt, hydrobromic acid salt, hydroiodic acid salt, trifluoromethanesulfonic acid salt, nonafluorobutanesulfonic acid salt, bis(trifluoromethanesulfonyl)imide acid salt, hexafluorophosphate salt, and tetrafluoroborate salt of sulfonium, phosphonium, ammonium, morpholinium, pyridinium, pyrrolidinium, and imidazolium. However, these salts (particularly, the ones with low molecular weight) are generally liable to hydrate, thereby causing a defect such that the salt is extracted with perspiration or by washing to lower the electric conductivity of a bio-electrode in which the living body contact layer is formed from a bio-electrode composition containing these salts. In addition, the tetrafluoroborate salt is highly toxic, and the other salts are highly water-soluble to easily permeate into skin, thereby causing an issue of rough dry skin (i.e., highly irritative to skin).

In neutralized salts formed from highly acidic acids, the ions are strongly polarized to improve the ionic conductivity. This is the reason why lithium salts of bis(trifluoromethanesulfonyl)imidic acid and tris(trifluoromethanesulfonyl)methide acid show high ionic conductivity as a lithium ion battery. On the other hand, the higher acidity makes the salt have stronger irritation to a body. That is, ionic conductivity and irritation to a body are in relation of trade-off. In a salt applied to a bio-electrode, however, higher ionic conductivity and lower irritation to a body have to be combined.

As the molecular weight of ionic compound increases, the permeability and the stimulus to skin tends to decrease. Accordingly, the ionic compound is preferably a polymer type with higher molecular weight. Thus the present inventors have conceived to polymerize this ionic compound by forming it to have a polymerizable double bond, and additionally to synthesize a copolymer with a silicon-containing monomer in order to improve water resistance such as resistance to perspiration from skin.

The present inventors have also conceived that the use of this salt mixed with adhesive (resin), such as a silicone type, an acrylic type, and a urethane type, makes it possible to achieve continuous adhesion to skin to obtain electric signals that is stable for a long time.

The inventors have diligently studied the above subjects and found that higher ionic conductivity alone is inadequate to form a bio-electrode with higher sensitivity, and higher electronic conductivity is also necessary; the electronic conductivity is improved efficiently by adding particles of carbon or metal; the addition of a metal powder is particularly effective and allows the bio-electrode to function as a highly sensitive bio-electrode with lower impedance; thereby bringing the present invention to completion.

That is, the present invention is a bio-electrode composition comprising:

(A) an ionic material; and (C) a metal powder;

the component (A) being a polymer compound comprising a repeating unit-a having a structure selected from the group consisting of an ammonium salt, a sodium salt, a potassium salt, and a silver salt of any of fluorosulfonic acid, fluorosulfonimide, and fluorosulfonamide.

Hereinafter, the present invention will be described specifically, but the present invention is not limited thereto.

<Bio-Electrode Composition>

The inventive bio-electrode composition contains (A) an ionic material and (C) a metal powder. Additionally, it is also possible to contain (B) a resin other than the component (A). Hereinafter, each component will be described more specifically.

[(A) Ionic Material (Salt)]

The salt to be added to the inventive bio-electrode composition as (A) the ionic material (conductive material) is a polymer compound containing the repeating unit-a having a structure selected from an ammonium salt, a sodium salt, a potassium salt, and a silver salt of any of fluorosulfonic acid, fluorosulfonimide, and fluorosulfonamide. The salt may be a polymer compound that has both of the repeating unit-a and the repeating unit-b having silicon.

The repeating unit-a can have at least one structure selected from the group consisting of structures shown by the following general formulae (1)-1 to (1)-4,

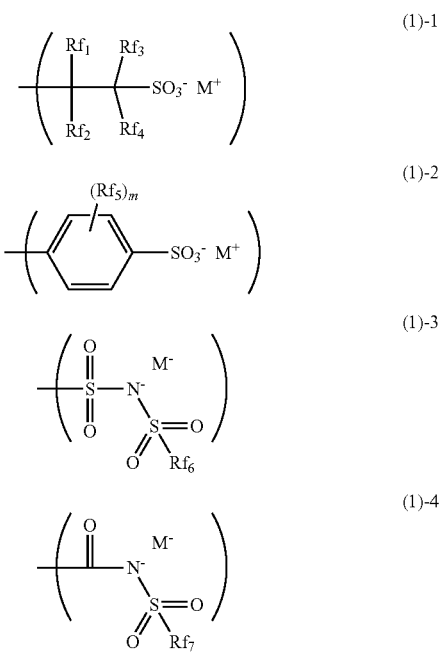

wherein $Rf_1$ and $Rf_2$ each represent a hydrogen atom, a fluorine atom, an oxygen atom, a methyl group, or a trifluoromethyl group, provided that when $Rf_1$ represents an oxygen atom, $Rf_2$ also represents the oxygen atom to form a carbonyl group together with a carbon atom bonded therewith; $Rf_3$ and $Rf_4$ each represent a hydrogen atom, a fluorine atom, or a trifluoromethyl group, provided that one or more of $Rf_1$ to $Rf_4$ is a fluorine atom or a trifluoromethyl group; $Rf_5$, $Rf_6$, and $Rf_7$ each represent a fluorine atom, or a linear or branched alkyl group having 1 to 4 carbon atoms, provided that one or more fluorine atoms are contained; "m" is an integer of 1 to 4; and $M^+$ is an ion selected from an ammonium ion, a sodium ion, a potassium ion, and a silver ion.

As at least one repeating unit selected from an ammonium salt, a sodium salt, a potassium salt, and a silver salt of fluorosulfonic acid shown by any of the general formula (1)-1 and (1)-2, fluorosulfonimide shown by the general formula (1)-3, and fluorosulfonamide shown by the general formula (1)-4, it is preferable to select one or more kinds of repeating units-a1 to -a7 shown by the following general formulae (2).

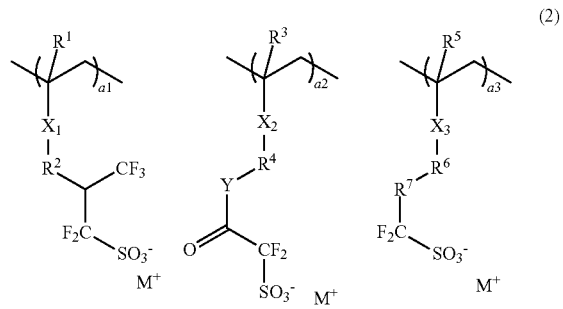

-continued

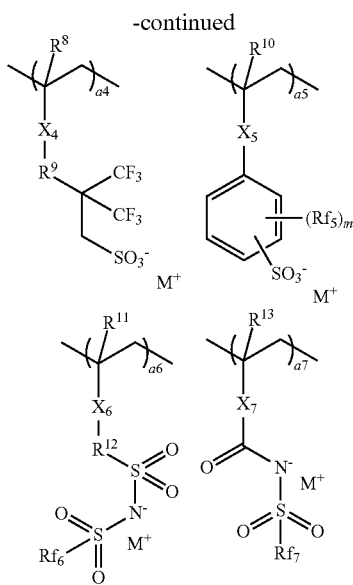

In the formulae, $R^1$, $R^3$, $R^5$, $R^8$, $R^{10}$, $R^{11}$, and $R^{13}$ each independently represent a hydrogen atom or a methyl group; $R^2$, $R^4$, $R^6$, $R^9$, and $R^{12}$ each independently represent any of a single bond, an ester group, or a linear, branched, or cyclic hydrocarbon group having 1 to 13 carbon atoms, optionally having either or both of an ether group and an ester group; $R^7$ represents a linear or branched alkylene group having 1 to 4 carbon atoms, and one or two of the hydrogen atoms in $R^7$ are optionally replaced with a fluorine atom; $X_1$, $X_2$, $X_3$, $X_4$, and $X_6$ each independently represent any of a single bond, a phenylene group, a naphthylene group, an ether group, an ester group, or an amide group; $X_5$ represents any of a single bond, an ether group, or an ester group; $X_7$ represents a single bond, an arylene group having 6 to 12 carbon atoms, or —C(=O)—O—$X_{10}$—; $X_{10}$ represents a linear, branched, or cyclic alkylene group having 1 to 12 carbon atoms, or a divalent aromatic hydrocarbon group having 6 to 10 carbon atoms, optionally having an ether group, a carbonyl group, or an ester group in $X_{10}$; Y represents an oxygen atom or an —$NR^{19}$— group, optionally bonded to $R^4$ to form a ring; $R^{19}$ represents a hydrogen atom, or a linear or branched alkyl group having 1 to 4 carbon atoms; "m" is an integer of 1 to 4; a1, a2, a3, a4, a5, a6, and a7 are numbers satisfying $0 \le a1 < 1.0$, $0 \le a2 < 1.0$, $0 \le a3 < 1.0$, $0 \le a4 < 1.0$, $0 \le a5 < 1.0$, $0 \le a6 < 1.0$, $0 \le a7 < 1.0$, and $0 < a1+a2+a3+a4+a5+a6+a7 < 1.0$; and $M^+$ is an ion selected from an ammonium ion, a sodium ion, a potassium ion, and a silver ion.

In case of containing the repeating unit-b having silicon in addition to the repeating unit-a, the repeating unit-b is preferably the repeating unit-b1 shown by the following general formula (2').

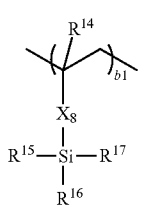

(2')

In the formula, $R^{14}$ represents a hydrogen atom or a methyl group; $X_8$ represents any of an arylene group having 6 to 12 carbon atoms, a —C(=O)—O—$R^{18}$— group, or a —C(=O)—NH—$R^{18}$— group; $R^{18}$ represents any of a single bond, a linear, branched, or cyclic alkylene group having 2 to 12 carbon atoms, or a phenylene group, optionally having one or more groups selected from an ether group, a carbonyl group, an ester group, and an amide group; $R^{15}$, $R^{16}$, and $R^{17}$ each represent a linear, branched, or cyclic alkyl group having 1 to 6 carbon atoms or an aryl group having 6 to 10 carbon atoms, with the alkyl group optionally having one or more species selected from a siloxane bond and a silicon atom in the chain, and the alkyl group and/or the aryl group optionally having a halogen atom; $R^{15}$ and $R^{16}$, or $R^5$, $R^{16}$, and $R^{17}$ are optionally bonded to each other to form a ring or a three dimensional structure; and b1 is a number satisfying $0 < b1 < 1.0$ and $0 < a1+a2+a3+a4+a5+a6+a7+b1 < 1.0$.

(Repeating Unit-a)

Among the repeating units-a1 to -a7 shown by the general formulae (2), the repeating units-a1 to -a5 can be obtained from the fluorosulfonic acid salt monomers exemplified below.

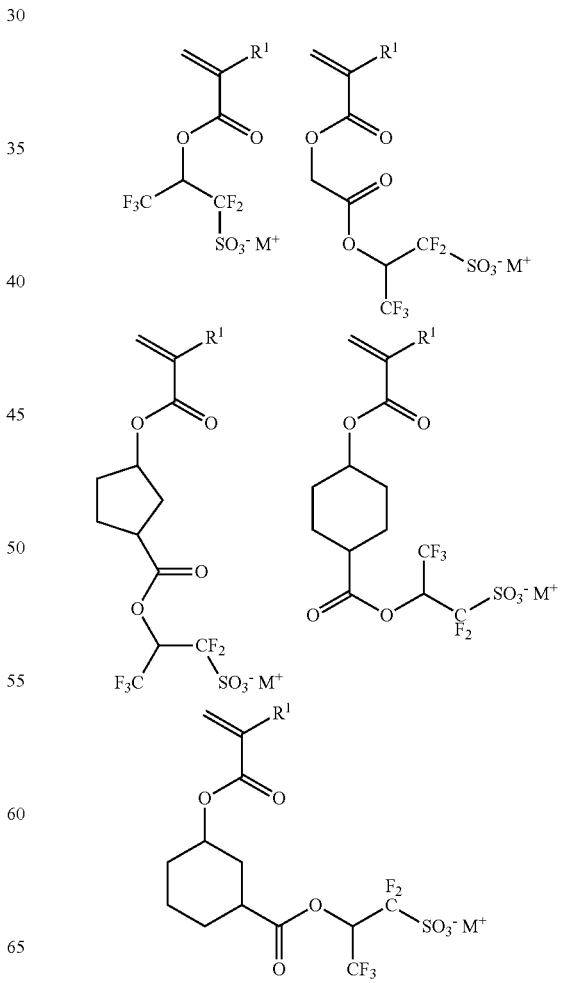

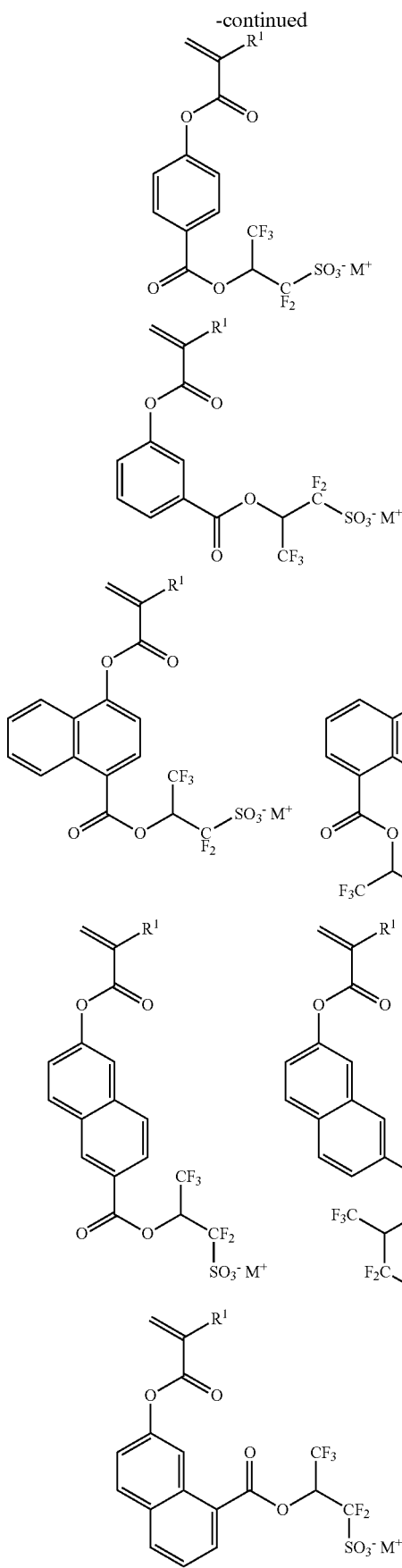
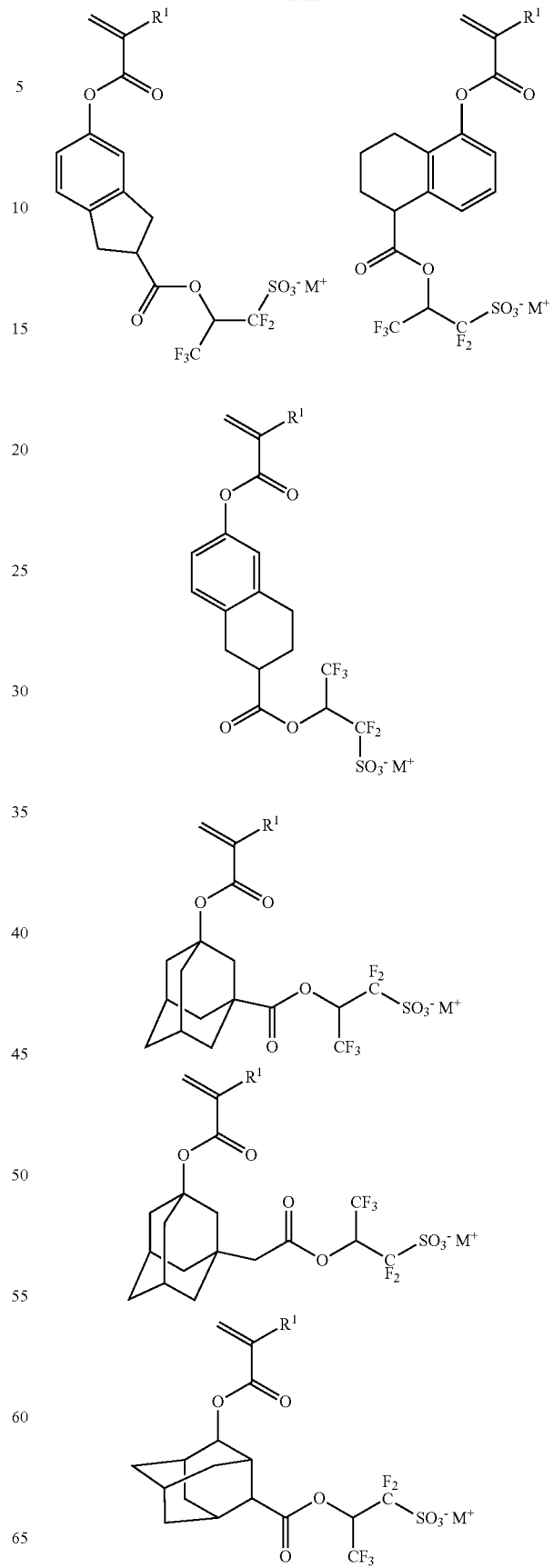

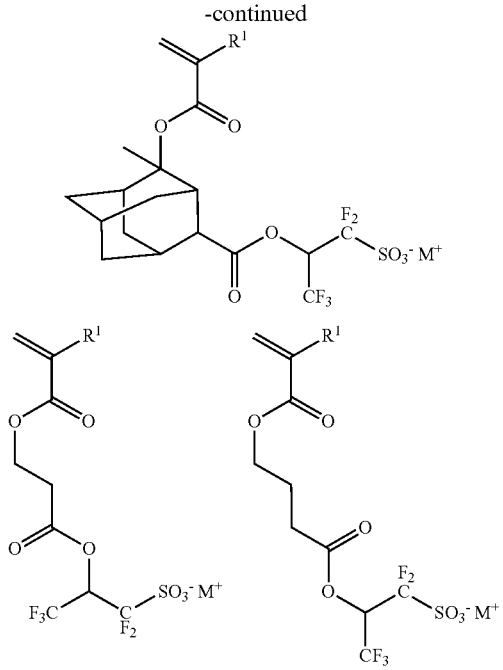
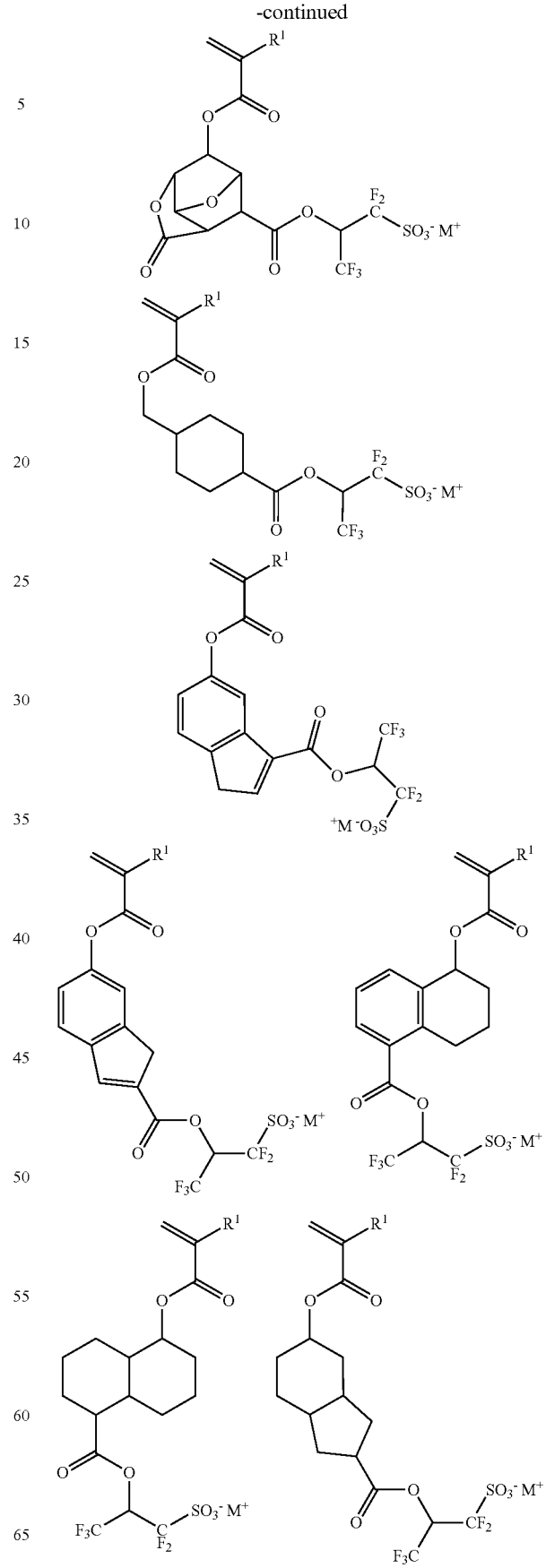

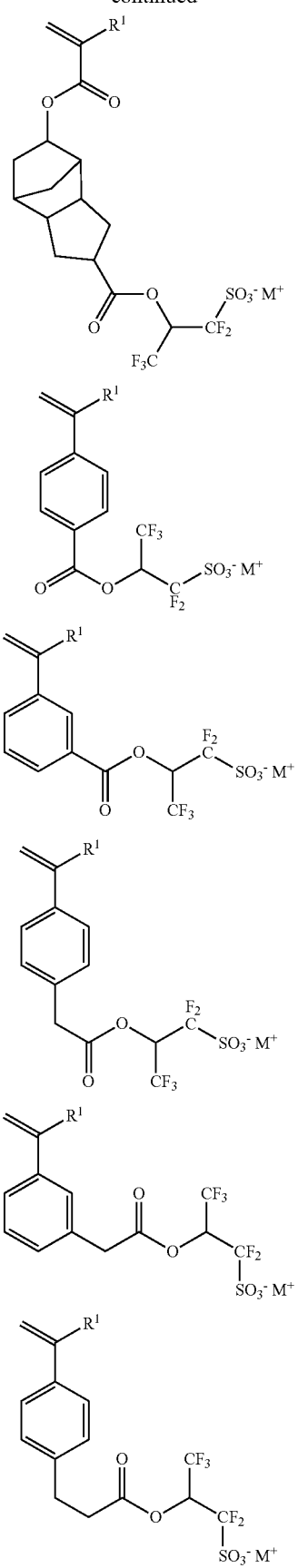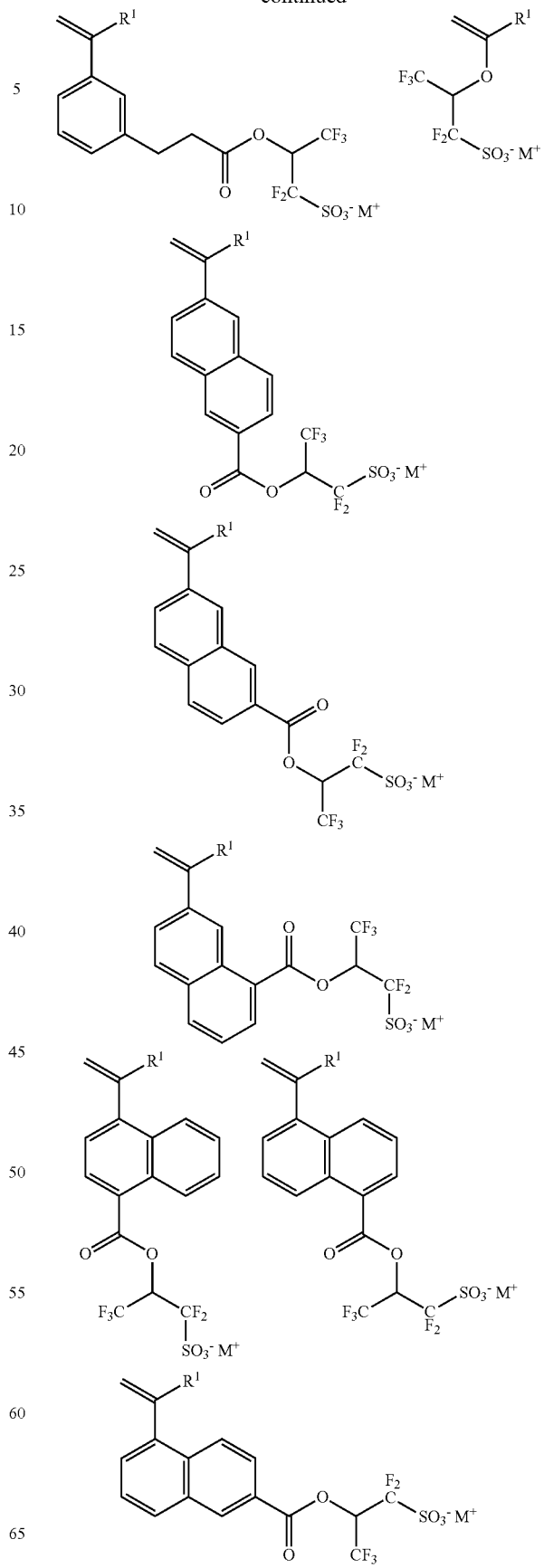

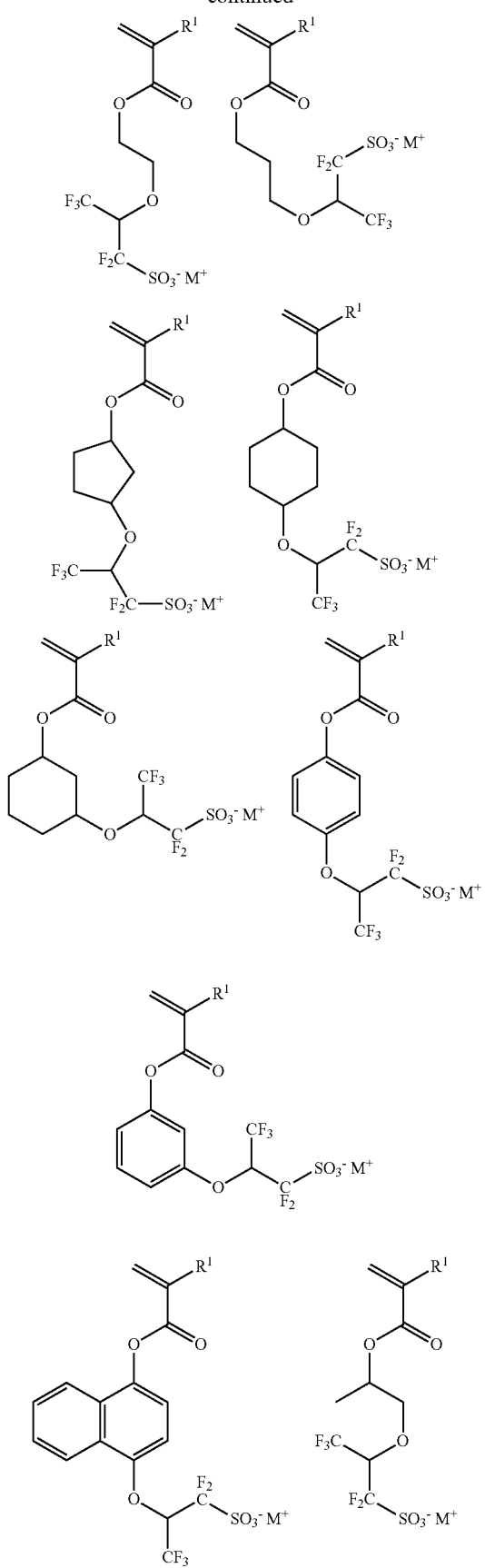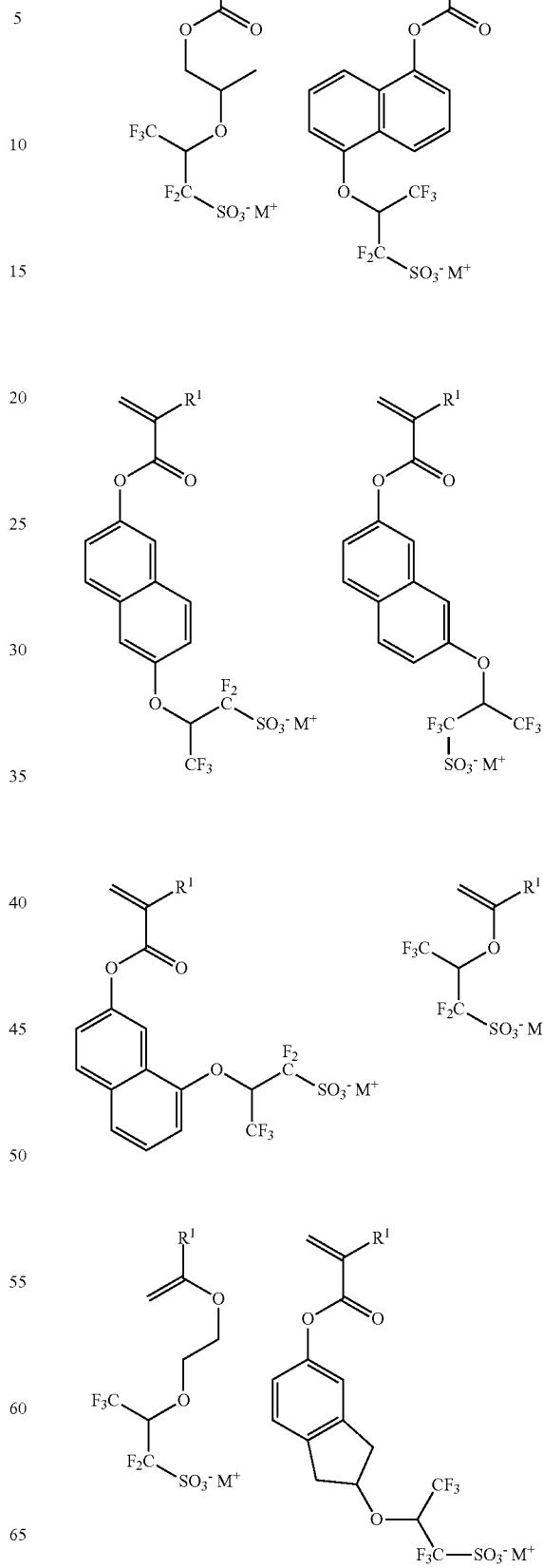

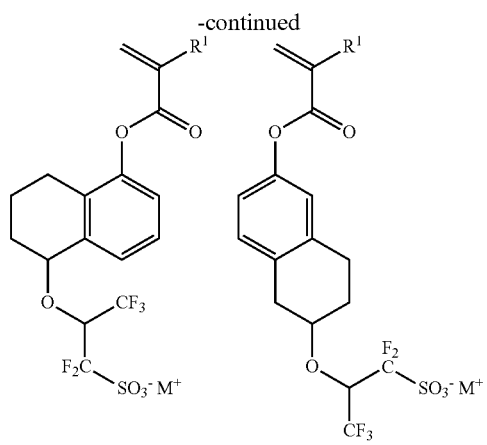
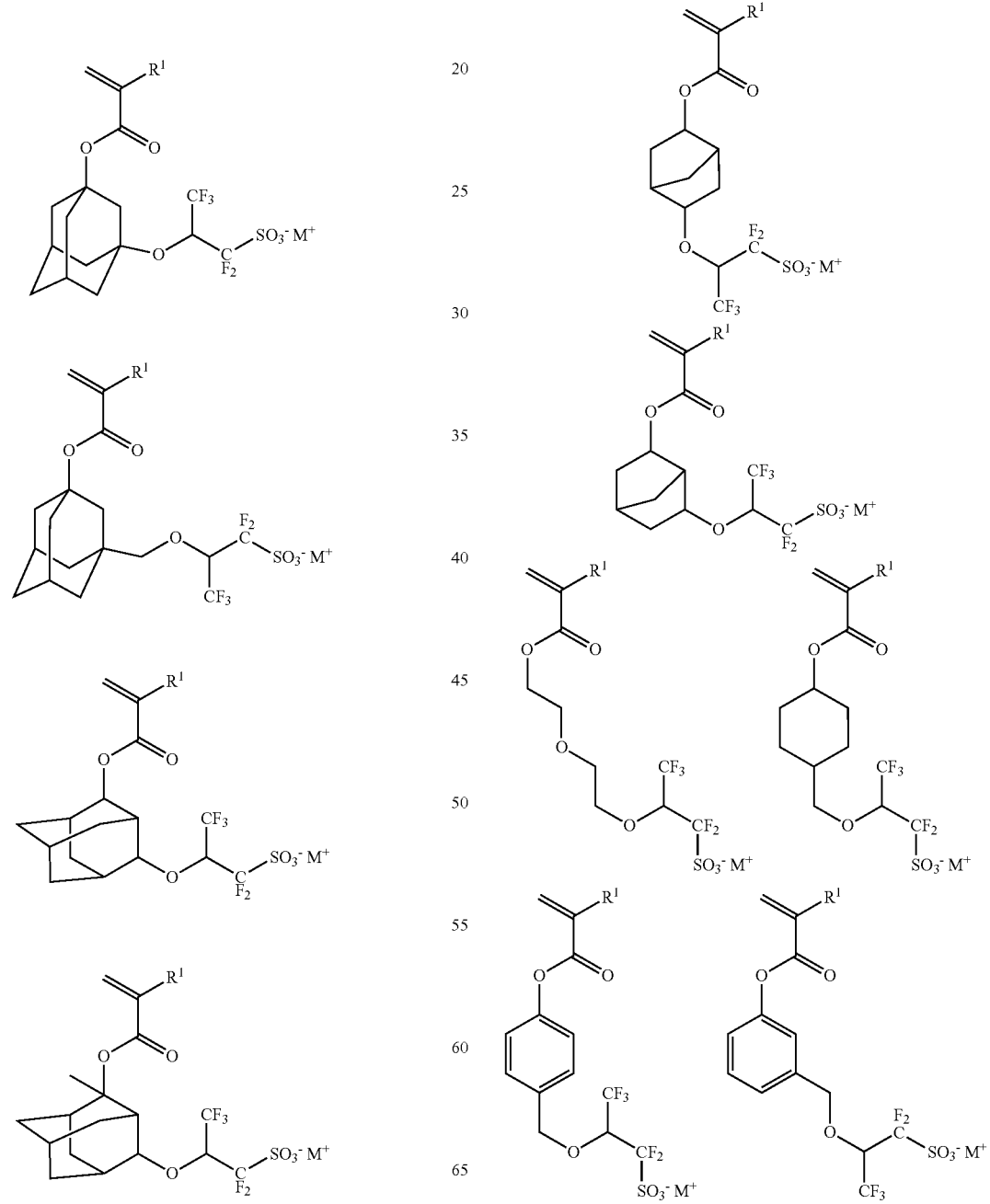

-continued
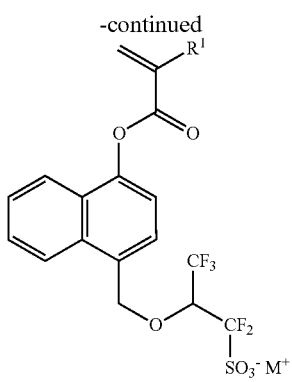
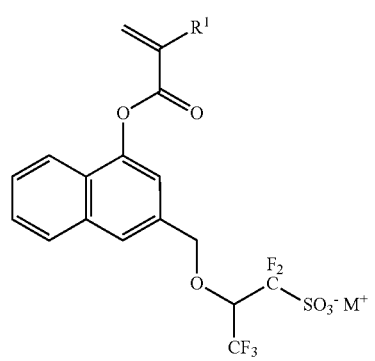
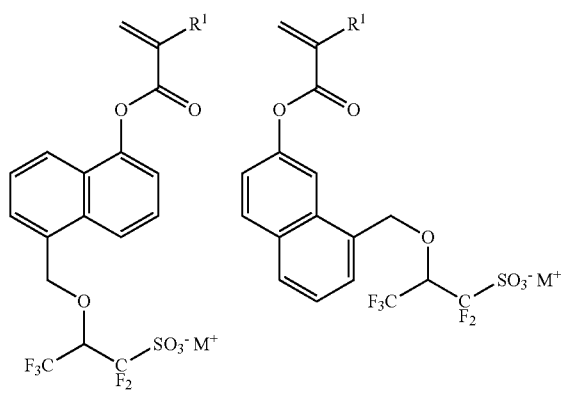
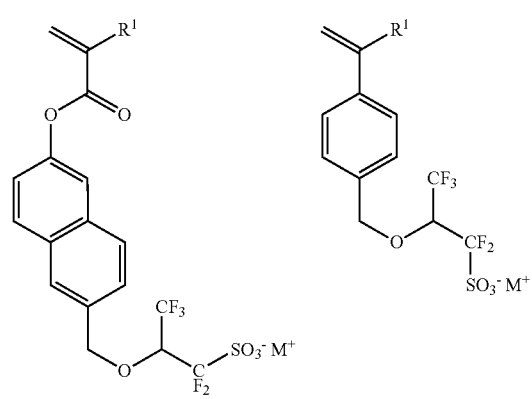
-continued
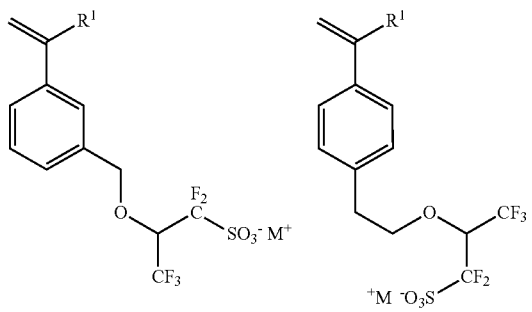
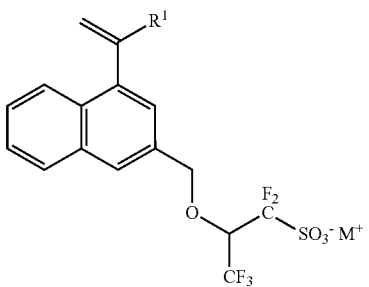
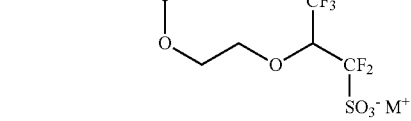
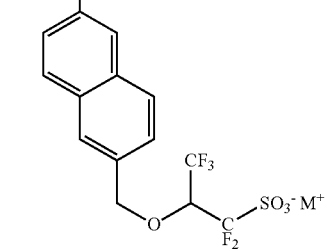
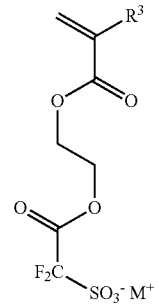

25
-continued
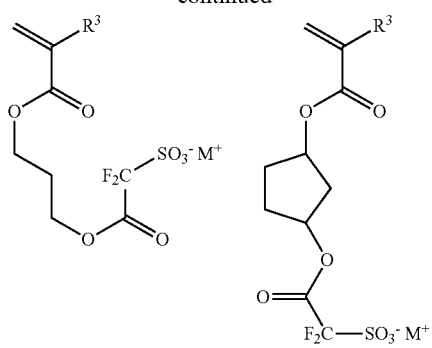
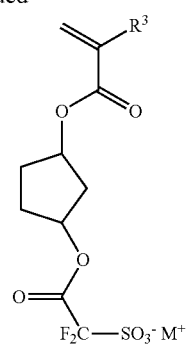
26
-continued
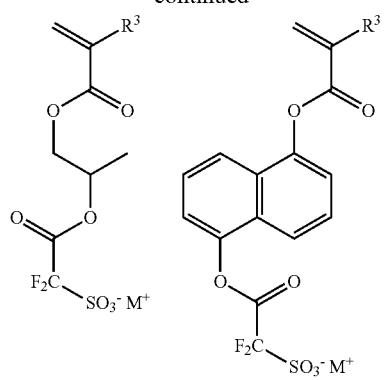
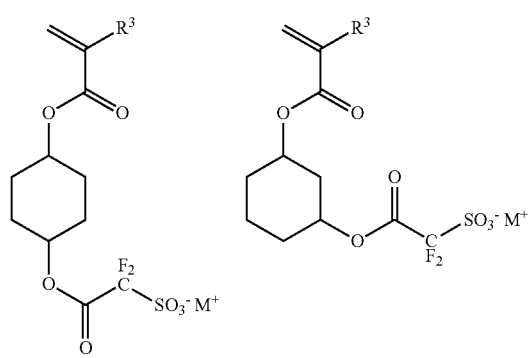
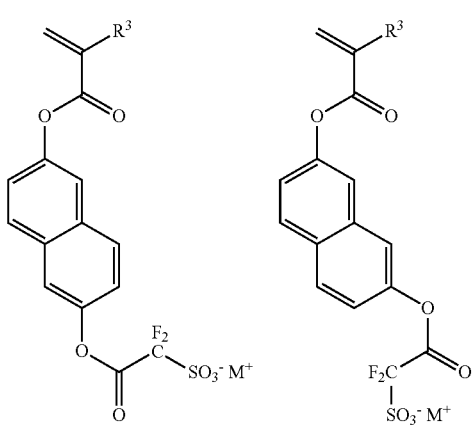
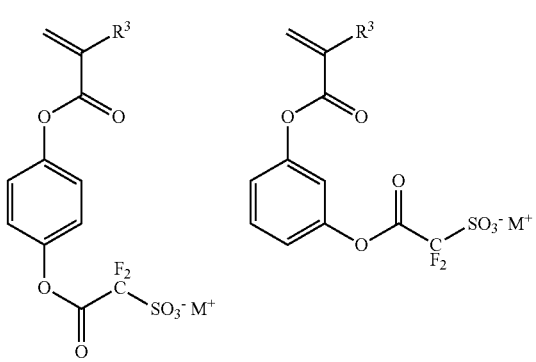
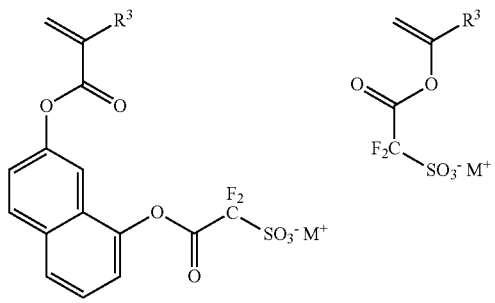
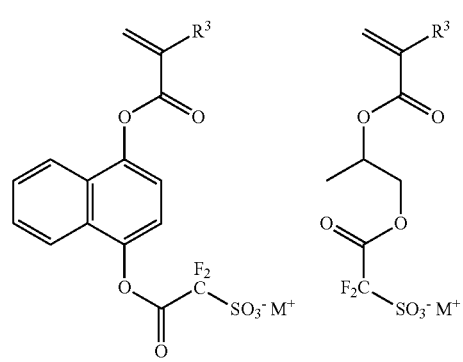
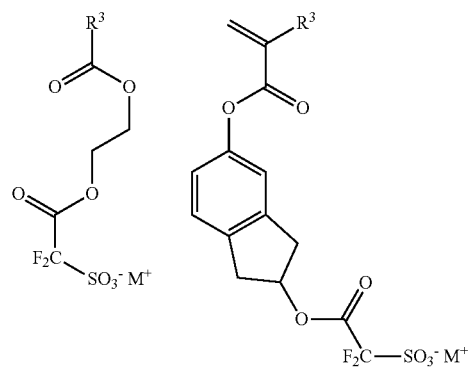

27
-continued
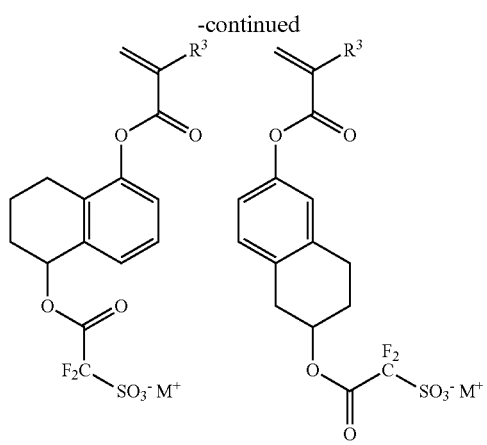
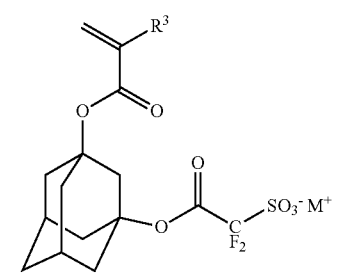
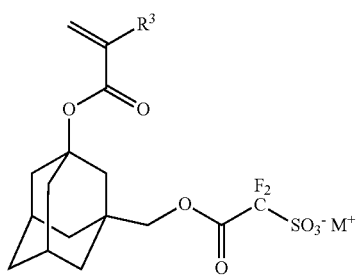
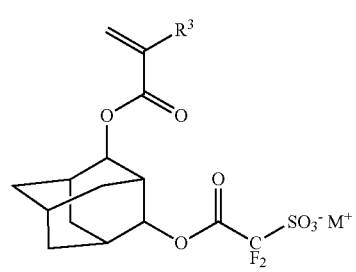
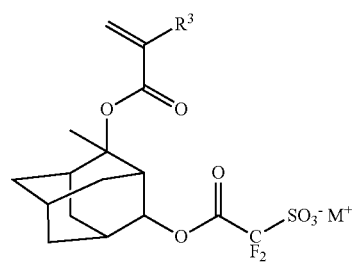
28
-continued
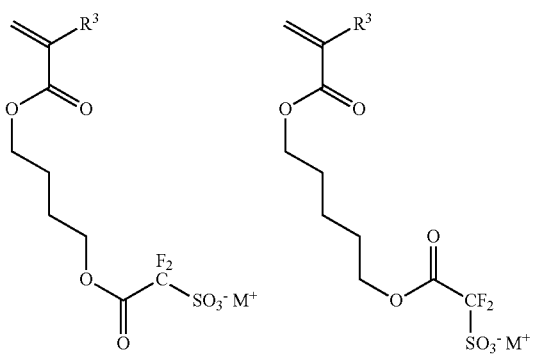
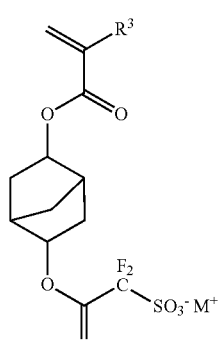
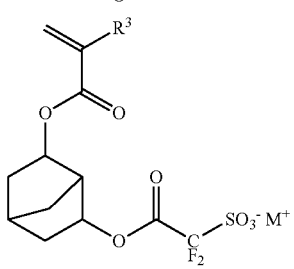
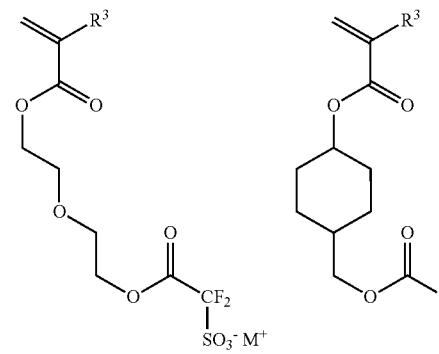
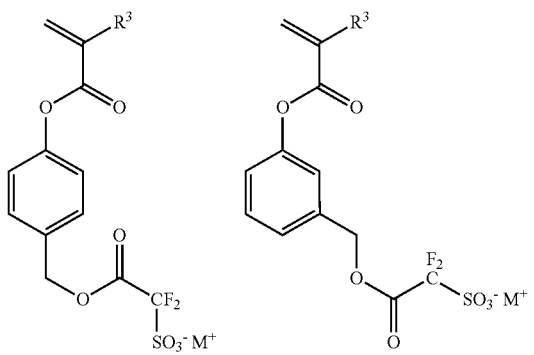

-continued
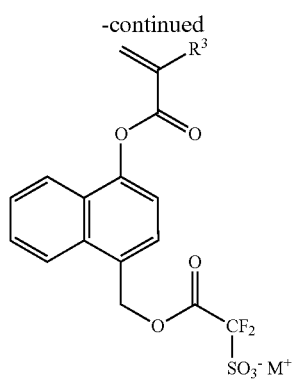
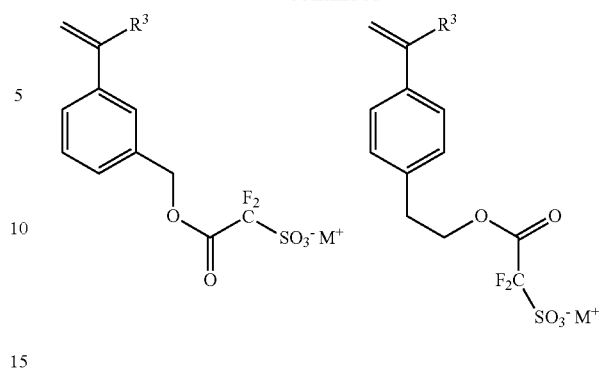
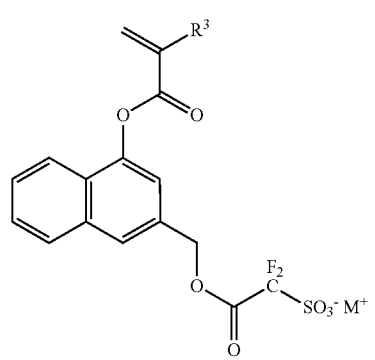
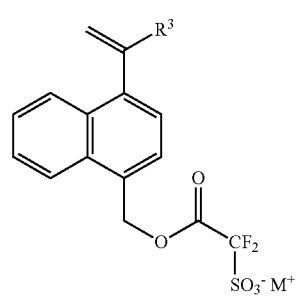
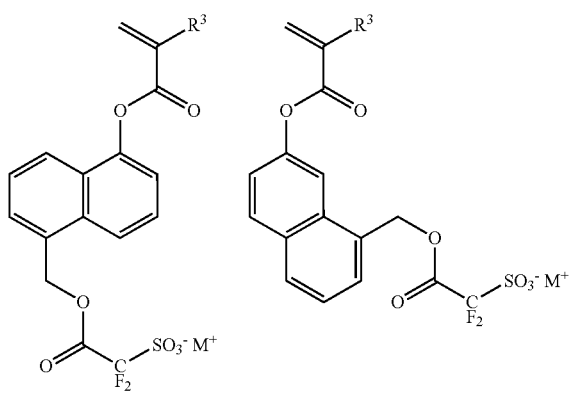
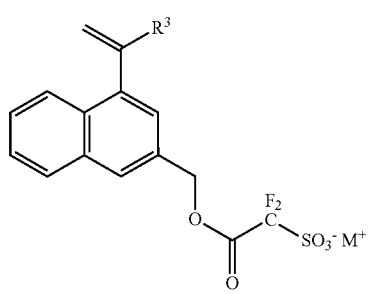
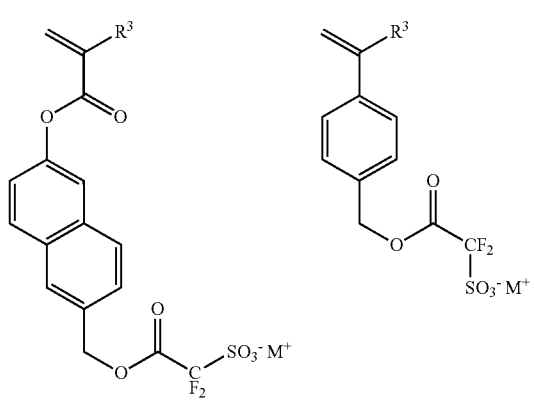
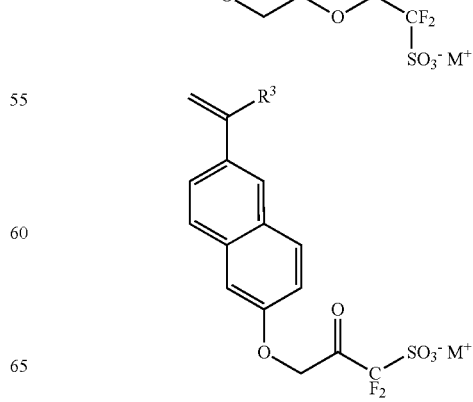

-continued
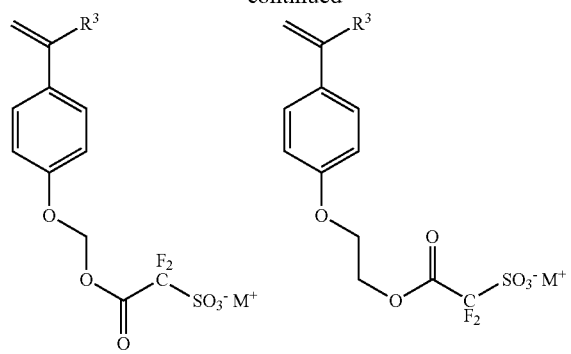
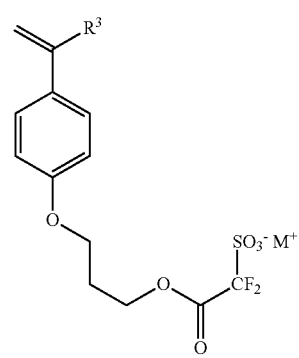
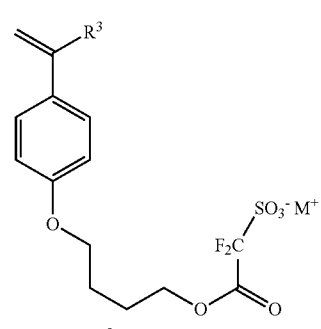
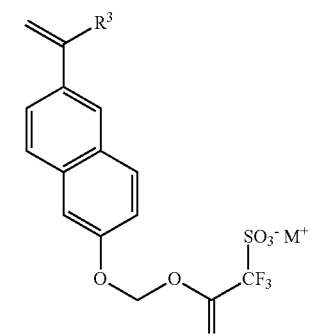
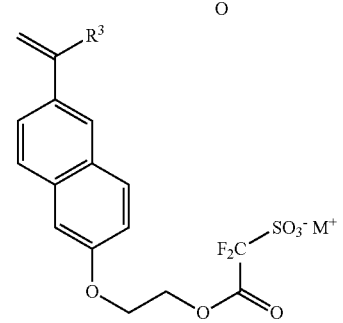
-continued
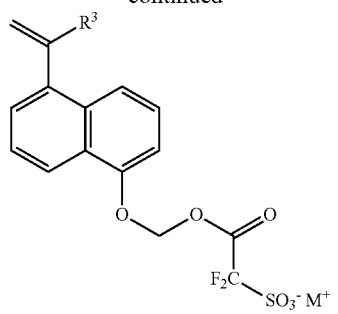
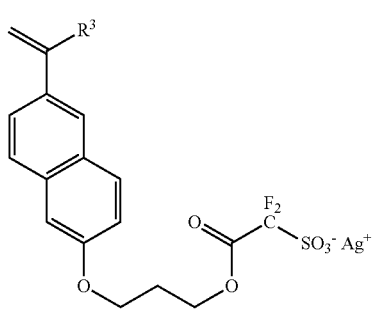
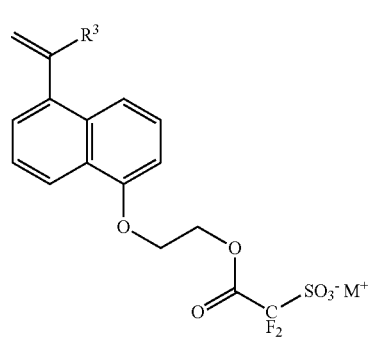
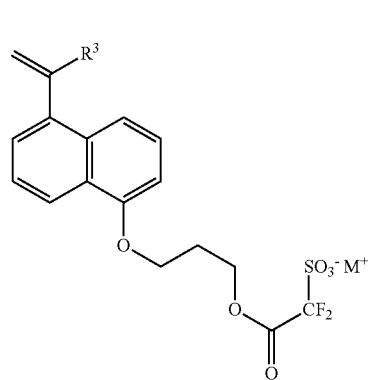
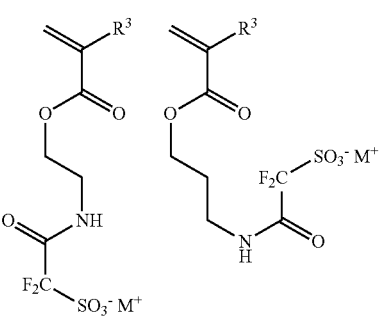

33
-continued
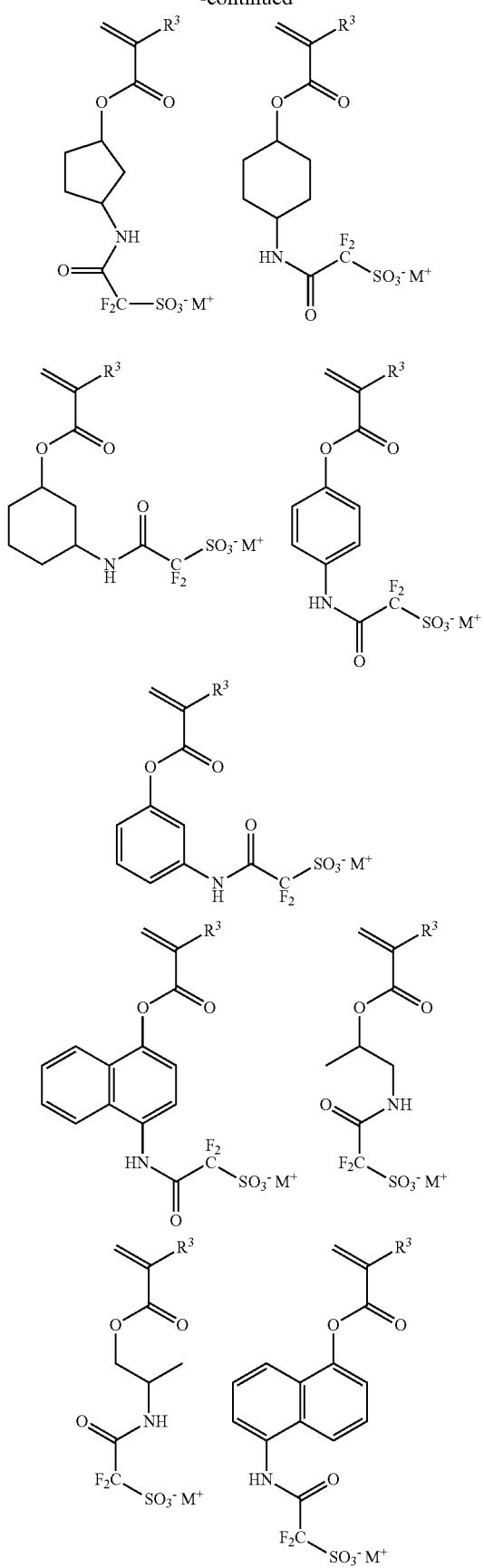
34
-continued
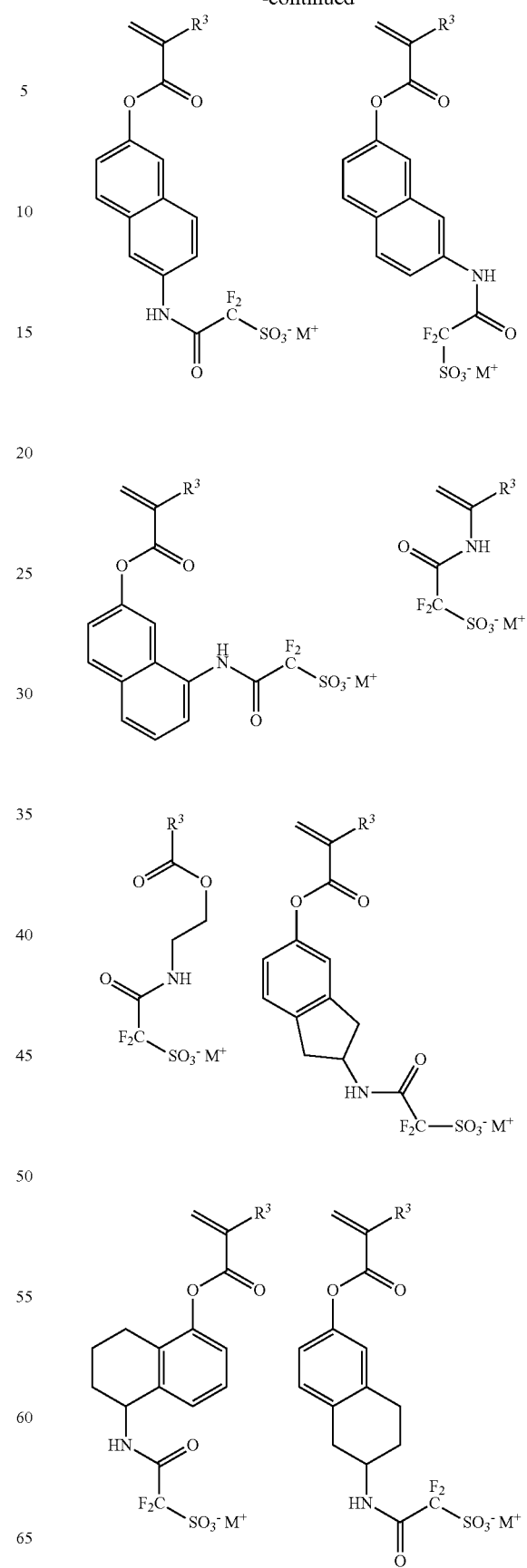

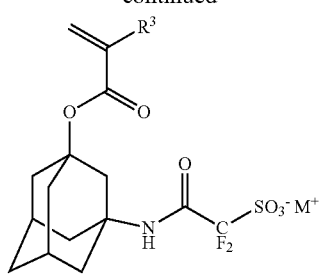
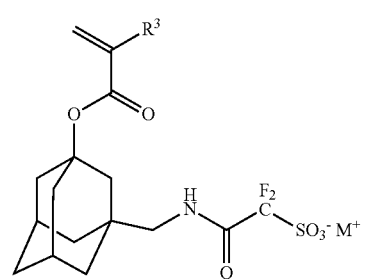
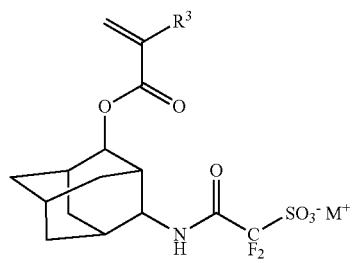
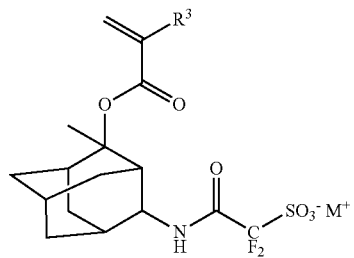
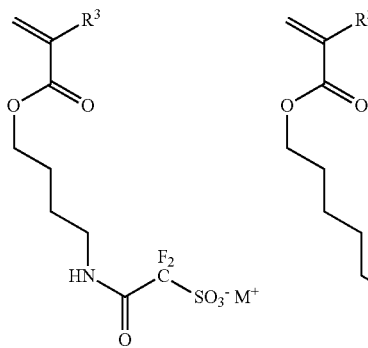
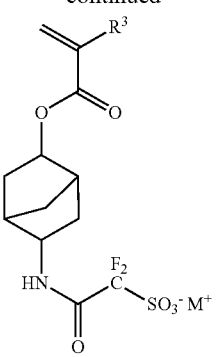
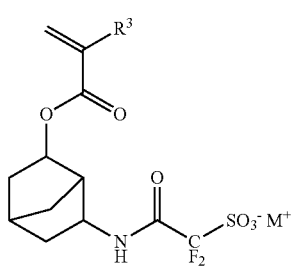
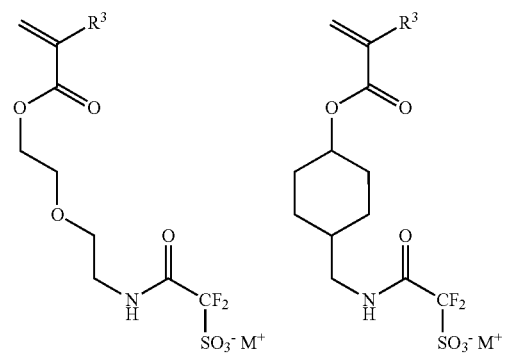
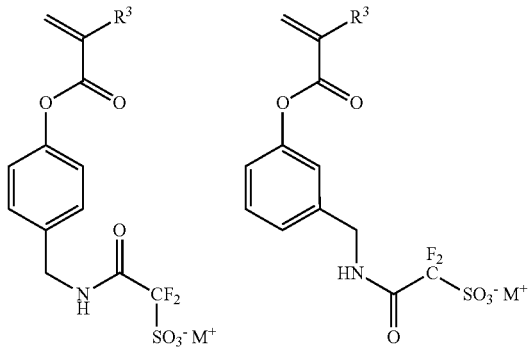
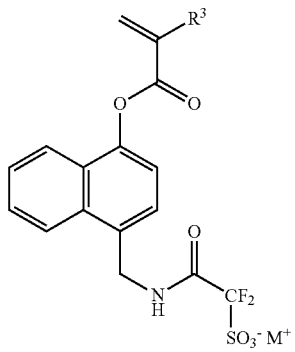

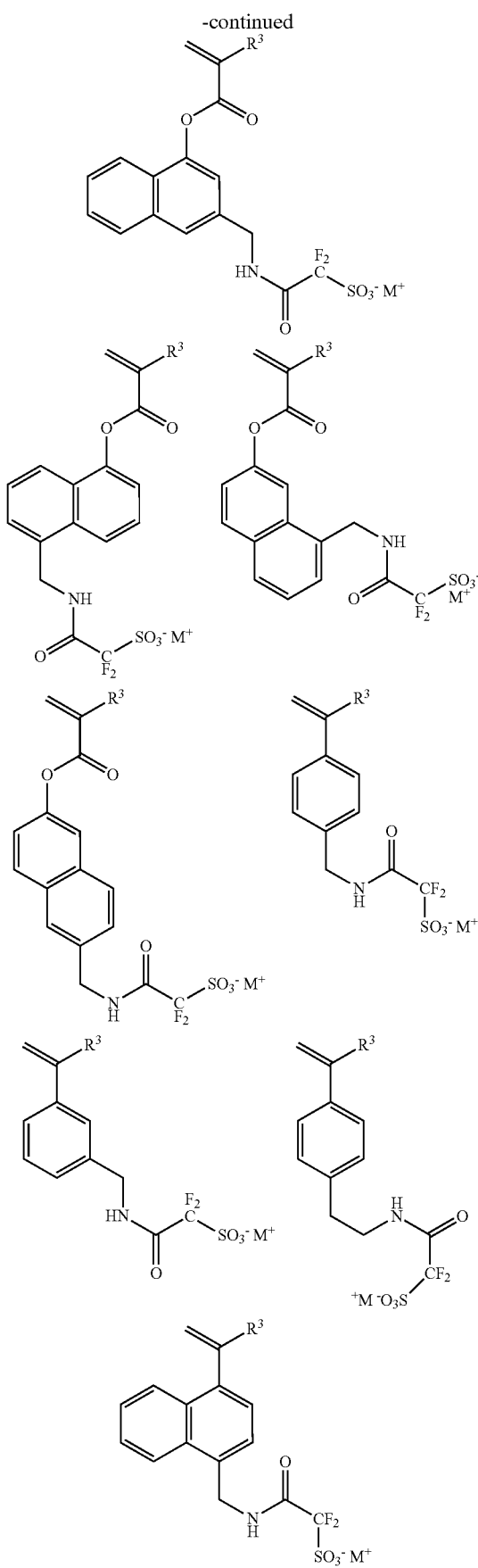
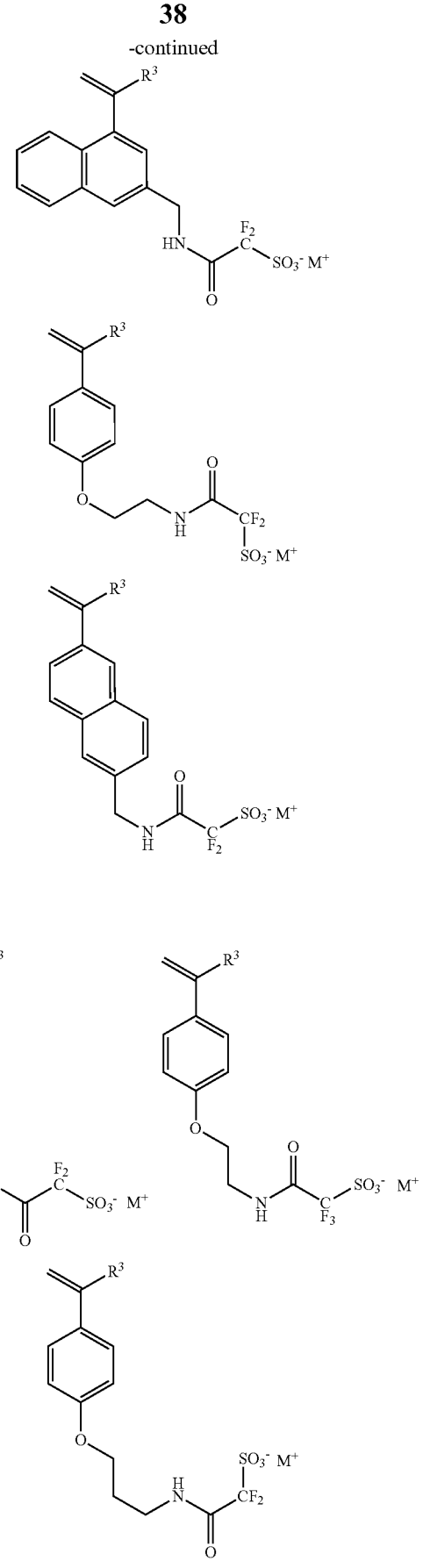

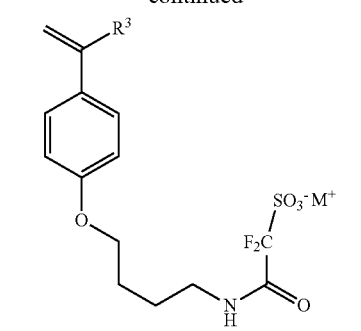
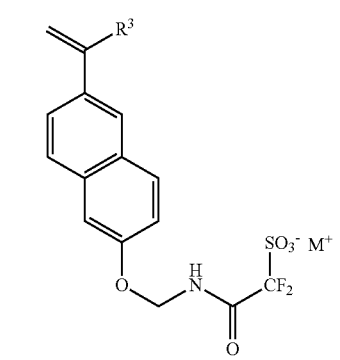
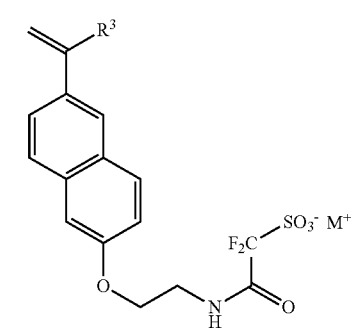
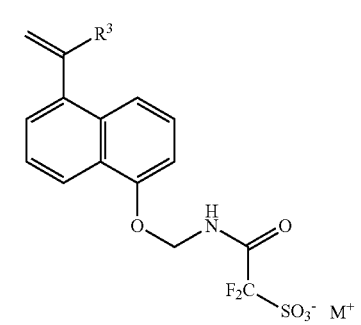
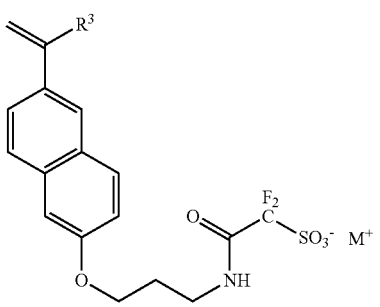
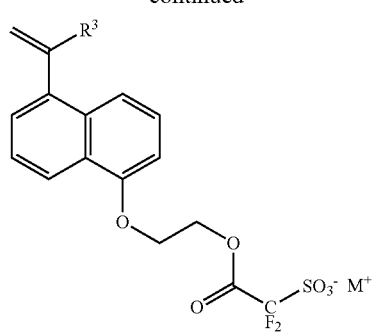
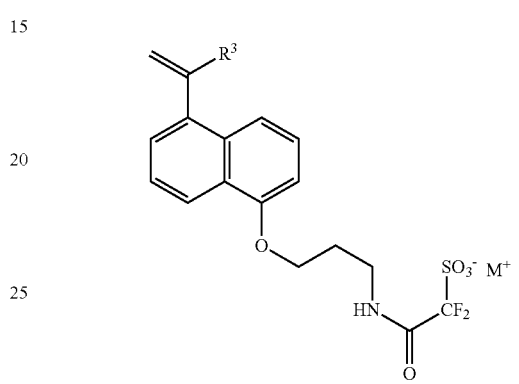
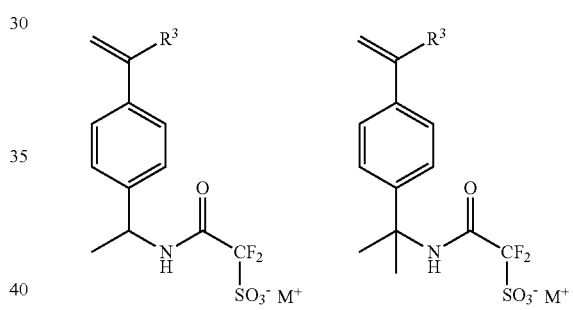
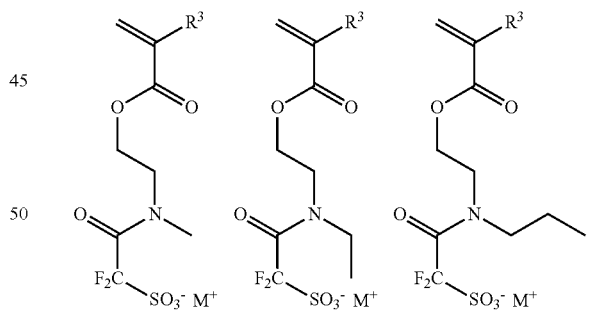
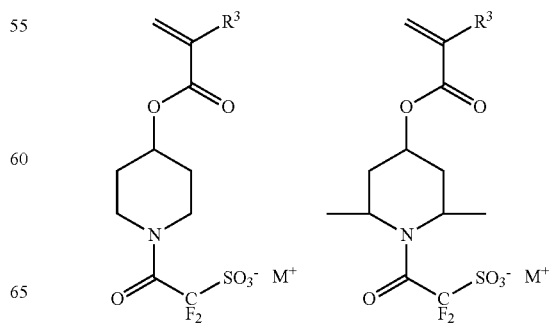

-continued
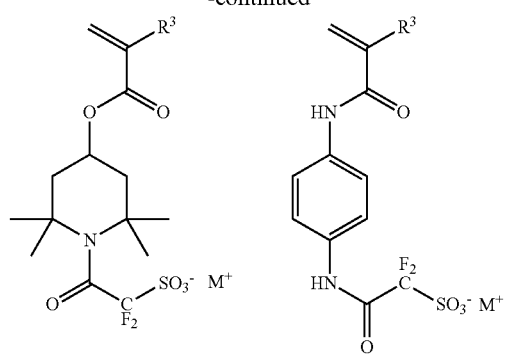
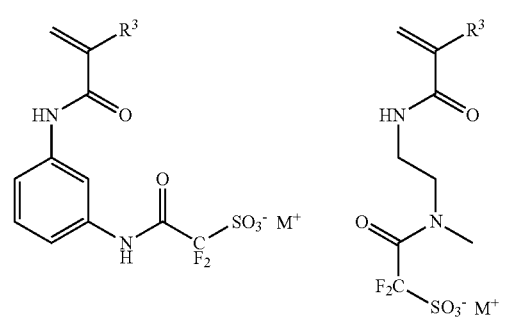
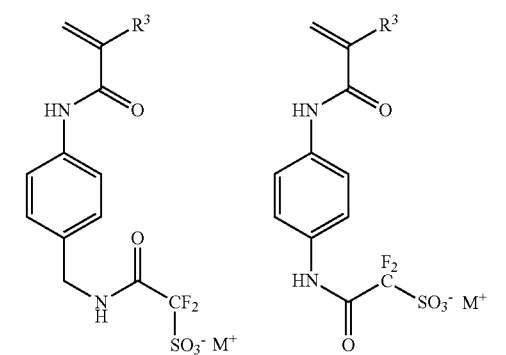
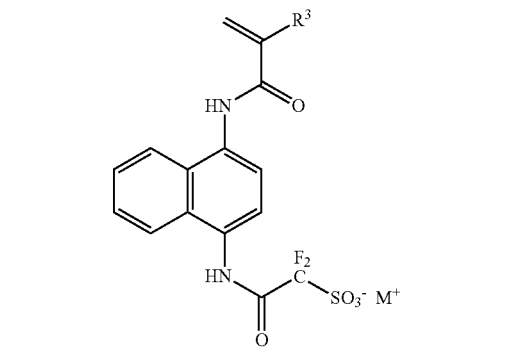
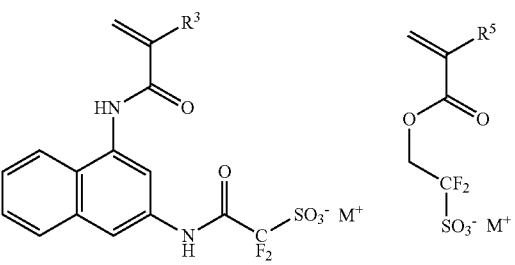
-continued
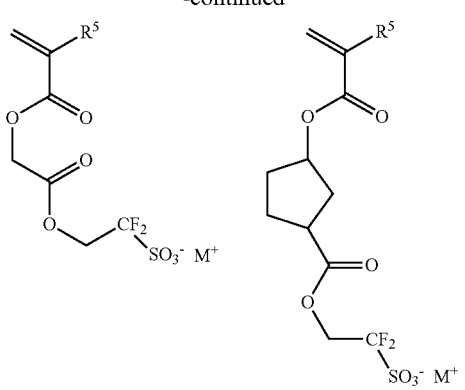
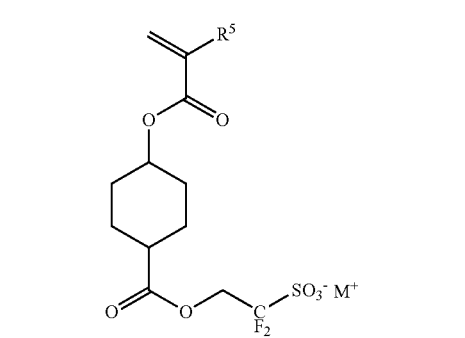
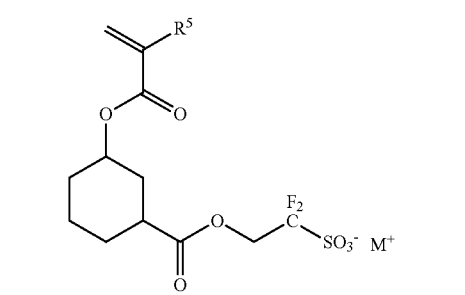
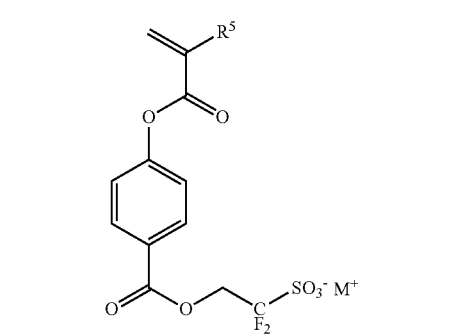
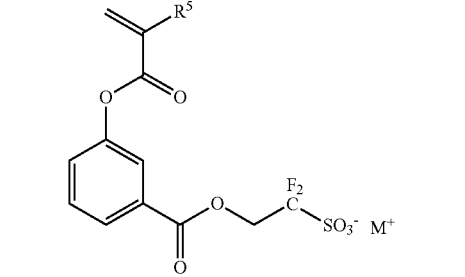

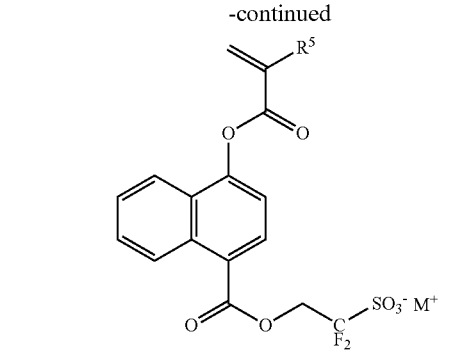
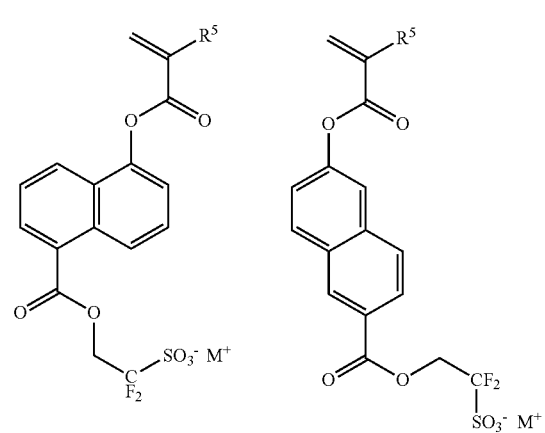
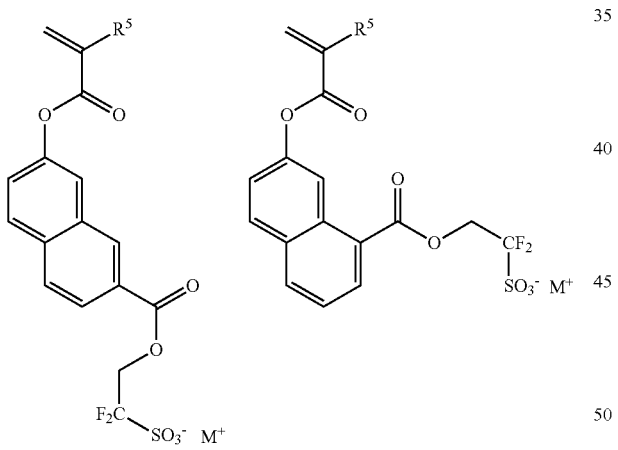
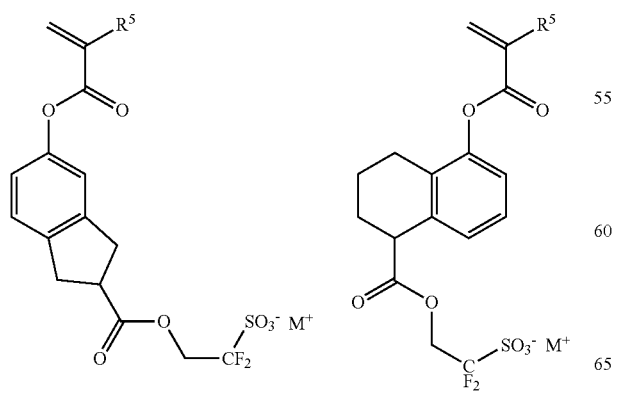
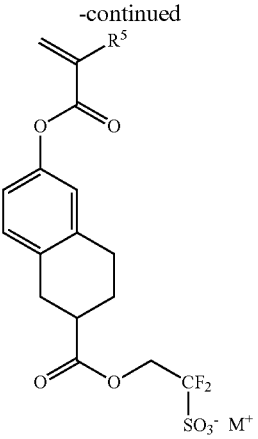
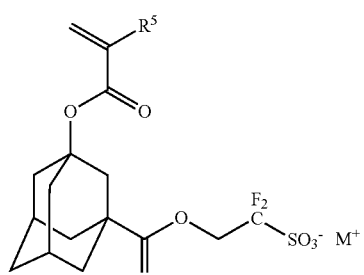
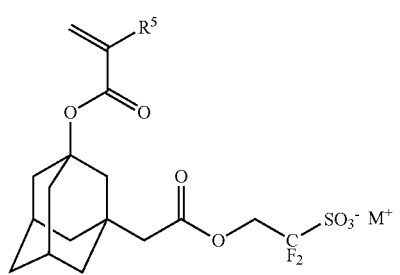
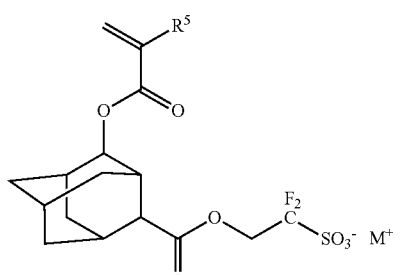
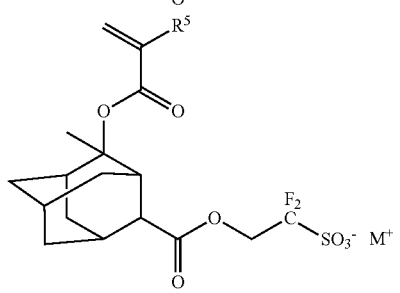

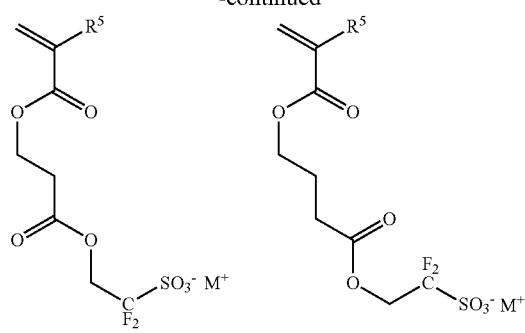
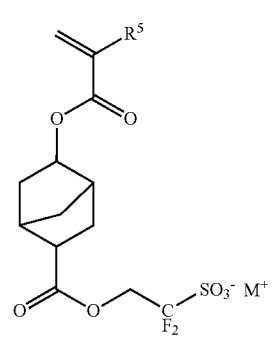
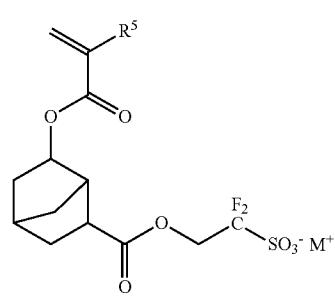
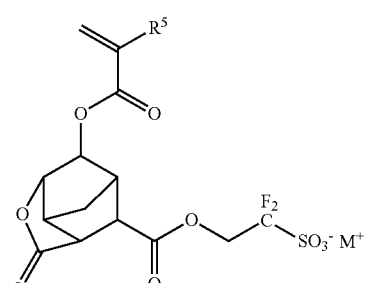
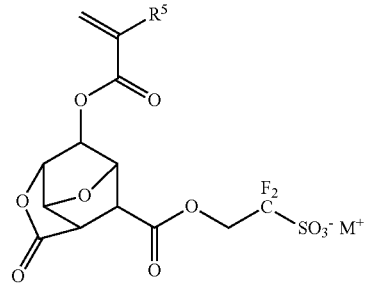
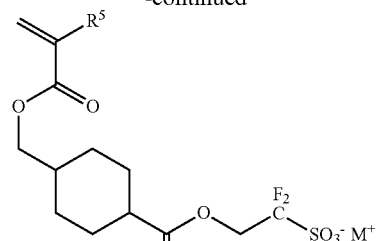
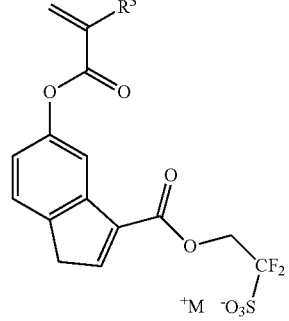
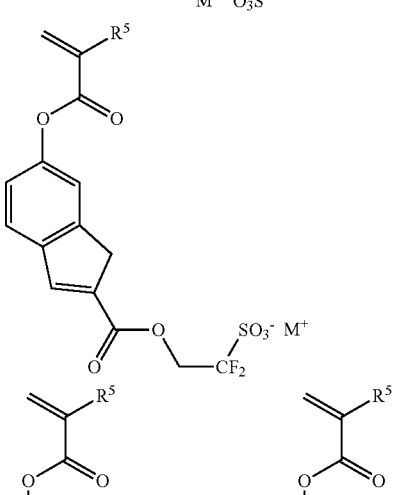
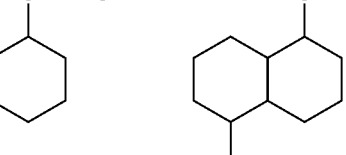
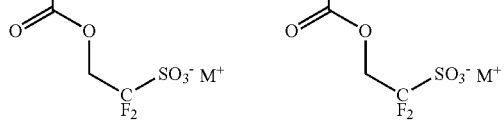
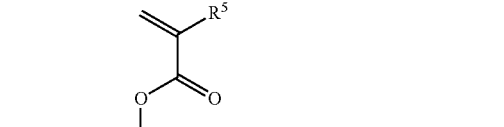
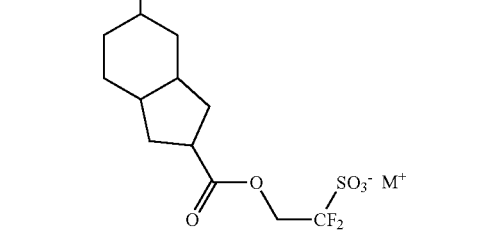

-continued
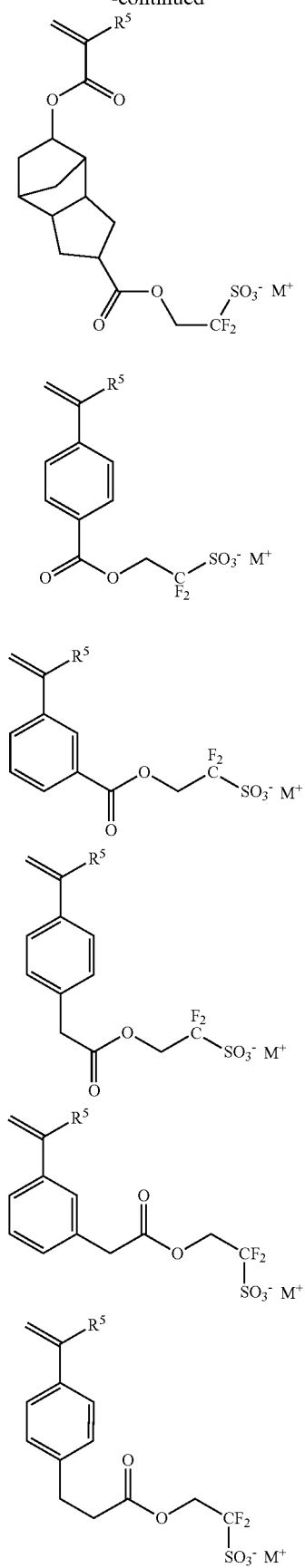
-continued
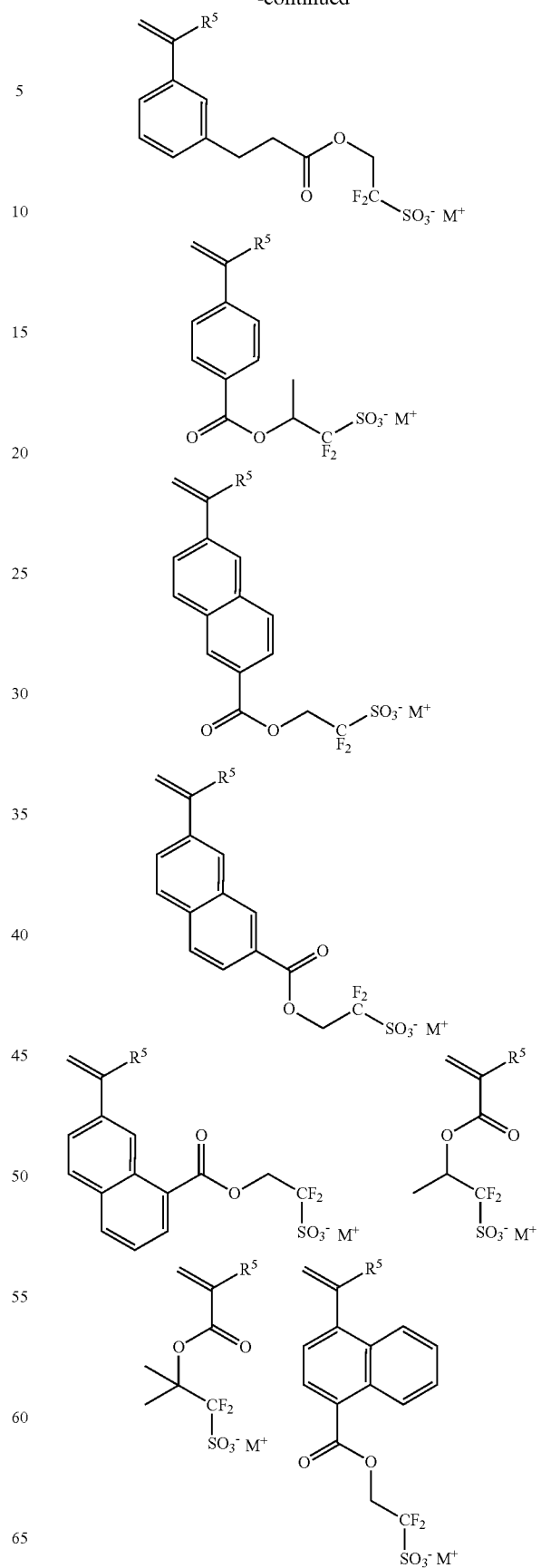

-continued
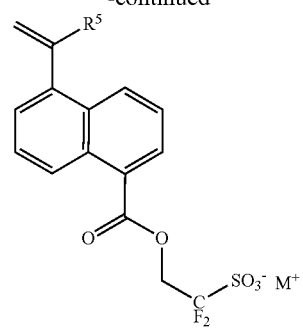
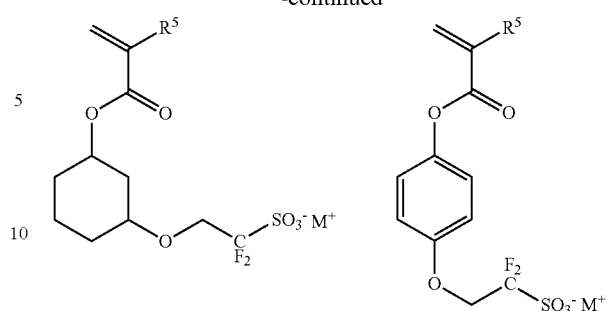
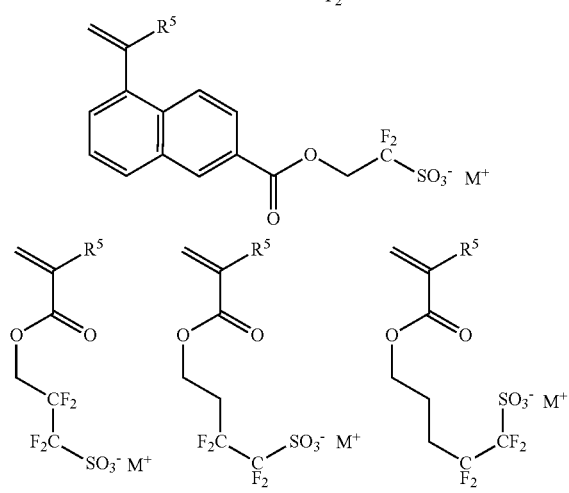
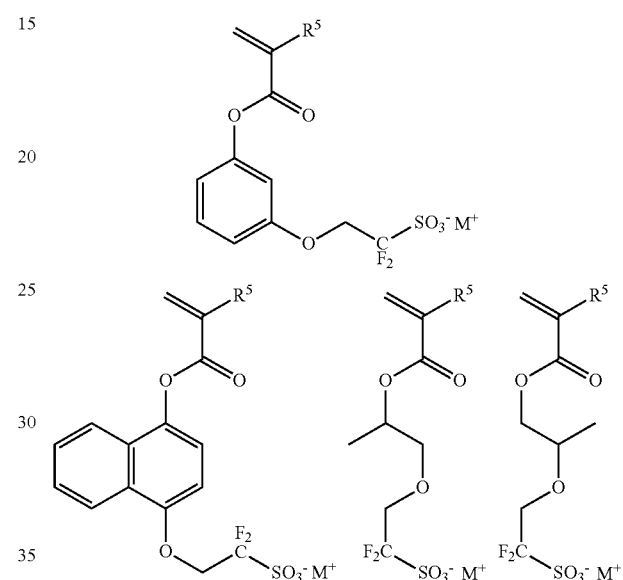
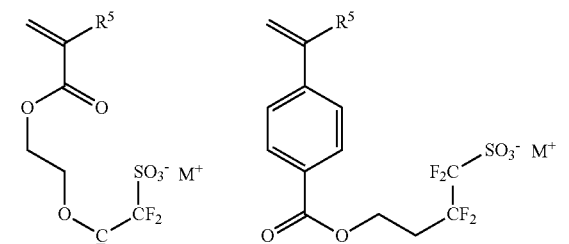
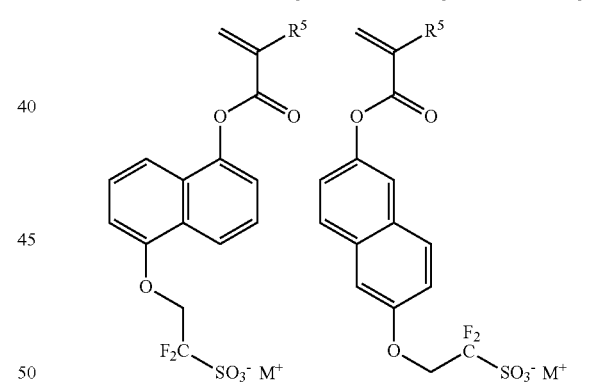
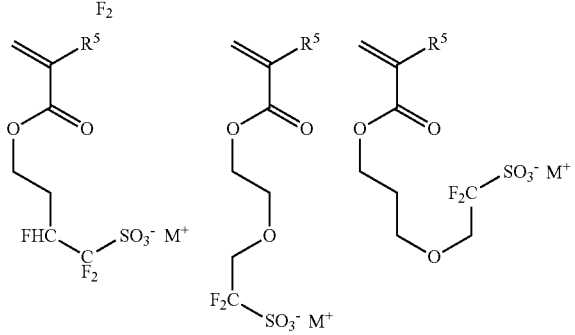
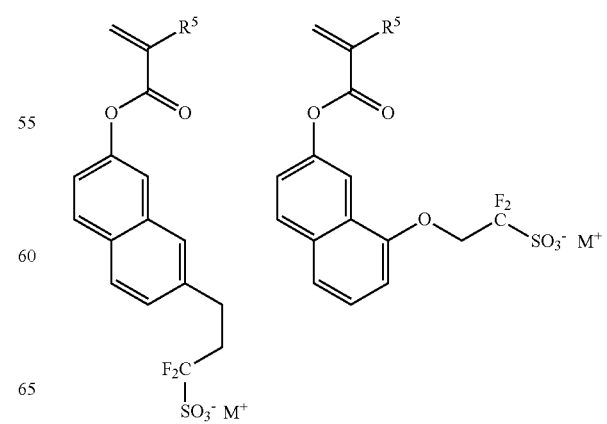
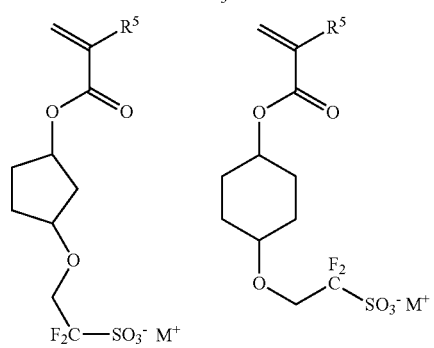

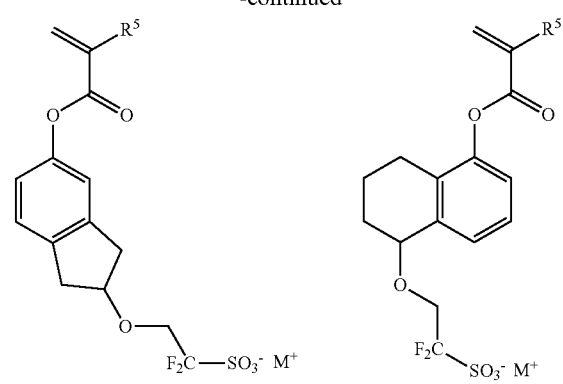
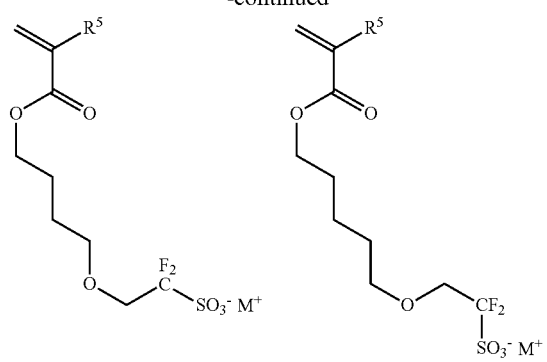
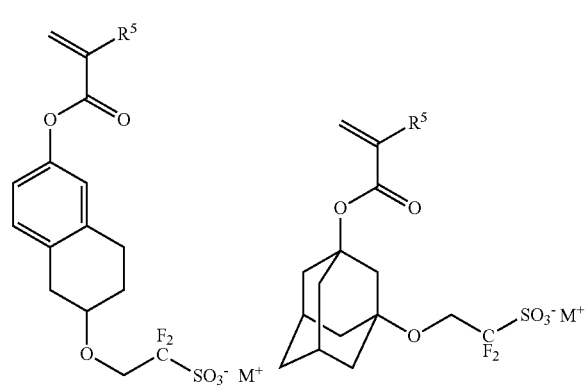
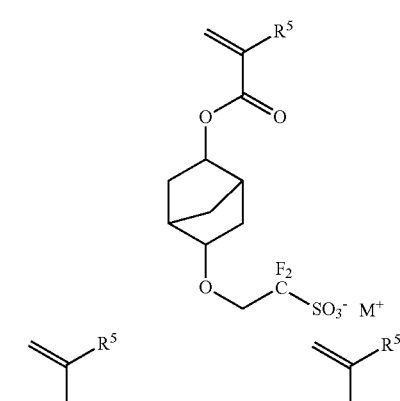
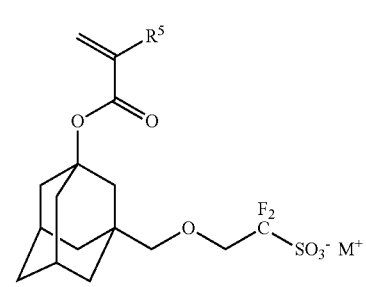
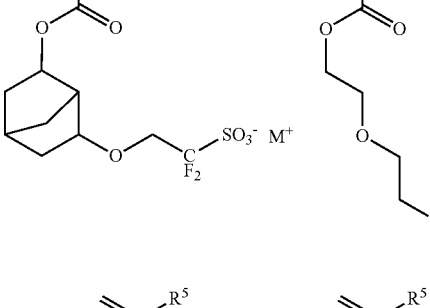
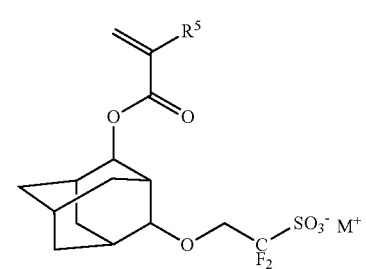
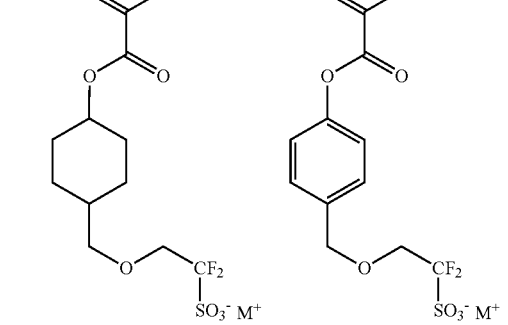
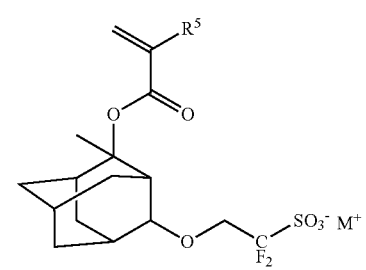
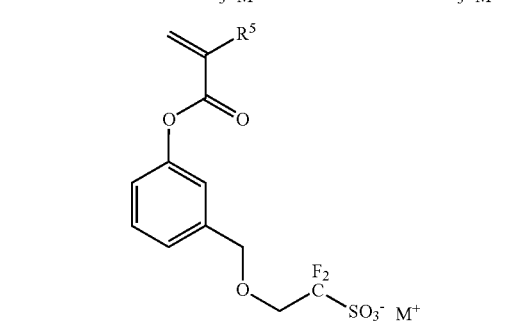

-continued
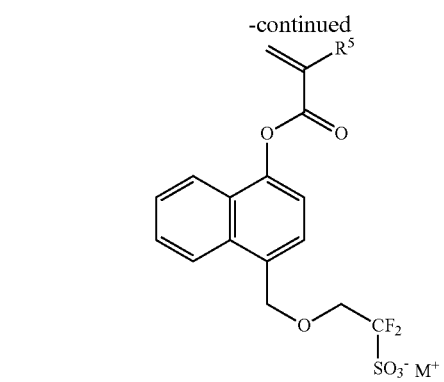
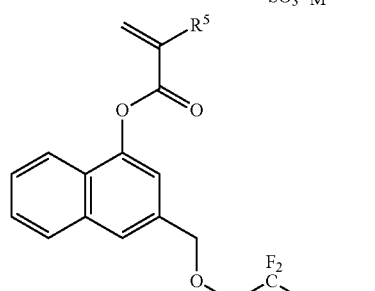
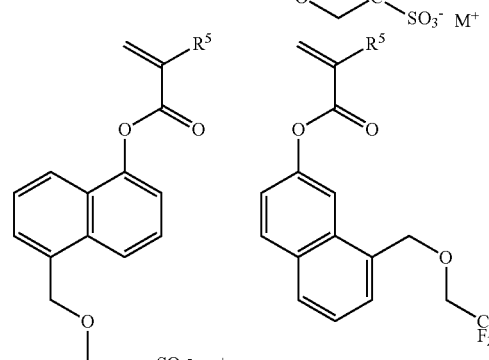
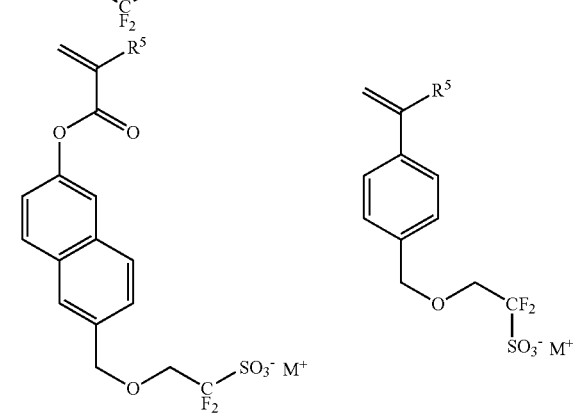
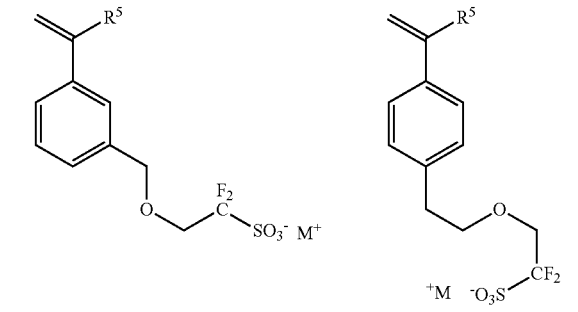
-continued
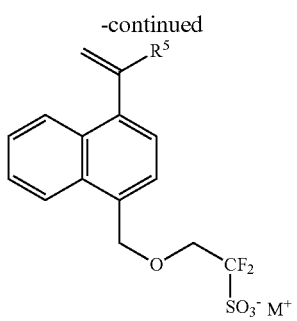
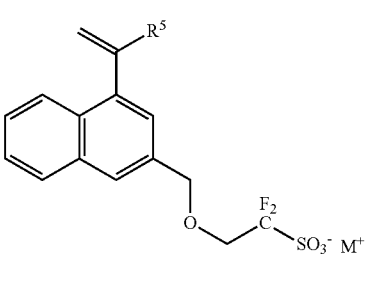
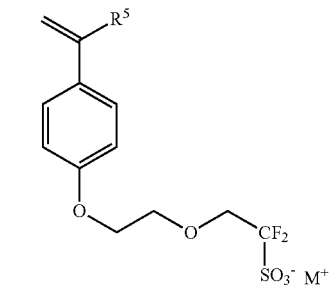
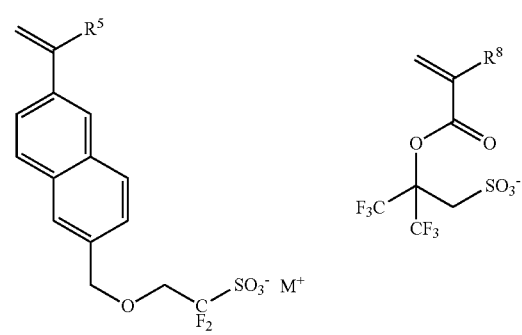
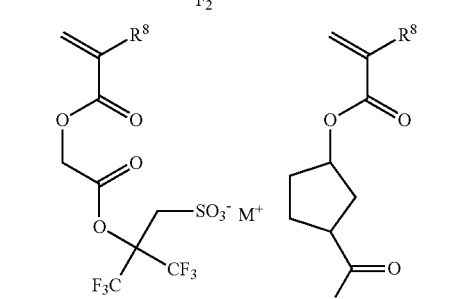
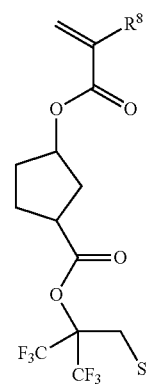

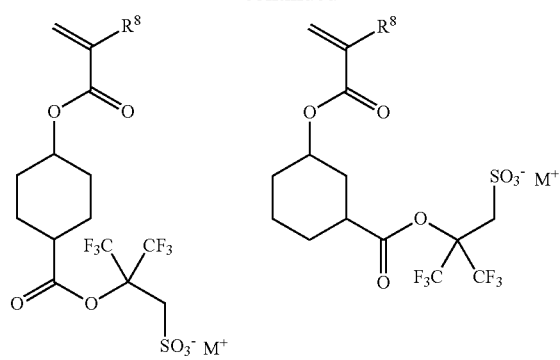
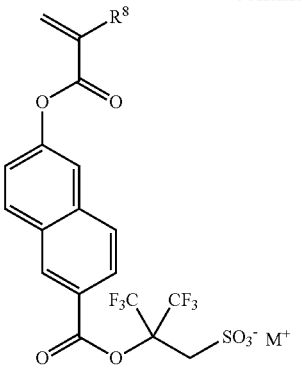
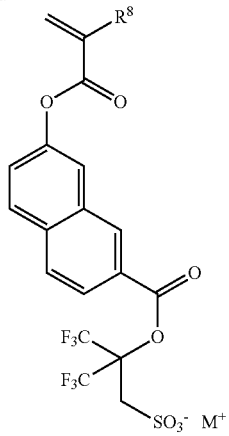
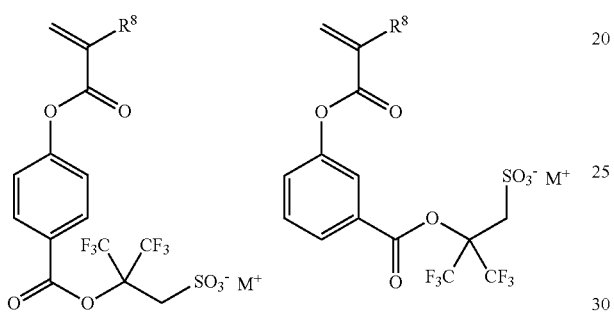
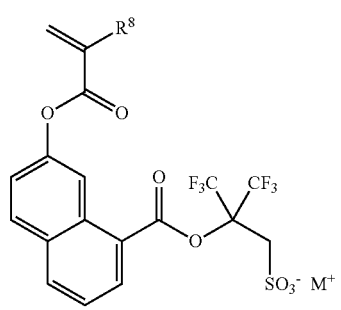
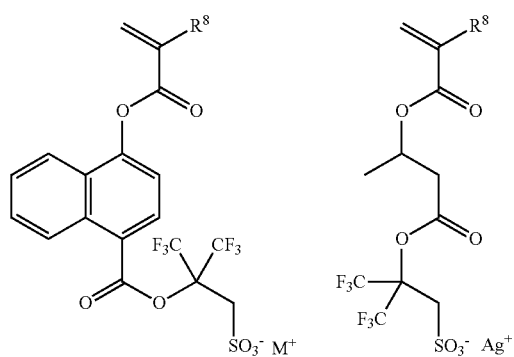
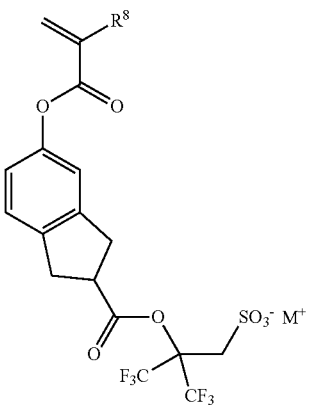
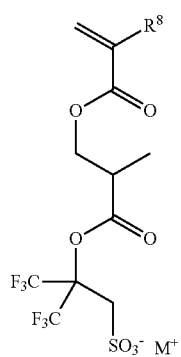
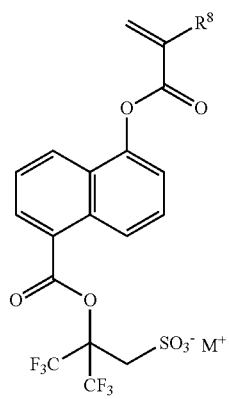
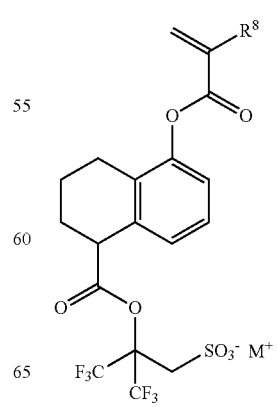
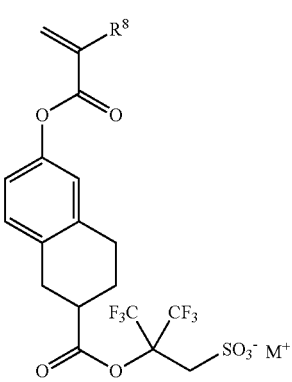

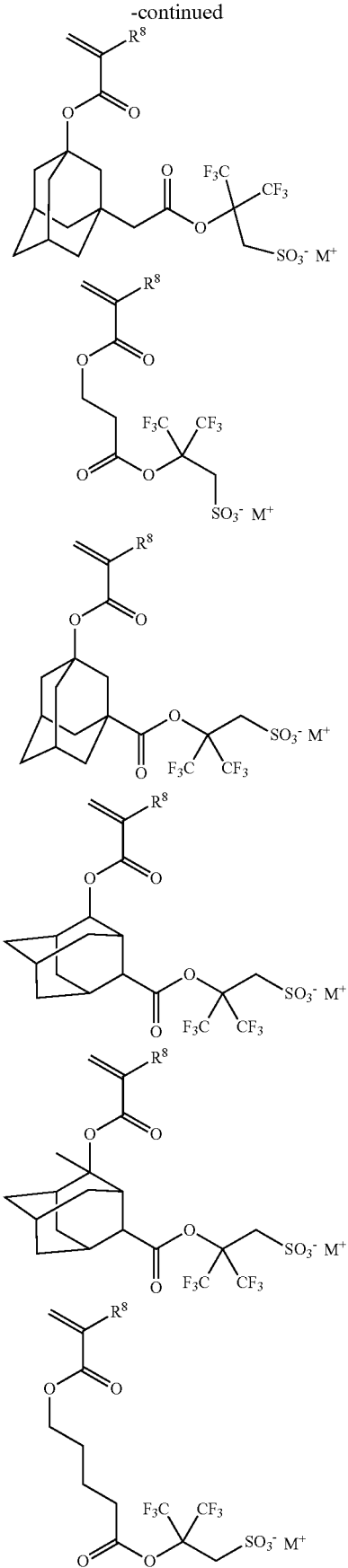
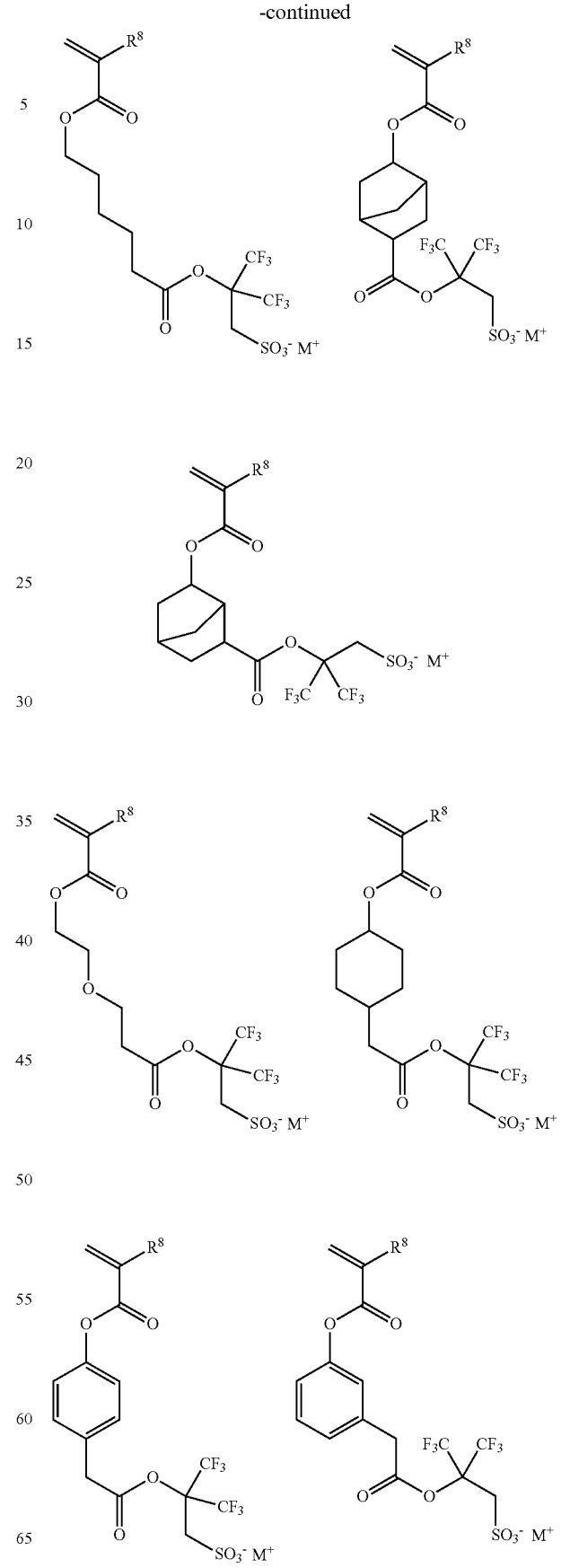

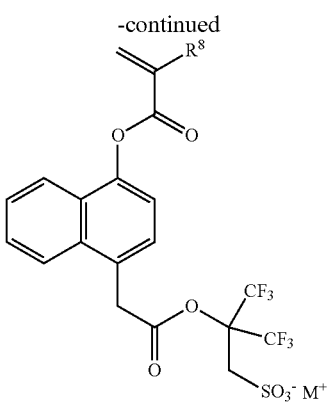
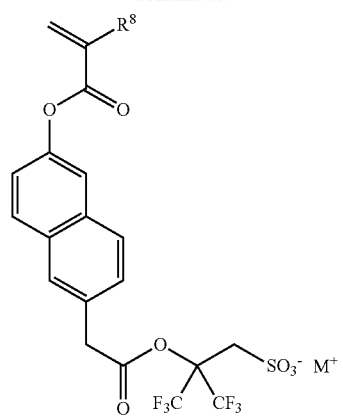
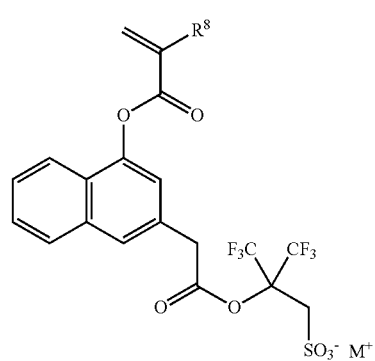
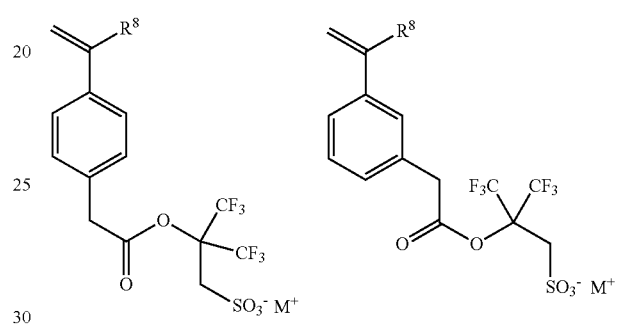
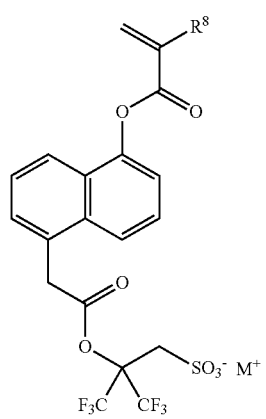
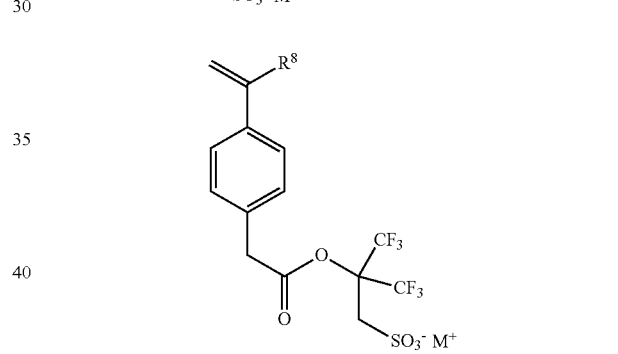
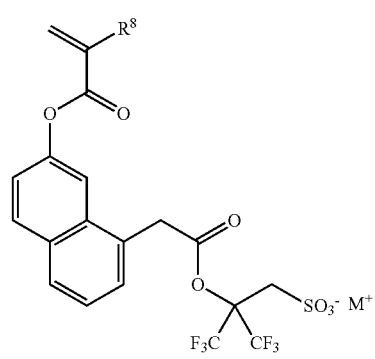
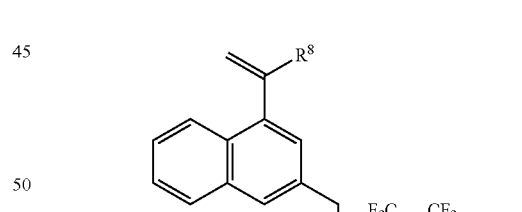
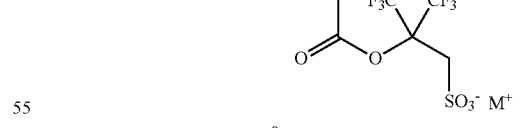
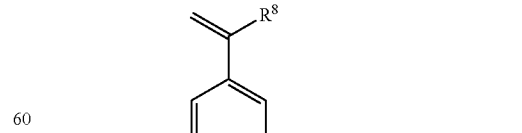
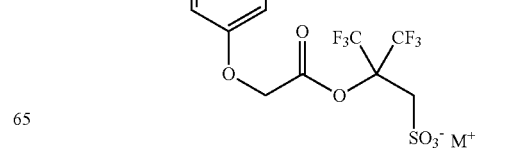
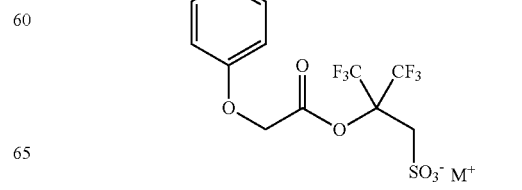

-continued
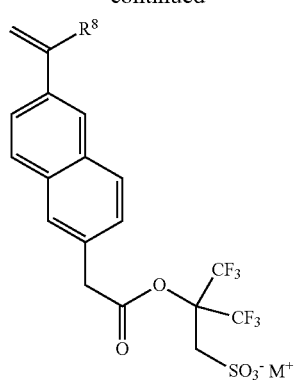
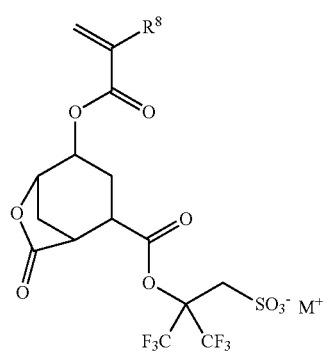
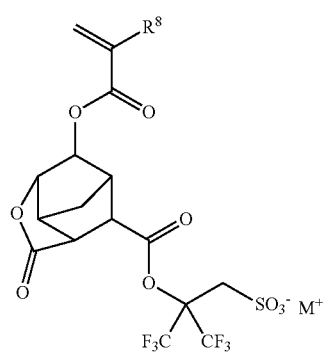
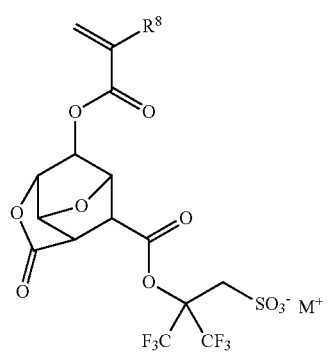
-continued
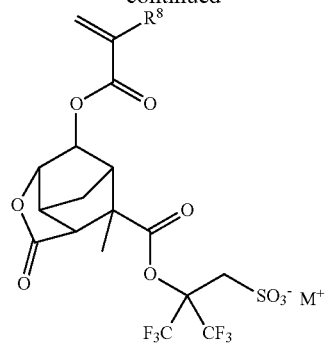
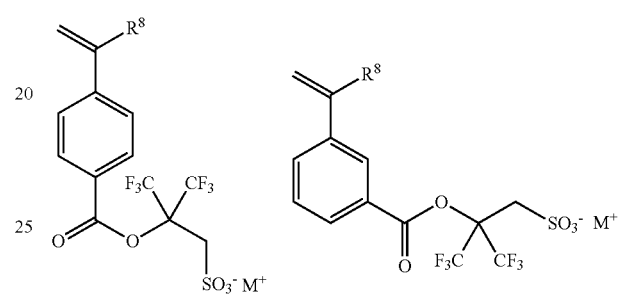
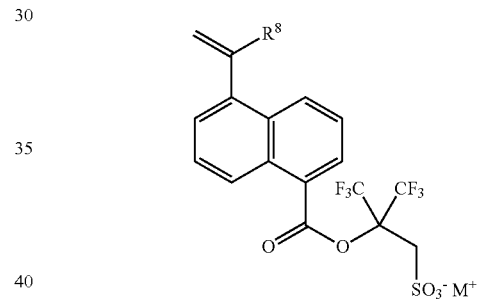
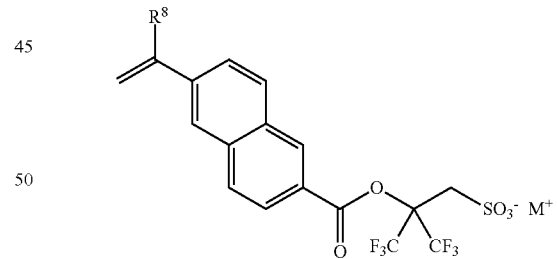
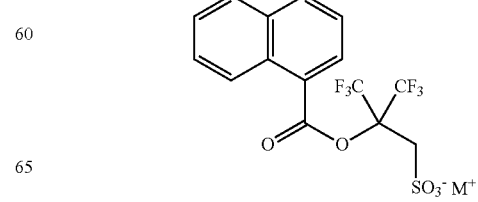

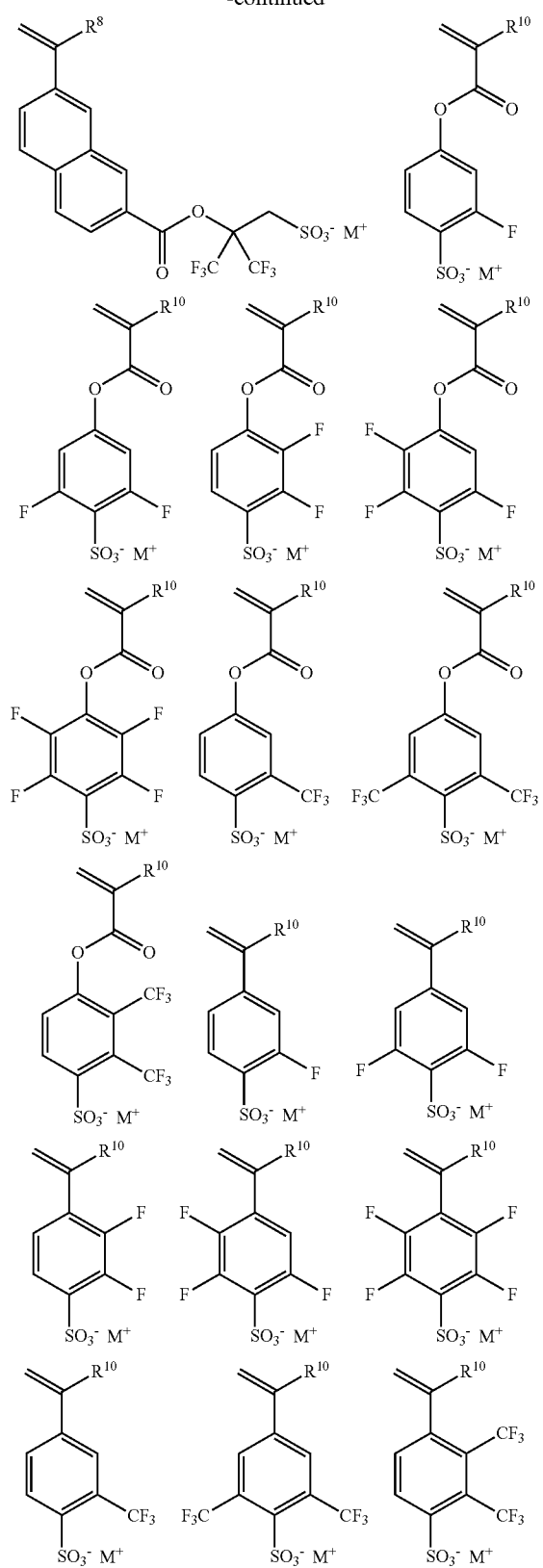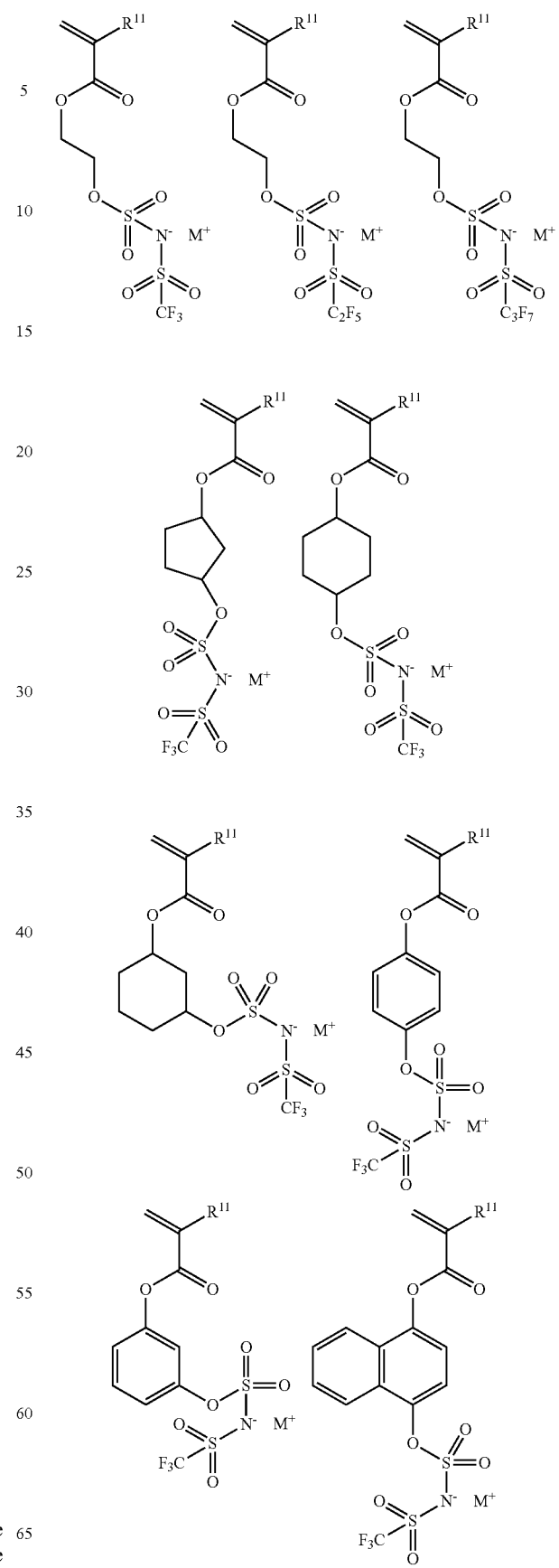
Illustrative examples of sulfonimide salt monomer to give the repeating unit-a6 of the above general formula include the following.

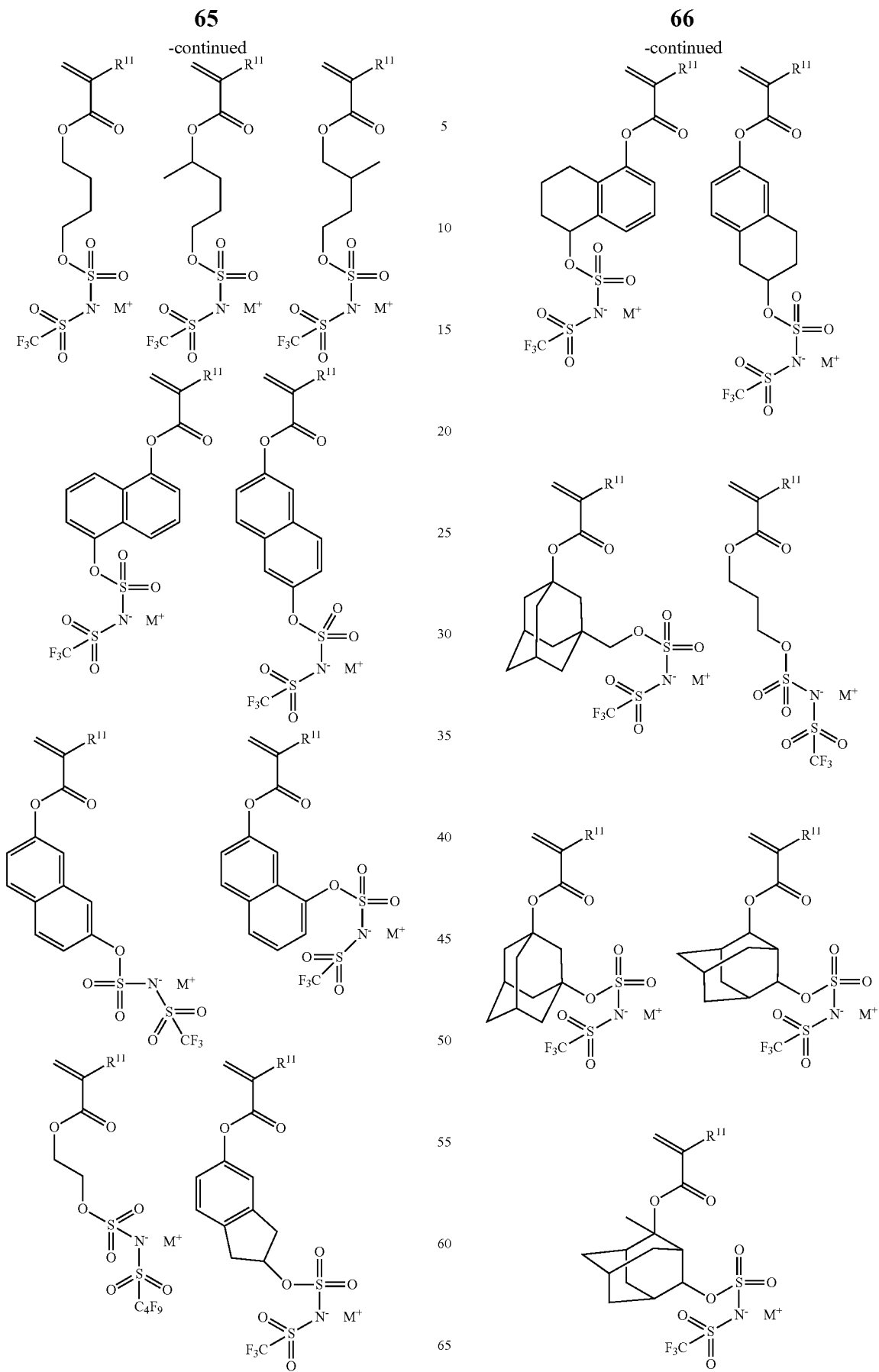

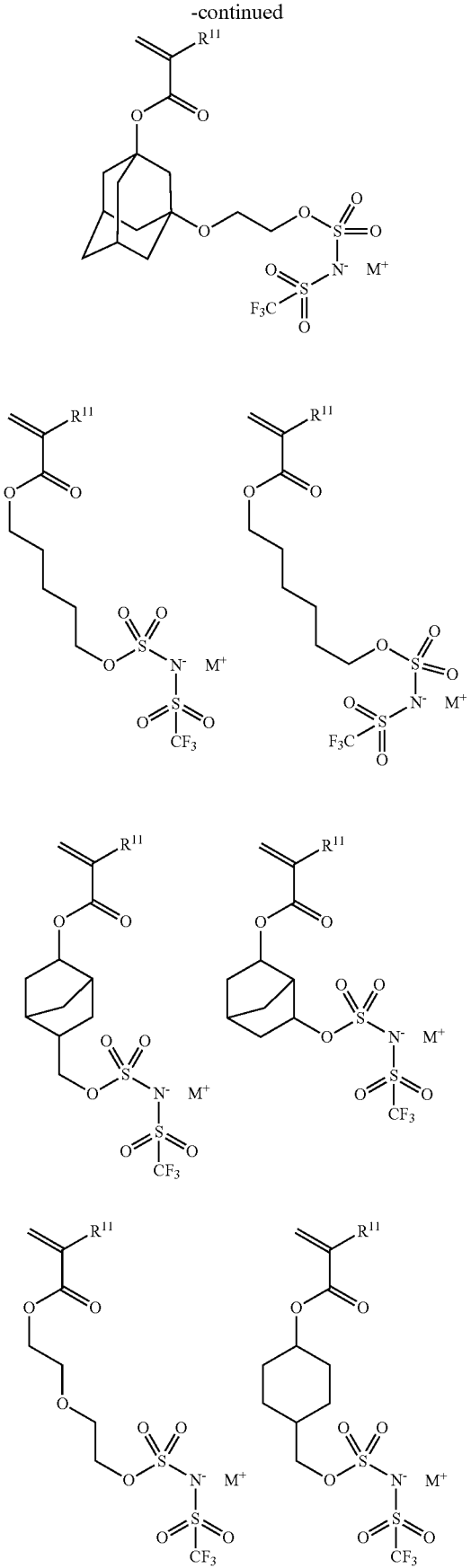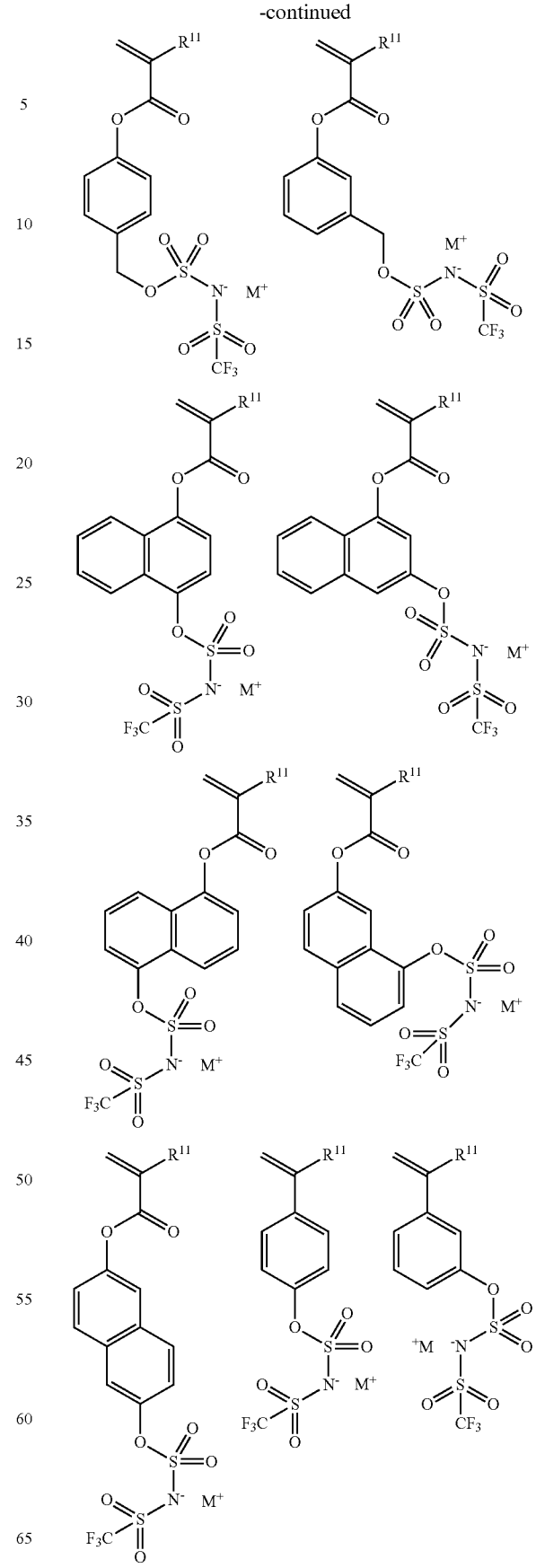

-continued
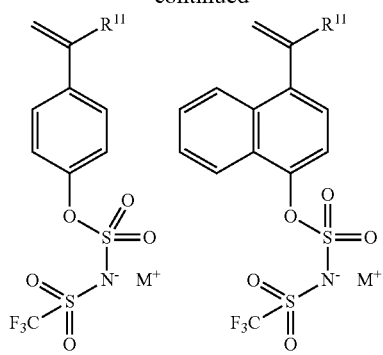
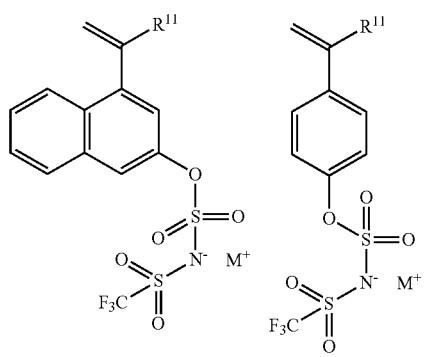
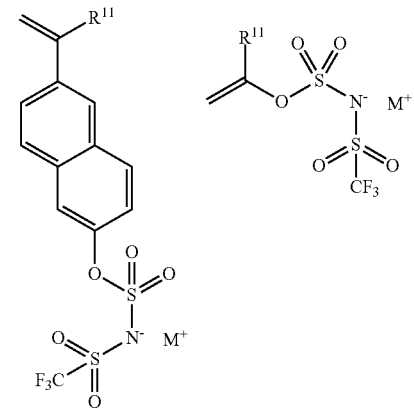
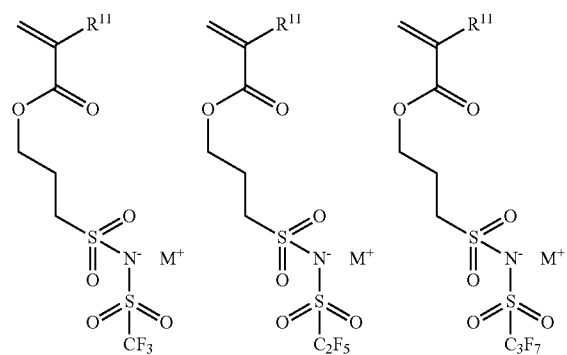
-continued
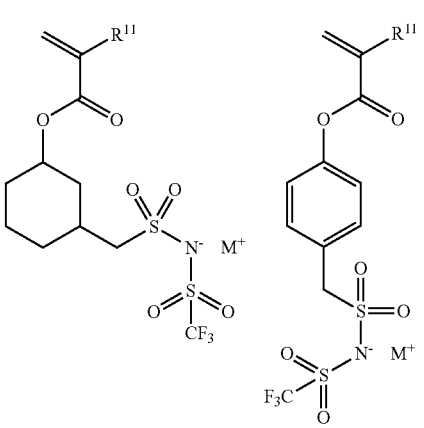
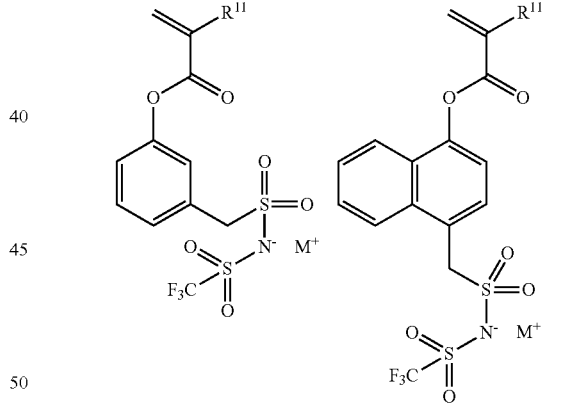
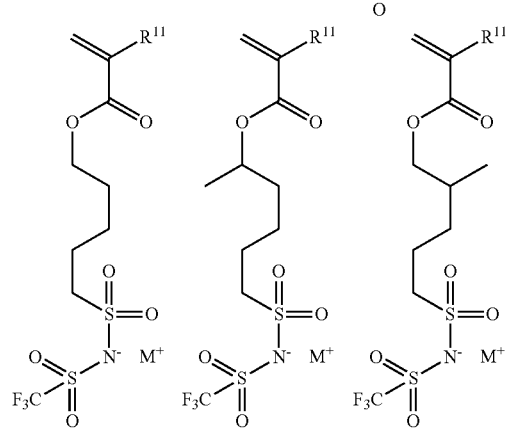

71
-continued
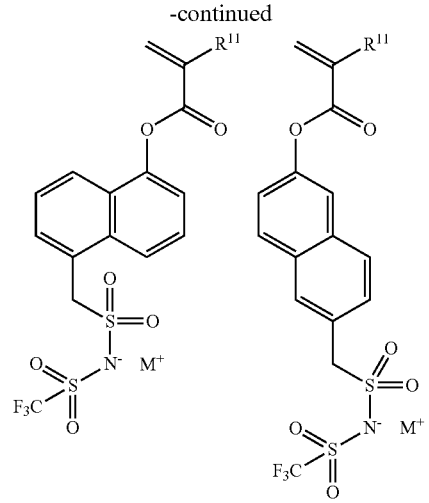
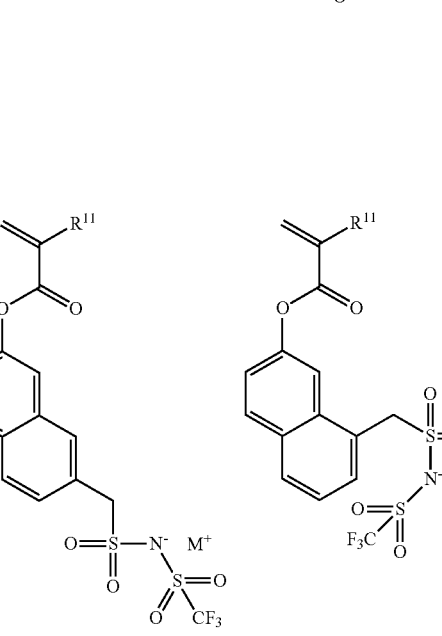
72
-continued
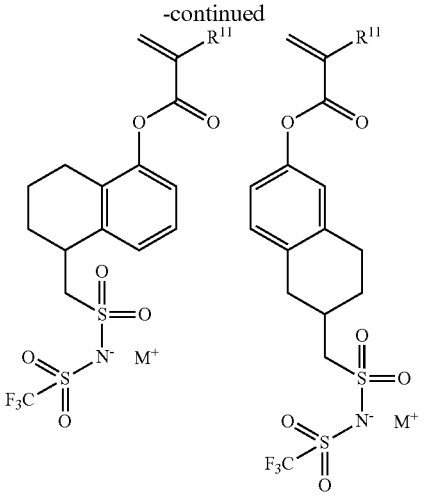
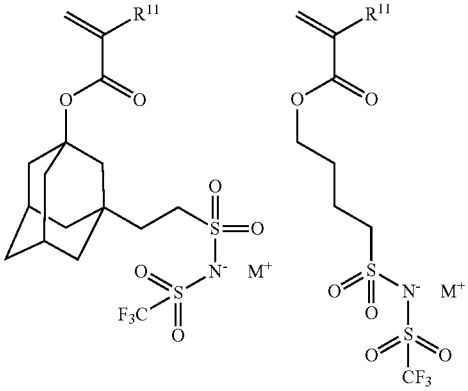
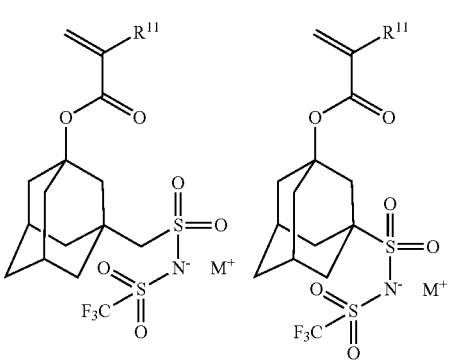
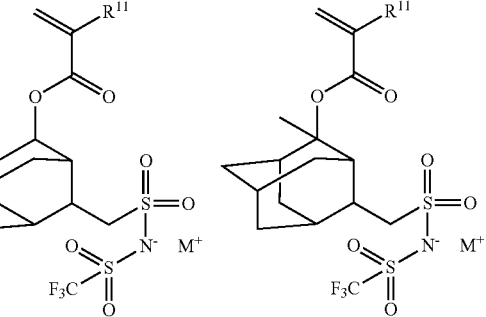

73 -continued
74 -continued
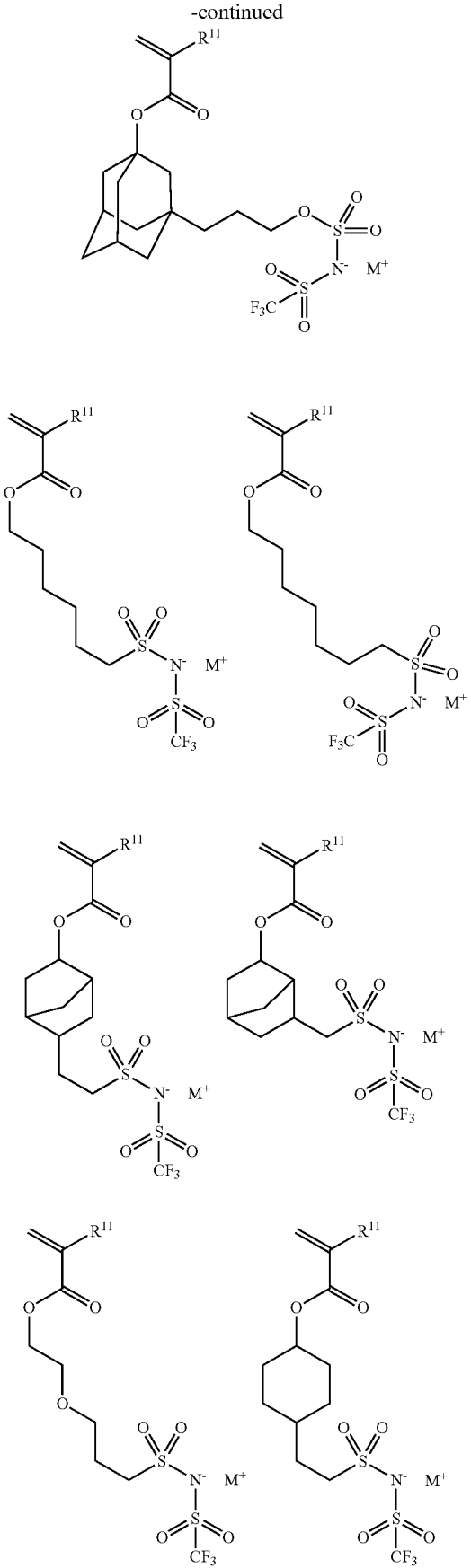
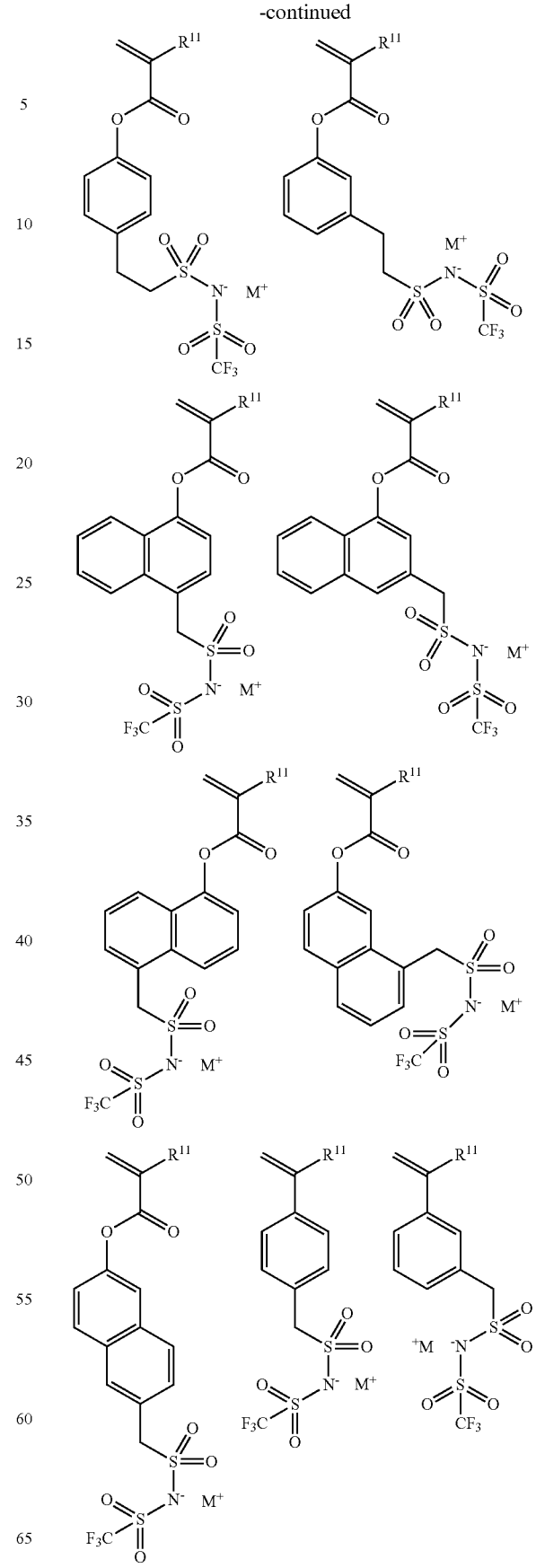

-continued
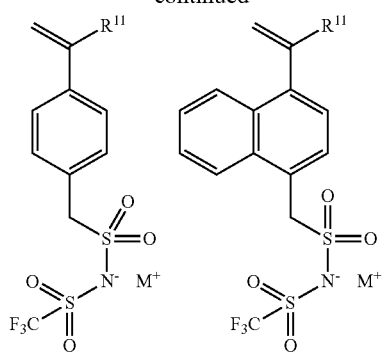
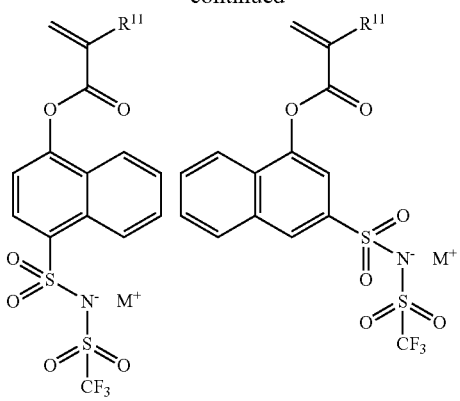
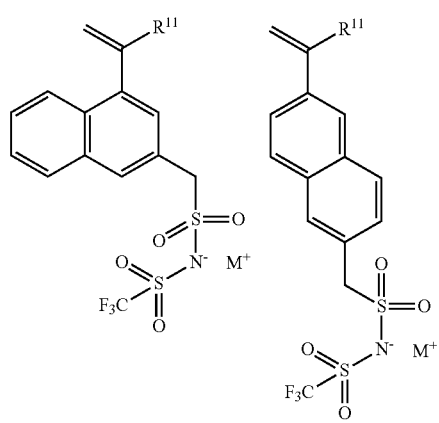
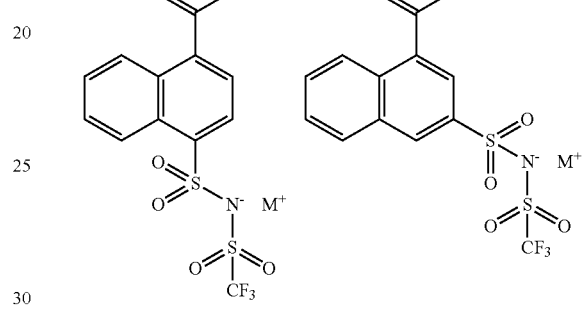
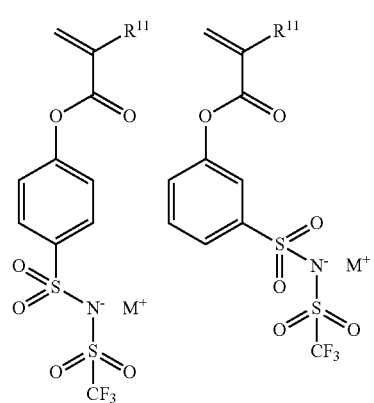
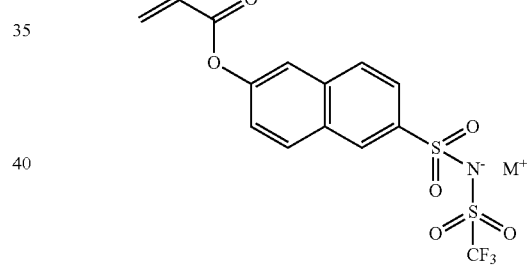
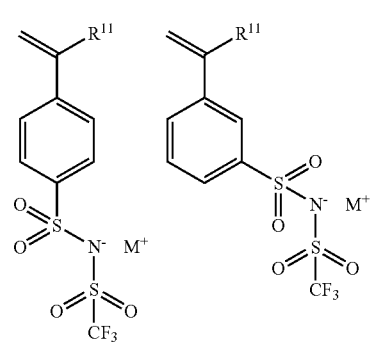
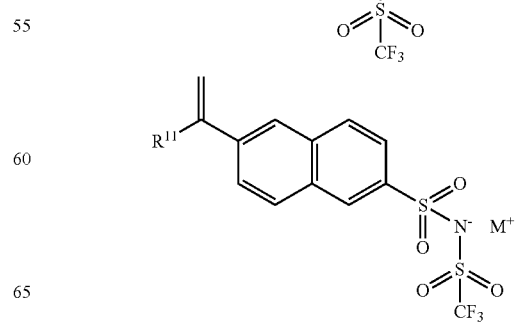

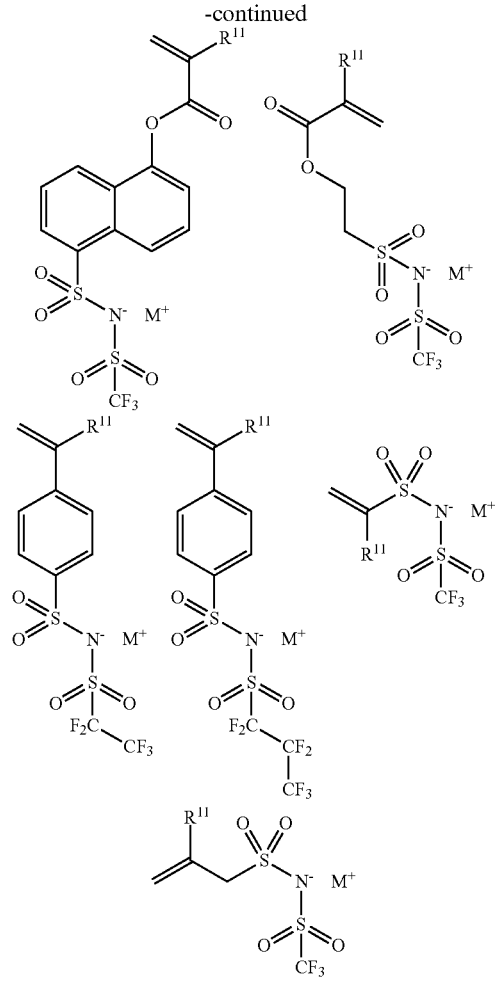
Illustrative examples of N-carbonylsulfonamide salt monomer to give the repeating unit-a7 of the above general formula include the following.
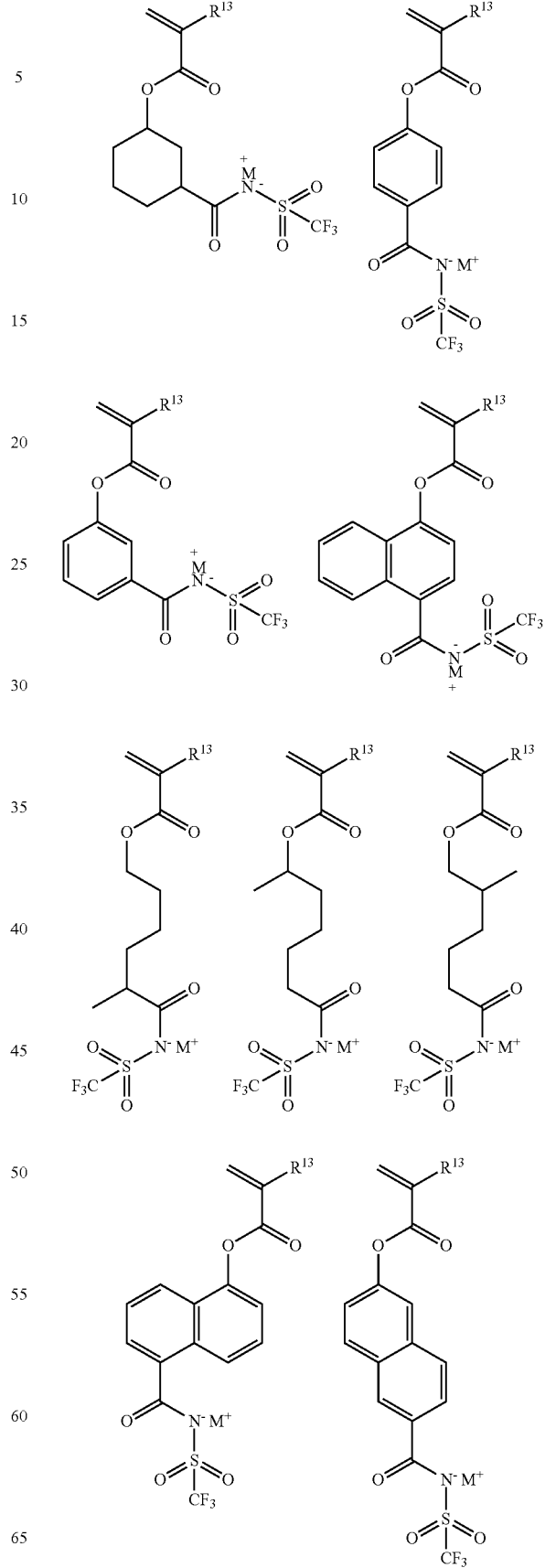

-continued
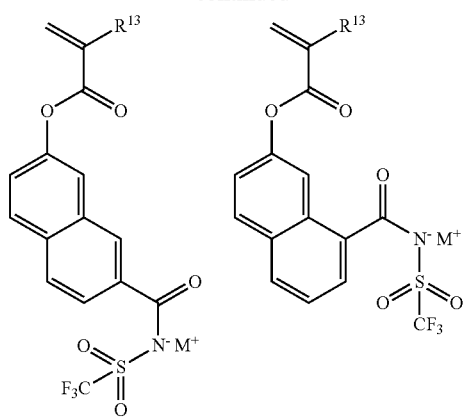
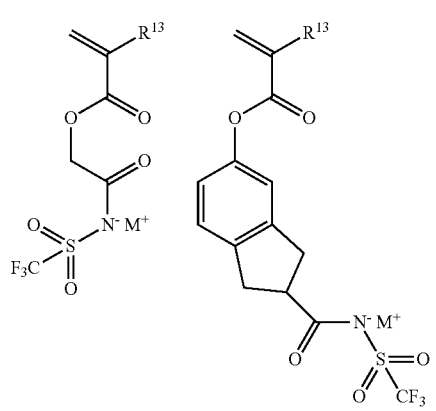
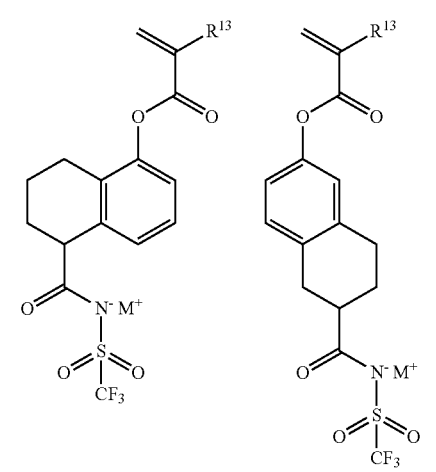
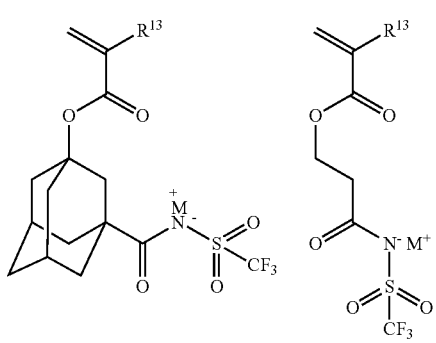
-continued
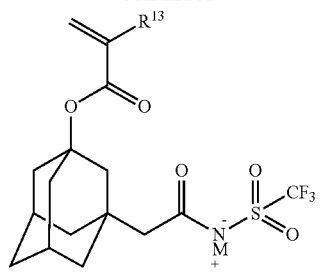
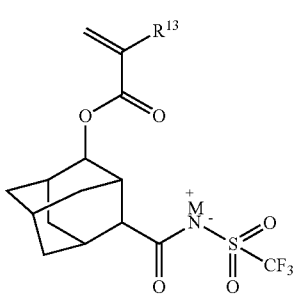
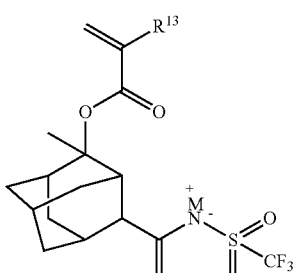
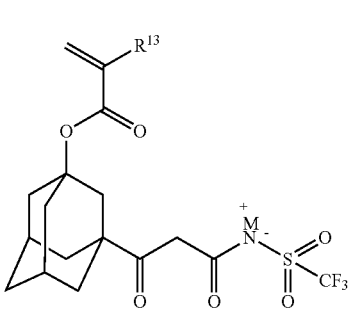
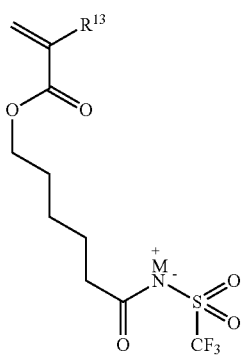

-continued

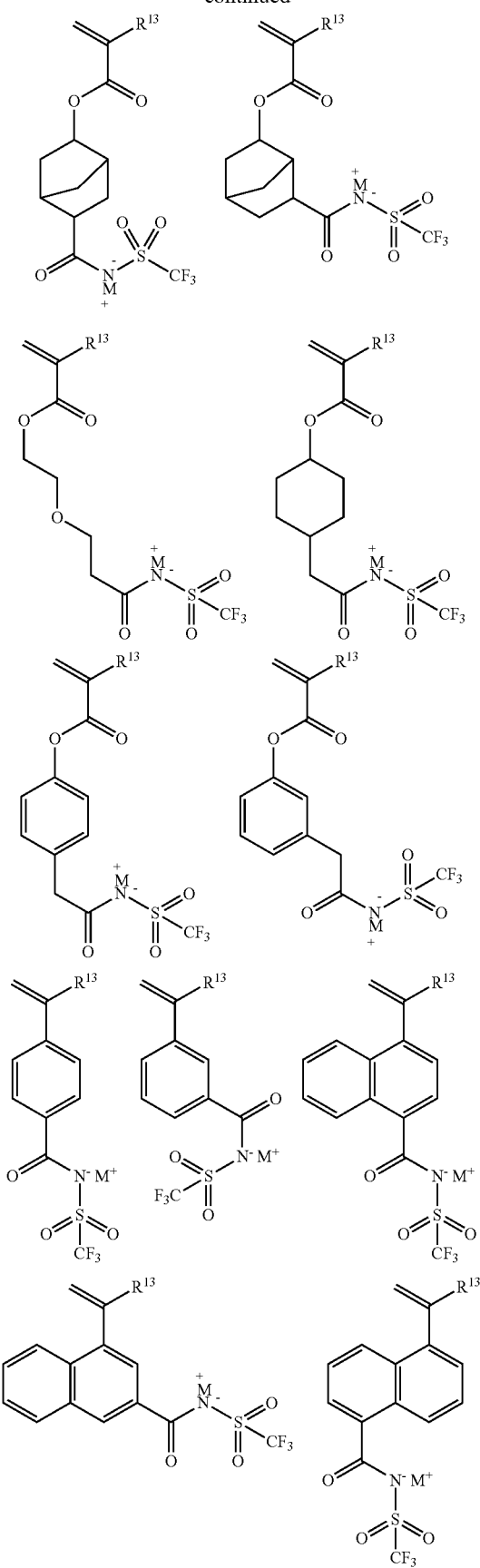

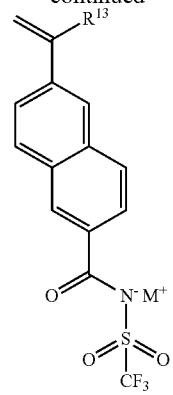

In the formulae, $R^1$, $R^3$, $R^5$, $R^8$, $R^{10}$, $R^{11}$, and $R^{13}$ each independently represent a hydrogen atom or a methyl group.

The component (A) preferably contains the ammonium ion (ammonium cation) shown by the following general formula (3) as $M^+$ in the repeating unit-a (repeating unit-a1).

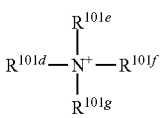

(3)

In the formula, $R^{101d}$, $R^{101e}$, $R^{101f}$, and $R^{101g}$ each represent a hydrogen atom, a linear, branched, or cyclic alkyl group having 1 to 12 carbon atoms, a linear, branched, or cyclic alkenyl group or alkynyl group having 2 to 12 carbon atoms, or an aromatic group having 4 to 20 carbon atoms, optionally having one or more species selected from an ether group, a carbonyl group, an ester group, a hydroxy group, an amino group, a nitro group, a sulfonyl group, a sulfinyl group, a halogen atom, and a sulfur atom; $R^{101d}$ and $R^{101e}$, or $R^{101d}$, $R^{101e}$, and $R^{101f}$ may form a ring together with a nitrogen atom bonded thereto, and in this case, $R^{101d}$ and $R^{101e}$, or $R^{101d}$, $R^{101e}$, and $R^{101f}$ represent an alkylene group having 3 to 10 carbon atoms, or form a heteroaromatic ring having a nitrogen atom in the formula within the ring.

Illustrative examples of the ammonium ion shown by the general formula (3) include the following.

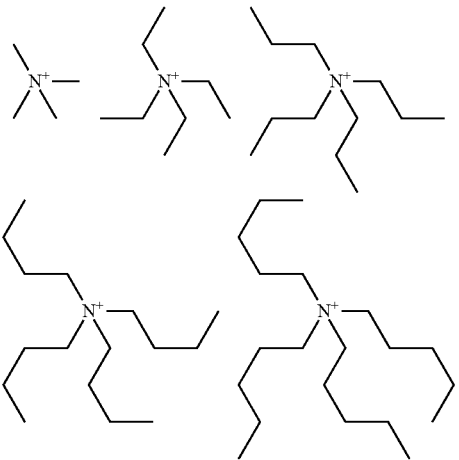

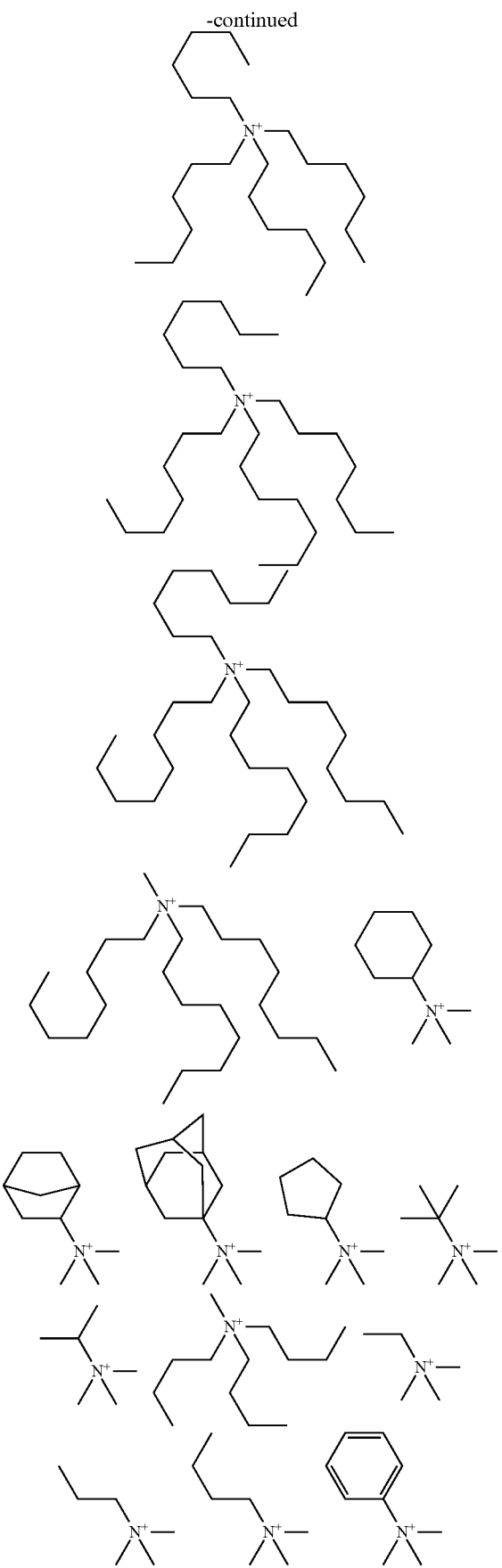
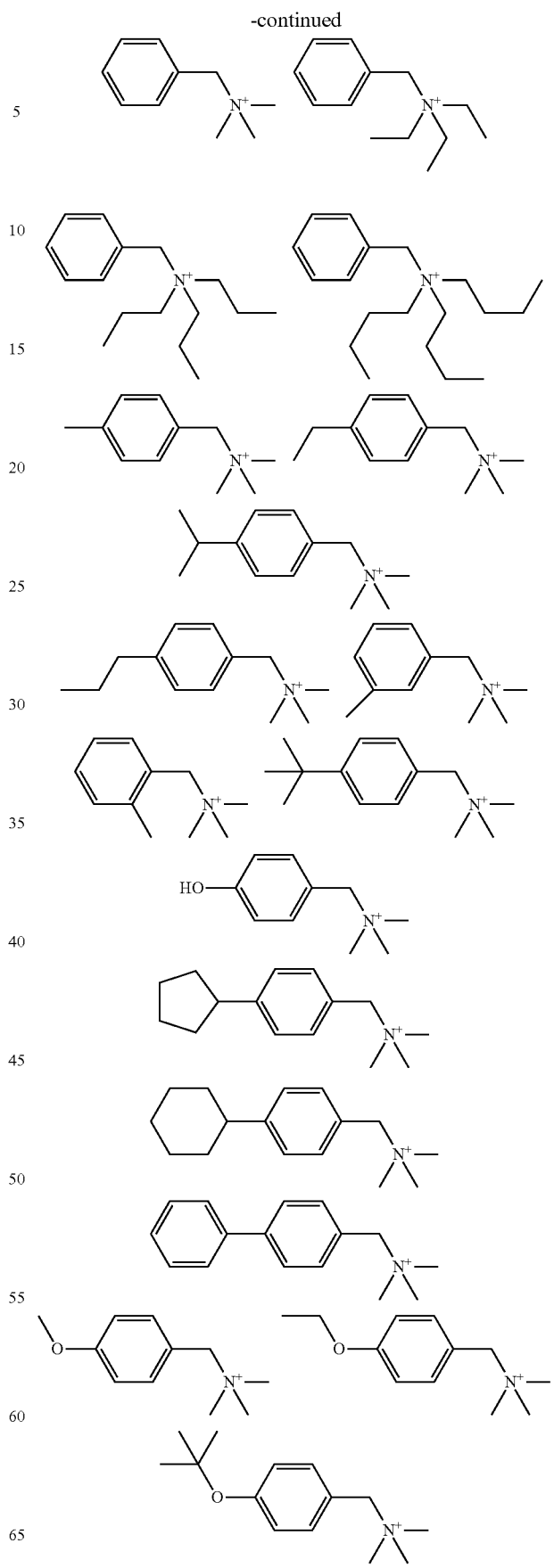

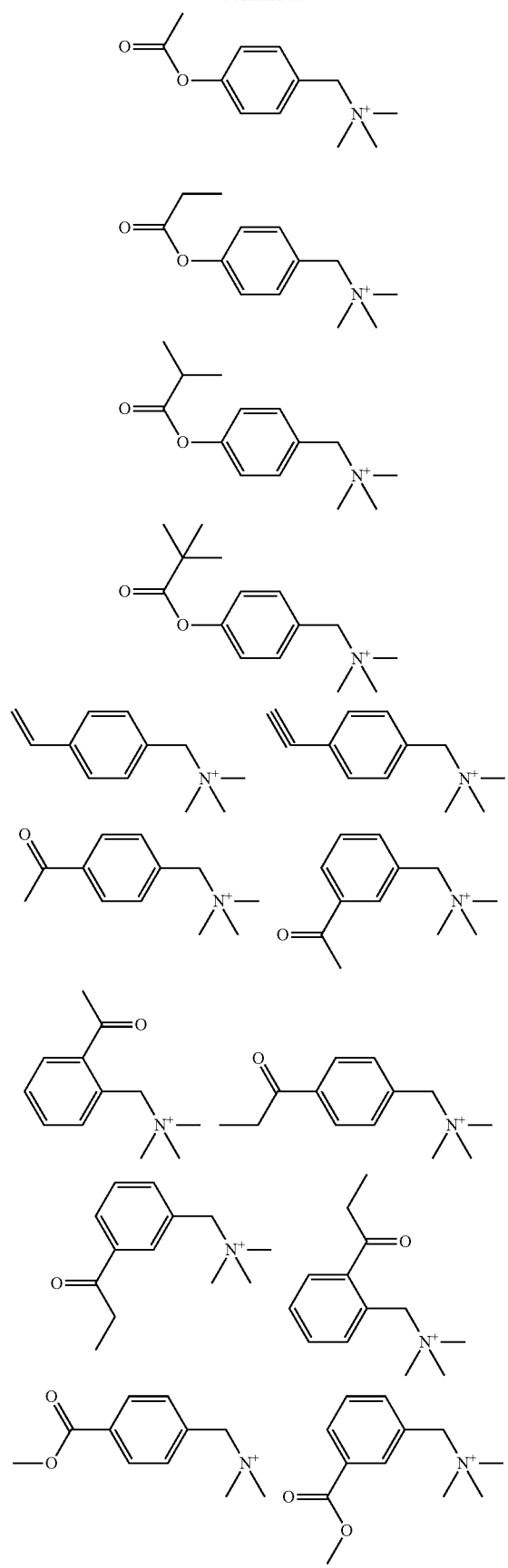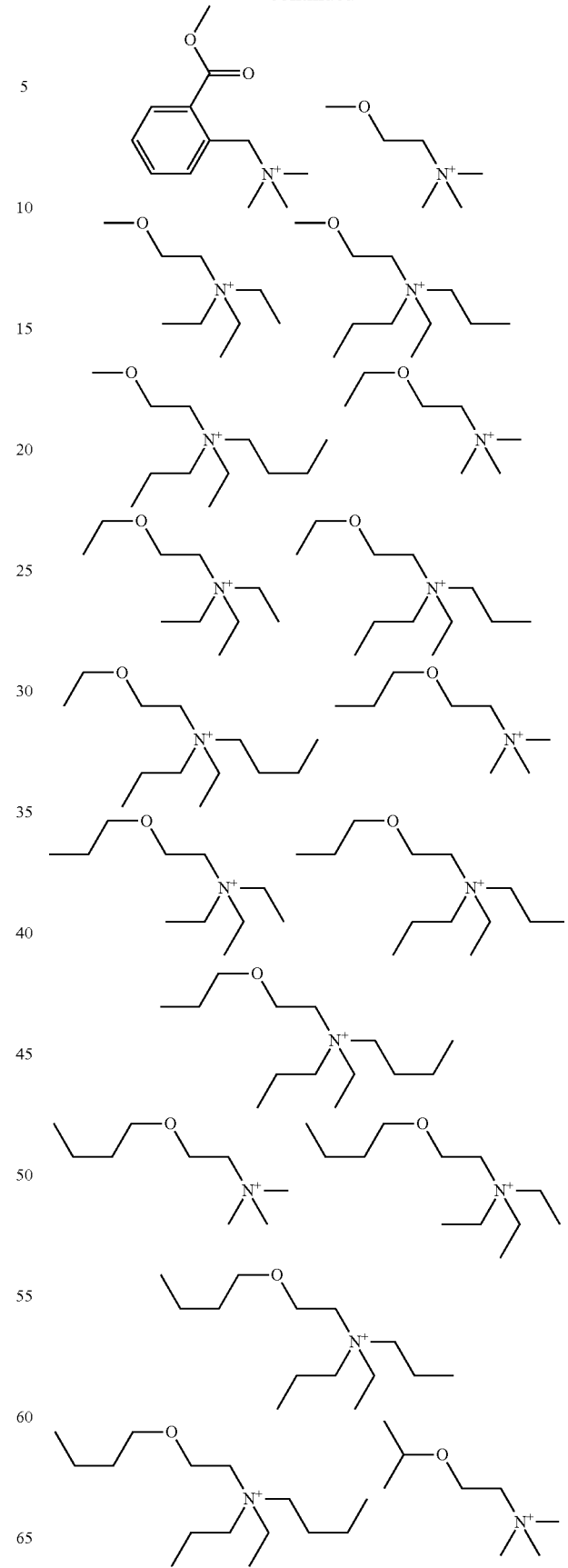

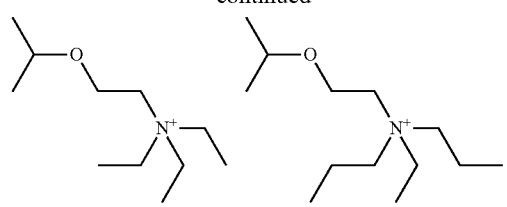
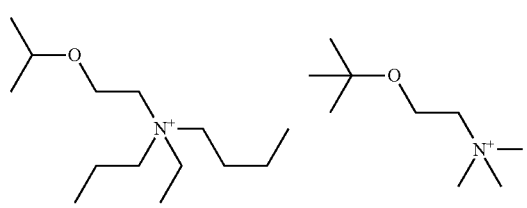
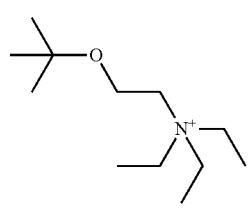
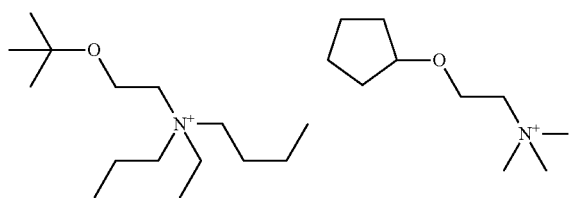
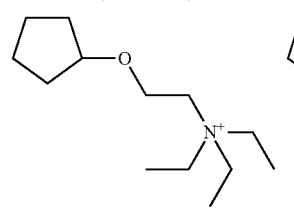
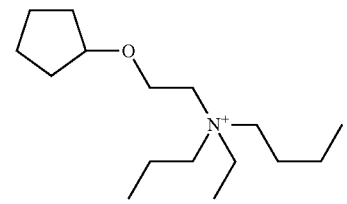
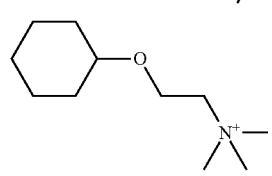
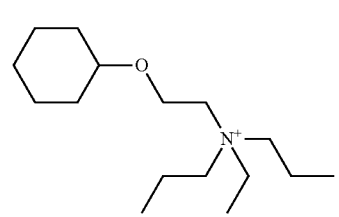
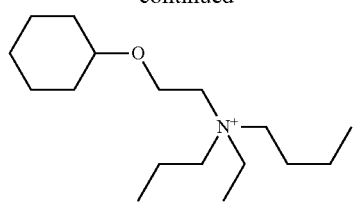
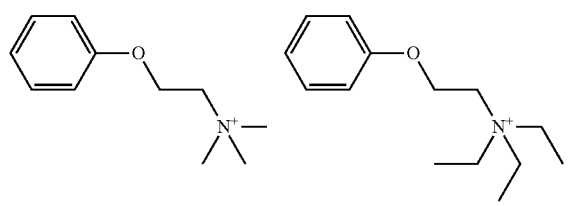
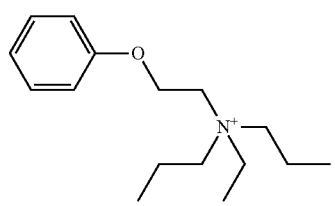
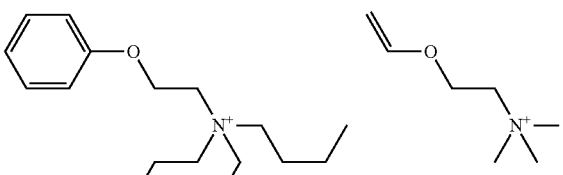
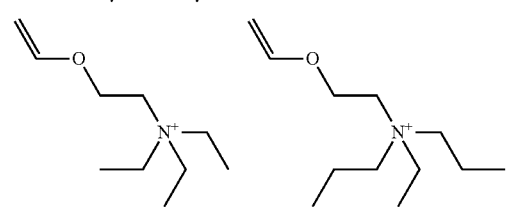
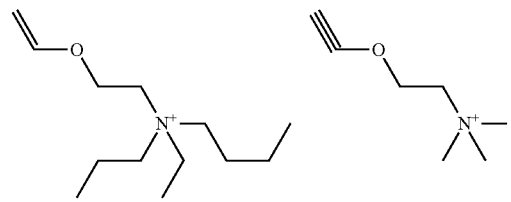
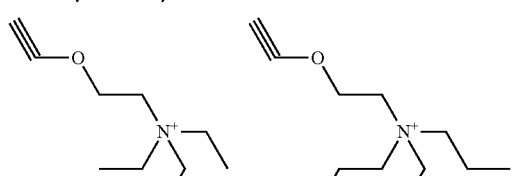
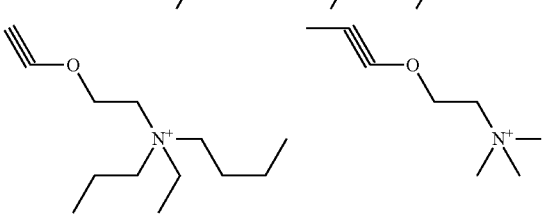

89
-continued
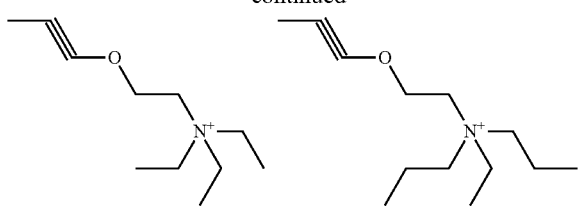
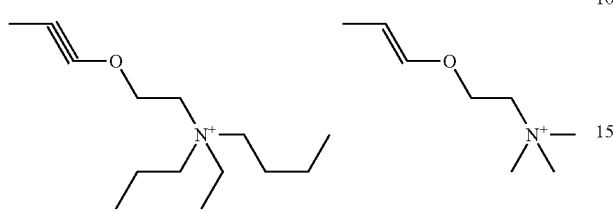
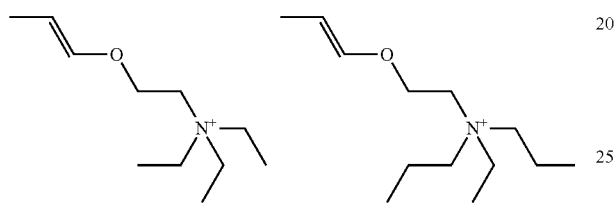
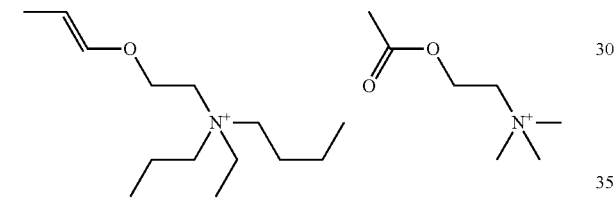
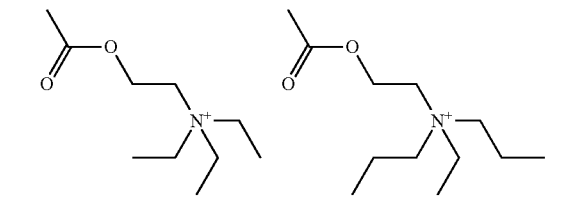
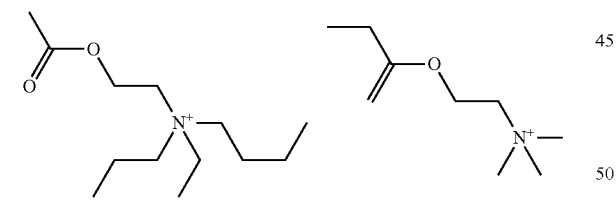
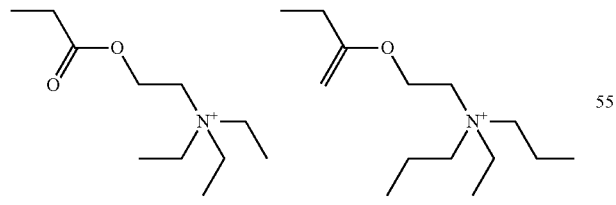
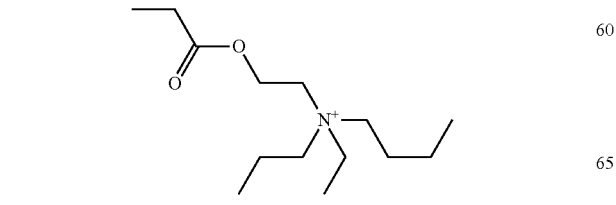
90
-continued
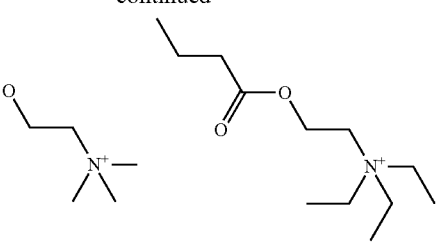
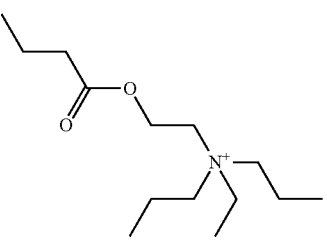
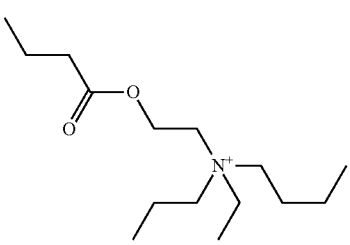
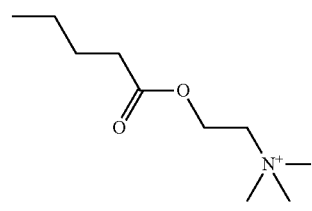
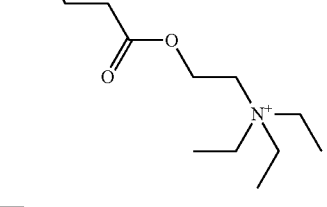
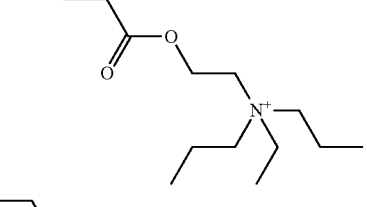
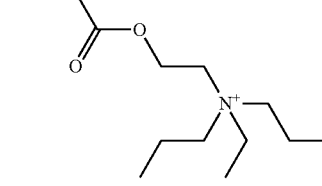

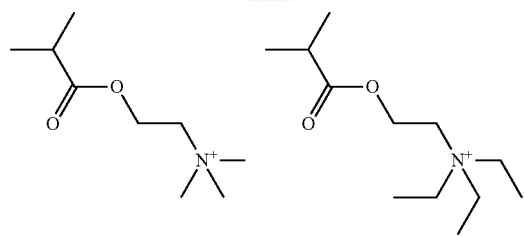
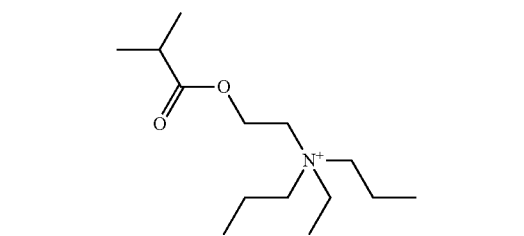
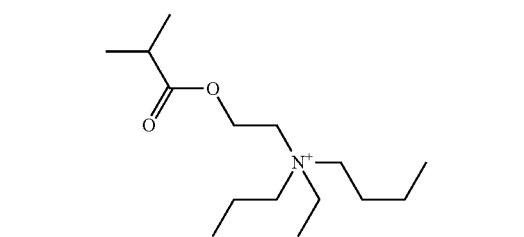
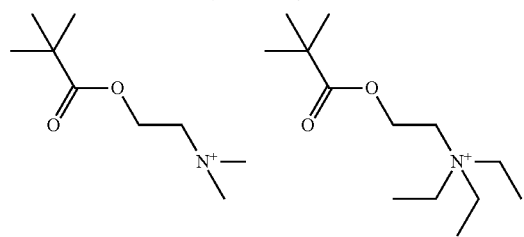
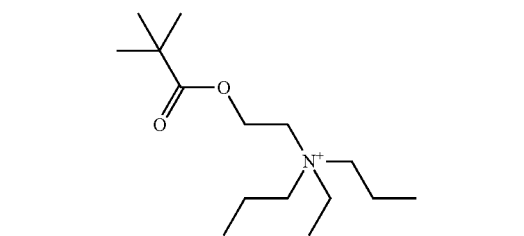
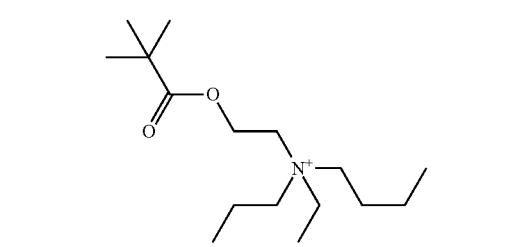
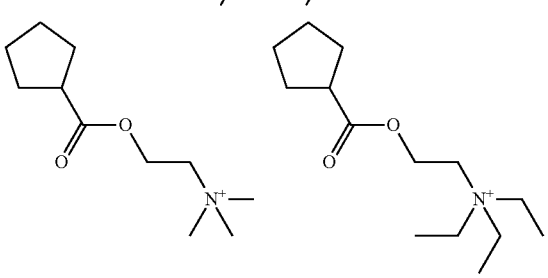
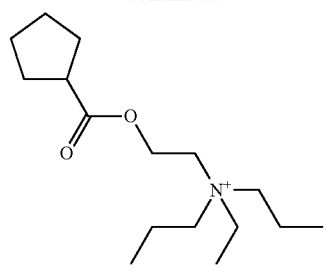
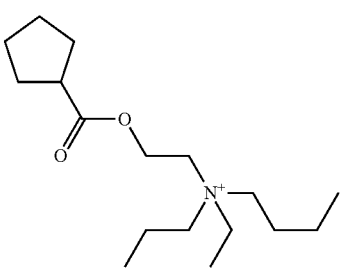
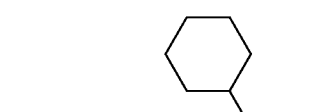
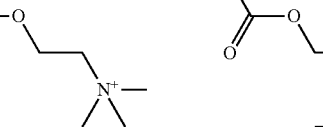
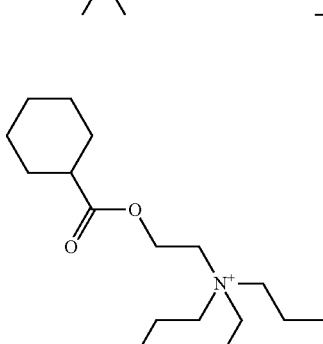
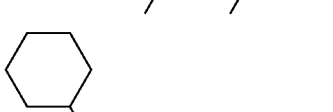
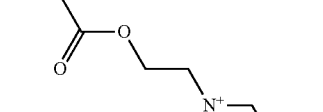
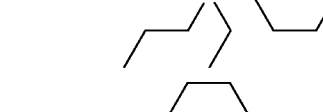
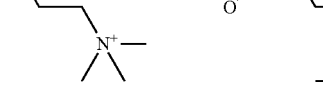

93
-continued
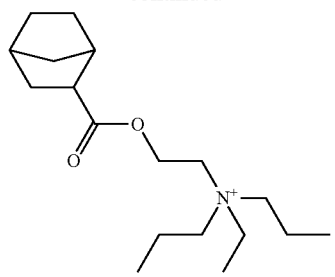
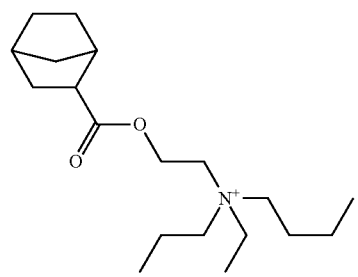
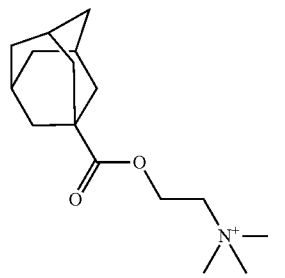
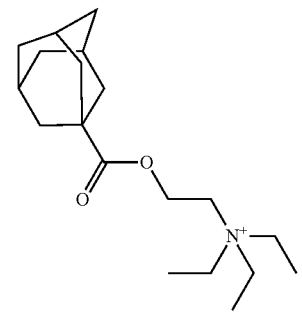
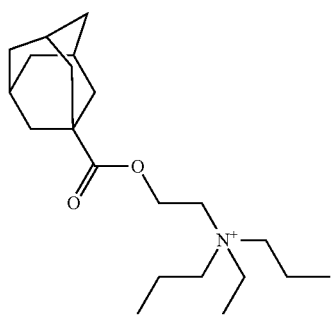
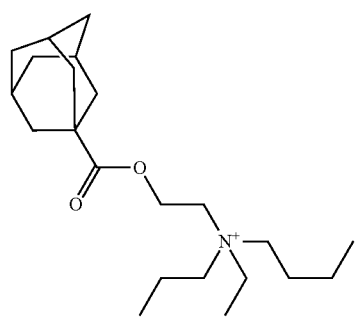
94
-continued
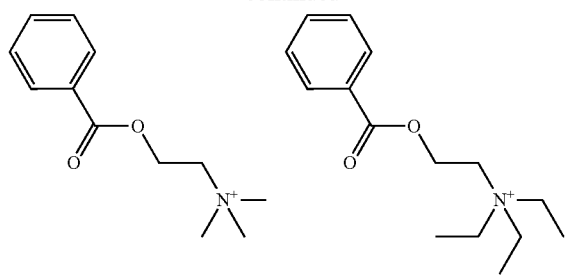
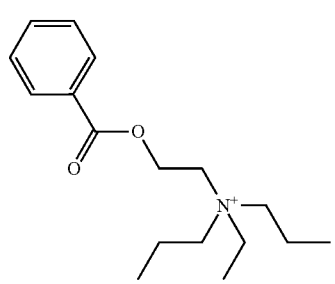
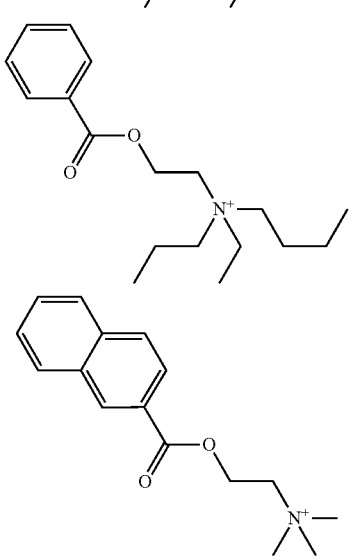
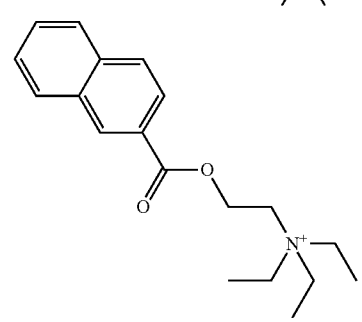
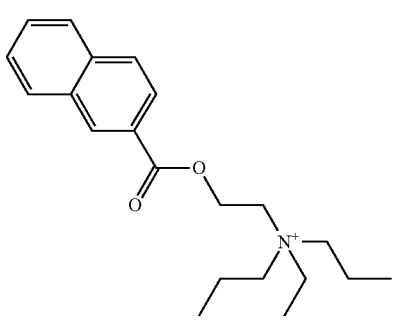

95
-continued
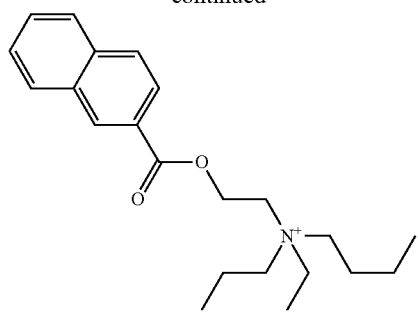
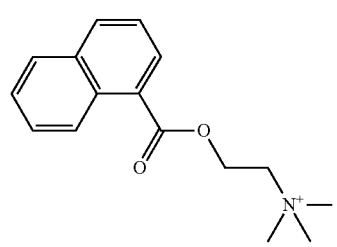
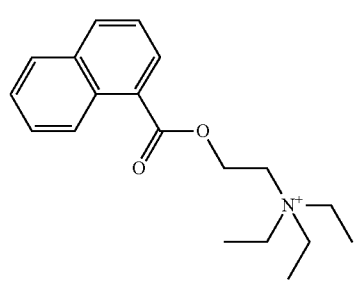
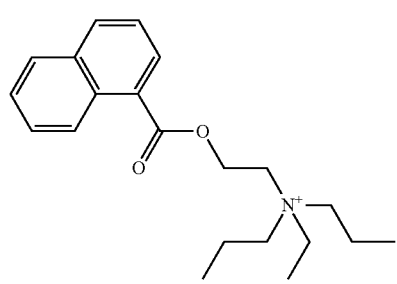
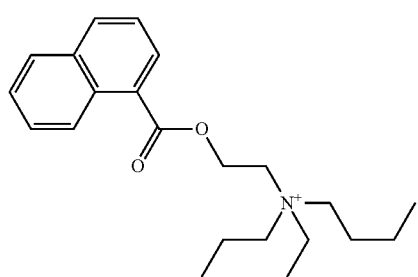
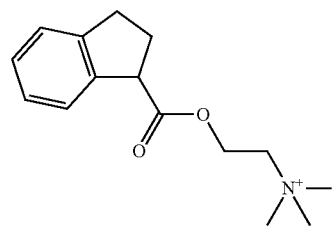
96
-continued
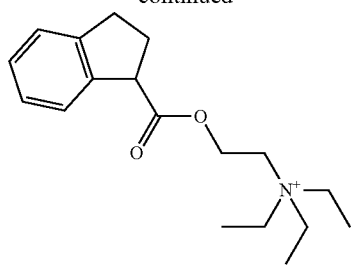
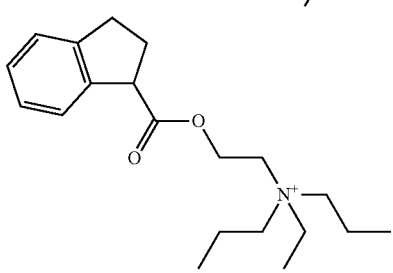
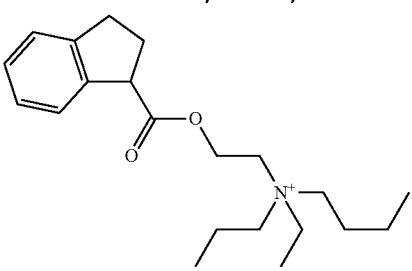
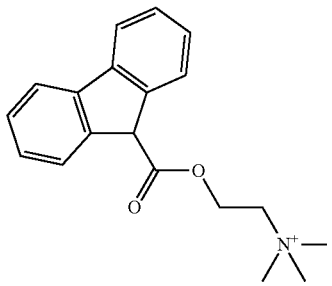
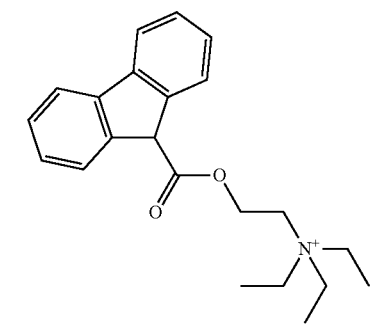
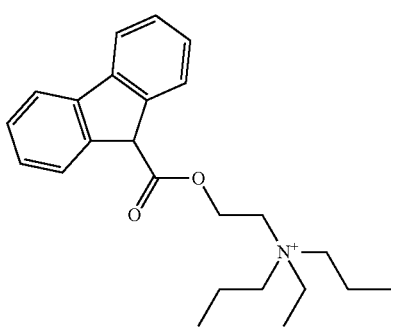

97
-continued
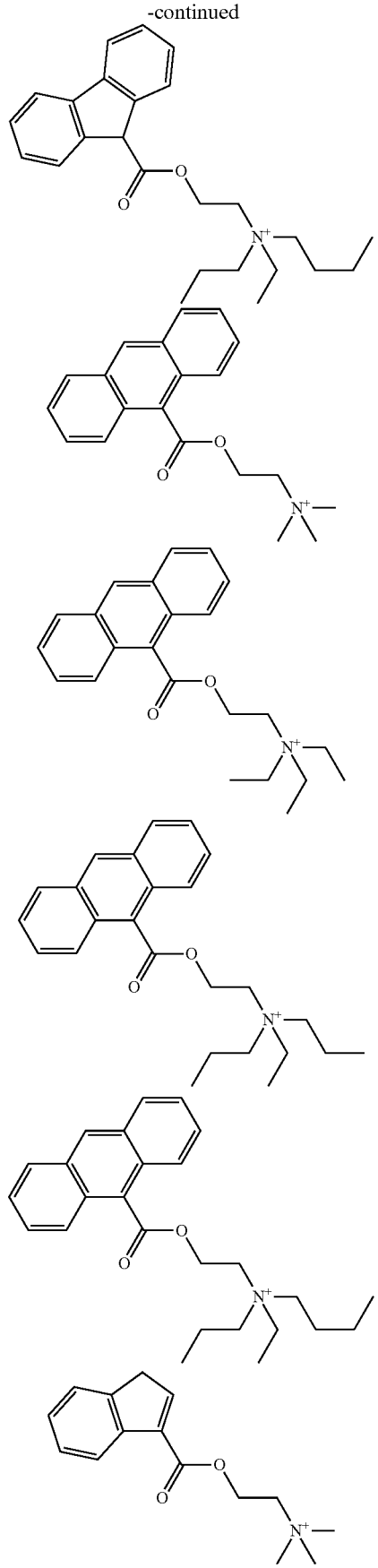
98
-continued
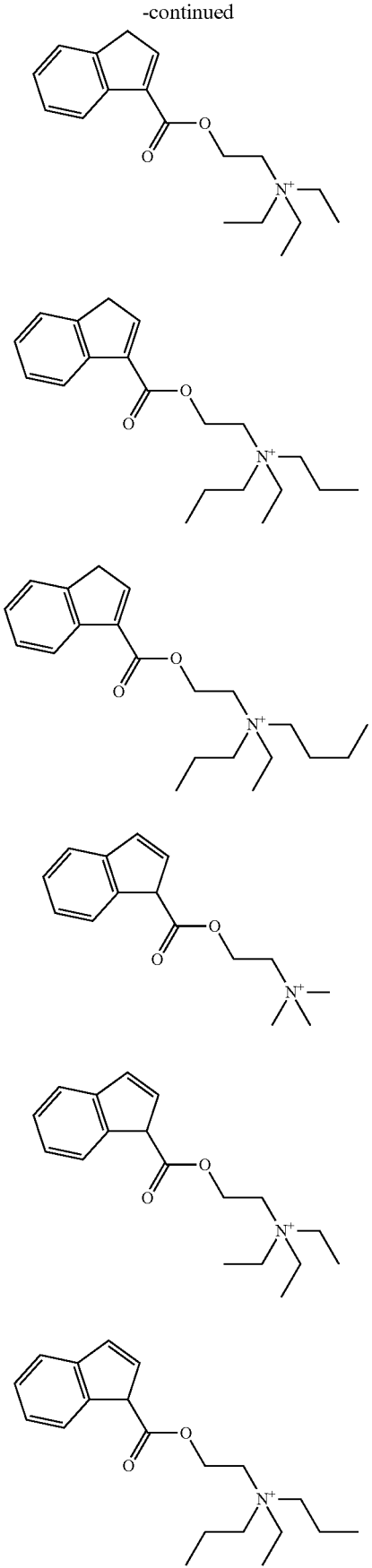

99
-continued
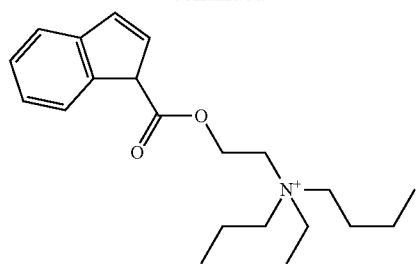
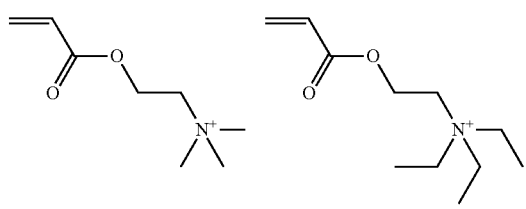
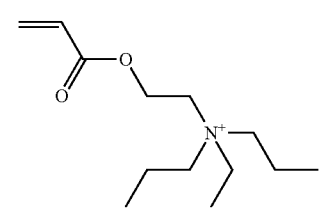
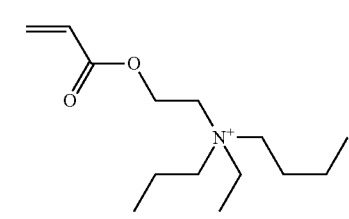
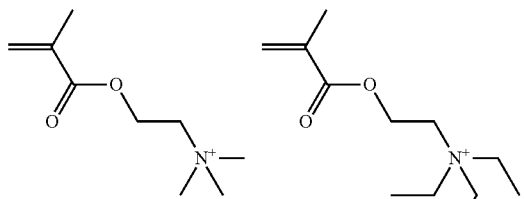
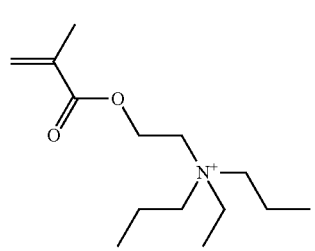
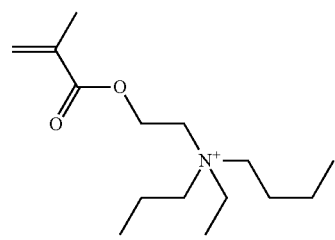
100
-continued
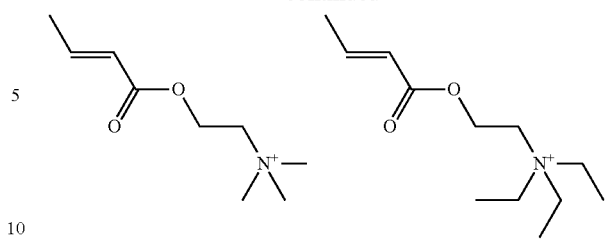
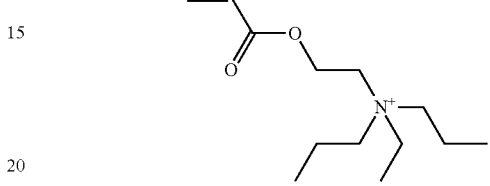
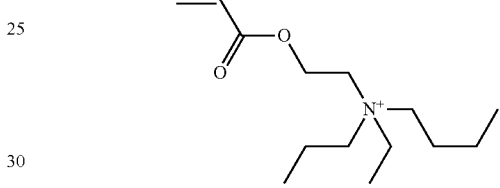
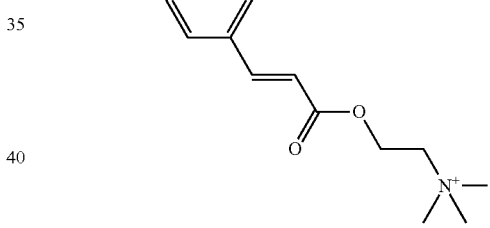
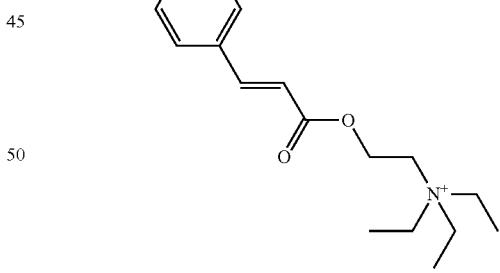
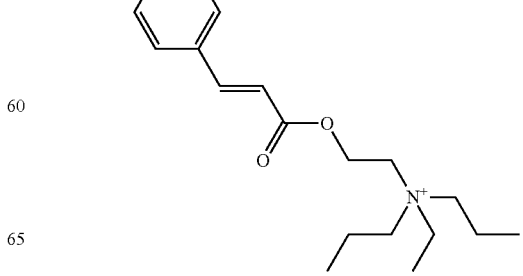

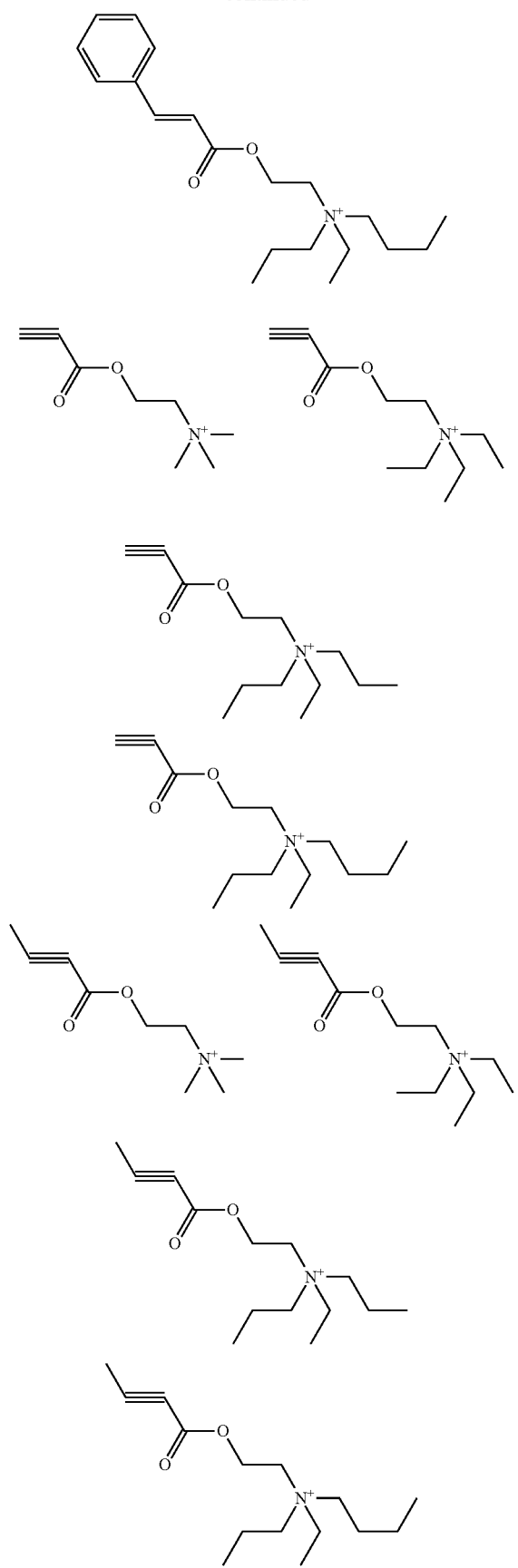
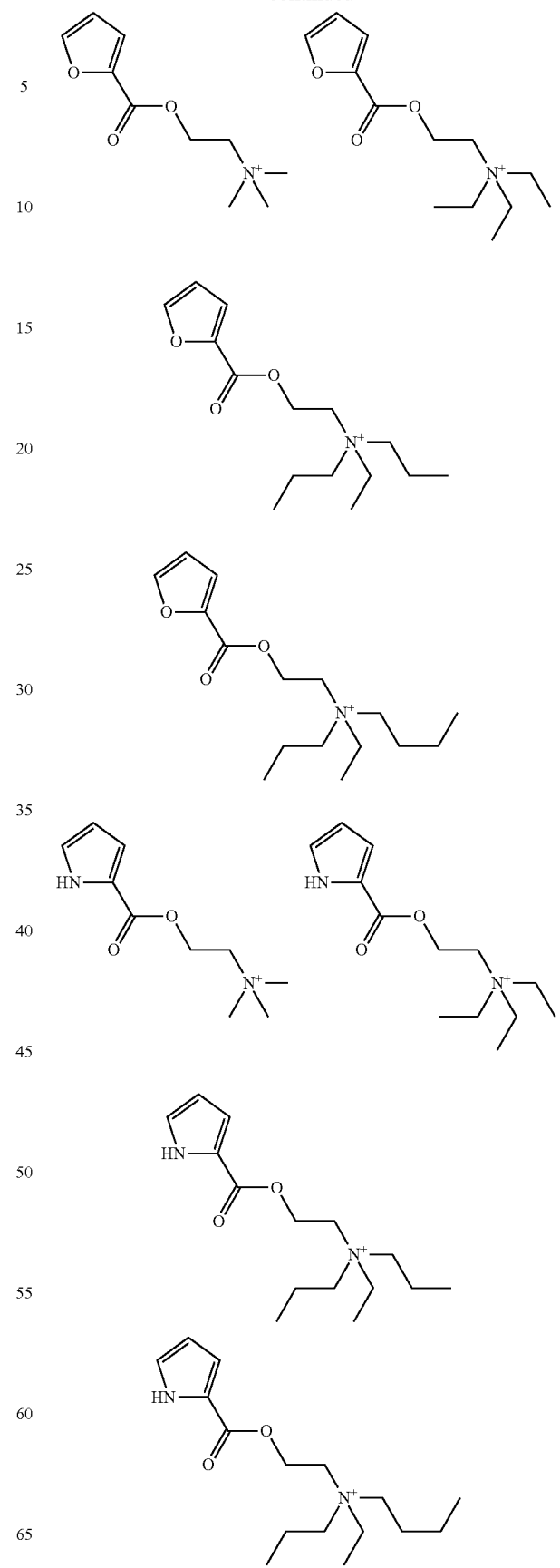

103
-continued
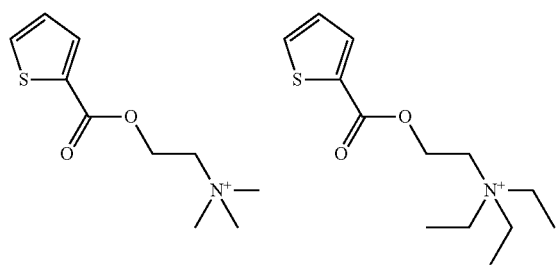
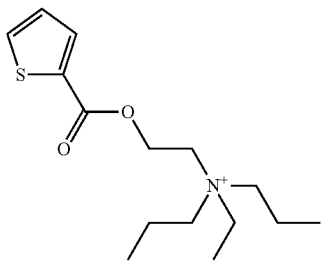
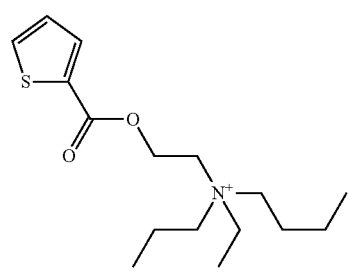
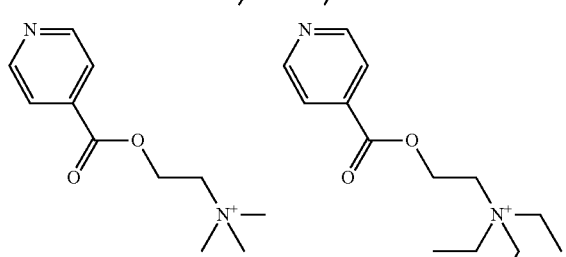
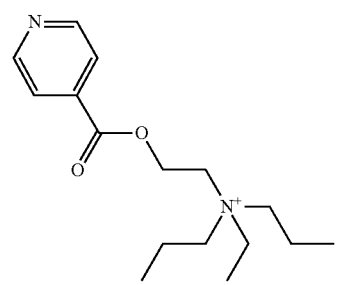
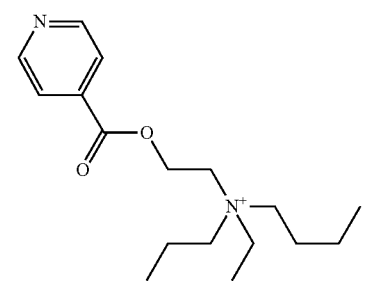
104
-continued
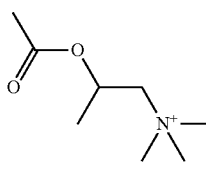
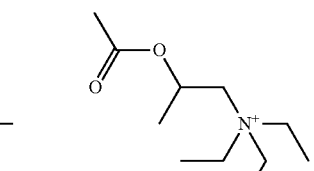
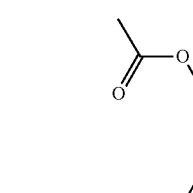
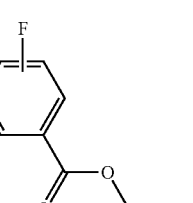
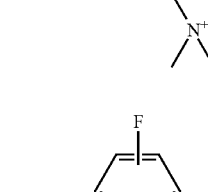
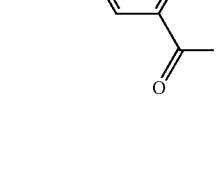
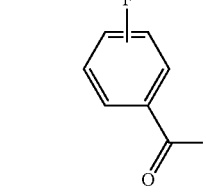

105
-continued
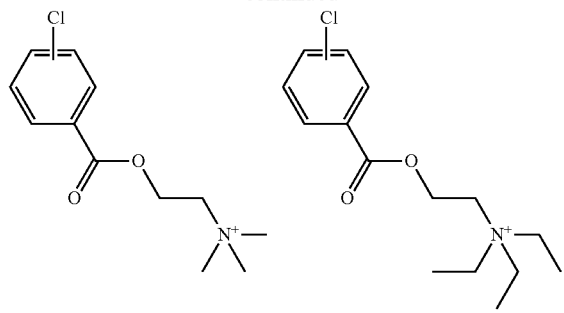
106
-continued
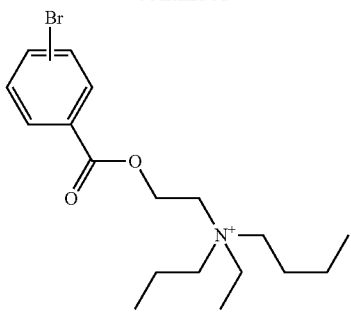
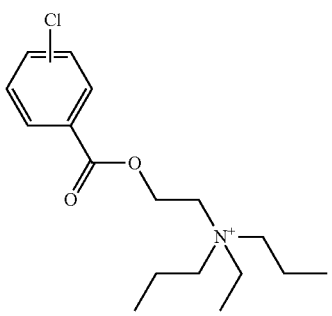
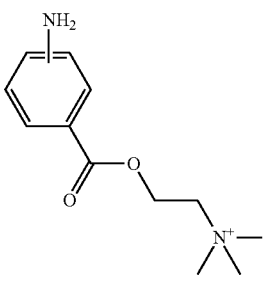
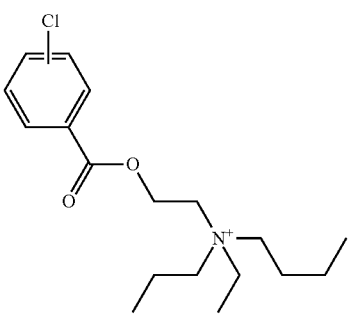
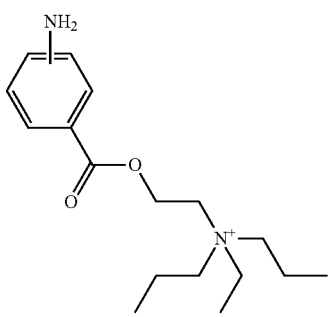
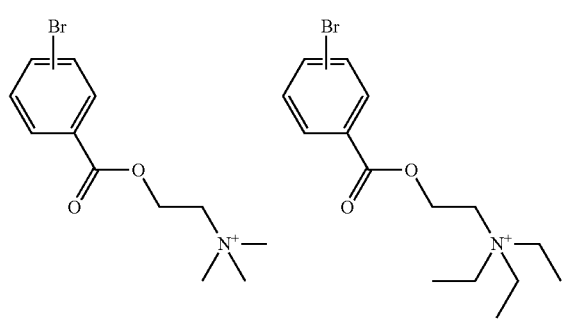
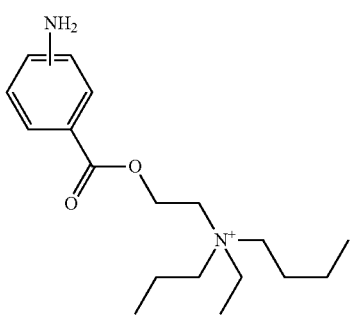
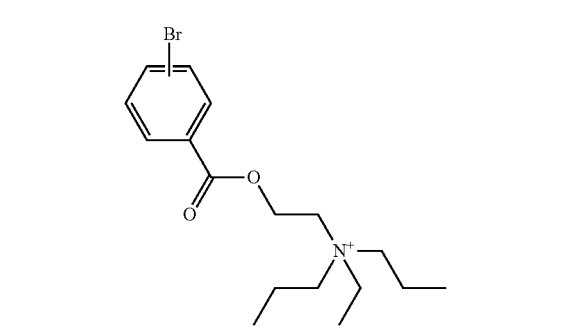
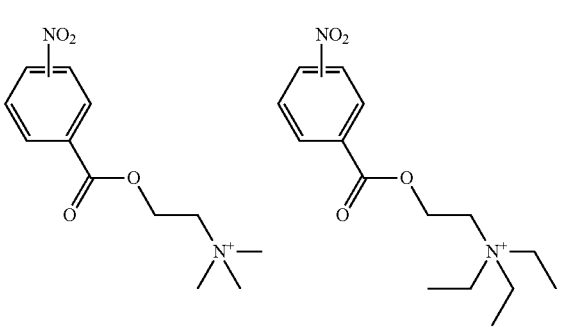

107
-continued
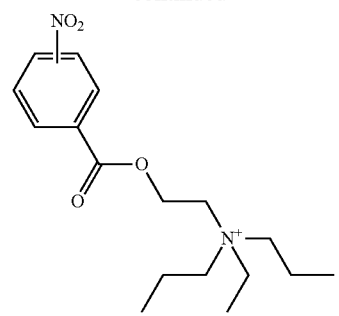
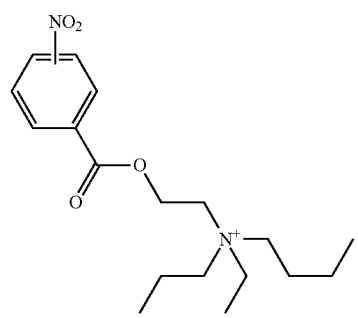
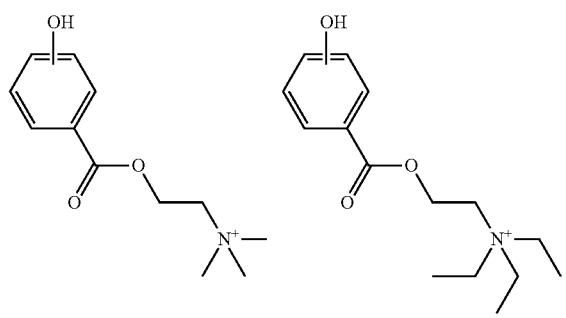
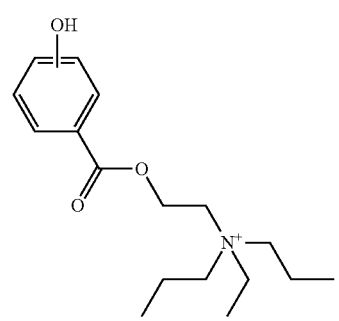
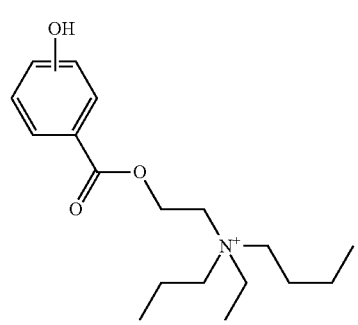
108
-continued
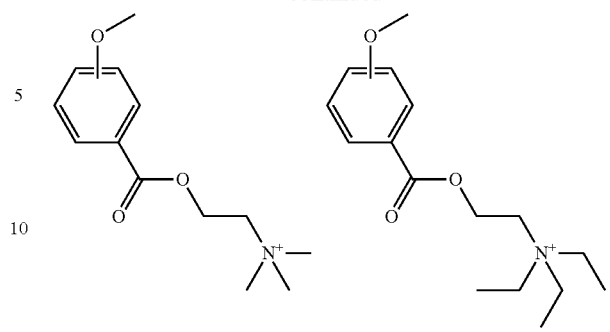
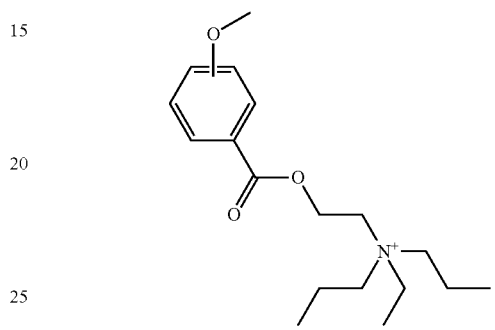
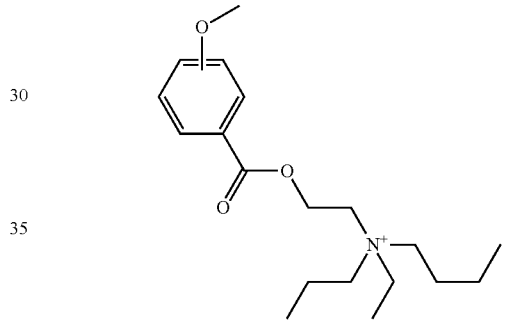
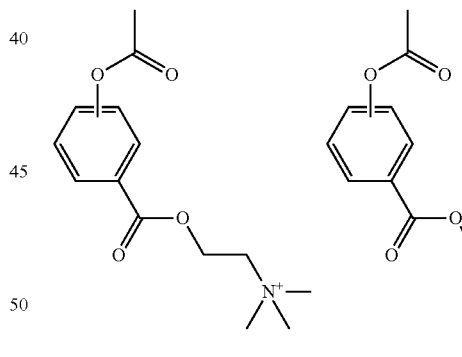
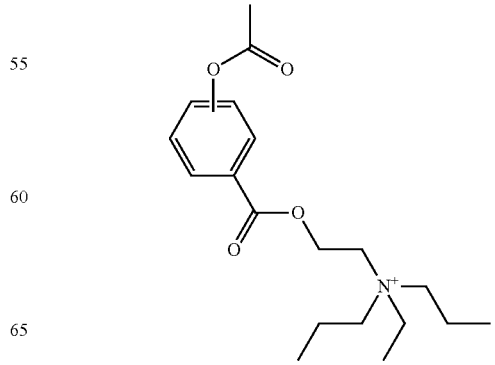

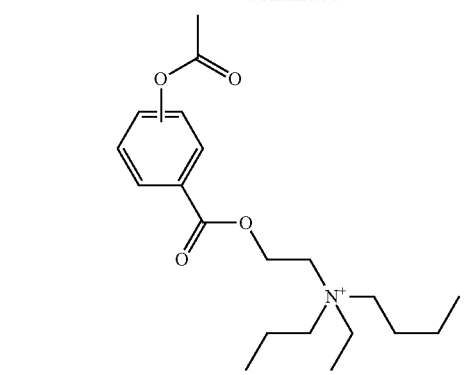
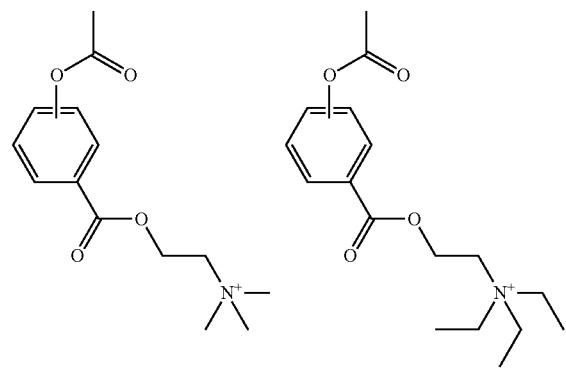
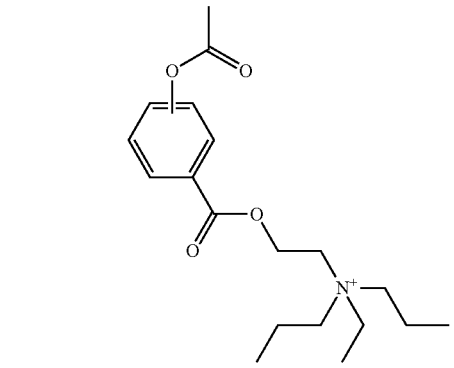
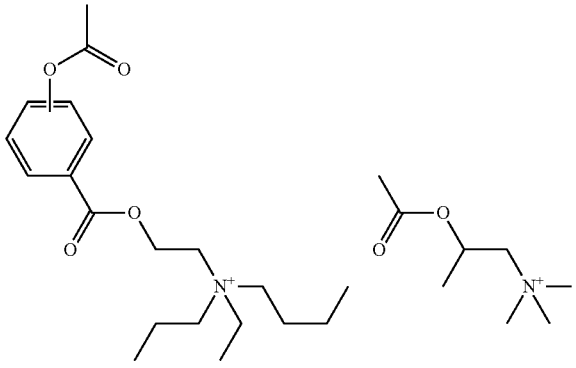
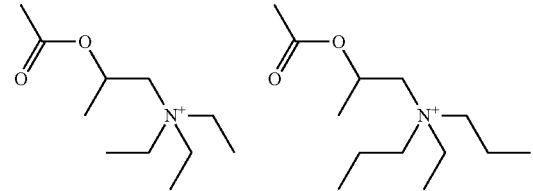
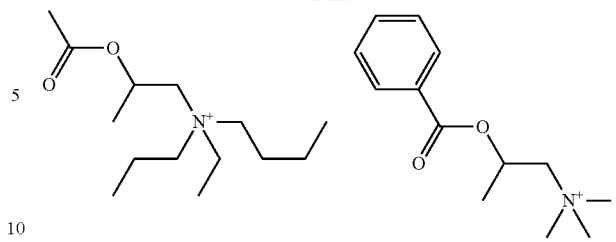
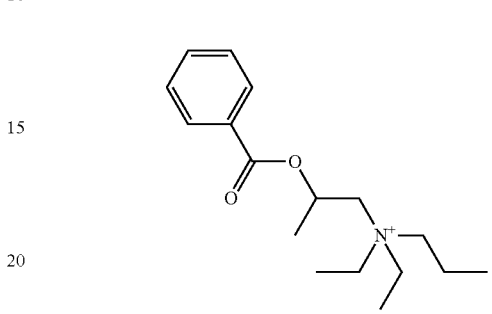
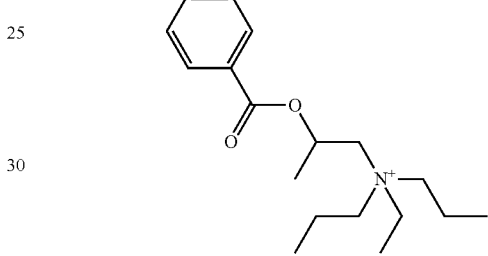
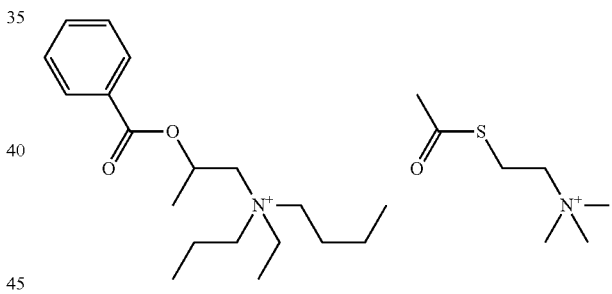
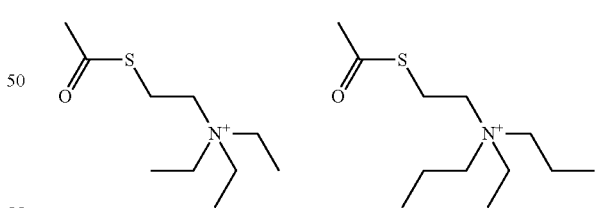
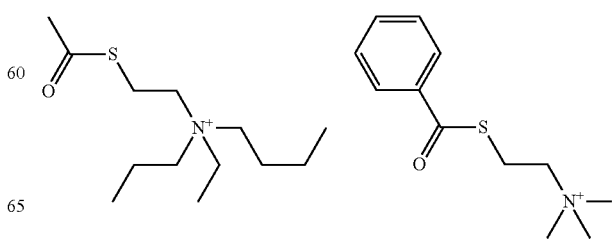

111
-continued
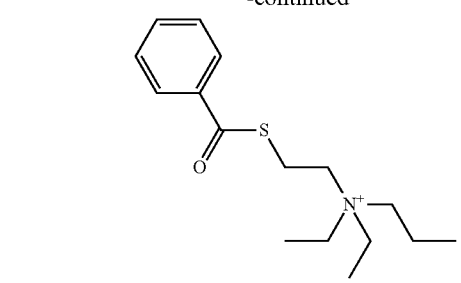
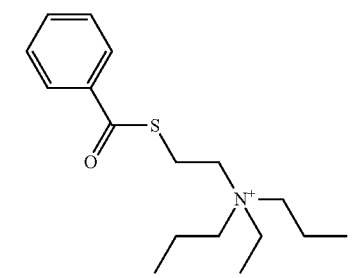
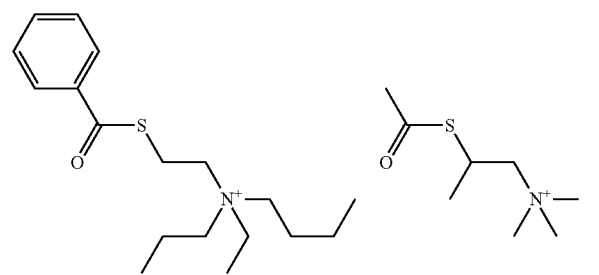
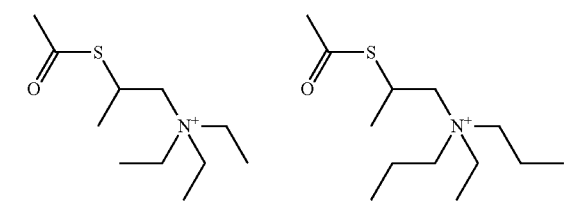
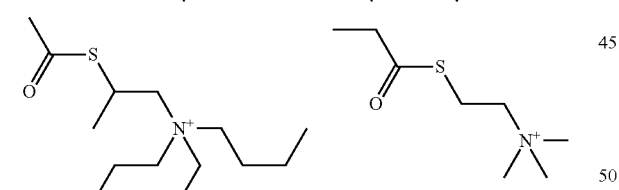
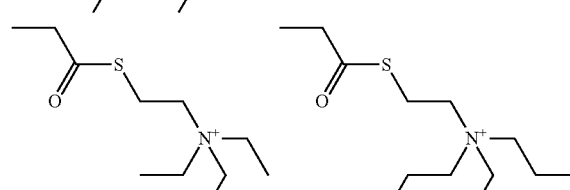
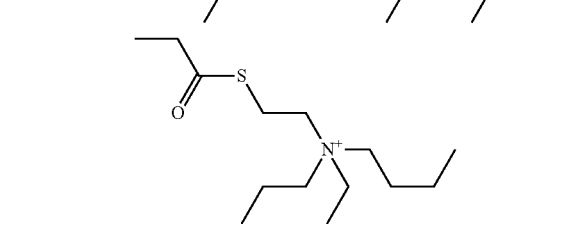
112
-continued
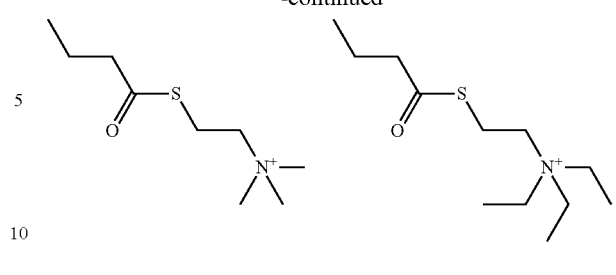
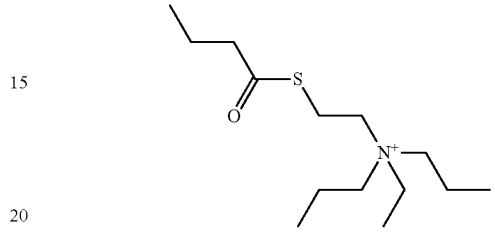
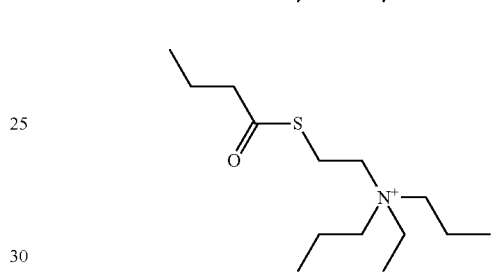
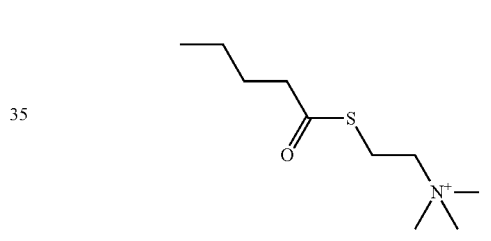
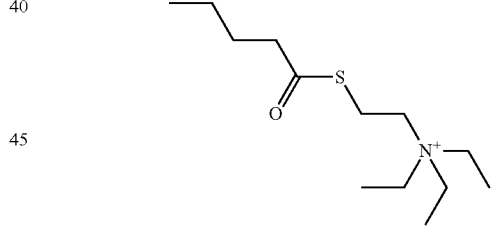
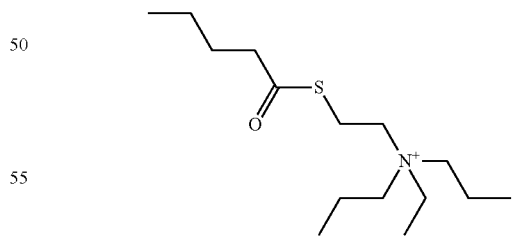
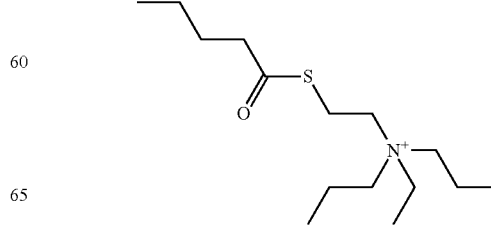

113
-continued
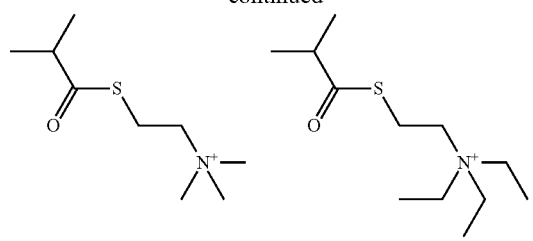
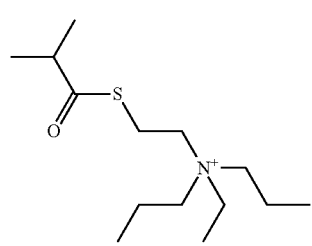
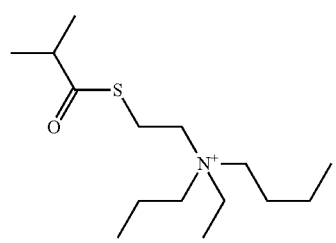
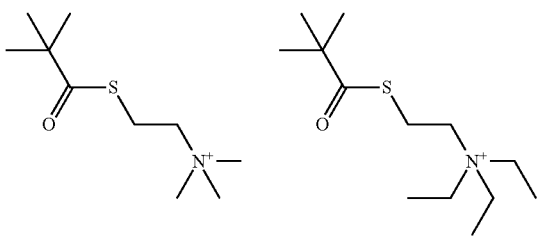
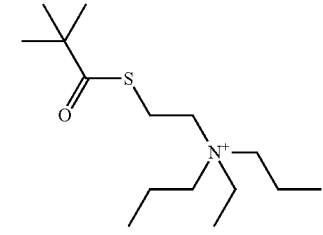
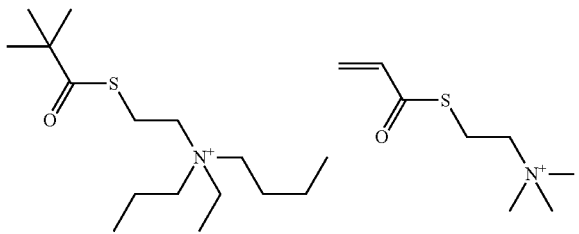
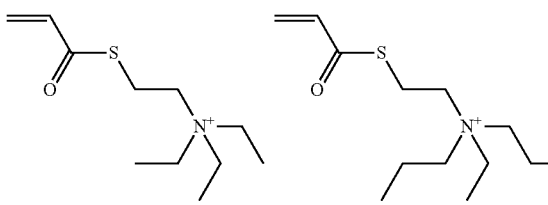
114
-continued
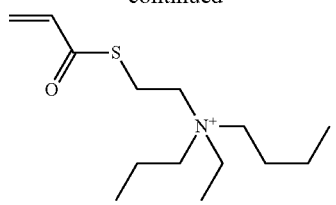
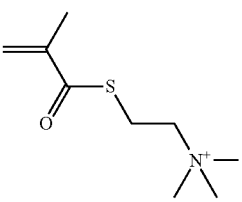
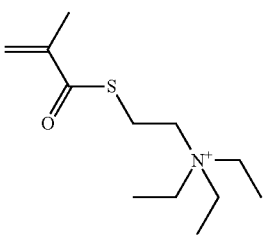
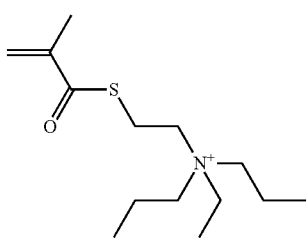
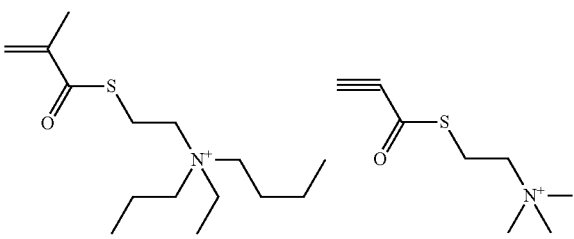
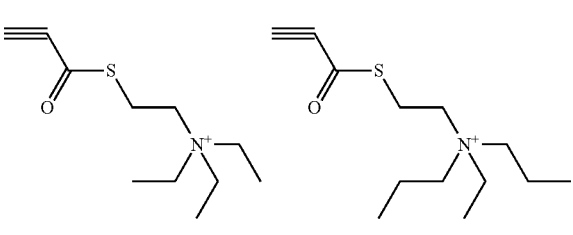
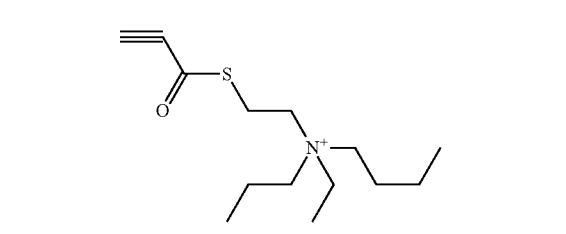
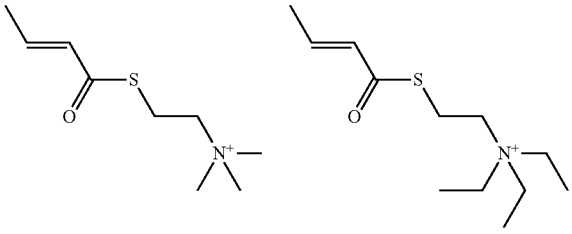

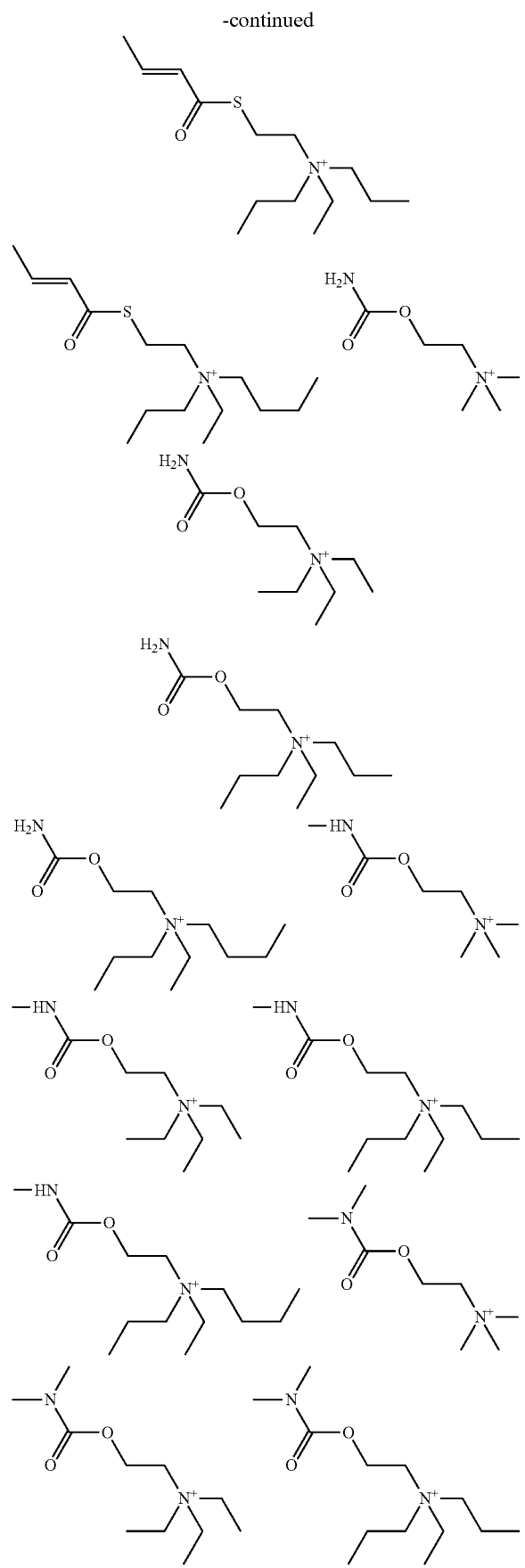
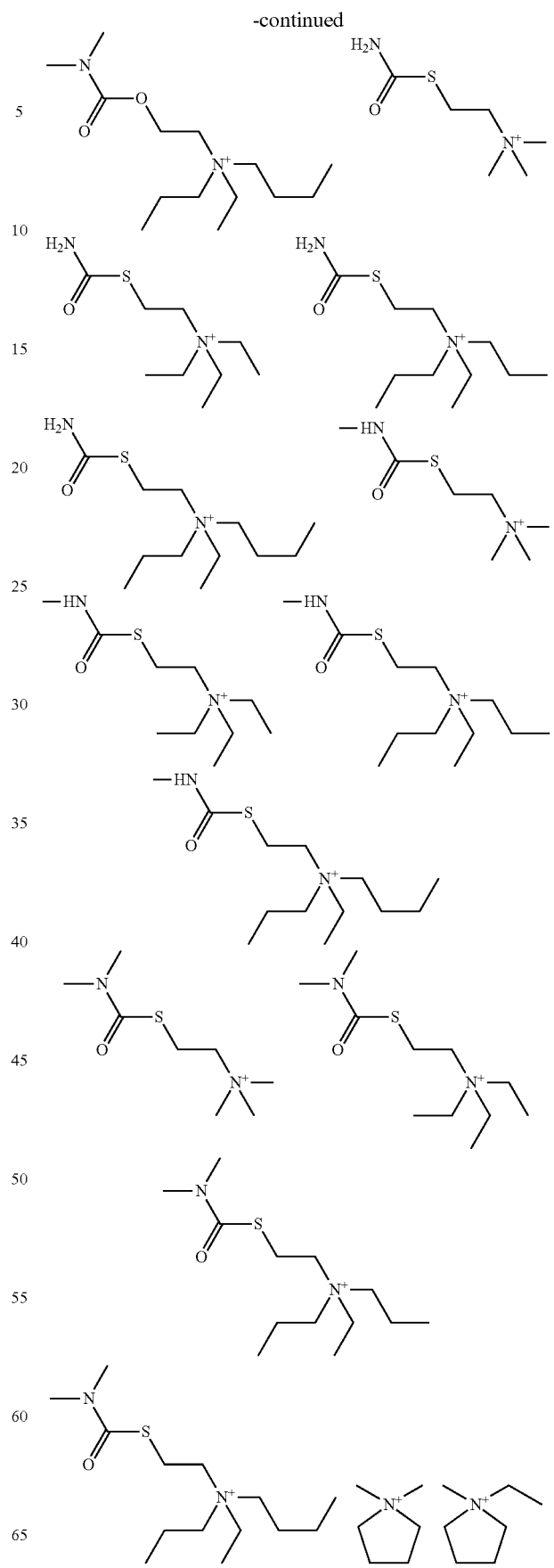

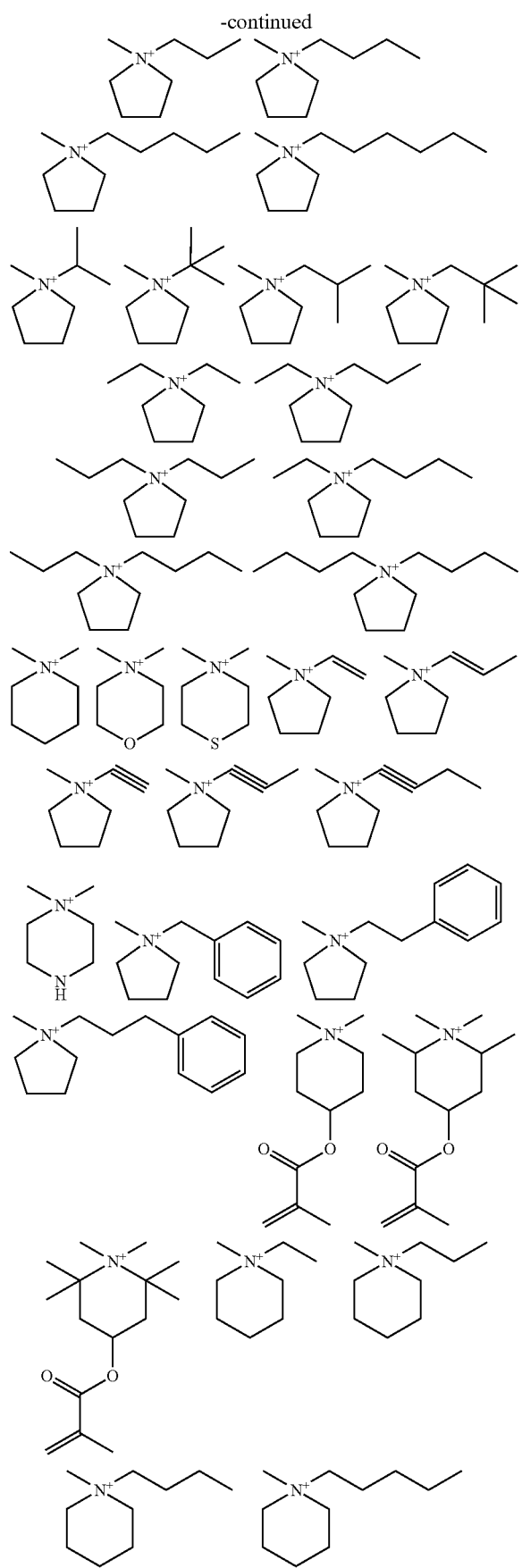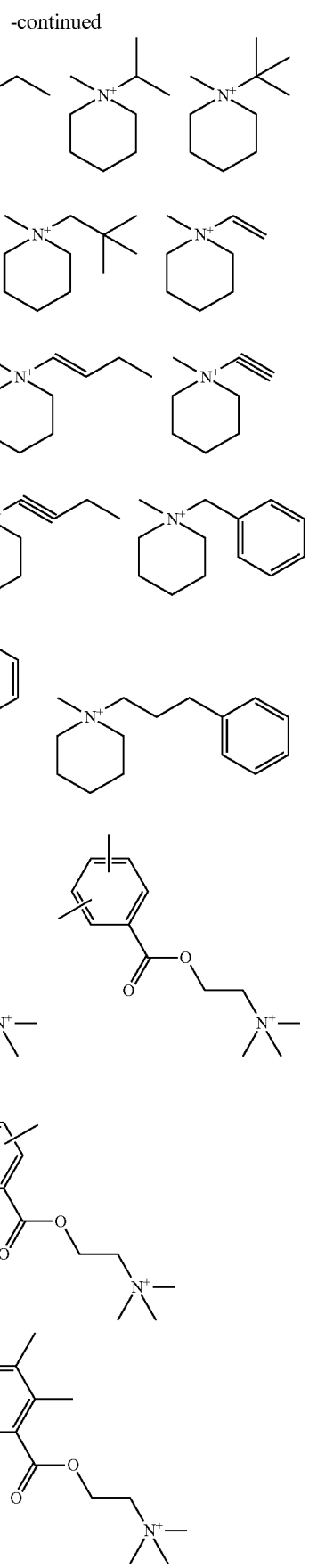

119
-continued
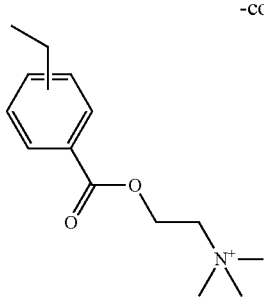 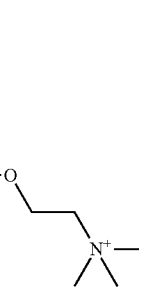
120
-continued
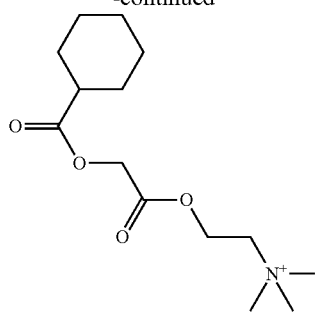
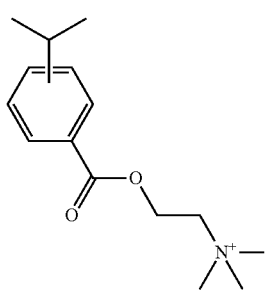
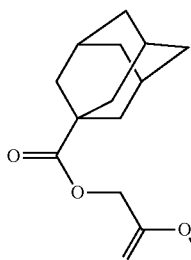
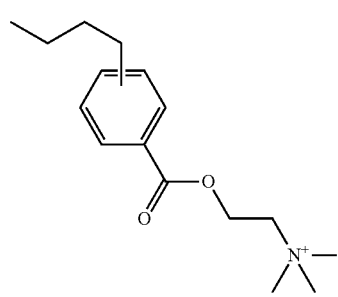
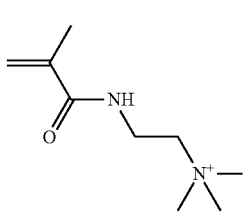 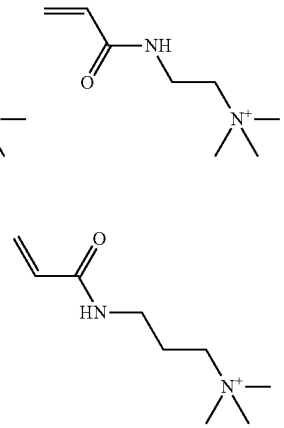
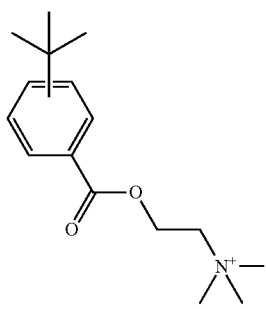
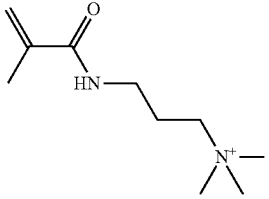
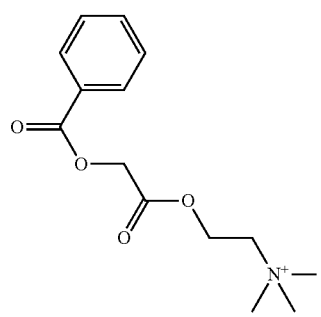

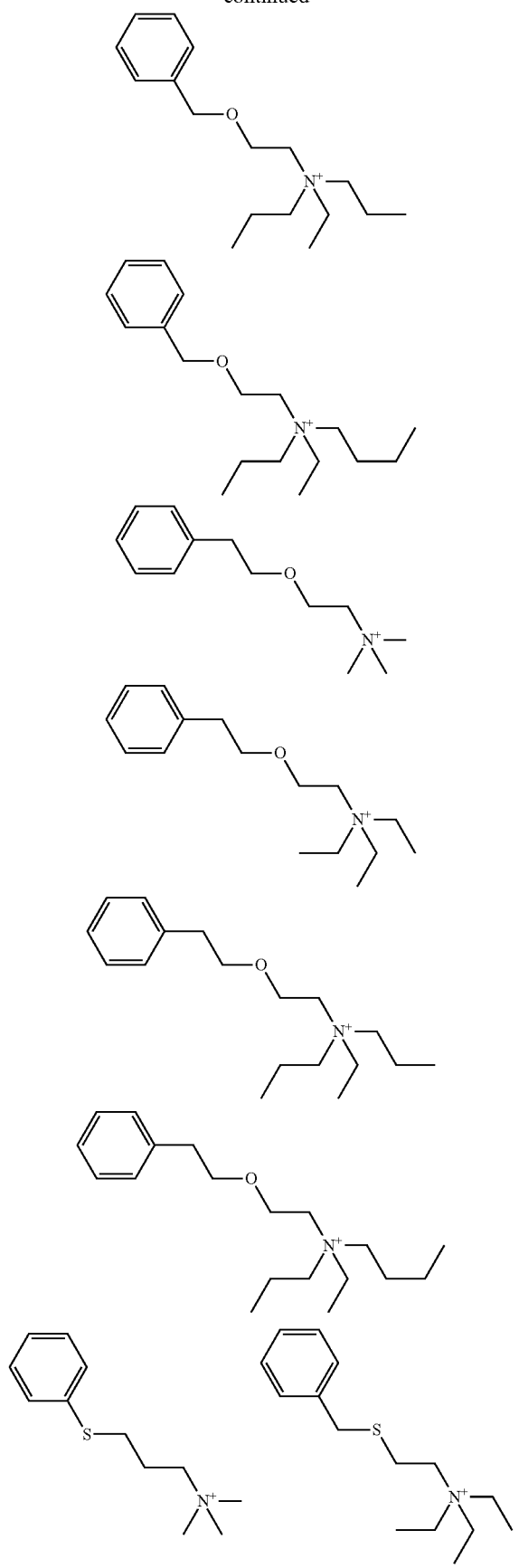
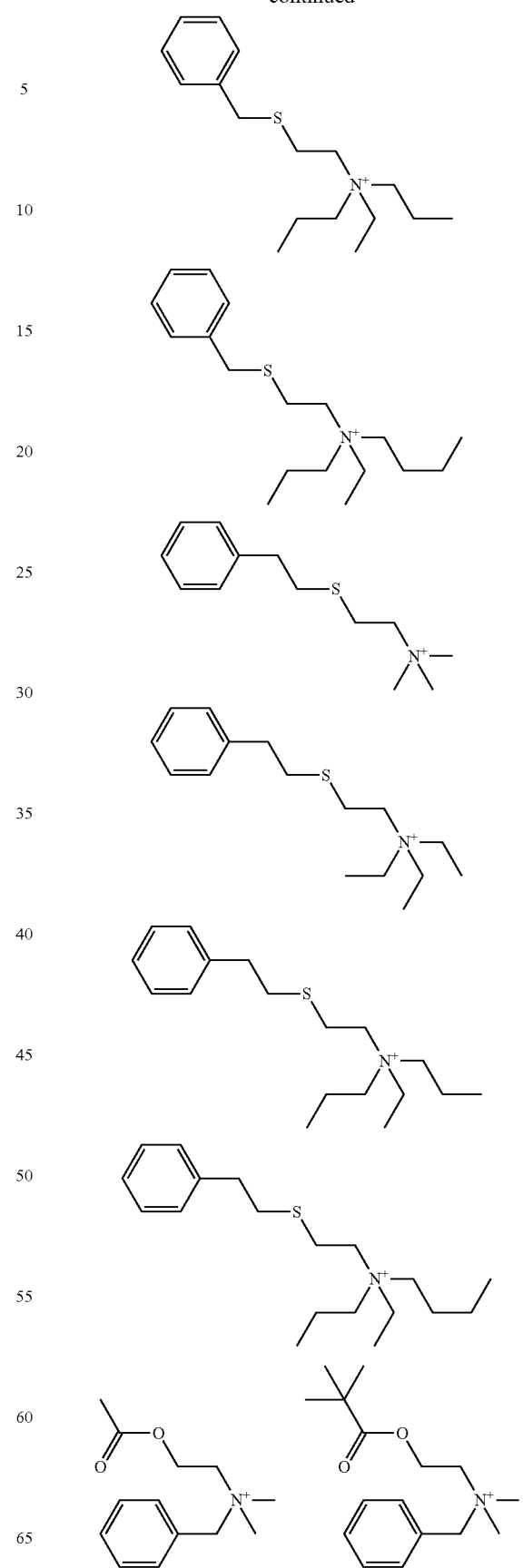

123
-continued
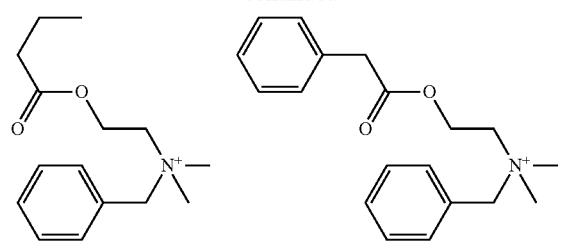
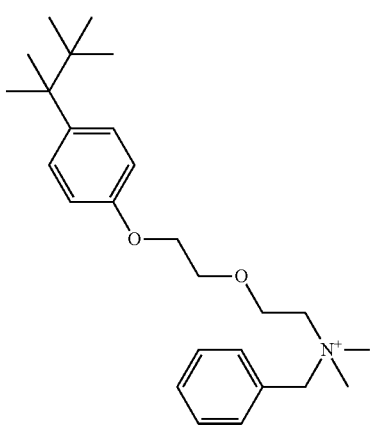
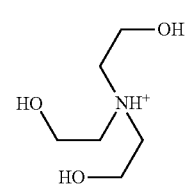
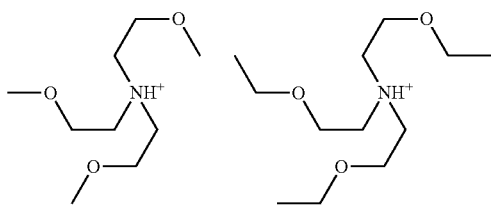
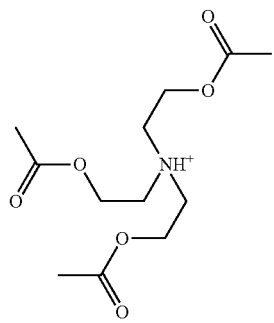
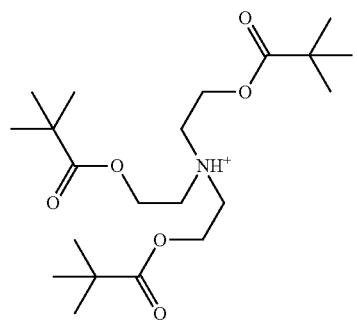
124
-continued
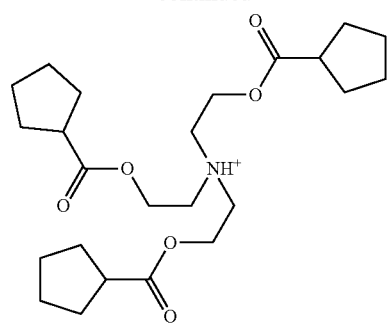
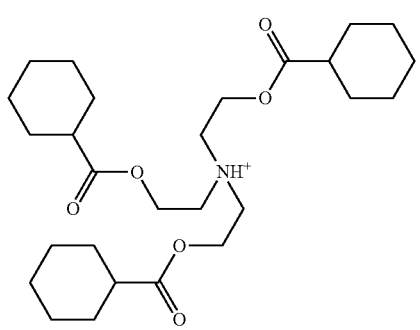
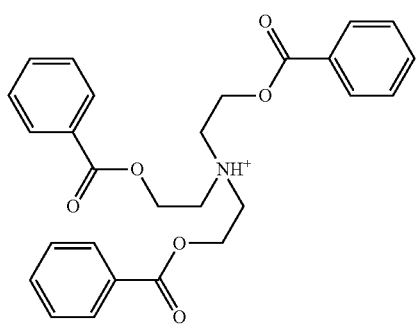
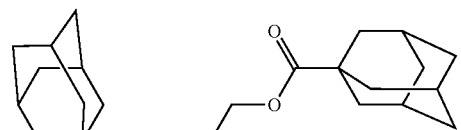
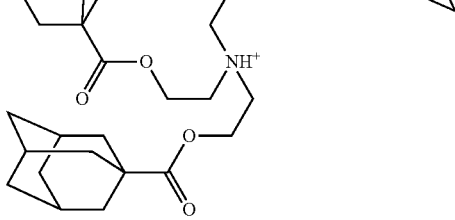
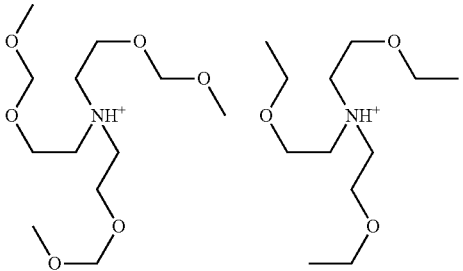

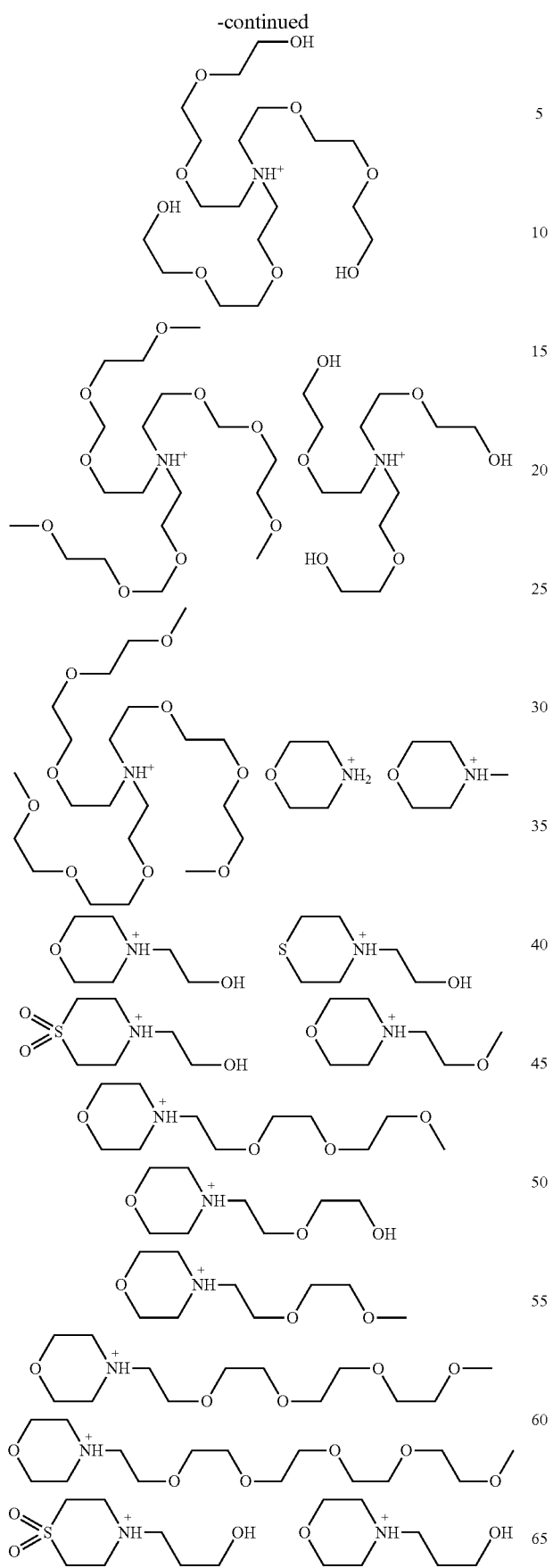
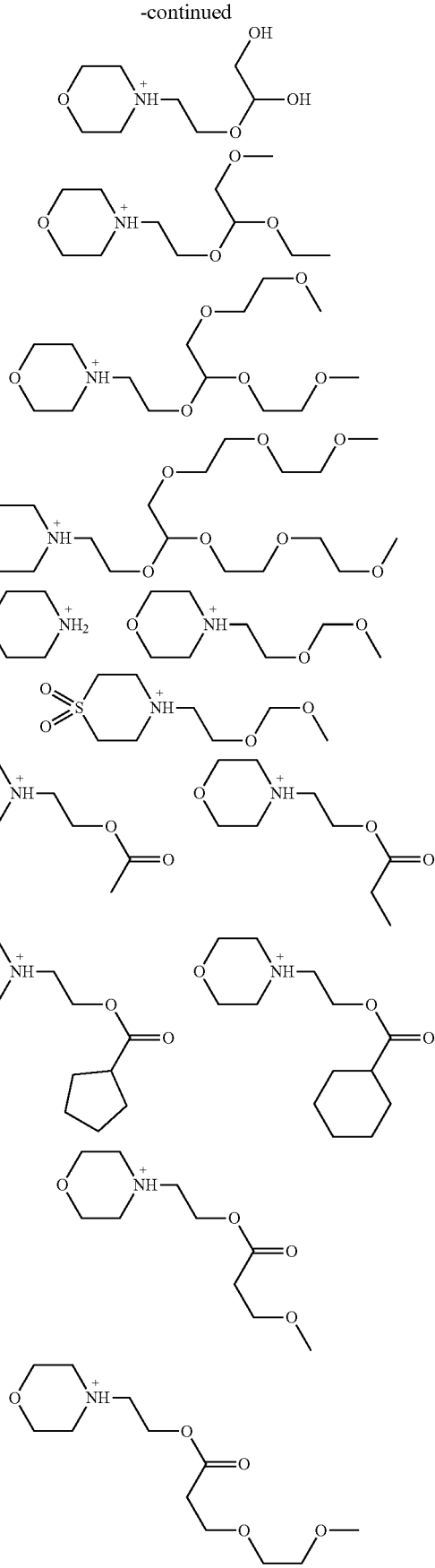

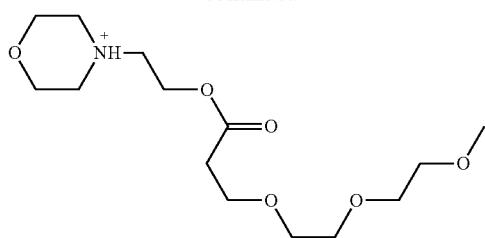

As the ammonium ion shown by the general formula (3), a tertiary or quaternary ammonium ion is particularly preferable.

(Repeating Unit-b)

The component (A) of the inventive bio-electrode composition can contain a repeating unit-b, which has silicon, in addition to the repeating unit(s) selected from the repeating units-a1 to -a7. The repeating unit-b is preferably the repeating unit-b1 shown by the following general formula (2'). Illustrative examples of a monomer to give the repeating unit-b1 include the following.

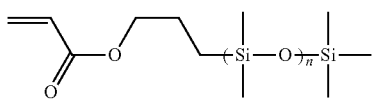

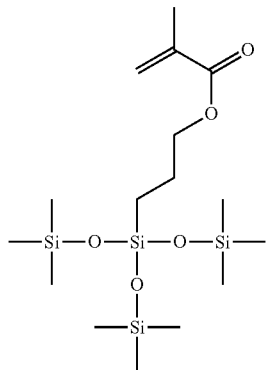
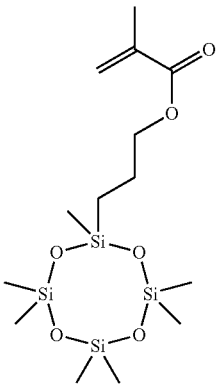

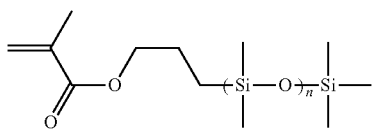

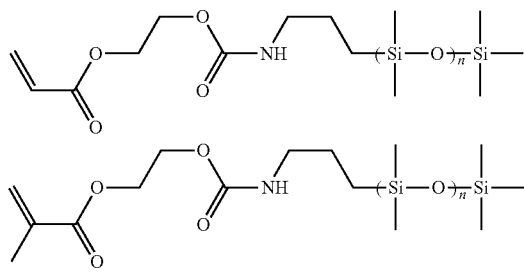

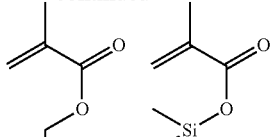

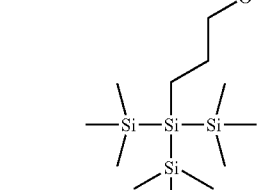

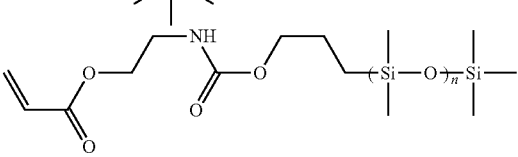

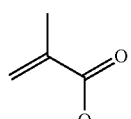

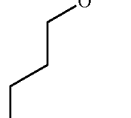

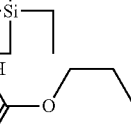

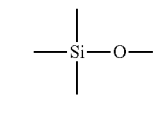

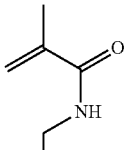

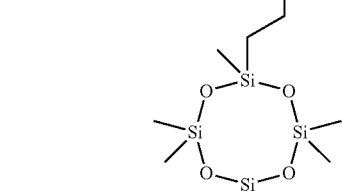

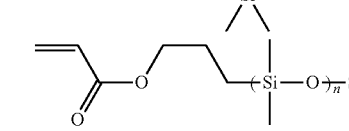

129
-continued

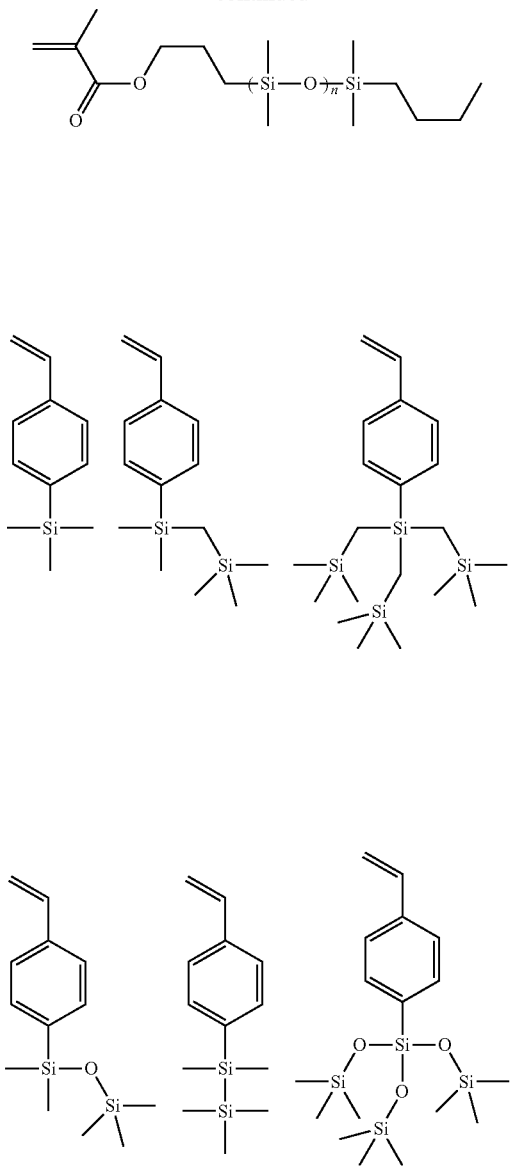

In the formulae, "n" is an integer of 0 to 100.

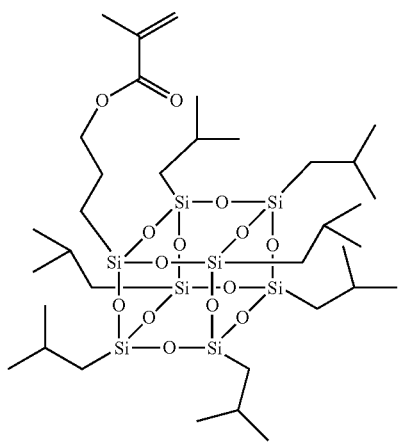

130
-continued

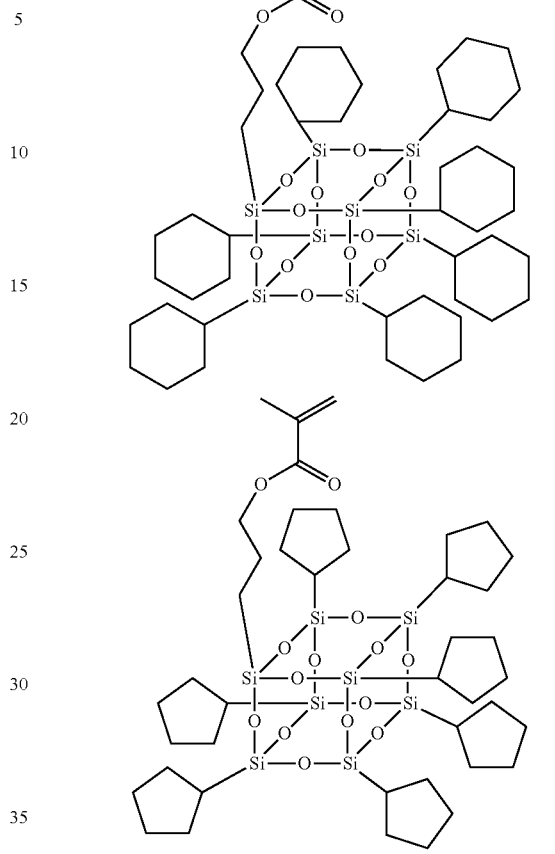

(Repeating Unit-c)

In the component (A) of the inventive bio-electrode composition, a repeating unit-c having a glyme chain can be copolymerized in addition to the repeating units-a and -b in order to improve the electric conductivity. Illustrative examples of the monomer to give the repeating unit-c having a glyme chain include the following.

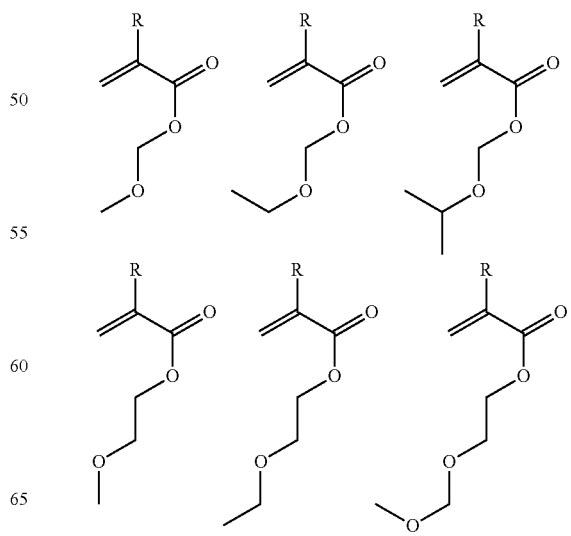

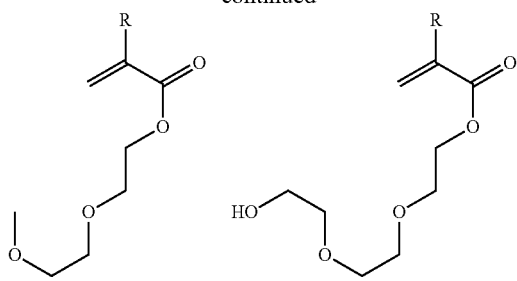
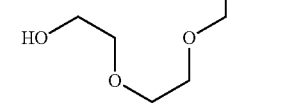
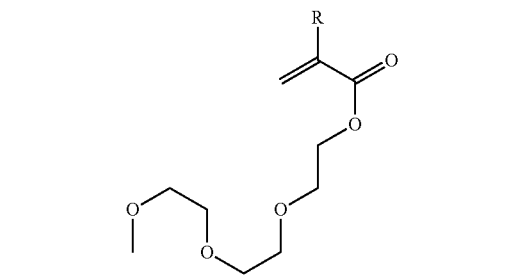
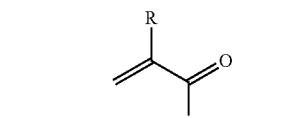
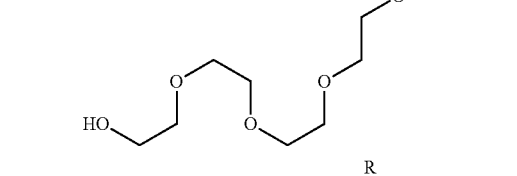
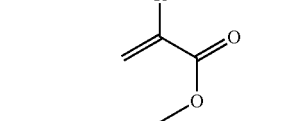
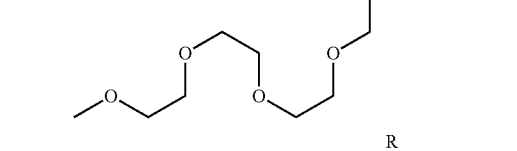
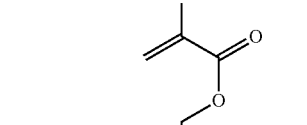
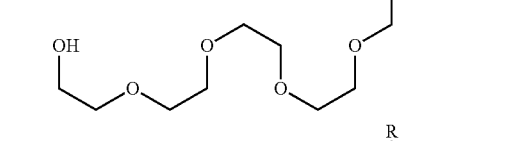
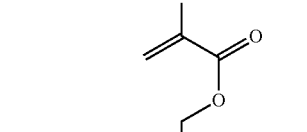
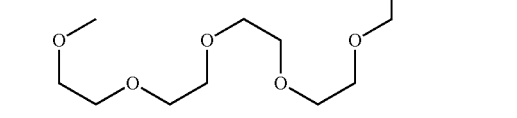
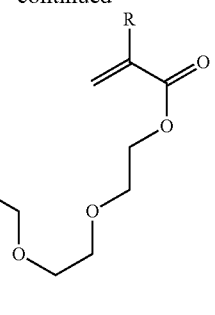
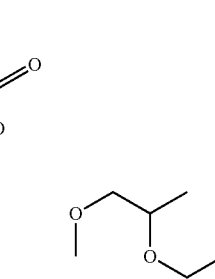
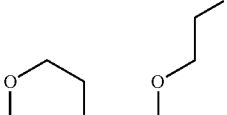
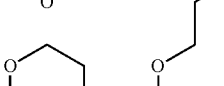
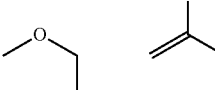
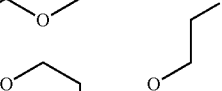
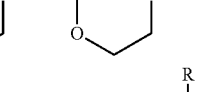
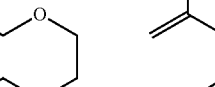
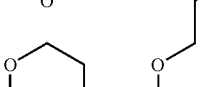
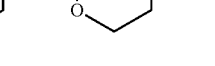

133
-continued
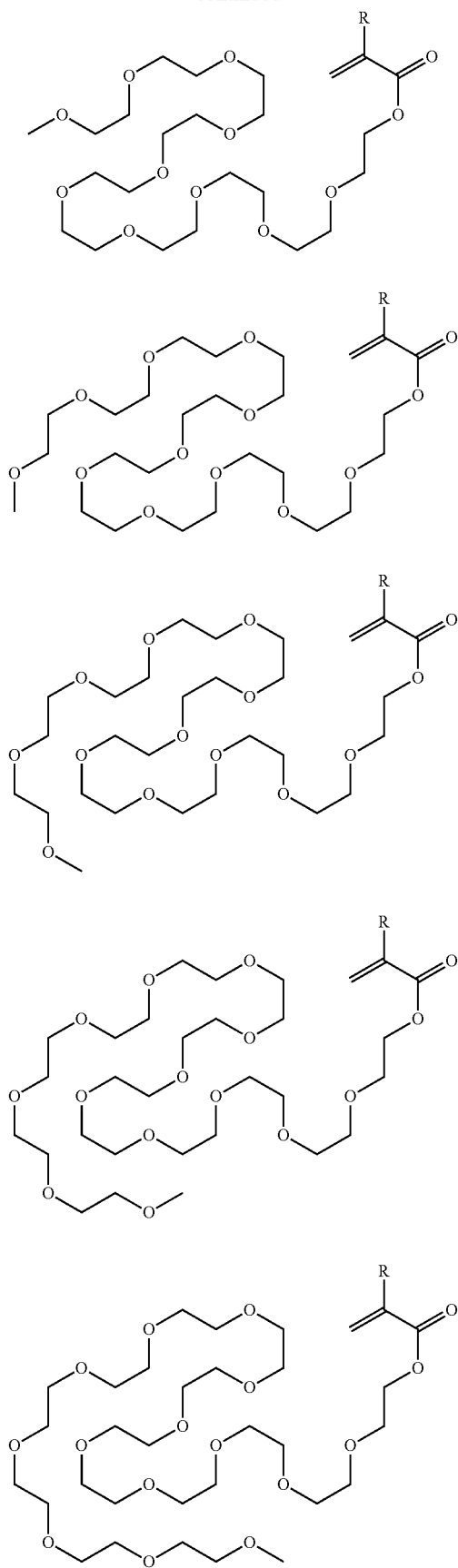
134
-continued
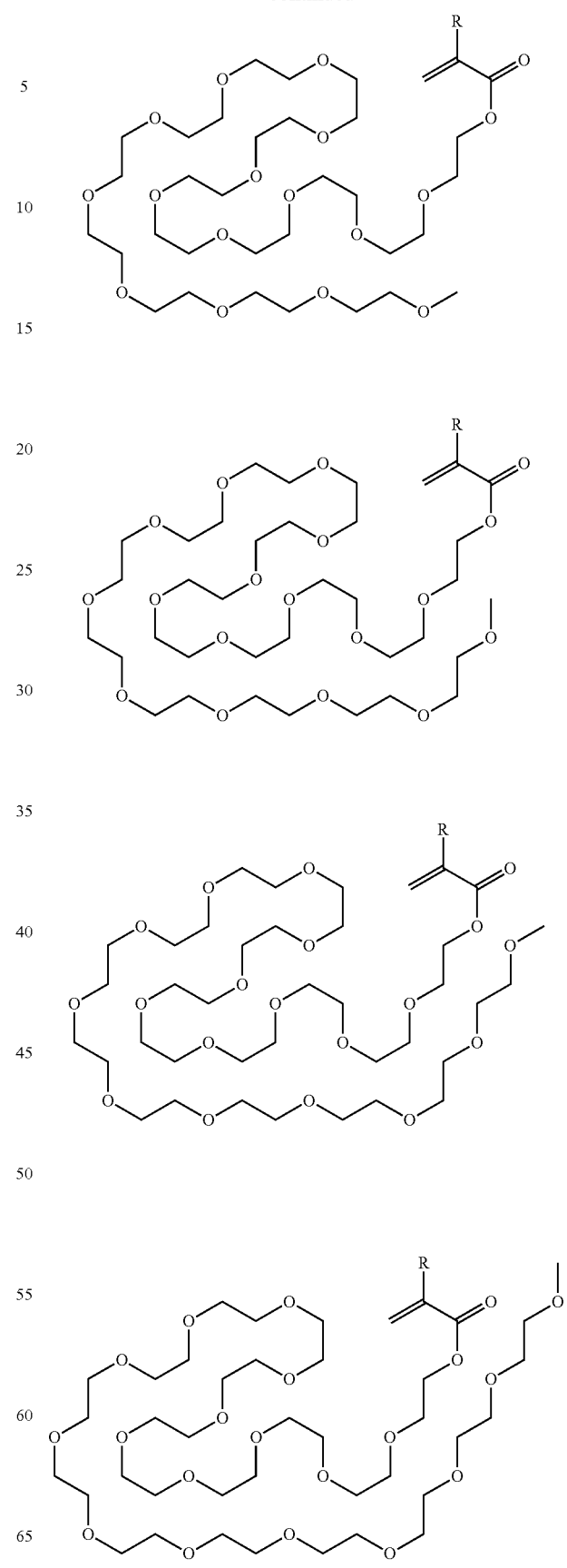

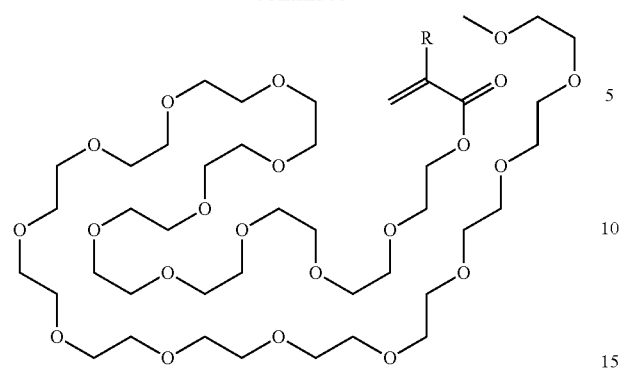
Wherein, R represents a methyl group or a hydrogen atom.
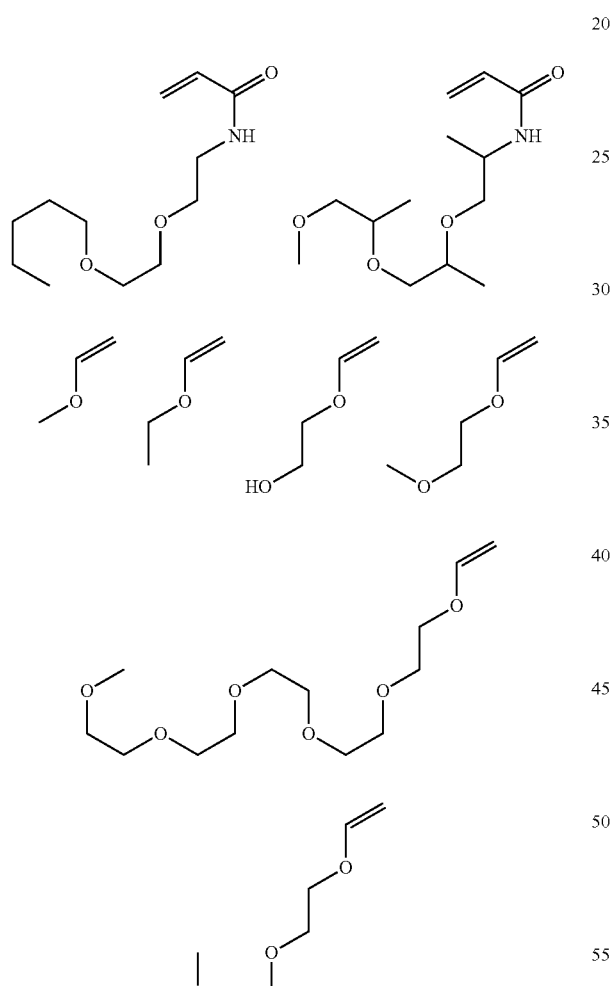
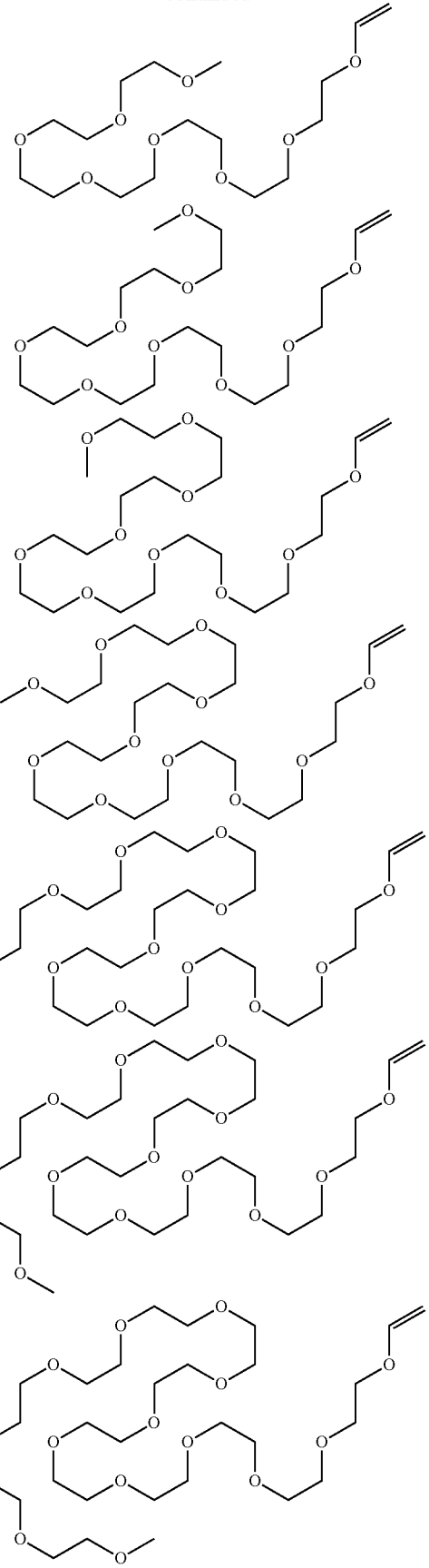

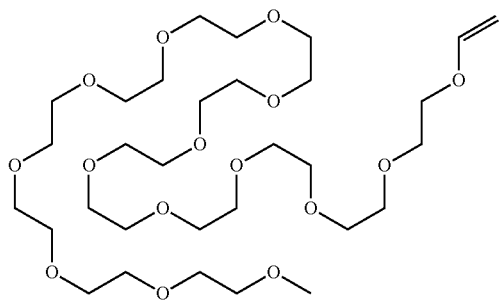
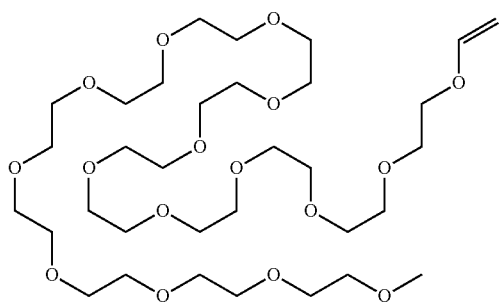
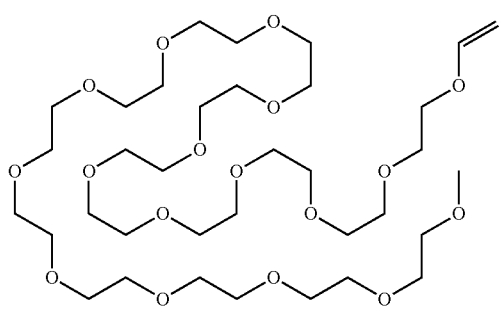
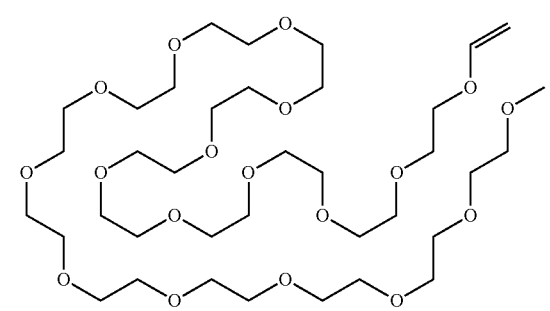
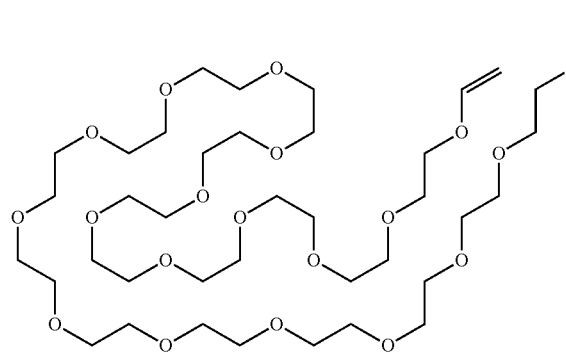
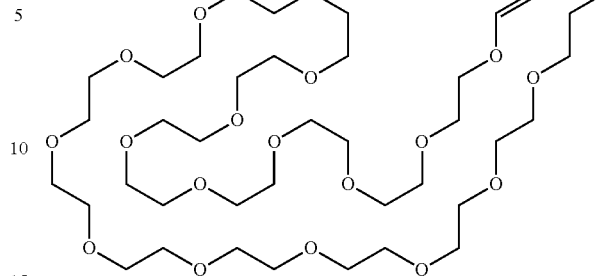
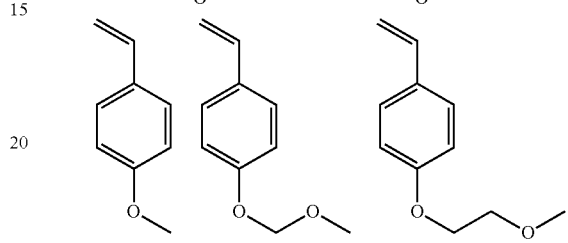
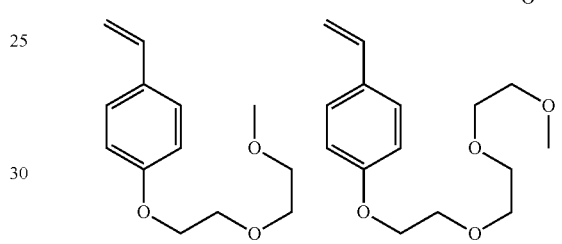
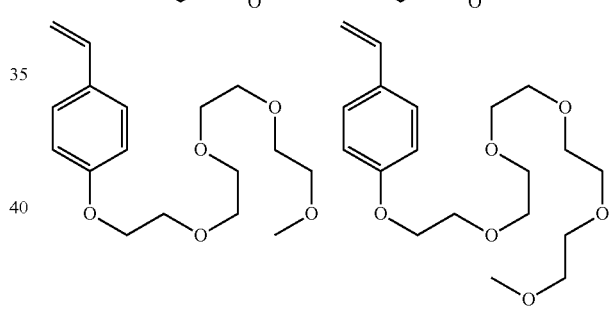
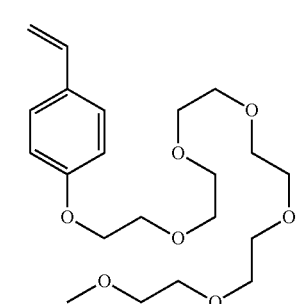
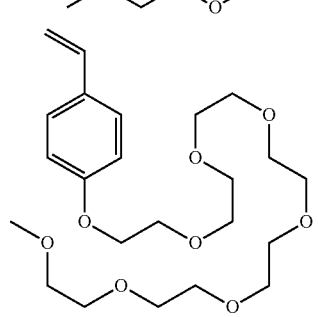

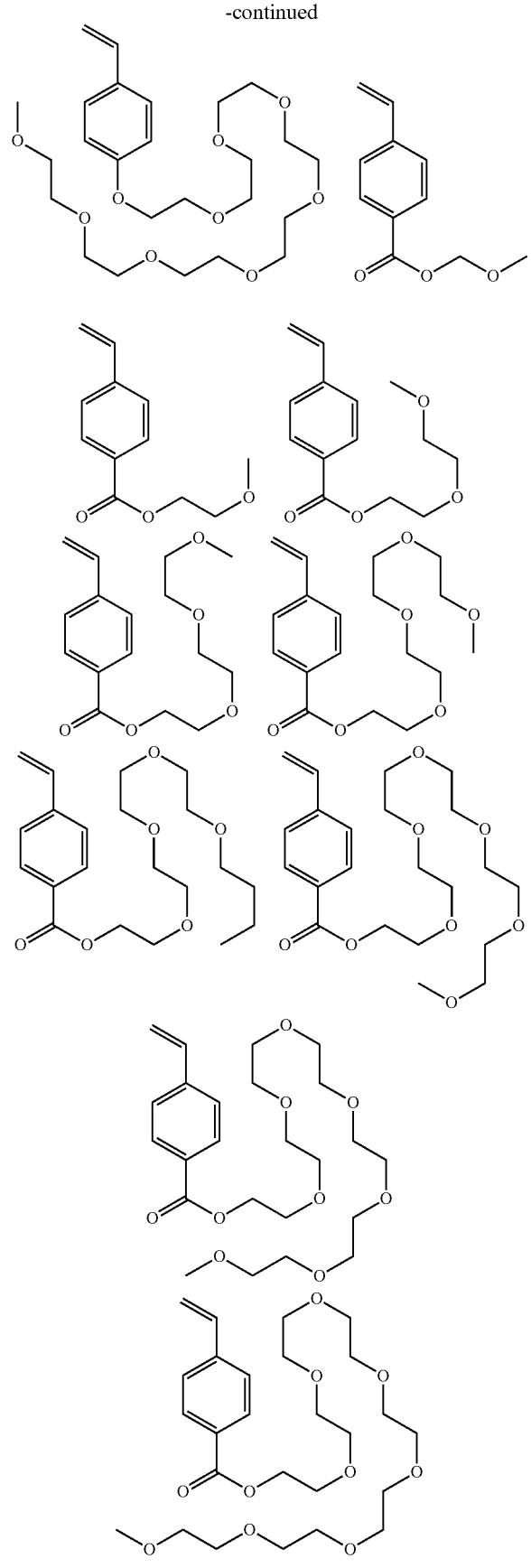
(Repeating Unit-d)
The polymer compound in the inventive bio-electrode composition can additionally contain a repeating unit-d to give adhesion properties.
Illustrative examples of the monomer to give the repeating unit-d include the following.
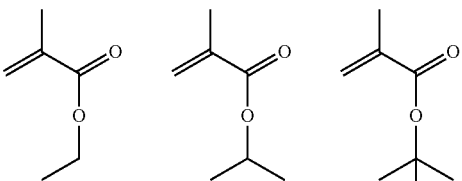
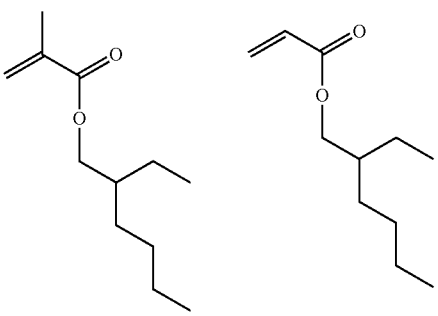
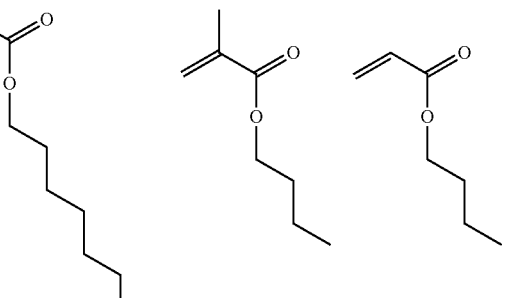
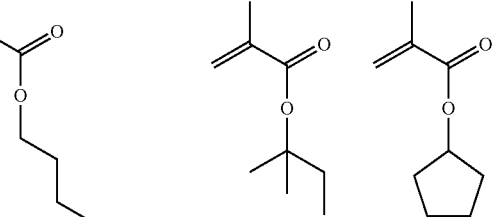
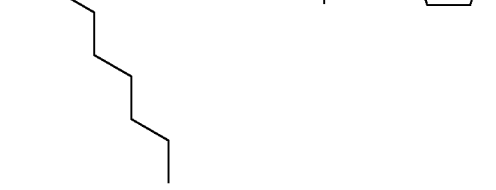

141
-continued
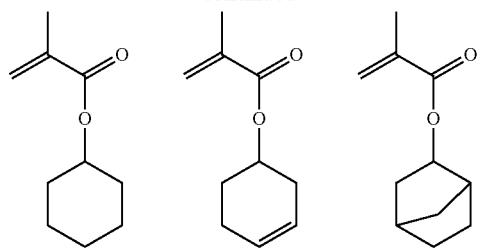
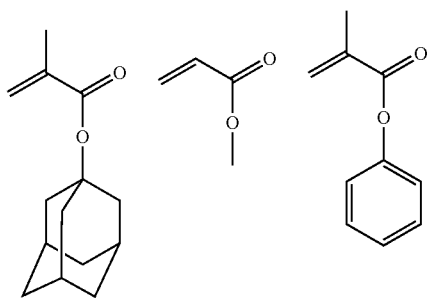
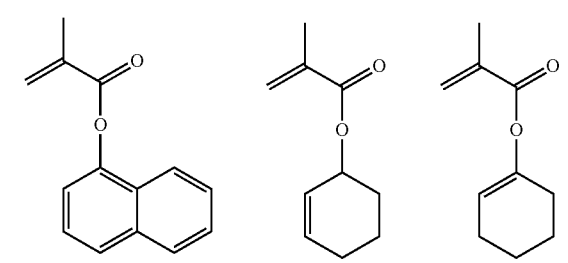
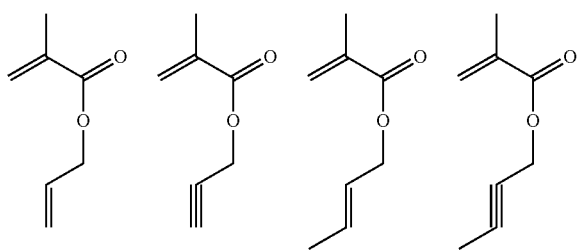
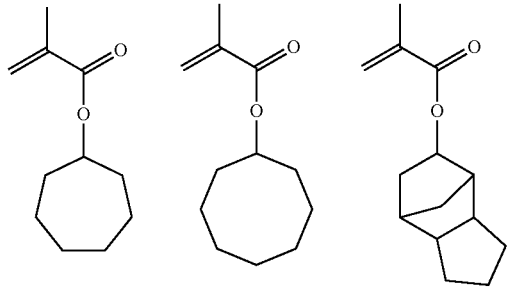
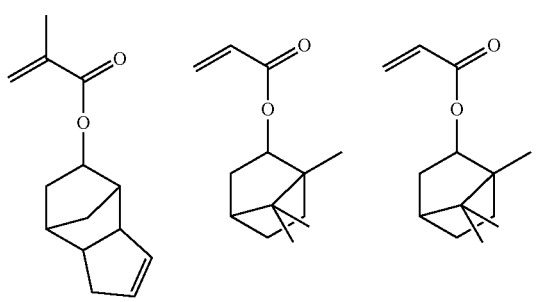
142
-continued
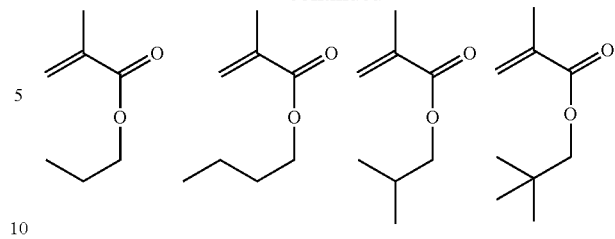
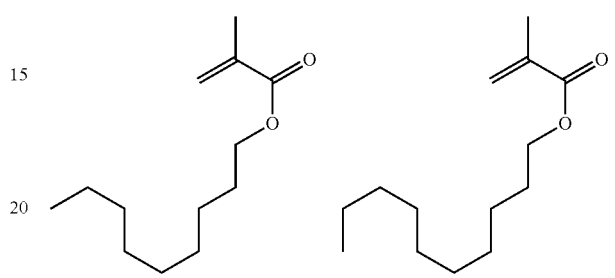
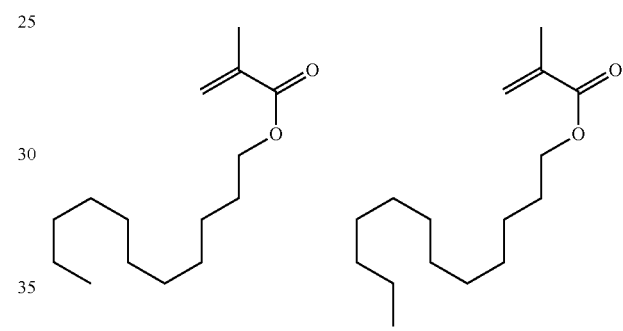
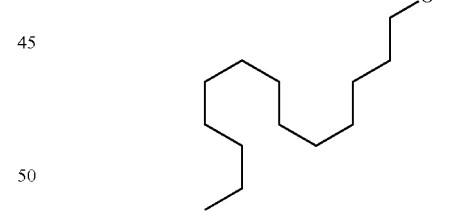
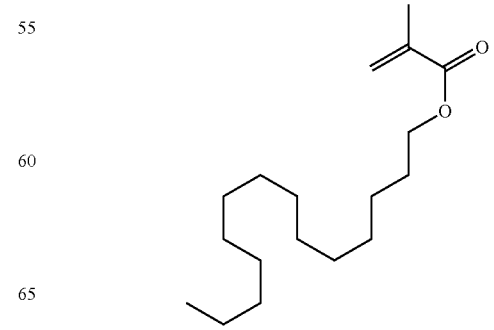

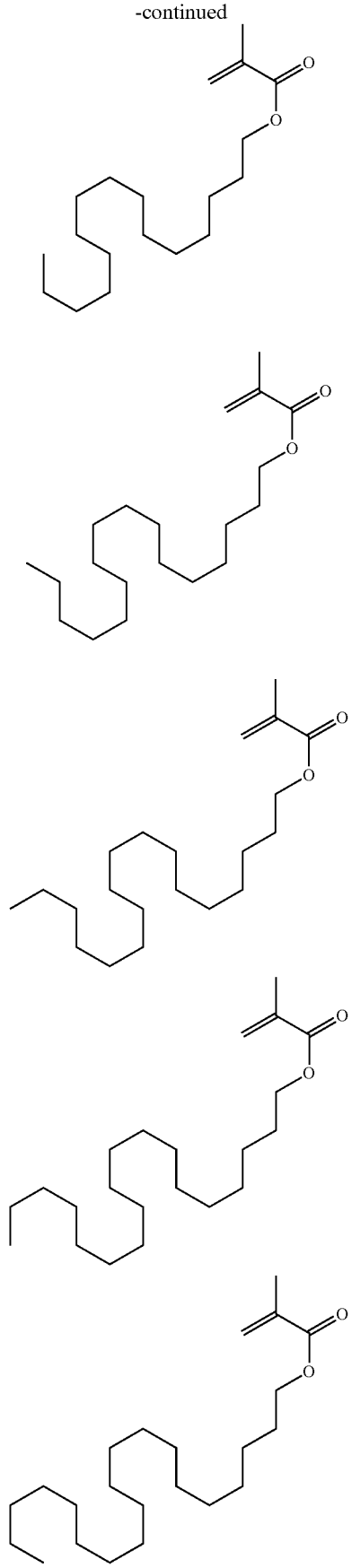
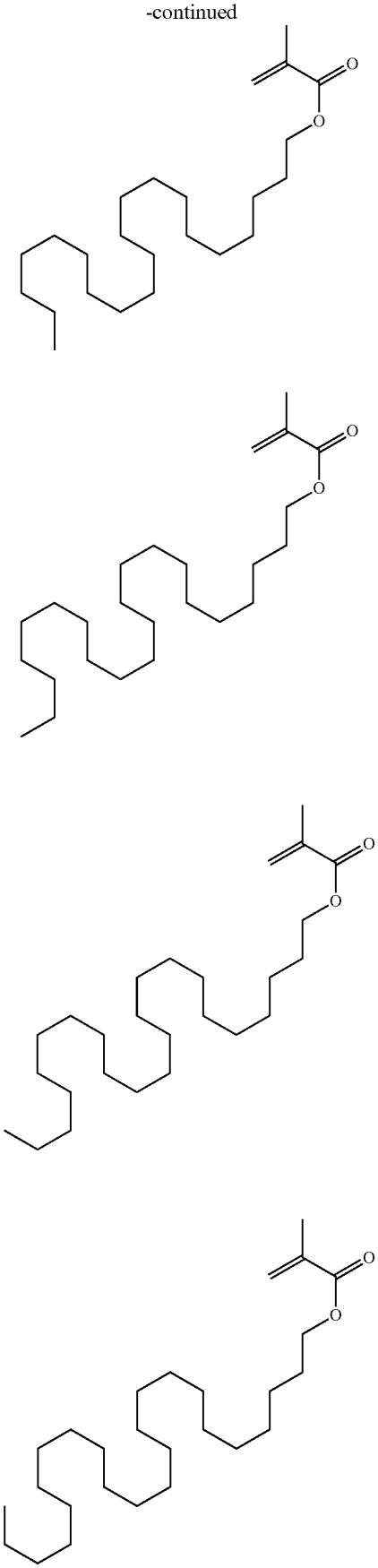

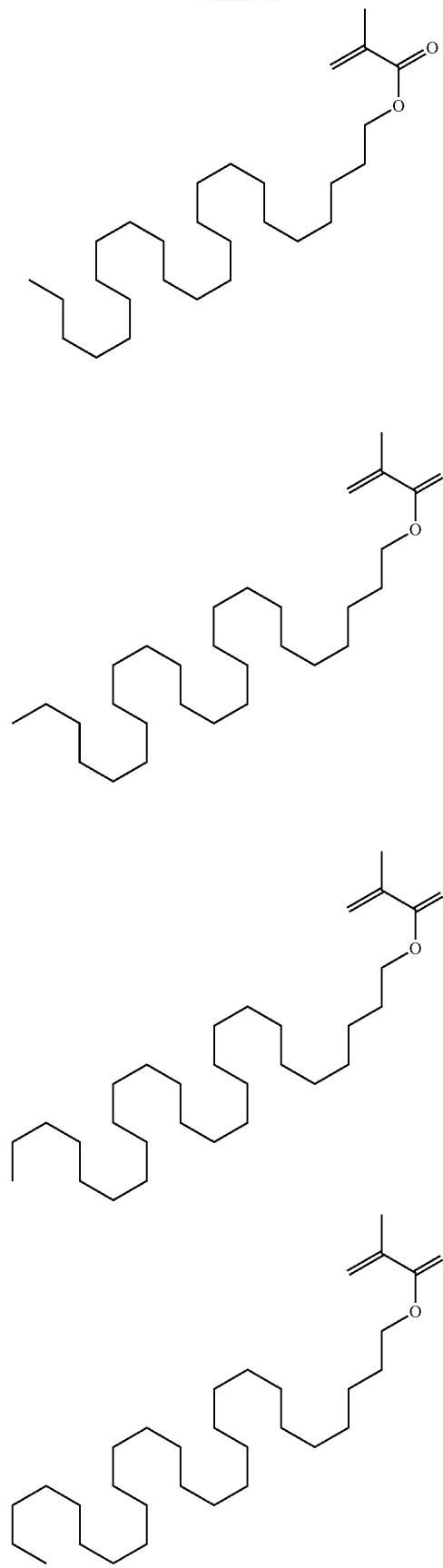
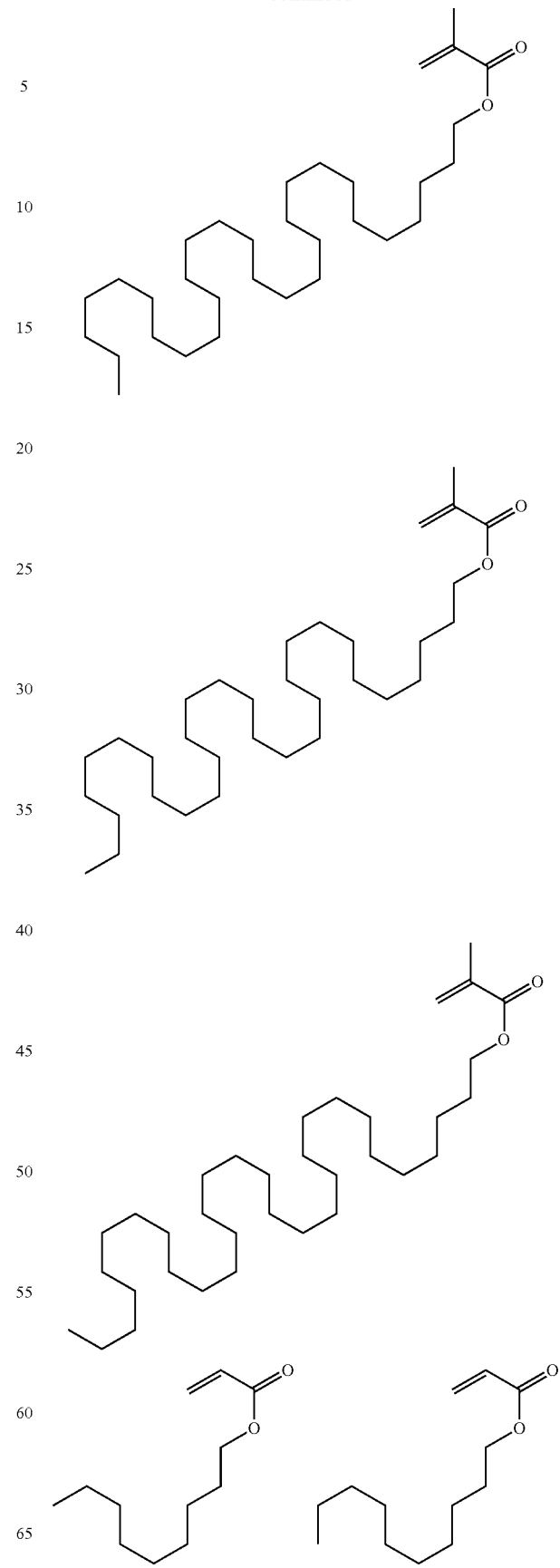

147
-continued
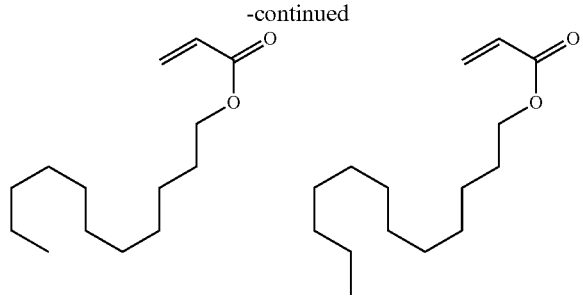
148
-continued
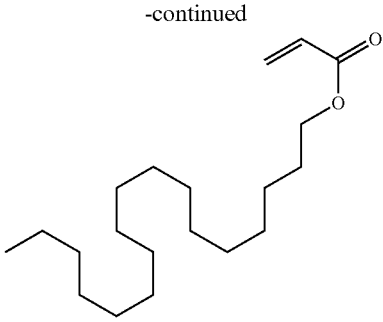
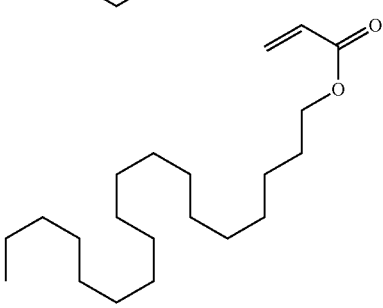
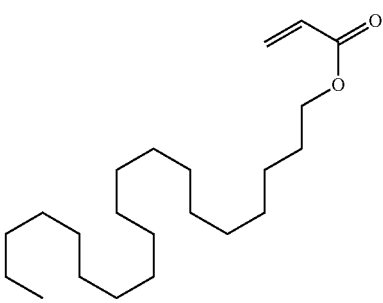
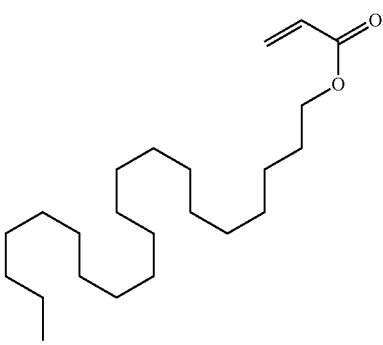
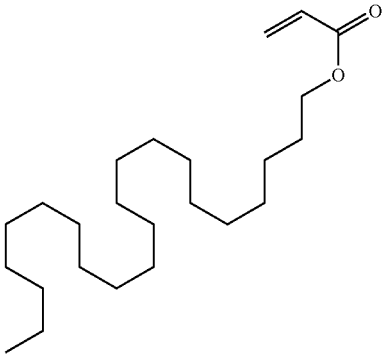

149 150

151
-continued
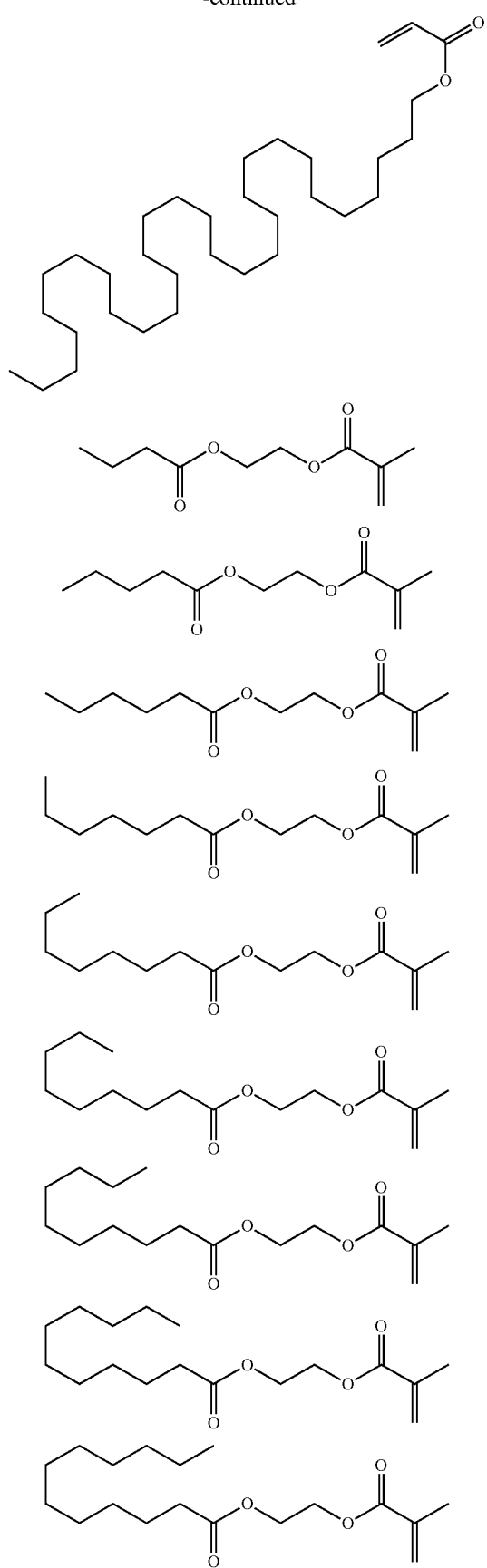
152
-continued
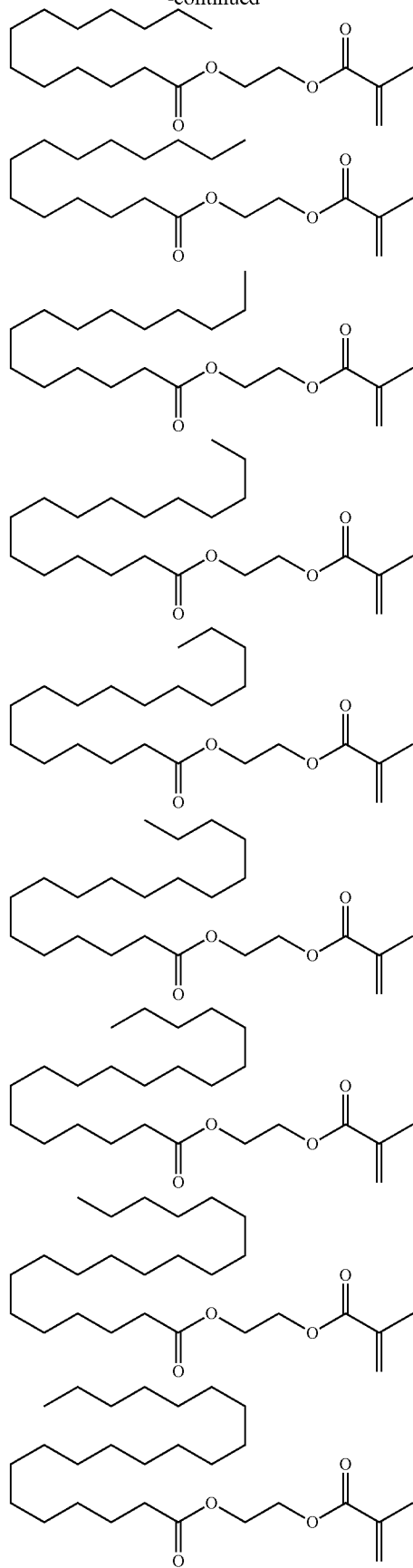

153
-continued
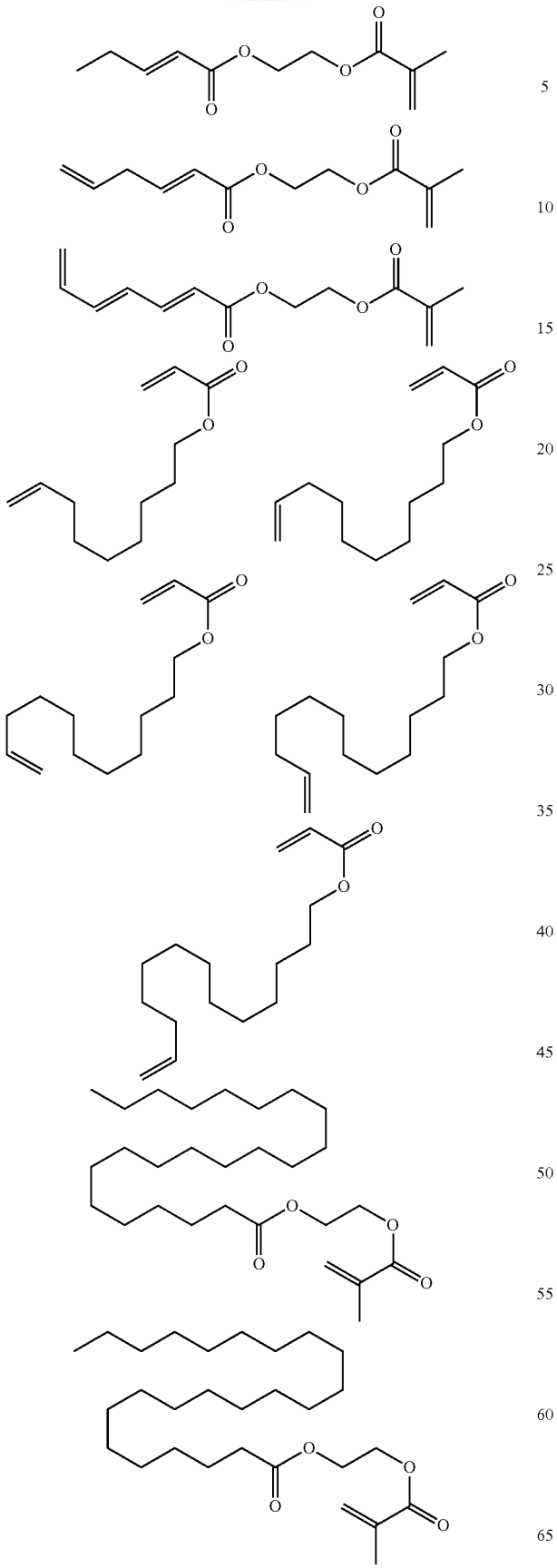
154
-continued
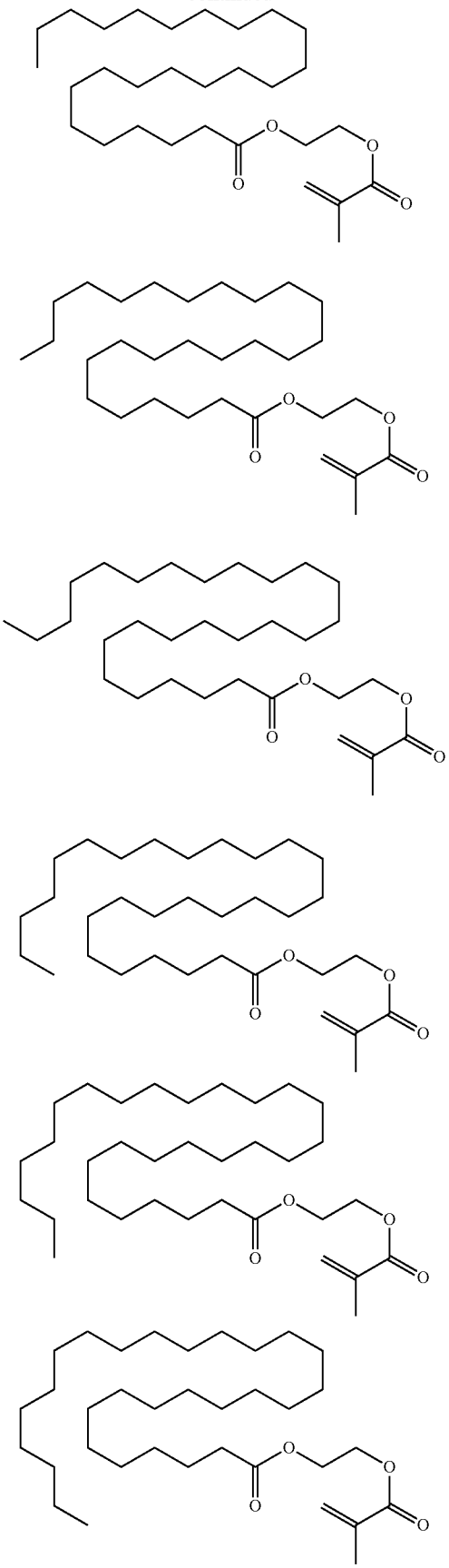

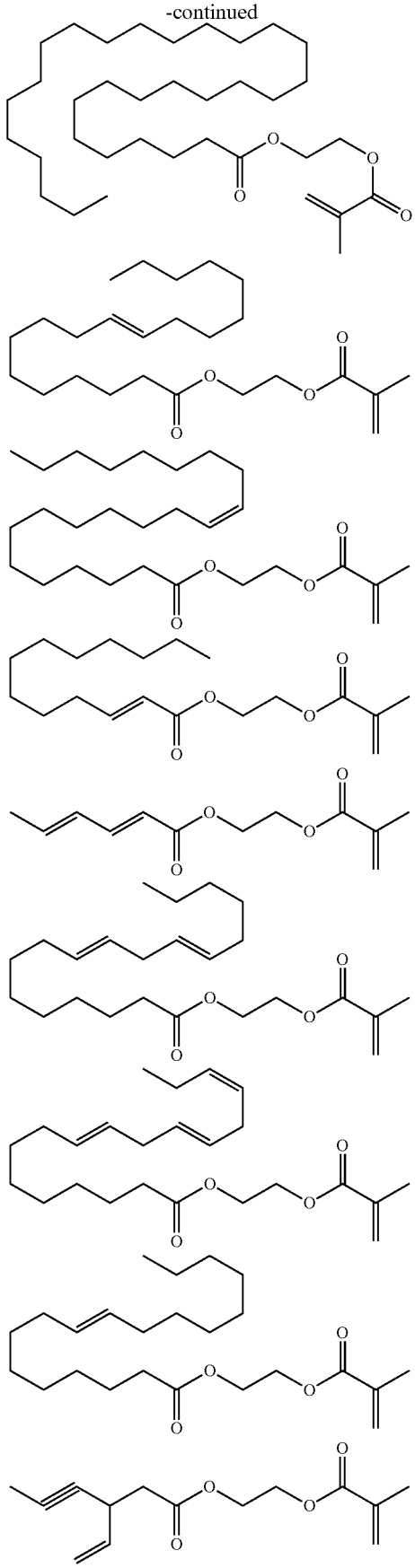
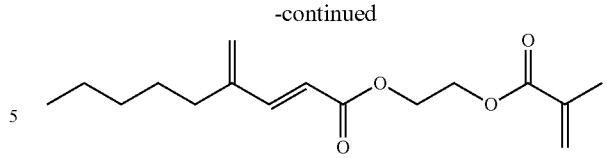
(Repeating Unit-e)
Additionally, it is also possible to copolymerize cross-linkable repeating unit-e. Illustrative examples of the cross-linkable repeating unit include a repeating unit having an oxirane ring or an oxetane ring.
The following examples are illustrative monomers to give the repeating unit-e having an oxirane ring or an oxetane ring.
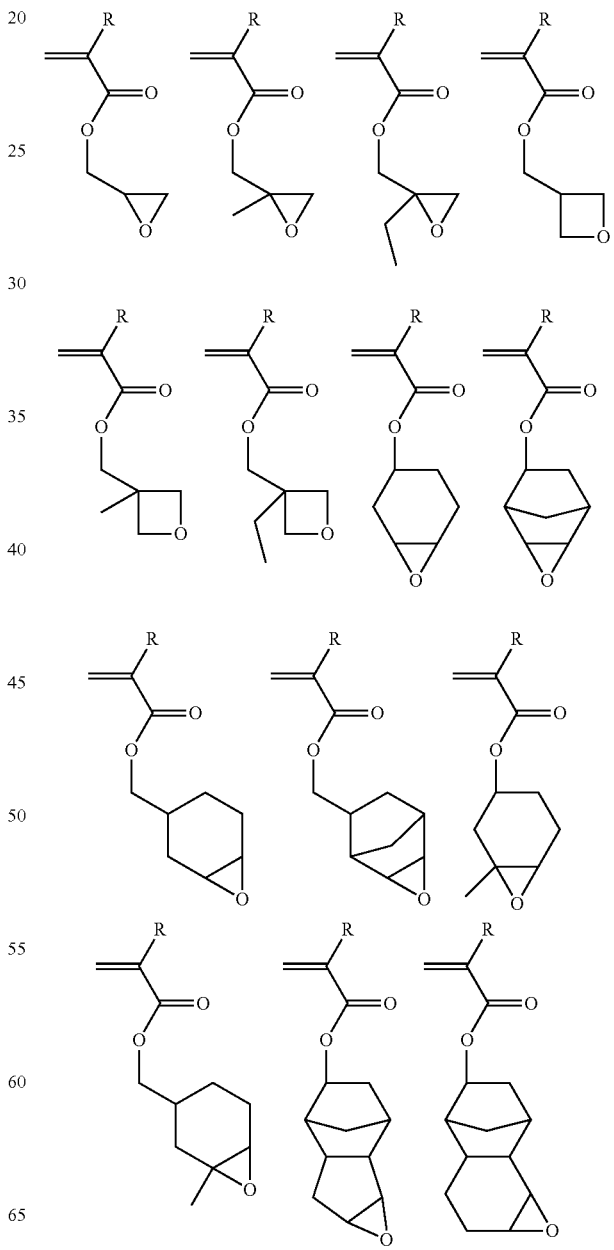

157
-continued
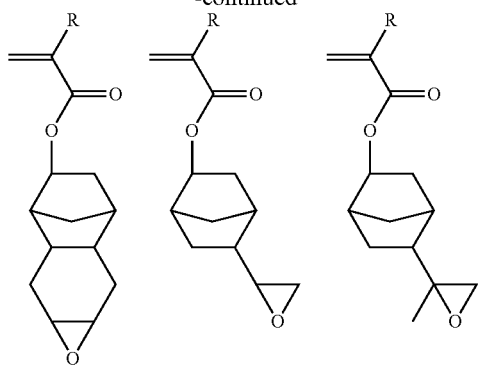
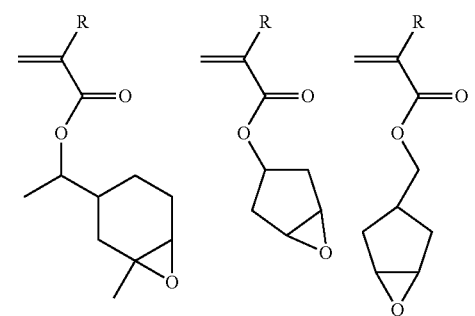
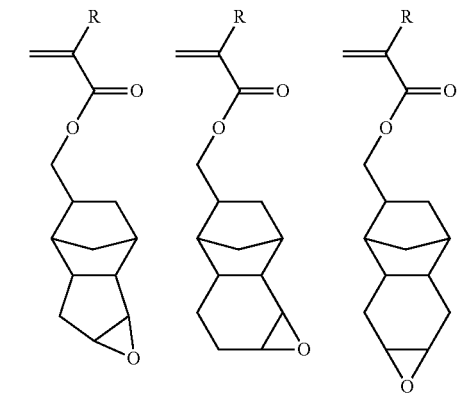
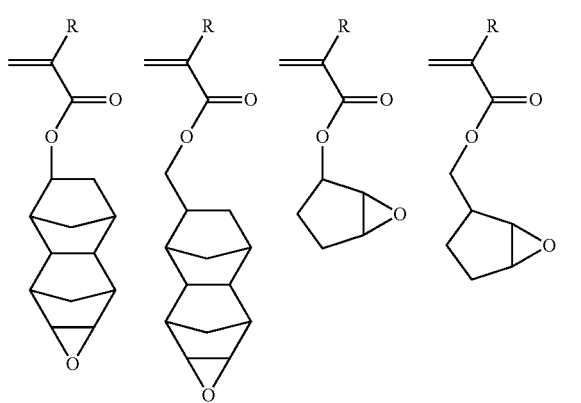
158
-continued
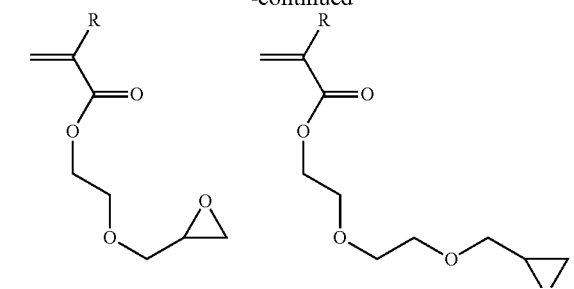
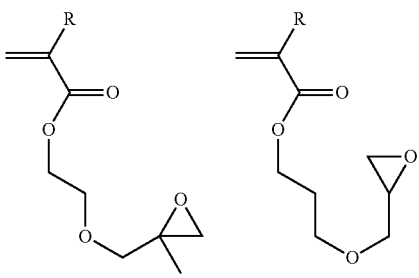
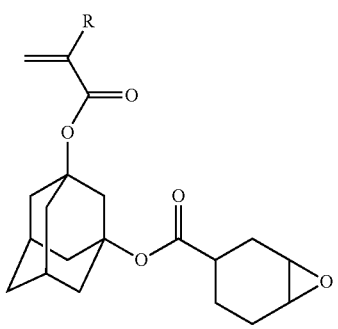
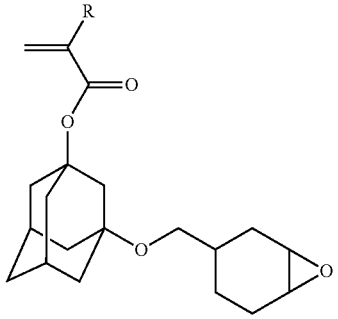
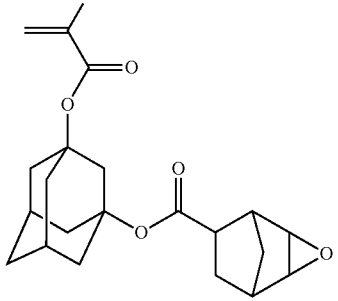

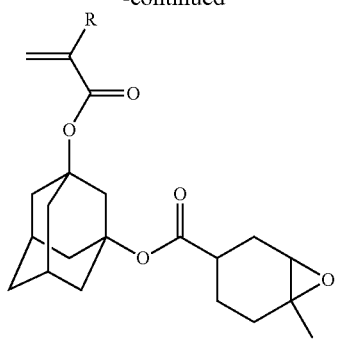
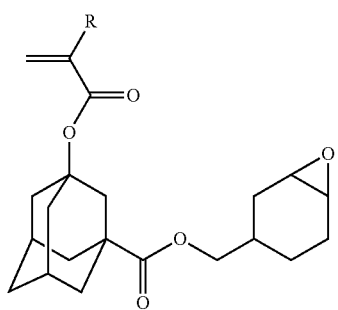
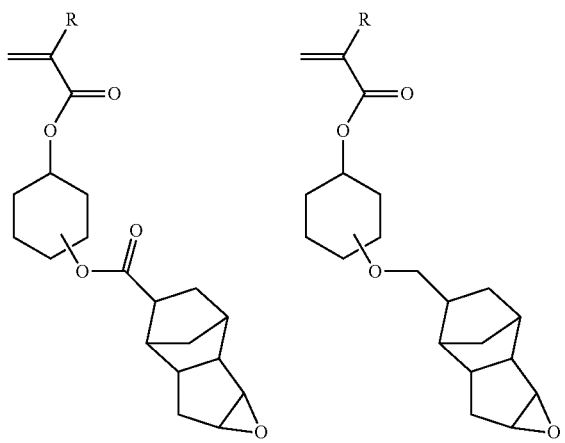
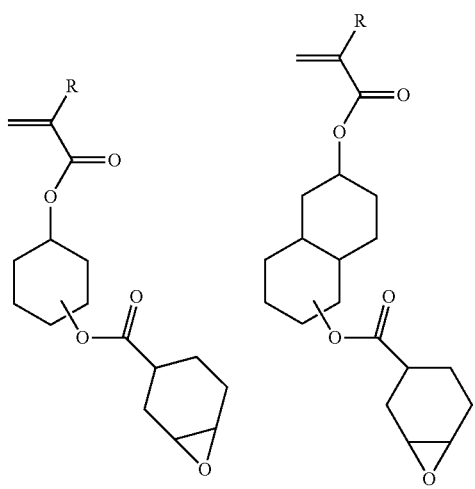
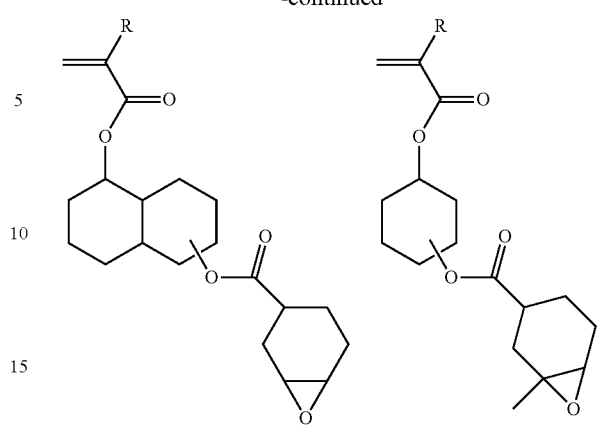
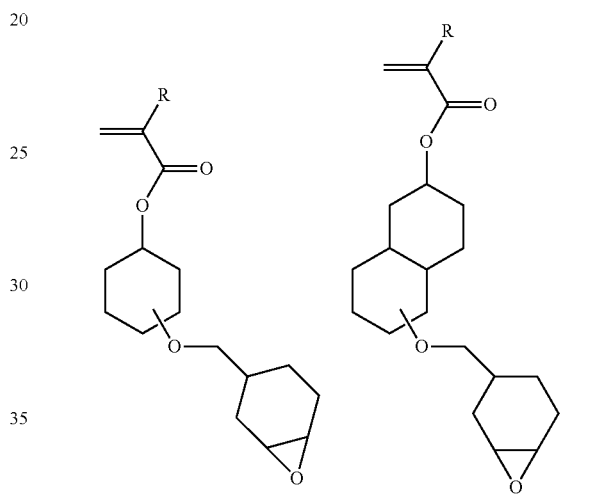
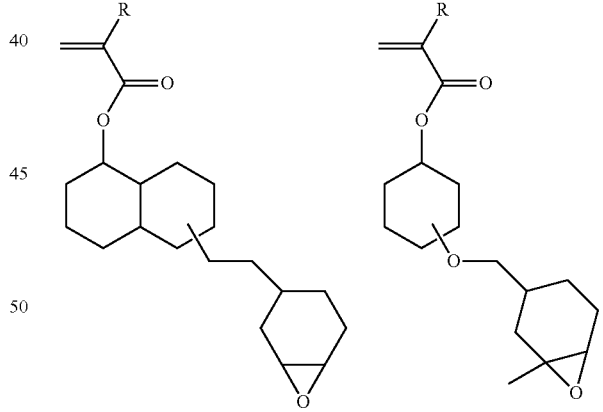
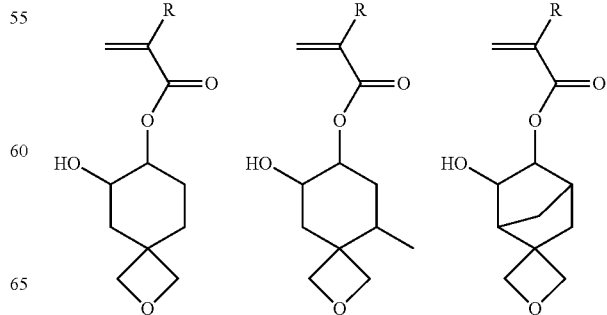

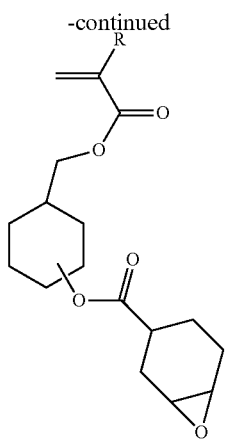

In these formulae, R represents a methyl group or a hydrogen atom.

As one of the method for synthesizing the polymer compound of the component (A) (ionic material), the copolymer compound can be obtained by a method of heat polymerization of desired monomer(s) among the monomers to give the repeating units-a (-a1 to -a7), together with -b (-b1), -c, -d, and -e in accordance with needs through addition of a radical polymerization initiator in an organic solvent.

As the organic solvent used in the polymerization, toluene, benzene, tetrahydrofuran, diethyl ether, dioxane and so on can be exemplified. Illustrative examples of the polymerization initiator include 2,2'-azobisisobutyronitrile (AIBN), 2,2'-azobis(2,4-dimethylvaleronitrile), dimethyl 2,2'-azobis(2-methylpropionate), benzoyl peroxide, and lauroyl peroxide. The temperature in heating is preferably 50 to 80° C., and the reaction time is preferably 2 to 100 hours, more preferably 5 to 20 hours.

The ratios of the repeating units-a1 to -a7, -b1, -c, -d, and -e are $0 \leq a1 < 1.0$, $0 \leq a2 < 1.0$, $0 \leq a3 < 1.0$, $0 \leq a4 < 1.0$, $0 \leq a5 < 1.0$, $0 \leq a6 < 1.0$, $0 \leq a7 < 1.0$, $0 < a1+a2+a3+a4+a5+a6+a7 < 1.0$, $0 \leq b1 < 1.0$, $0 \leq c < 1.0$, $0 \leq d < 1.0$, and $0 \leq e < 0.5$; preferably $0 \leq a1 \leq 0.9$, $0 \leq a2 \leq 0.9$, $0 \leq a3 \leq 0.9$, $0 \leq a4 \leq 0.9$, $0 \leq a5 \leq 0.9$, $0 \leq a6 \leq 0.9$, $0 \leq a7 \leq 0.9$, $0.01 \leq a1+a2+a3+a4+a5+a6+a7 \leq 0.9$, $0.05 \leq b1 \leq 0.9$, $0 \leq c \leq 0.8$, $0 \leq d \leq 0.6$, and $0 \leq e < 0.4$; and more preferably $0 \leq a1 \leq 0.8$, $0 \leq a2 \leq 0.8$, $0 \leq a3 \leq 0.8$, $0 \leq a4 \leq 0.8$, $0 \leq a5 \leq 0.8$, $0 \leq a6 \leq 0.8$, $0 \leq a7 \leq 0.8$, $0.02 \leq a1+a2+a3+a4+a5+a6+a7 \leq 0.8$, $0.1 \leq b1 \leq 0.8$, $0 \leq c \leq 0.7$, $0 \leq d \leq 0.5$, and $0 \leq e < 0.3$.

Incidentally, $a1+a2+a3+a4+a5+a6+a7+b1+c+d+e=1$, for example, means that the total amount of repeating units-a1, -a2, -a3, -a4, -a5, -a6, -a7, -b1, -c, -d, and -e is 100 mol % on the basis of the total amount of the whole repeating units in a polymer compound that contains repeating units-a1, -a2, -a3, -a4, -a5, -a6, -a7, -b1, -c, -d, and -e; and $a1+a2+a3+a4+a5+a6+a7+b1+c+d+e<1$ means that the total amount of repeating units-a1, -a2, -a3, -a4, -a5, -a6, -a7, -b1, -c, -d, and -e is less than 100 mol % on the basis of the total amount of the whole repeating units, and another repeating unit(s) is contained in addition to the repeating units-a1, -a2, -a3, -a4, -a5, -a6, -a7, -b1, -c, -d, and -e.

Regarding the molecular weight of the component (A), the weight average molecular weight is preferably 500 or more, more preferably 1,000 or more and 1,000,000 or less, further preferably 2,000 or more and 500,000 or less. Regarding the ionic monomer that is not incorporated into the component (A) after polymerization (residual monomer), this can be prevented from permeating to skin in a biocompatibility test to cause allergy when the amount is smaller. Accordingly, it is preferable to decrease the amount of residual monomer(s). The amount of residual monomer(s) is preferably 10 parts by mass or less on the basis of 100 parts by mass of the whole component (A).

In the inventive bio-electrode composition when it contains the component (B), which will be described later, the amount of the component (A) is preferably 0.1 to 300 parts by mass, more preferably 1 to 200 parts by mass on the basis of 100 parts by mass of the component (B). The component (A) may be used singly or in admixture of two or more kinds.

[(B) Resin Other than Component (A)]

The component (B), which is added to the inventive bio-electrode composition in accordance with needs, is a component for preventing elution of the salt by being compatibilized with (A) the ionic material (salt), for holding an electric conductivity improver such as metal powders, and for achieving adhesion. When the component (A) itself is curable and capable of preventing elution of the salt and holding the electric conductivity improver such as a metal powder, and has adhesion, the component (B) is inessential. It is to be noted that the component (B) may be any of a resin other than the component (A) and is preferably either or both of a thermosetting resin and a photo-curable resin, particularly one or more resins selected from silicone base, acrylic base, and urethane base resins.

The adherent (adhesive) silicone base resin include an addition-curable (addition reaction-curable) type and a radical curable (radical crosslinking reaction-curable) type. As the addition-curable type, it is possible to use one that contains diorganosiloxane having an alkenyl group(s), an MQ resin having an $R_3SiO_{0.5}$ unit and an $SiO_2$ unit, organohydrogenpolysiloxane having a plurality of SiH groups, a platinum catalyst, an addition reaction inhibitor, and organic solvent, for example, described in JP 2015-193803A. As the radical curable type, it is possible to use one that contains diorganopolysiloxane with or without an alkenyl group, an MQ resin having an $R_3SiO_{0.5}$ unit and an $SiO_2$ unit, organic peroxide, and organic solvent, for example, described in JP 2015-193803A. Herein, R represents a substituted or unsubstituted monovalent hydrocarbon group having 1 to 10 carbon atoms.

It is also possible to use a polysiloxane-resin integrated compound that is formed by condensation reaction of an MQ resin and polysiloxane having silanol at the terminal or the side chain of the polymer. The MQ resin contains many silanol and improves adhesion by addition of it, but does not bind to polysiloxane in molecular level because it is not crosslinkable. The adhesion can be increased by integrating the polysiloxane and the resin as described above.

The silicone resin may contain modified siloxane that has a group selected from an amino group, an oxirane group, an oxetane group, a polyether group, a hydroxy group, a carboxy group, a mercapto group, a methacryl group, an acryl group, a phenol group, a silanol group, a carboxylic anhydride group, an aryl group, an aralkyl group, an amide group, an ester group, and a lactone ring. The addition of modified siloxane improves dispersibility of the component (A) in the silicone resin. The modified siloxane may be modified at any part such as the one terminal, the both terminals, or the side chain of the siloxane.

As the adherent acrylic base resin, it is possible to use one having hydrophilic (meth)acrylic ester and hydrophobic long chain (meth)acrylic ester as the repeating units described in JP 2016-011338A, for example. In some cases, it is also possible to copolymerize (meth)acrylic ester having a functional group or (meth)acrylic ester having a siloxane bond.

As the adherent urethane base resin, it is possible to use one having a urethane bond with a polyether bond, a polyester bond, a polycarbonate bond, or a siloxane bond described in JP 2016-065238A, for example.

In the inventive bio-electrode composition, the component (B) preferably has high compatibility with the component (A) to prevent lowering of the electric conductivity due to elution of the component (A) from the living body contact layer. In the inventive bio-electrode composition, the component (B) preferably has high adhesion to the electro-conductive base material to prevent peeling of the living body contact layer from the electro-conductive base material. In order to increase the compatibility of the resin with the electro-conductive base material and the salt, the use of a resin with high polarity is effective. Illustrative examples of such a resin include resin having one or more moieties selected from an ether bond, an ester bond, an amide bond, an imide bond, an urethane bond, a thiourethane bond, and a thiol group; as well as a polyacrylic resin, a polyamide resin, a polyimide resin, a polyurethane resin, and a polythiourethane resin. On the other hand, the living body contact layer is in contact with a living body, thereby being susceptible to perspiration. Accordingly, in the inventive bio-electrode composition, the component (B) preferably has high repellency, and is hardly hydrolyzed. To make the resin be highly repellent and hardly hydrolyzed, the use of a silicon-containing resin is effective.

The silicon atom-containing polyacrylic resin includes a polymer that has a silicone main chain and a polymer that has a silicon atom(s) on the side chain, each of which can be suitably used. As the polymer that has a silicone main chain, silsesquioxane or siloxane having a (meth)acrylpropyl group and so on can be used. In this case, an addition of a photoradical generator allows the (meth)acryl moiety to polymerize to cure.

As the silicon atom-containing polyamide resin, it is possible to suitably use polyamide silicone resins described in JP 2011-079946A and U.S. Pat. No. 5,981,680, for example. Such a polyamide silicone resin can be synthesized by combining a silicone or non-silicone compound having amino groups at the both terminals and a non-silicone or silicone compound having carboxy groups at the both terminals.

It is also possible to use polyamic acid before cyclization thereof, which is obtained by reacting carboxylic anhydride and amine. The carboxy group of the polyamic acid may be crosslinked by using a crosslinking agent such as an epoxy type and an oxetane type. It is also possible to esterify the carboxy group with hydroxyethyl (meth)acrylate to perform photoradical crosslinking of the (meth)acrylate moiety.

As the silicon atom-containing polyimide resin, it is possible to suitably use polyimide silicone resins described in JP 2002-332305A, for example. Although polyimide resins have very high viscosity, the viscosity can be decreased by blending a (meth)acrylic monomer as a solvent and a crosslinking agent.

Illustrative examples of the silicon atom-containing polyurethane resin include polyurethane silicone resins. These polyurethane silicone resins can be crosslinked through urethane bond by blending a compound having isocyanate groups at the both terminals and a compound having a hydroxy group(s) at the terminal(s), followed by heating thereof. In this case, a silicon atom(s) (siloxane bond) have to be contained in either or both of the compound having isocyanate groups at the both terminals and the compound having a hydroxy group(s) at the terminal(s). Alternatively, an urethane (meth)acrylate monomer and polysiloxane can be blended and photo-crosslinked as described in JP 2005-320418A. It is also possible to photo-crosslink a polymer having both of a siloxane bond(s) and an urethane bond(s), with the terminal having a (meth)acrylate group(s).

The silicon atom-containing polythiourethane resin can be obtained by reaction of a compound having a thiol group(s) and a compound having an isocyanate group(s), provided that either of them have to contain a silicon atom(s). It can also be photo-cured if (meth)acrylate groups are contained at the terminals.

The silicone base resin is improved in compatibility with the foregoing salt by adding modified siloxane that has a group selected from an amino group, an oxirane group, an oxetane group, a polyether group, a hydroxy group, a carboxy group, a mercapto group, a methacryl group, an acryl group, a phenol group, a silanol group, a carboxylic anhydride group, an aryl group, an aralkyl group, an amide group, an ester group, and a lactone ring in addition to the diorganosiloxane having an alkenyl group(s), the MQ resin having an $R_3SiO_{0.5}$ unit and an $SiO_2$ unit, and the organohydrogenpolysiloxane having a plurality of SiH groups.

As will be described later, the living body contact layer is a cured material of the bio-electrode composition. Curing the same improves the adhesion of the living body contact layer to both of skin and the electro-conductive base material. The curing means is not limited, and common means can be used, including crosslinking reaction by either or both of heat and light, an acid catalyst, or a base catalyst. The crosslinking reaction can be performed by appropriately selecting a crosslinking method described in "Kakyou hannou handbook (handbook of crosslinking reaction)", Chapter 2, pages 51-371, Yasuharu Nakamura, Maruzen shuppan (2013).

The diorganosiloxane having an alkenyl group(s) and organohydrogenpolysiloxane having a plurality of SiH groups can be crosslinked through an addition reaction with a platinum catalyst.

Illustrative examples of the platinum catalyst include platinum-based catalysts such as platinic chloride, alcohol solution of platinic chloride, reaction product of platinic chloride and alcohol, reaction product of platinic chloride and an olefin compound, reaction product of platinic chloride and vinyl group-containing siloxane, a platinum-olefin complex, a complex of platinum and vinyl group-containing siloxane; platinum group metal-based catalysts such as a rhodium complex and a ruthenium complex. These catalysts may be used after dissolved or dispersed in alcohol solvent, hydrocarbon solvent, or siloxane solvent.

The amount of platinum catalyst is preferably in a range of 5 to 2,000 ppm, particularly in a range of 10 to 500 ppm on the basis of 100 parts by mass of the resin.

When the addition curable silicone resin is used, an addition reaction inhibitor may be added. This addition reaction inhibitor is added as a quencher to prevent the platinum catalyst from acting in the solvent or under a low temperature circumstance after forming the coating film and before heat curing. Illustrative examples thereof include 3-methyl-1-butyn-3-ol, 3-methyl-1-pentyn-3-ol, 3,5-dimethyl-1-hexyn-3-ol, 1-ethynylcyclohexanol, 3-methyl-3-trimethylsiloxy-1-butyne, 3-methyl-3-trimethylsiloxy-1-pentyne, 3,5-dimethyl-3-trimethylsiloxy-1-hexyne, 1-ethynyl-1-trimethylsiloxycyclohexane, bis(2,2-dimethyl- 3-butynoxy)dimethylsilane, 1,3,5,7-tetramethyl-1,3,5,7-tetravinylcyclotetrasiloxane, and 1,1,3,3-tetramethyl-1,3-divinyldisiloxane.

The amount of addition reaction inhibitor is preferably in a range of 0 to 10 parts by mass, particularly in a range of 0.05 to 3 parts by mass on the basis of 100 parts by mass of the resin.

Illustrative examples of photo-curing method include a method of adding a photoradical generator to generate radical by light, together with using a resin having a (meth) acrylate terminal(s) or an olefin terminal(s) or adding a crosslinking agent with the terminal(s) being (meth)acrylate, olefin, or a thiol group(s); and a method of adding a photo-acid generator to generate acid by light, together with using a resin or a crosslinking agent having an oxirane group(s), an oxetane group(s), or a vinyl ether group(s).

Illustrative examples of the photoradical generator include acetophenone, 4,4'-dimethoxybenzyl, benzyl, benzoin, benzophenone, 2-benzoylbenzoic acid, 4,4'-bis(dimethylamino)benzophenone, 4,4'-bis(diethylamino)benzophenone, benzoin methyl ether, benzoin ethyl ether, benzoin isopropyl ether, benzoin butyl ether, benzoin isobutyl ether, 4-benzoylbenzoic acid, 2,2'-bis(2-chlorophenyl)-4,4',5,5'-tetraphenyl-1,2'-biimidazole, methyl 2-benzoylbenzoic acid, 2-(1,3-benzodioxole-5-yl)-4,6-bis(trichloromethyl)-1,3,5-triazine, 2-benzyl-2-(dimethylamino)-4'-morpholinobutyrophenone, 4,4'-dichlorobenzophenone, 2,2-diethoxyacetophenone, 2,2-dimethoxy-2-phenylacetophenone, 2,4-diethylthioxanthene-9-one, diphenyl(2,4,6-trimethylbenzoyl)phosphine oxide (BAPO), 1,4-dibenzoylbenzene, 2-ethylanthraquinone, 1-hydroxycyclohexyl phenyl ketone, 2-hydroxy-2-methylpropiophenone, 2-hydroxy-4'-(2-hydroxyethoxy)-2-methylpropiophenone, 2-isonitrosopropiophenone, and 2-phenyl-2-(p-toluenesulfonyloxy)acetophenone.

The curing can also be performed by adding a radical generator of a heat decomposition type. Illustrative examples of the thermal radical generator include 2,2'-azobis(isobutyronitrile), 2,2'-azobis(2,4-dimethylvaleronitrile), 2,2'-azobis(2-methylbutyronitrile), 2,2'-azobis(methylpropionamidine) hydrochloride, 2,2'-azobis[2-(2-imidazolin-2-yl)propane] hydrochloride, 2,2'-azobis(4-methoxy-2,4-dimethylvaleronitrile), 2,2'-azobis(cyclohexane-1-carbonitrile), 1[(1-cyano-1-methylethyl)azo]formamide, 2,2'-azobis[2-methyl-N-(2-hydroxyethyl)propionamide], 2,2'-azobis[N-(2-propenyl)-2-methylpropionamide], 2,2'-azobis(N-butyl-2-methylpropionamide), dimethyl-2,2'-azobis(isobutylate), 4,4'-azobis(4-cyanopentanoic acid), dimethyl-2,2'-azobis(2-methylpropionate), benzoyl peroxide, tert-butyl hydroperoxide, cumene hydroperoxide, di-tert-butyl peroxide, di-tert-amyl peroxide, di-n-butyl peroxide, and dicumyl peroxide.

Illustrative examples of the photo-acid generator include sulfonium salt, iodonium salt, sulfonyldiazomethane, N-sulfonyloxyimide, and oxime-O-sulfonate type acid generators. Specific examples of the photo-acid generator is described in paragraphs [0122] to [0142] of JP 2008-111103A, together with JP 2009-080474A.

The amount of radical generator or photo-acid generator is preferably in a range of 0.1 to 50 parts by mass on the basis of 100 parts by mass of the resin.

Among them, particularly preferable resin of the component (B) contains a silicone resin having an $R_xSiO_{(4-x)/2}$ unit (wherein, R represents a substituted or unsubstituted monovalent hydrocarbon group having 1 to 10 carbon atoms, and "x" is a number in a range of 2.5 to 3.5) and an $SiO_2$ unit, diorganosiloxane having an alkenyl group, and organohydrogenpolysiloxane having an SiH group.

It is to be noted that when the component (A) itself is curable, the curing method and additives described above can be appropriately applied in accordance with needs.

[(C) Metal Powder]

The inventive bio-electrode composition preferably contains a metal powder selected from gold, silver, platinum, copper, tin, titanium, nickel, aluminum, tungsten, molybdenum, ruthenium, chromium, and indium as the component (C) in order to improve electronic conductivity. The amount of the metal powder is preferably in a range of 1 to 100 parts by mass, more preferably 1 to 50 parts by mass on the basis of 100 parts by mass of the resin (the whole of the component (A) and the component (B)).

As the kind of the metal powder, gold, silver, and platinum are preferable in view of electric conductivity; and silver, copper, tin, titanium, nickel, aluminum, tungsten, molybdenum, ruthenium, and chromium are preferable in view of cost. In view of biocompatibility, noble metals are preferable. On the whole of these viewpoints, silver, copper, tin, and titanium is most preferable.

The metal powder may have any shape, such as a spherical shape, a disk shape, a flaky shape, and a needle shape. The addition of flaky powder brings highest electric conductivity and is preferable thereby. The metal powder is preferably a flake having relatively lower density and larger specific surface area with a size of 100 μm or less, a tapped density of 5 $g/cm^3$ or less, and a specific surface area of 0.5 $m^2/g$ or more.

[Carbon Material]

As an electric conductivity improver, a carbon material can be added in addition to the metal powder. The carbon material may be exemplified by carbon black, carbon nanotube, carbon fiber, and the like. The carbon nanotube may be either single layer or multilayer, and the surface may be modified with an organic group(s). The amount of carbon material is preferably in a range of 1 to 50 parts by mass on the basis of 100 parts by mass of the resin (the whole of the component (A) and the component (B)).

[Tackifier]

The inventive bio-electrode composition may contain a tackifier in order to have adhesion to a living body. Illustrative examples of such a tackifier include silicone resin, as well as non-crosslinkable siloxane, non-crosslinkable poly (meth)acrylate, and non-crosslinkable polyether.

[Organic Solvent]

The inventive bio-electrode composition may contain organic solvent. Illustrative examples of the organic solvent include aromatic hydrocarbon solvent such as toluene, xylene, cumene, 1,2,3-trimethylbenzene, 1,2,4-trimethylbenzene, 1,3,5-trimethylbenzene, styrene, α-methylstyrene, butylbenzene, sec-butylbenzene, isobutylbenzene, cymene, diethylbenzene, 2-ethyl-p-xylene, 2-propyltoluene, 3-propyltoluene, 4-propyltoluene, 1,2,3,5-tetramethyltoluene, 1,2,4,5-tetramethyltoluene, tetrahydronaphthalene, 4-phenyl-1-butene, tert-amylbenzene, amylbenzene, 2-tert-butyltoluene, 3-tert-butyltoluene, 4-tert-butyltoluene, 5-isopropyl-m-xylene, 3-methylethylbenzene, tert-butyl-3-ethylbenzene, 4-tert-butyl-o-xylene, 5-tert-butyl-m-xylene, tert-butyl-p-xylene, 1,2-diisopropylbenzene, 1,3-diisopropylbenzene, 1,4-diisopropylbenzene, dipropylbenzene, pentamethylbenzene, hexamethylbenzene, hexylbenzene, and 1,3,5-triethylbenzene; aliphatic hydrocarbon solvent such as n-heptane, isoheptane, 3-methylhexane, 2,3-dimethylpentane, 3-ethylpentane, 1,6-heptadiene, 5-methyl-1-hexyn, norbornane, norbornene, dicyclopentadiene, 1-methyl-1,4-cyclohexadiene, 1-heptyne, 2-heptyne, cycloheptane, cycloheptene, 1,3-dimethylcyclopentane, ethylcyclopentane, methylcyclohexane, 1-methyl-1-cyclohexene, 3-methyl-1-cyclohexene, methylenecyclohexane, 4-methyl-1-cyclohexene, 2-methyl-1-hexene, 2-methyl-2-hexene, 1-heptene, 2-heptene, 3-heptene, n-octane, 2,2-dimethylhexane, 2,3-dimethylhexane, 2,4-dimethylhexane, 2,5-dimethylhexane, 3,3-dimethylhexane, 3,4-dimethylhexane, 3-ethyl-2-methylpentane, 3-ethyl-3-methylpentane, 2-methylheptane, 3-methylheptane, 4-methylheptane, 2,2,3-trimethylpentane, 2,2,4-trimethylpentane, cyclooctane, cyclooctene, 1,2-dimethylcyclohexane, 1,3-dimethylcyclohexane, 1,4-dimethylcyclohexane, ethylcyclohexane, vinylcyclohexane, isopropylcyclopentane, 2,2-dimethyl-3-hexene, 2,4-dimethyl-1-hexene, 2,5-dimethyl-1-hexene, 2,5-dimethyl-2-hexene, 3,3-dimethyl-1-hexene, 3,4-dimethyl-1-hexene, 4,4-dimethyl-1-hexene, 2-ethyl-1-hexene, 2-methyl-1-heptene, 1-octene, 2-octene, 3-octene, 4-octene, 1,7-octadiene, 1-octyne, 2-octyne, 3-octyne, 4-octyne, n-nonane, 2,3-dimethylheptane, 2,4-dimethylheptane, 2,5-dimethylheptane, 3,3-dimethylheptane, 3,4-dimethylheptane, 3,5-dimethylheptane, 4-ethylheptane, 2-methyloctane, 3-methyloctane, 4-methyloctane, 2,2,4,4-tetramethylpentane, 2,2,4-trimethylhexane, 2,2,5-trimethylhexane, 2,2-dimethyl-3-heptene, 2,3-dimethyl-3-heptene, 2,4-dimethyl-1-heptene, 2,6-dimethyl-1-heptene, 2,6-dimethyl-3-heptene, 3,5-dimethyl-3-heptene, 2,4,4-trimethyl-1-hexene, 3,5,5-trimethyl-1-hexene, 1-ethyl-2-methylcyclohexane, 1-ethyl-3-methylcyclohexane, 1-ethyl-4-methylcyclohexane, propylcyclohexane, isopropylcyclohexane, 1,1,3-trimethylcyclohexane, 1,1,4-trimethylcyclohexane, 1,2,3-trimethylcyclohexane, 1,2,4-trimethylcyclohexane, 1,3,5-trimethylcyclohexane, allylcyclohexane, hydrindane, 1,8-nonadiene, 1-nonyne, 2-nonyne, 3-nonyne, 4-nonyne, 1-nonene, 2-nonene, 3-nonene, 4-nonene, n-decane, 3,3-dimethyloctane, 3,5-dimethyloctane, 4,4-dimethyloctane, 3-ethyl-3-methylheptane, 2-methylnonane, 3-methylnonane, 4-methylnonane, tert-butylcyclohexane, butylcyclohexane, isobutylcyclohexane, 4-isopropyl-1-methylcyclohexane, pentylcyclopentane, 1,1,3,5-tetramethylcyclohexane, cyclododecane, 1-decene, 2-decene, 3-decene, 4-decene, 5-decene, 1,9-decadiene, decahydronaphthalene, 1-decyne, 2-decyne, 3-decyne, 4-decyne, 5-decyne, 1,5,9-decatriene, 2,6-dimethyl-2,4,6-octatriene, limonene, myrcene, 1,2,3,4,5-pentamethylcyclopentadiene, α-phellandrene, pinene, terpinene, tetrahydrodicyclopentadiene, 5,6-dihydrodicyclopentadiene, 1,4-decadiyne, 1,5-decadiyne, 1,9-decadiyne, 2,8-decadiyne, 4,6-decadiyne, n-undecane, amylcyclohexane, 1-undecene, 1,10-undecadiene, 1-undecyne, 3-undecyne, 5-undecyne, tricyclo[6.2.1.02'7]undeca-4-ene, n-dodecane, 2-methylundecane, 3-methylundecane, 4-methylundecane, 5-methylundecane, 2,2,4,6,6-pentamethylheptane, 1,3-dimethyladamantane, 1-ethyladamantane, 1,5,9-cyclododecatriene, 1,2,4-trivinylcyclohexane, and isoparaffin; ketone solvent such as cyclohexanone, cyclopentanone, 2-octanone, 2-nonanone, 2-heptanone, 3-heptanone, 4-heptanone, 2-hexanone, 3-hexanone, diisobutyl ketone, methylcyclohexanone, and methyl n-pentyl ketone; alcohol solvent such as 3-methoxybutanol, 3-methyl-3-methoxybutanol, 1-methoxy-2-propanol, and 1-ethoxy-2-propanol; ether solvent such as propylene glycol monomethyl ether, ethylene glycol monomethyl ether, propylene glycol monoethyl ether, ethylene glycol monoethyl ether, propylene glycol dimethyl ether, diethylene glycol dimethyl ether, diisopropyl ether, diisobutyl ether, diisopentyl ether, di-n-pentyl ether, methyl cyclopentyl ether, methyl cyclohexyl ether, di-n-butyl ether, di-sec-butyl ether, di-sec-pentyl ether, di-tert-amyl ether, di-n-hexyl ether, and anisole; ester solvent such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, propylene glycol mono-tert-butyl ether acetate; lactone solvent such as γ-butyrolactone.

The amount of organic solvent is preferably in a range of 10 to 50,000 parts by mass on the basis of 100 parts by mass of the resin (the whole of the component (A) and the component (B)).

As described above, the inventive bio-electrode composition makes it possible to form a living body contact layer for a bio-electrode that is capable of conducting electric signals from skin efficiently to a device (i.e., excellent in electric conductivity), free from the risk of causing allergies even when it is worn on skin for a long time (i.e., excellent in biocompatibility), light-weight, manufacturable at low cost, and free from large lowering of the electric conductivity even though it is wetted with water or dried. It is possible to improve the electric conductivity still more by adding a carbon material, and to manufacture a bio-electrode with particularly high adhesion and stretchability by combining a resin with adhesion and stretchability. Furthermore, it is possible to improve the stretchability and adhesion to skin by additives, and to control the stretchability and adhesion by adjusting the composition of the resin and the thickness of the living body contact layer appropriately.

<Bio-Electrode>

The present invention also provides a bio-electrode comprising an electro-conductive base material and a living body contact layer formed on the electro-conductive base material; wherein the living body contact layer is a cured material of the inventive bio-electrode composition described above.

Hereinafter, the bio-electrode having a living body contact layer composed of a cured material of the bio-electrode composition (hereinafter, also referred to as "the inventive bio-electrode") will be specifically described by reference to the FIGS., but the present invention is not limited thereto.

FIG. 1 is a schematic sectional view showing an example of the inventive bio-electrode. The bio-electrode 1 of FIG. 1 has the electro-conductive base material 2 and the living body contact layer 3 formed on the electro-conductive base material 2. The living body contact layer 3 is a layer in which the ionic polymer (ionic material) 4 and the metal powder 5a are dispersed in the resin 6. In accordance with needs, the carbon material 5b can be added as an electric conductivity improver in addition to the metal powder 5a. Incidentally, FIG. 1 shows a case of containing the resin 6, but the resin 6 is inessential. In this case, the living body contact layer 3 is composed of the ionic polymer 4 and the metal powders 5a dispersed therein (the ionic polymer 4 is combined with the resin 6).

When using the bio-electrode 1 of FIG. 1 like this, electric signals are picked from the living body 7 through the ionic polymer 4 and the metal powder 5a while bringing the living body contact layer 3 (i.e., the layer in which the ionic polymer 4 and the metal powders 5a are dispersed in the resin 6 or the layer in which the metal powders 5a are dispersed in the ionic polymer 4) into contact with the living body 7, and then conducted to a sensor device etc. (not shown) through the electro-conductive base material 2 as shown in FIG. 2. As described above, the inventive bio-electrode is capable of coping with both electric conductivity and biocompatibility by using the ionic polymer (ionic material) described above and obtaining electric signals from skin stably in high sensitivity because the contact area with skin is kept constant due to the adhesion thereof. Incidentally, 5b in FIGS. 1 and 2 is a carbon material (e.g., carbon nanotube).

Hereinafter, each component composing the inventive bio-electrode will be described more specifically.

[Electro-Conductive Base Material]

The inventive bio-electrode comprises an electro-conductive base material. This electro-conductive base material is usually connected electrically with a sensor device and so on, and conducts electrical signals picked from a living body through the living body contact layer to the sensor device and so on.

As the electro-conductive base material, any electro-conductive material can be used without being limited to particular ones. However, it is preferable to comprise one or more species selected from gold, silver, silver chloride, platinum, aluminum, magnesium, tin, tungsten, iron, copper, nickel, stainless steel, chromium, titanium, and carbon, for example.

The electro-conductive base material may be a hard electro-conductive substrate, an electro-conductive film having flexibility, a cloth with the surface being coated with electro-conductive paste, or a cloth into which electro-conductive polymer is kneaded without being limited to particular substrates. The electro-conductive base material may be flat, uneven, or mesh-form of woven metal wires, which can be appropriately selected in accordance with the use of the bio-electrode.

[Living Body Contact Layer]

The inventive bio-electrode comprises a living body contact layer formed on the electro-conductive base material. This living body contact layer is a part to be actually in contact with a living body when using the bio-electrode, and has electric conductivity and adhesion. The living body contact layer is a cured material of the inventive bio-electrode composition described above, that is to say, an adherent resin layer containing (A) the ionic material (salt) and (C) the metal powder, together with additives such as the component (B) in accordance with needs.

The living body contact layer preferably has adhesion in a range of 0.5 N/25 mm or more and 20 N/25 mm or less. The adhesion is commonly measured by the method shown in JIS Z 0237, in which a metal substrate such as a stainless steel (SUS) substrate or a polyethylene terephthalate (PET) substrate can be used as a base material or, alternatively, human skin can be used for measuring. Human skin has lower surface energy compared to metals and various plastics, which is as low as that of Teflon (registered trade mark), and is hard to adhere.

The living body contact layer of the bio-electrode preferably has a thickness of 1 μm or more and 5 mm or less, more preferably 2 μm or more and 3 mm or less. As the living body contact layer is thinner, the adhesion lowers, but the flexibility is improved, and the weight decreases to improve the compatibility with skin. The thickness of the living body contact layer can be selected based on the balance of adhesion and texture.

The inventive bio-electrode may be provided with an adherent film separately on the living body contact layer as previous bio-electrodes (e.g., the bio-electrode described in JP 2004-033468A) in order to prevent peeling off of the bio-electrode from a living body during the use. When the adherent film is prepared separately, the adherent film may be formed by using a raw material for the adherent film such as an acrylic type, a urethane type, and a silicone type. Particularly, the silicone type is suitable because of the high transparency of oxygen, which enables dermal respiration while pasting the same, the high water repellency, which decreases lowering of adhesion due to perspiration, and the low irritation to skin. It is to be noted that the inventive bio-electrode does not necessarily require the adherent film that is prepared separately described above, because peeling off from a living body can be prevented by adding tackifier to the bio-electrode composition or using a resin having good adhesion to a living body as described above.

When the inventive bio-electrode is used as a wearable device, wiring between the bio-electrode and a sensor device, and other components are not limited to particular ones. For example, it is possible to apply the ones described in JP 2004-033468A.

As described above, the inventive bio-electrode is capable of conducting electric signals from skin efficiently to a device (i.e., excellent in electric conductivity), free from the risk of causing allergies even when it is worn on skin for a long time (i.e., excellent in biocompatibility), light-weight, manufacturable at low cost, and free from large lowering of the electric conductivity even though it is wetted with water or dried, because the living body contact layer is formed from a cured material of the inventive bio-electrode composition described above. It is possible to improve the electric conductivity still more by adding a metal powder, and to manufacture a bio-electrode with higher adhesion and stretchability by combining a resin that has adhesion and stretchability. It is also possible to improve the stretchability and adhesion to skin by additives, and to control the stretchability and adhesion by adjusting the composition of the resin and the thickness of the living body contact layer appropriately. Accordingly, the inventive bio-electrode described above is particularly suitable as a bio-electrode used for a medical wearable device.

<Method for Manufacturing Bio-Electrode>

The present invention also provides a method for manufacturing a bio-electrode having an electro-conductive base material and a living body contact layer formed on the electro-conductive base material, comprising: applying the inventive bio-electrode composition described above onto the electro-conductive base material; and curing the bio-electrode composition; thereby forming the living body contact layer.

Incidentally, the electro-conductive base material, the bio-electrode composition, etc. used for the inventive method for manufacturing a bio-electrode may be the same as those described above.

The method for applying the bio-electrode composition onto the electro-conductive base material is not limited to particular ones; and dip coating, spray coating, spin coating, roll coating, flow coating, doctor coating, screen printing, flexographic printing, gravure printing, and inkjet printing are suitable, for example.

The method for curing the resin can be appropriately selected based on a kind of the component (B) used for the bio-electrode composition without being limited to particular methods. For example, the bio-electrode composition is preferably cured by either or both of heat and light. The foregoing bio-electrode composition can also be cured by adding a catalyst to generate acid or base to the bio-electrode composition, which causes a crosslinking reaction.

In case of heating, the temperature is not particularly limited and may be appropriately selected based on a kind of the component (B) used for the bio-electrode composition, but is preferably about 50 to 250° C., for example.

When the heating and light irradiation are combined, it is possible to perform the heating and the light irradiation simultaneously, to perform the heating after the light irradiation, or to perform the light irradiation after the heating. It is also possible to perform air-drying to evaporate solvent before heating the coating film.

As described above, the inventive method for manufacturing a bio-electrode makes it possible to manufacture the inventive bio-electrode easily and at low cost, with the bio-electrode being excellent in electric conductivity and biocompatibility, light-weight, and free from large lowering of the electric conductivity even though it is wetted with water or dried.

EXAMPLE

Hereinafter, the present invention will be specifically described by giving Examples and Comparative Examples, but the present invention is not limited thereto. Incidentally, "Me" represents a methyl group, and "Vi" represents a vinyl group in the below.

Ionic polymers 1 to 13, which were blended to bio-electrode composition solutions as an ionic material (electro-conductive material), were synthesized as follows. Each 30 mass % monomer solution in PGMEA was introduced into a reaction vessel and mixed. The reaction vessel was cooled to −70° C. under a nitrogen atmosphere, and subjected to vacuum degassing and nitrogen blowing, which were repeated for three times. After raising the temperature to room temperature, azobisisobutyronitrile (AIBN) was added thereto as a polymerization initiator in an amount of 0.01 mole per 1 mole of the whole monomers, this was warmed to a temperature of 60° C. and then allowed to react for 15 hours. The composition of obtained polymer was identified by $^1$H-NMR after drying the solvent. The molecular weight (Mw) and the dispersity (Mw/Mn) of obtained polymer were determined by gel permeation chromatography (GPC) using tetrahydrofuran (THF) as a solvent. Thus synthesized Ionic polymers 1 to 13 are shown below.

Ionic polymer 1

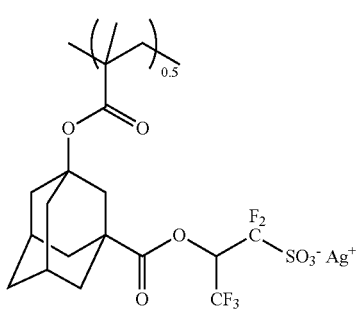

Mw = 36,400
Mw/Mn = 2.11

Ionic polymer 2

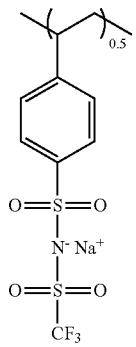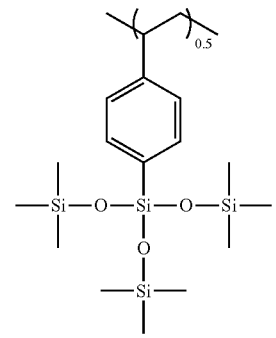

Mw = 24,800
Mw/Mn = 1.99

Ionic polymer 3

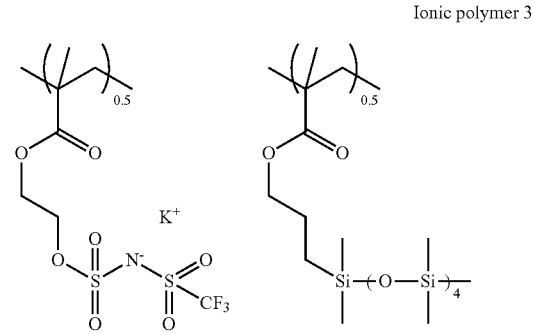

Mw = 48,100
Mw/Mn = 1.87

The repeating number in the formula shows the average value.

Ionic polymer 4

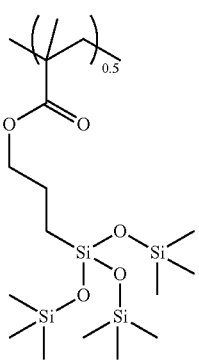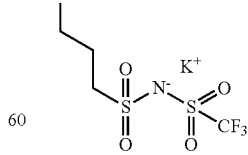

Mw = 31,600
Mw/Mn = 2.10

The repeating number in the formula shows the average value.

Ionic polymer 5
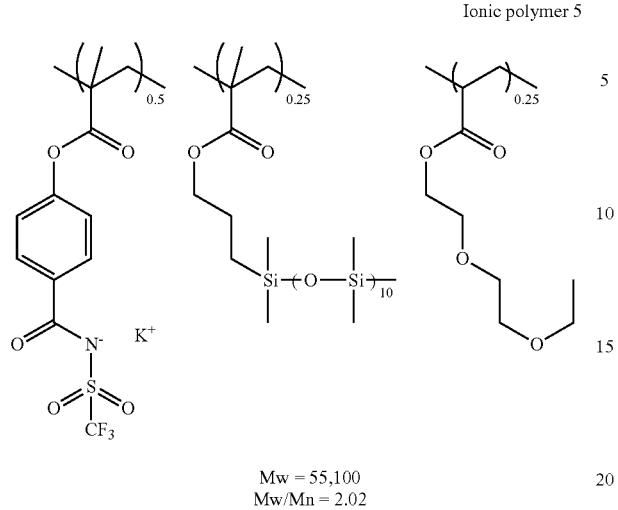
Mw = 55,100
Mw/Mn = 2.02
The repeating number in the formula shows the average value.
Ionic polymer 6
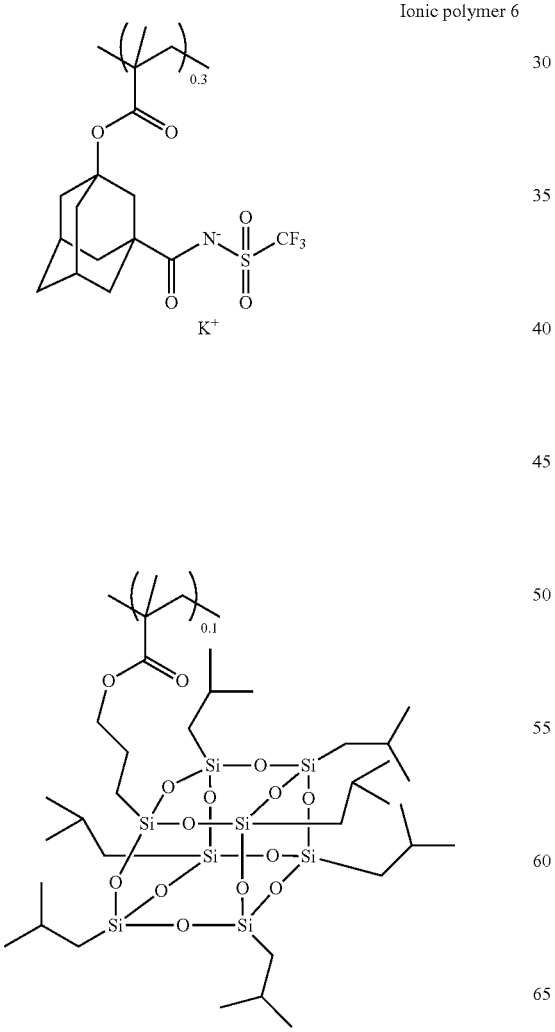
Ionic polymer 7
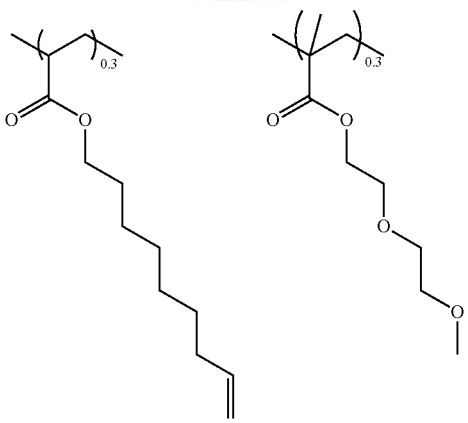
Mw = 26,100
Mw/Mn = 1.99
Mw = 56,500
Mw/Mn = 2.22
The repeating number in the formula shows the average value.

Ionic polymer 8

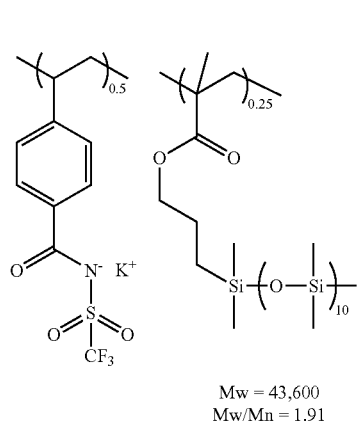

Mw = 43,600
Mw/Mn = 1.91

The repeating number in the formula shows the average value.

Ionic polymer 9

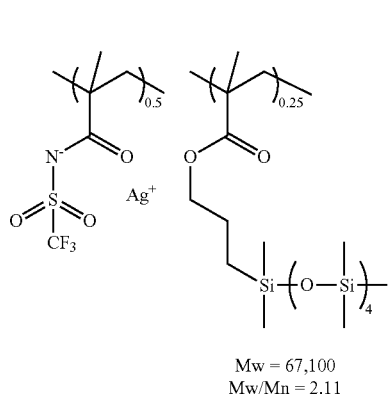

Mw = 67,100
Mw/Mn = 2.11

The repeating number in the formula shows the average value.

Ionic polymer 10

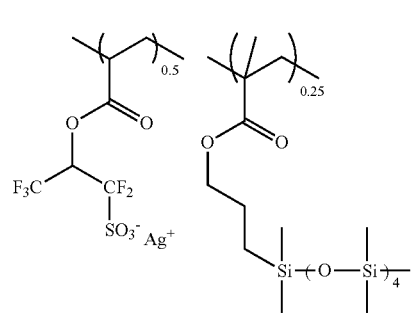

Mw = 78,300
Mw/Mn = 2.11

The repeating number in the formula shows the average value.

Ionic polymer 11

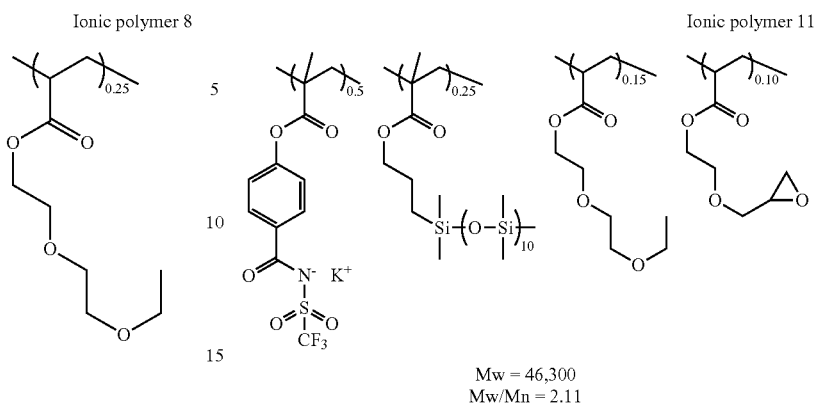

Mw = 46,300
Mw/Mn = 2.11

The repeating number in the formula shows the average value.

Ionic polymer 12

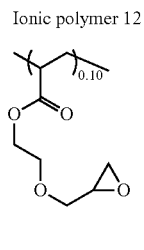

Mw = 64,600
Mw/Mn = 1.94

The repeating number in the formula shows the average value.

Ionic polymer 13

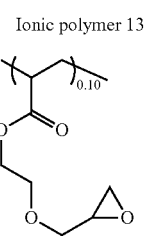

Mw = 46,500
Mw/Mn = 1.91

Comparative salts 1 to 3, which were blended as an ionic material to the bio-electrode composition solutions of Comparative Examples, are shown below.

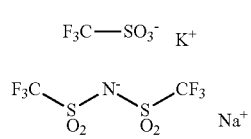

Comparative salt 1

Comparative salt 2

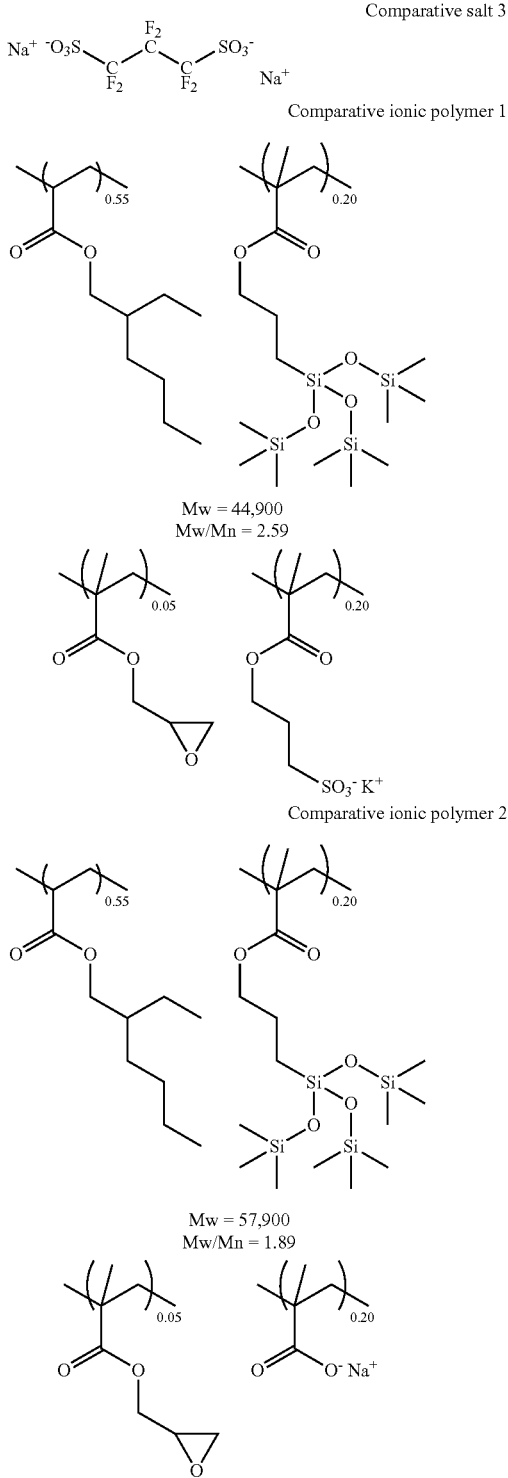

Comparative salt 3

Comparative ionic polymer 1

Mw = 44,900
Mw/Mn = 2.59

Comparative ionic polymer 2

Mw = 57,900
Mw/Mn = 1.89

Siloxane compounds 1 to 4, which were blended to the bio-electrode composition solutions as a silicone base resin, are shown below.

(Siloxane Compound 1)

Siloxane compound 1 was vinyl group-containing polydimethylsiloxane having an alkenyl group-content of 0.007 mol/100 g in which the terminals of molecular chain were blocked with $SiMe_2Vi$ groups, with the 30% toluene solution having a viscosity of 27,000 mPa·s.

(Siloxane Compound 2)

Siloxane compound 2 was a 60% toluene solution of polysiloxane of MQ resin composed of an $Me_3SiO_{0.5}$ unit and an $SiO_2$ unit ($Me_3SiO_{0.5}$ unit/$SiO_2$ unit=0.8).

(Siloxane Compound 3)

Siloxane compound 3 was a polydimethylsiloxane-bonded MQ resin obtained by heating a solution composed of 40 parts by mass of vinyl group-containing polydimethylsiloxane having an alkenyl group-content of 0.007 mol/100 g in which the terminals of molecular chain were blocked with OH groups, with the 30% toluene solution having a viscosity of 42,000 mPa·s; 100 parts by mass of 60% toluene solution of polysiloxane of MQ resin composed of an $Me_3SiO_{0.5}$ unit and an $SiO_2$ unit ($Me_3SiO_{0.5}$ unit/$SiO_2$ unit=0.8); and 26.7 parts by mass of toluene with refluxing for 4 hours, followed by cooling.

(Siloxane Compound 4)

As methylhydrogensilicone oil, KF-99 manufactured by Shin-Etsu Chemical Co., Ltd. was used.

As a silicone base resin, KF-353 manufactured by Shin-Etsu Chemical Co., Ltd. was used, which is polyether type silicone oil with the side chain being modified with polyether.

Acrylic polymer blended as an acrylic base polymer to the bio-electrode composition solution is shown below.

Acrylic polymer 1

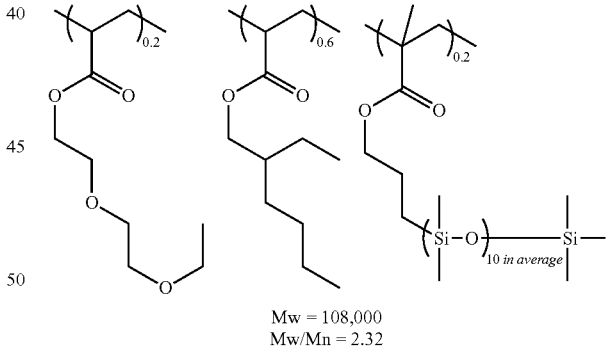

Acrylic polymer 1

Mw = 108,000
Mw/Mn = 2.32

The repeating number in the formula shows the average value.

Silicone-urethane acrylates 1, which was blended to the bio-electrode composition solutions as a silicone base, acrylic base, or urethane base resin, are shown below.

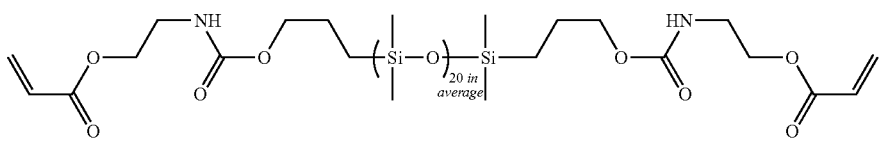

Silicone-urethane acrylate 1

The repeating number in the formula shows the average value.

Organic solvents, which were blended to the bio-electrode composition solutions, are shown below.
PGMEA: propylene glycol-1-monomethyl ether-2-acetate
PGME: propylene glycol-1-monomethyl ether
PGEE: propylene glycol-1-monoethyl ether The following are (C) metal powders, a radical generator, a platinum catalyst, and electric conductivity improvers (carbon black and carbon nanotube) blended to the bio-electrode composition solution as an additive.

Metal Powders:
Silver powder: silver flake manufactured by Sigma-Aldrich Co. LLC., with the diameter of 10 μm
Gold powder: gold powder manufactured by Sigma-Aldrich Co. LLC., with the diameter of 10 μm or less
Tin powder: tin powder manufactured by Sigma-Aldrich Co. LLC., with the diameter of 45 μm or less
Titanium powder: titanium powder manufactured by Sigma-Aldrich Co. LLC., with the diameter of 45 μm or less
Copper powder: copper powder manufactured by Sigma-Aldrich Co. LLC., with the diameter of 45 μm or less
Radical generator: V-601 manufactured by FUJI FILM Wako Pure Chemical Corporation
Platinum catalyst: CAT-PL-50T manufactured by Shin-Etsu Chemical Co., Ltd.
Carbon black: DENKA BLACK HS-100 manufactured by Denka Co., Ltd.
Multilayer carbon nanotube: manufactured by Sigma-Aldrich Co. LLC., with the diameter of 110 to 170 nm and the length of 5 to 9 μm Examples 1 to 21, Comparative Examples 1 to 7

On the basis of each composition described in Tables 1-1 and 1-2 as well as Table 2, the ionic material (salt), the resin, the organic solvent, and the additive (radical generator, platinum catalyst, electric conductivity improver) were blended to prepare each bio-electrode composition solution (Bio-electrode composition solutions 1 to 21, Comparative bio-electrode composition solutions 1 to 7).

TABLE 1-1

| Bio-electrode composition solution | Ionic material (parts by mass) | Resins (parts by mass) | Organic solvent (parts by mass) | Additives (parts by mass) |
|---|---|---|---|---|
| Bio-electrode composition solution 1 | Ionic polymer 1 (20) | Siloxane compound 1 (40) Siloxane compound 2 (100) Siloxane compound 4 (3) | toluene (30) | CAT-PL-50T (1.5) Silver powder (10) |
| Bio-electrode composition solution 2 | Ionic polymer 2 (20) | Siloxane compound 3 (126) Siloxane compound 4 (3) | heptane (30) PGMEA (14) | CAT-PL-50T (0.7) Silver powder (5) Carbon black (5) |
| Bio-electrode composition solution 3 | Ionic polymer 3 (22.5) | Siloxane compound 1 (40) Siloxane compound 2 (100) Siloxane compound 4 (3) | toluene (30) PGMEA (14) | CAT-PL-50T (0.7) Silver powder (5) Carbon black (5) |
| Bio-electrode composition solution 4 | Ionic polymer 4 (20) | Siloxane compound 1 (40) Siloxane compound 2 (100) Siloxane compound 4 (3) | toluene (30) PGMEA (14) | CAT-PL-50T (0.7) Silver powder (5) Carbon black (5) |
| Bio-electrode composition solution 5 | Ionic polymer 5 (20) | Siloxane compound 3 (126) Siloxane compound 4 (3) | toluene (44) | CAT-PL-50T (1.0) Silver powder (5) Carbon black (5) |
| Bio-electrode composition solution 6 | Ionic polymer 6 (20) | Siloxane compound 3 (126) Siloxane compound 4 (3) KF-353 (26) | toluene (30) 2-heptanone (14) | CAT-PL-50T (2.0) Silver powder (5) Carbon black (5) |
| Bio-electrode composition solution 7 | Ionic polymer 7 (25) | Siloxane compound 3 (126) Siloxane compound 4 (3) | toluene (30) PGME (14) | CAT-PL-50T (1.0) Silver powder (5) Carbon black (5) |
| Bio-electrode composition solution 8 | Ionic polymer 8 (24) | Siloxane compound 3 (126) Siloxane compound 4 (3) | toluene (30) PGME (14) | CAT-PL-50T (1.5) Silver powder (5) Carbon black (5) |
| Bio-electrode composition solution 9 | Ionic polymer 8 (24) | Siloxane compound 3 (126) Siloxane compound 4 (3) | toluene (30) PGME (14) | CAT-PL-50T (1.5) Silver powder (5) Multilayer carbon nanotube (3) |
| Bio-electrode composition solution 10 | Ionic polymer 1 (20) | Acrylic polymer 1 (60) Silicone-urethane acrylate 1 (20) | PGMEA (100) | Radical generator V-601 (4) Silver powder (10) |
| Bio-electrode composition solution 11 | Ionic polymer 1 (20) | Acrylic polymer 1 (55) Silicone-urethane acrylate 1 (25) | PGMEA (100) | Radical generator V-601 (4) Gold powder (10) |
| Bio-electrode composition solution 12 | Ionic polymer 9 (25) | Siloxane compound 3 (126) Siloxane compound 4 (3) | toluene (30) PGEE (14) | CAT-PL-50T (1.5) Silver powder (5) Carbon black (5) |

TABLE 1-1-continued

| Bio-electrode composition solution | Ionic material (parts by mass) | Resins (parts by mass) | Organic solvent (parts by mass) | Additives (parts by mass) |
|---|---|---|---|---|
| Bio-electrode composition solution 13 | Ionic polymer 10 (25) | Siloxane compound 3 (126) Siloxane compound 4 (3) | toluene (30) PGEE (14) | CAT-PL-50T (1.5) Silver powder (5) Carbon black (5) |
| Bio-electrode composition solution 14 | Ionic polymer 8 (24) | Siloxane compound 3 (126) Siloxane compound 4 (3) | toluene (30) PGEE (14) | CAT-PL-50T (1.5) Tin powder (10) |
| Bio-electrode composition solution 15 | Ionic polymer 8 (24) | Siloxane compound 3 (126) Siloxane compound 4 (3) | toluene (30) cyclopentanone (14) | CAT-PL-50T (1.5) Tin powder (5) Carbon black (5) |
| Bio-electrode composition solution 16 | Ionic polymer 8 (24) | Siloxane compound 3 (126) Siloxane compound 4 (3) | toluene (30) cyclopentanone (14) | CAT-PL-50T (1.5) Titanium powder (10) |
| Bio-electrode composition solution 17 | Ionic polymer 8 (24) | Siloxane compound 3 (126) Siloxane compound 4 (3) | toluene (30) cyclopentanone (14) | CAT-PL-50T (1.5) Titanium powder (5) Carbon black (5) |
| Bio-electrode composition solution 18 | Ionic polymer 8 (24) | Siloxane compound 3 (126) Siloxane compound 4 (3) | toluene (30) cyclopentanone (14) | CAT-PL-50T (1.5) Copper powder (10) |

TABLE 1-2

| Bio-electrode composition solution | Ionic material (parts by mass) | Resins (parts by mass) | Organic solvent (parts by mass) | Additives (parts by mass) |
|---|---|---|---|---|
| Bio-electrode composition solution 19 | Ionic polymer 11 (80) | — | cyclopentanone (40) | Silver powder (40) |
| Bio-electrode composition solution 20 | Ionic polymer 12 (80) | — | cyclopentanone (40) | Silver powder (40) |
| Bio-electrode composition solution 21 | Ionic polymer 13 (80) | — | cyclopentanone (40) | Silver powder (40) |

TABLE 2

| Bio-electrode composition solution | Ionic material (parts by mass) | Resins (parts by mass) | Organic solvent (parts by mass) | Additives (parts by mass) |
|---|---|---|---|---|
| Comparative bio-electrode composition solution 1 | Comparative salt 1 (4.7) | Siloxane compound 3 (126) Siloxane compound 4 (3) | toluene (30) PGME (14) | CAT-PL-50T (1.5) Silver powder (5) Carbon black (5) |
| Comparative bio-electrode composition solution 2 | Comparative salt 2 (8.2) | Siloxane compound 3 (126) Siloxane compound 4 (3) | toluene (30) PGME (14) | CAT-PL-50T (1.5) Silver powder (5) Carbon black (5) |
| Comparative bio-electrode composition solution 3 | Comparative salt 3 (8.4) | Siloxane compound 3 (126) Siloxane compound 4 (3) | toluene (30) PGME (14) | CAT-PL-50T (1.5) Silver powder (5) Carbon black (5) |
| Comparative bio-electrode composition solution 4 | — | Siloxane compound 3 (126) Siloxane compound 4 (3) | toluene (30) PGME (14) | CAT-PL-50T (1.5) Silver powder (5) Carbon black (5) |
| Comparative bio-electrode composition solution 5 | Ionic polymer 1 (100) | Siloxane compound 3 (126) Siloxane compound 4 (3) | toluene (30) PGME (14) | CAT-PL-50T (1.5) |
| Comparative bio-electrode composition solution 6 | Comparative ionic polymer 1 (20) | Siloxane compound 3 (126) Siloxane compound 4 (3) | toluene (30) PGME (14) | CAT-PL-50T (1.0) Silver powder (5) Carbon black (5) |

TABLE 2-continued

| Bio-electrode composition solution | Ionic material (parts by mass) | Resins (parts by mass) | Organic solvent (parts by mass) | Additives (parts by mass) |
|---|---|---|---|---|
| Comparative bio-electrode composition solution 7 | Comparative ionic polymer 2 (20) | Siloxane compound 3 (126) Siloxane compound 4 (3) | toluene (30) PGME (14) | CAT-PL-50T (1.0) Silver powder (5) Carbon black (5) |

(Evaluation of Electric Conductivity)

Each bio-electrode composition solution (adhesive solution) was applied onto an aluminum disk having a diameter of 3 cm and a thickness of 0.2 mm by using an applicator. This was air-dried at room temperature for 6 hours and then baked at 120° C. for 30 minutes under a nitrogen atmosphere by using an oven to be cured, thereby producing four pieces of bio-electrodes for each bio-electrode composition solution. Thus obtained bio-electrode had the living body contact layer 3 at one side and the aluminum disk 8 at the other side as an electro-conductive base material as shown in FIGS. 3A and 3B. Then, the copper wiring 9 was pasted on the surface of the aluminum disk 8 with self-adhesive tape at the side that had not been coated with the living body contact layer to form a lead-out electrode, which was connected to an impedance measurement apparatus as shown in FIG. 3B. Two pieces of the bio-electrodes 1' were pasted on a human arm at a distance of 15 cm from each other such that the side of each living body contact layer was in contact with the skin of the human arm as shown in FIG. 4. The initial impedance was measured while altering the frequency by using an AC impedance measurement apparatus SI1260 manufactured by Solartron. Then, the remained two pieces of the bio-electrodes were immersed in pure water for 1 hour, and used for measuring the impedance on skin by the same method described above after drying the water. Each impedance at the frequency of 1,000 Hz is shown in Table 3.

(Evaluation of Adhesion)

Each bio-electrode composition solution was applied onto a polyethylene naphthalate (PEN) substrate having a thickness of 100 μm by using an applicator. This was air dried at room temperature for 6 hours, followed by curing through baking at 120° C. for 30 minutes under a nitrogen atmosphere by using an oven to produce an adhesive film. From this adhesive film, a tape with a width of 25 mm was cut out. This was pressed to a stainless (SUS304) board and allowed to stand at room temperature for 20 hours. Then, the force (N/25 mm) for peeling the tape, which had been produced from the adhesive film, from the stainless board was measured at an angle of 180° and a speed of 300 mm/min by using a tensile tester. The results are shown in Table 3.

(Measurement of Thickness of Living Body Contact Layer)

On each bio-electrode produced in the evaluation test of electric conductivity described above, the thickness of the living body contact layer was measured by using a micrometer. The results are shown in Table 3.

TABLE 3

| Example | Adhesive solution (to be in contact with body) | Adhesion (N/25 mm) | Thickness of resin (μm) | Initial impedance (Ω) | Impedance after water im-mersion (Ω) |
|---|---|---|---|---|---|
| Example 1 | Adhesive solution 1 | 3.0 | 420 | $3.8\ E^4$ | $3.3\ E^4$ |
| Example 2 | Adhesive solution 2 | 3.0 | 390 | $5.8\ E^4$ | $5.5\ E^4$ |
| Example 3 | Adhesive solution 3 | 3.2 | 540 | $2.1\ E^4$ | $2.9\ E^4$ |
| Example 4 | Adhesive solution 4 | 3.1 | 460 | $1.1\ E^4$ | $1.2\ E^4$ |
| Example 5 | Adhesive solution 5 | 3.4 | 520 | $3.1\ E^4$ | $3.9\ E^4$ |
| Example 6 | Adhesive solution 6 | 3.2 | 460 | $3.0\ E^4$ | $3.1\ E^4$ |
| Example 7 | Adhesive solution 7 | 3.1 | 510 | $6.9\ E^4$ | $7.0\ E^4$ |
| Example 8 | Adhesive solution 8 | 3.3 | 610 | $2.5\ E^4$ | $3.4\ E^4$ |
| Example 9 | Adhesive solution 9 | 2.1 | 520 | $3.2\ E^4$ | $3.9\ E^4$ |
| Example 10 | Adhesive solution 10 | 2.9 | 630 | $5.2\ E^4$ | $5.3\ E^4$ |
| Example 11 | Adhesive solution 11 | 3.3 | 680 | $6.4\ E^4$ | $6.8\ E^4$ |
| Example 12 | Adhesive solution 12 | 3.2 | 510 | $3.1\ E^4$ | $3.6\ E^4$ |
| Example 13 | Adhesive solution 13 | 3.2 | 550 | $3.1\ E^4$ | $3.6\ E^4$ |
| Example 14 | Adhesive solution 14 | 3.1 | 420 | $8.8\ E^4$ | $8.3\ E^4$ |
| Example 15 | Adhesive solution 15 | 3.0 | 440 | $7.8\ E^4$ | $6.5\ E^4$ |
| Example 16 | Adhesive solution 16 | 3.2 | 470 | $7.1\ E^4$ | $7.9\ E^4$ |
| Example 17 | Adhesive solution 17 | 3.0 | 490 | $6.1\ E^4$ | $7.3\ E^4$ |
| Example 18 | Adhesive solution 18 | 3.1 | 580 | $9.1\ E^4$ | $8.9\ E^4$ |
| Example 19 | Adhesive solution 19 | 1.1 | 320 | $5.1\ E^4$ | $5.3\ E^4$ |
| Example 20 | Adhesive solution 20 | 1.3 | 280 | $4.1\ E^4$ | $4.9\ E^4$ |
| Example 21 | Adhesive solution 21 | 2.1 | 290 | $5.1\ E^4$ | $5.3\ E^4$ |
| Comparative Example 1 | Comparative adhesive solution 1 | 2.3 | 520 | $4.2\ E^4$ | $5.3\ E^5$ |
| Comparative Example 2 | Comparative adhesive solution 2 | 2.2 | 530 | $5.2\ E^4$ | $7.3\ E^5$ |
| Comparative Example 3 | Comparative adhesive solution 3 | 2.6 | 520 | $5.1\ E^4$ | $8.3\ E^5$ |
| Comparative Example 4 | Comparative adhesive solution 4 | 2.6 | 560 | $1.1\ E^5$ | $1.1\ E^5$ |
| Comparative Example 5 | Comparative adhesive solution 5 | 4.6 | 370 | $1.9\ E^6$ | $1.8\ E^6$ |

TABLE 3-continued

| Example | Adhesive solution (to be in contact with body) | Adhesion (N/25 mm) | Thickness of resin (μm) | Initial impedance (Ω) | Impedance after water im-mersion (Ω) |
|---|---|---|---|---|---|
| Comparative Example 6 | Comparative adhesive solution 6 | 4.1 | 530 | $9.9 \text{ E}^6$ | $9.8 \text{ E}^6$ |
| Comparative Example 7 | Comparative adhesive solution 7 | 3.8 | 430 | $9.1 \text{ E}^6$ | $8.8 \text{ E}^6$ |

As shown in Table 3, Examples 1 to 18, the living body contact layer of which was formed by using the inventive bio-electrode composition containing the salt (ionic material) with a particular structure and resins, exhibited lower initial impedance and did not cause large change in impedance after the bio-electrodes were immersed to water and dried. That is, Examples 1 to 18 each gave a bio-electrode that had high initial electric conductivity and did not cause large lowering of the electric conductivity even though it was wetted with water or dried. These bio-electrodes of Examples 1 to 18 had good adhesion similar to that of bio-electrode of Comparative Examples 1 to 3, in which previous salt and resin were blended, and was light-weight, excellent in biocompatibility, and manufacturable at low cost.

Examples 19 to 21, in which each living body contact layer was formed using the inventive bio-electrode composition containing a salt (ionic material) without containing a resin, also exhibited lower initial impedance and did not cause large change in impedance even though it was wetted with water or dried. That is, each of Examples 19 to 21 also gave a bio-electrode that had high initial electric conductivity and did not cause large lowering of the electric conductivity even though it was wetted with water or dried. This reveals that the component (B) is inessential in the present invention. In each of Examples 19 to 21, the metal powders were successfully contained in an amount of 50 parts by mass on the basis of 100 parts by mass of the ionic material, which was larger than in Examples 1 to 18. These bio-electrodes in Examples 19 to 21 were adhesive enough for the actual use, light-weight, excellent in biocompatibility, and manufacturable at low cost.

On the other hand, in each Comparative Examples 1 to 3, the living body contact layer of which was formed by using a bio-electrode composition containing previous salt and resins, the initial impedance was low, but large increase of the impedance occurred such that the order of magnitude was changed after water immersion and drying. That is, each of Comparative Examples 1 to 3 only gave a bio-electrode, the electric conductivity of which was largely decreased when it was wetted by water and dried, although the initial electric conductivity was high.

Comparative Example 4, in which the living body contact layer was formed by using a bio-electrode composition that contained resins without containing salt, did not cause large increase of impedance by an order of magnitude after it was immersed to water and dried because it did not contain salt, but the initial impedance was high. That is, Comparative Example 4 only gave a bio-electrode with low initial electric conductivity.

In cases of forming a living body contact layer without containing metal powders (Comparative Example 5) and forming a living body contact layer in which a polymer salt with lower acidity had been added (Comparative Examples 6 and 7), each initial impedance was high.

As described above, it was revealed that the bio-electrode, with the living body contact layer being formed by using the inventive bio-electrode composition, was excellent in electric conductivity, biocompatibility, and adhesion to an electro-conductive base material; excellent in holding the ionic material to prevent large lowering of electric conductivity even though it was wetted with water or dried; light-weight; and manufacturable at low cost.

It is to be noted that the present invention is not restricted to the foregoing embodiment. The embodiment is just an exemplification, and any examples that have substantially the same feature and demonstrate the same functions and effects as those in the technical concept described in claims of the present invention are included in the technical scope of the present invention.

The invention claimed is:
1. A bio-electrode composition comprising:
(A) an ionic material;
(B) a resin other than the ionic material (A); and
(C) a metal powder;
the ionic material (A) being a polymer compound comprising a repeating unit-a having a structure selected from the group consisting of salts of an ammonium, a sodium, a potassium, and a silver of one or more of fluorosulfonic acid, fluorosulfonimide, and fluorosulfonamide,
the resin (B) containing a silicone resin, diorganosiloxane and organohydrogenpolysiloxane,
wherein the silicone resin has both units of an $R_xSiO_{(4-x)/2}$ unit, wherein R represents a substituted or unsubstituted monovalent hydrocarbon group having 1 to 10 carbon atoms, and "x" is a number in a range of 2.5 to 3.5, and an $SiO_2$ unit, the diorganosiloxane has an alkenyl group, and the organohydrogenpolysiloxane has an SiH group.
2. The bio-electrode composition according to claim 1, wherein the repeating unit-a is a repeating unit having at least one structure selected from the group consisting of structures shown by the following general formulae (1)-1 to (1)-4,

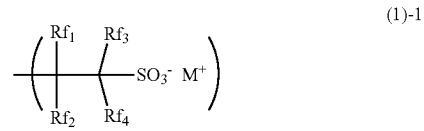

(1)-1

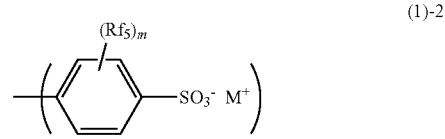

(1)-2

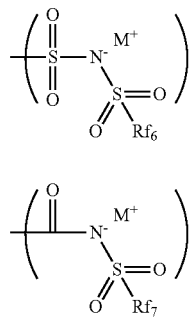
(1)-3

(1)-4 wherein $Rf_1$ and $Rf_2$ each represent a hydrogen atom, a fluorine atom, an oxygen atom, a methyl group, or a trifluoromethyl group, provided that when $Rf_1$ represents an oxygen atom, $Rf_2$ also represents the oxygen atom to form a carbonyl group together with a carbon atom bonded therewith; $Rf_3$ and $Rf_4$ each represent a hydrogen atom, a fluorine atom, or a trifluoromethyl group, provided that one or more of $Rf_1$ to $Rf_4$ is a fluorine atom or a trifluoromethyl group; $Rf_5$, $Rf_6$, and $Rf_7$ each represent a fluorine atom, or a linear or branched alkyl group having 1 to 4 carbon atoms, provided that one or more fluorine atoms are contained; "m" is an integer of 1 to 4; and $M^+$ is an ion selected from the group consisting of an ammonium ion, a sodium ion, a potassium ion, and a silver ion.

3. The bio-electrode composition according to claim 1, wherein the repeating unit-a is at least one repeating unit selected from repeating units shown by the following general formulae (2),

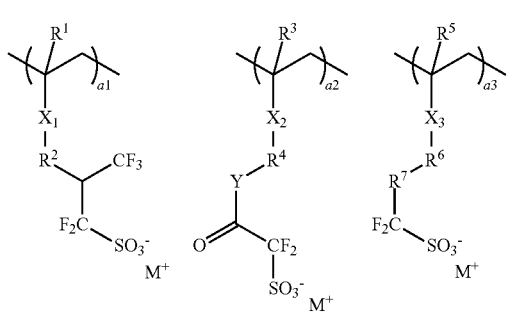
(2)

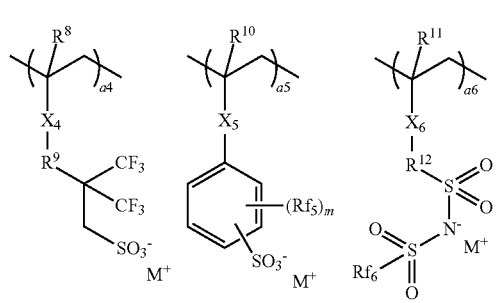

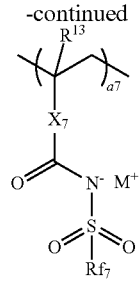

wherein $R^1$, $R^3$, $R^5$, $R^8$, $R^{10}$, $R^{11}$, and $R^{13}$ each independently represent a hydrogen atom or a methyl group; $R^2$, $R^4$, $R^6$, $R^9$, and $R^{12}$ each independently represent any of a single bond, an ester group, or a linear, branched, or cyclic hydrocarbon group having 1 to 13 carbon atoms, optionally having either or both of an ether group and an ester group; $R^7$ represents a linear or branched alkylene group having 1 to 4 carbon atoms, and one or two of the hydrogen atoms in $R^7$ are optionally replaced with a fluorine atom; $X_1$, $X_2$, $X_3$, $X_4$, and $X_6$ each independently represent any of a single bond, a phenylene group, a naphthylene group, an ether group, an ester group, or an amide group; $X_5$ represents any of a single bond, an ether group, or an ester group; $X_7$ represents a single bond, an arylene group having 6 to 12 carbon atoms, or —C(=O)—O—$X_{10}$—; $X_{10}$ represents a linear, branched, or cyclic alkylene group having 1 to 12 carbon atoms, or a divalent aromatic hydrocarbon group having 6 to 10 carbon atoms, optionally having an ether group, a carbonyl group, or an ester group in $X_{10}$; Y represents an oxygen atom or an —$NR^{19}$— group, optionally bonded to $R^4$ to form a ring; $R^{19}$ represents a hydrogen atom, or a linear or branched alkyl group having 1 to 4 carbon atoms; "m" is an integer of 1 to 4; a1, a2, a3, a4, a5, a6, and a7 are numbers defined in terms of mole fractions satisfying $0 \leq a1 < 1.0$, $0 \leq a2 < 1.0$, $0 \leq a3 < 1.0$, $0 \leq a4 < 1.0$, $0 \leq a5 < 1.0$, $0 \leq a6 < 1.0$, $0 \leq a7 < 1.0$, and $0 < a1+a2+a3+a4+a5+a6+a7 < 1.0$; and $M^+$ is an ion selected from the group consisting of an ammonium ion, a sodium ion, a potassium ion, and a silver ion.

4. The bio-electrode composition according to claim 2, wherein the repeating unit-a is at least one repeating unit selected from repeating units shown by the following general formulae (2),

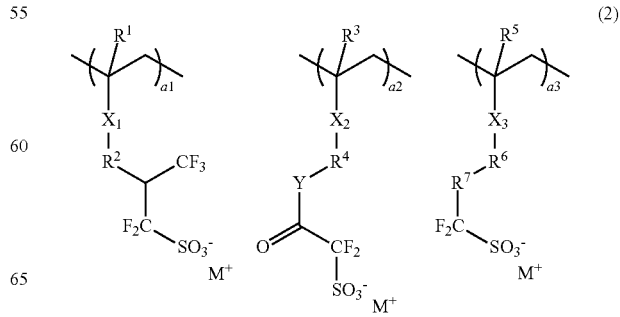
(2)

-continued

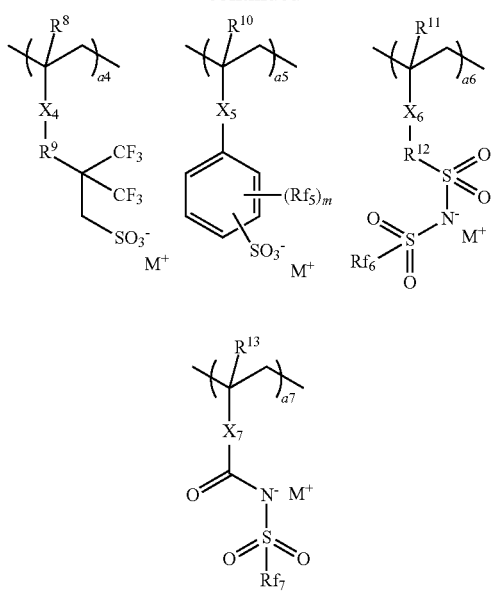

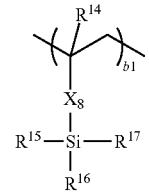

(2')

wherein $R^{14}$ represents a hydrogen atom or a methyl group; $X_8$ represents any of an arylene group having 6 to 12 carbon atoms, a —C(=O)—O—$R^{18}$- group, or a —C(=O)—NH—$R^{18}$- group; $R^{18}$ represents any of a single bond, a linear, branched, or cyclic alkylene group having 2 to 12 carbon atoms, or a phenylene group, optionally having one or more groups selected from the group consisting of an ether group, a carbonyl group, an ester group, and an amide group; $R^{15}$, $R^{16}$, and $R^{17}$ each represent a linear, branched, or cyclic alkyl group having 1 to 6 carbon atoms or an aryl group having 6 to 10 carbon atoms, with the alkyl group optionally having at least one of a siloxane bond and/or a silicon atom in a chain of the alkyl group, and the alkyl group and/or the aryl group optionally having a halogen atom; $R^{15}$ and $R^{16}$, or $R^{15}$, $R^{16}$, and $R^{17}$ are optionally bonded to each other to form a ring or a three dimensional structure; and b1 is a number defined in terms of mole fraction satisfying 0<b1<1.0.

wherein $R^1$, $R^3$, $R^5$, $R^8$, $R^{10}$, $R^{11}$, and $R^{13}$ each independently represent a hydrogen atom or a methyl group; $R^2$, $R^4$, $R^6$, $R^9$, and $R^{12}$ each independently represent any of a single bond, an ester group, or a linear, branched, or cyclic hydrocarbon group having 1 to 13 carbon atoms, optionally having either or both of an ether group and an ester group; $R^7$ represents a linear or branched alkylene group having 1 to 4 carbon atoms, and one or two of the hydrogen atoms in $R^7$ are optionally replaced with a fluorine atom; $X_1$, $X_2$, $X_3$, $X_4$, and $X_6$ each independently represent any of a single bond, a phenylene group, a naphthylene group, an ether group, an ester group, or an amide group; $X_5$ represents any of a single bond, an ether group, or an ester group; $X_7$ represents a single bond, an arylene group having 6 to 12 carbon atoms, or —C(=O)—O—$X_{10}$—; $X_{10}$ represents a linear, branched, or cyclic alkylene group having 1 to 12 carbon atoms, or a divalent aromatic hydrocarbon group having 6 to 10 carbon atoms, optionally having an ether group, a carbonyl group, or an ester group in $X_{10}$; Y represents an oxygen atom or an —$NR^{19}$— group, optionally bonded to $R^4$ to form a ring; $R^{19}$ represents a hydrogen atom, or a linear or branched alkyl group having 1 to 4 carbon atoms; "m" is an integer of 1 to 4; a1, a2, a3, a4, a5, a6, and a7 are numbers defined in terms of mole fractions satisfying 0≤a1<1.0, 0≤a2<1.0, 0≤a3<1.0, 0≤a4<1.0, 0≤a5<1.0, 0≤a6<1.0, 0≤a7<1.0, and 0<a1+a2+a3+a4+a5+a6+a7<1.0; and $M^+$ is an ion selected from the group consisting of an ammonium ion, a sodium ion, a potassium ion, and a silver ion.

5. The bio-electrode composition according to claim 1, wherein the ionic material (A) has a repeating unit-b having silicon in addition to the repeating unit-a.

6. The bio-electrode composition according to claim 5, wherein the repeating unit-b having silicon is shown by the following general formula (2'), 7. The bio-electrode composition according to claim 1, wherein the ionic material (A) has the repeating unit-a that has an ammonium salt structure with the ammonium salt containing an ammonium ion shown by the following general formula (3),

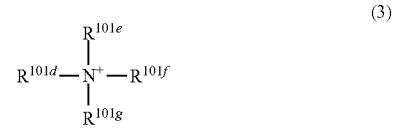

(3)

wherein $R^{101d}$, $R^{101e}$, $R^{101f}$, and $R^{101g}$ each represent a hydrogen atom, a linear, branched, or cyclic alkyl group having 1 to 12 carbon atoms, a linear, branched, or cyclic alkenyl group or alkynyl group having 2 to 12 carbon atoms, or an aromatic group having 4 to 20 carbon atoms, with each group optionally having one or more species selected from the group consisting of an ether group, a carbonyl group, an ester group, a hydroxy group, an amino group, a nitro group, a sulfonyl group, a sulfinyl group, a halogen atom, and a sulfur atom; $R^{101d}$ and $R^{101e}$, or $R^{101d}$, $R^{101e}$, and $R^{101f}$ are optionally bonded to each other together with the nitrogen atom bonded therewith to form a ring in which $R^{101d}$ and $R^{101e}$, or $R^{101d}$, $R^{101e}$, and $R^{101f}$ are each an alkylene group having 3 to 10 carbon atoms, or to form a heteroaromatic ring having the nitrogen atom in the formula within the ring.

8. The bio-electrode composition according to claim 1, further comprising an organic solvent.

9. The bio-electrode composition according to claim 1, wherein the metal powder (C) is a powder of a metal selected from the group consisting of gold, silver, platinum, copper, tin, titanium, nickel, aluminum, tungsten, molybdenum, ruthenium, chromium, and indium.

10. The bio-electrode composition according to claim 9, wherein the metal powder (C) is a silver powder, a copper powder, a tin powder, or a titanium powder.

11. The bio-electrode composition according to claim 1, further comprising a carbon material in addition to the metal powder (C).

12. The bio-electrode composition according to claim 11, wherein the carbon material is either or both of carbon black and carbon nanotube.

13. A method for manufacturing a bio-electrode having an electro-conductive base material and a living body contact layer formed on the electro-conductive base material, comprising:
applying the bio-electrode composition according to claim 1 onto the electro-conductive base material; and
curing the bio-electrode composition; thereby forming the living body contact layer.

14. The method for manufacturing a bio-electrode according to claim 13, wherein the electro-conductive base material comprises one or more species selected from the group consisting of gold, silver, silver chloride, platinum, aluminum, magnesium, tin, tungsten, iron, copper, nickel, stainless steel, chromium, titanium, and carbon.

15. A bio-electrode composition comprising:
(A) an ionic material; and
(C) a metal powder;
the ionic material (A) being a polymer compound comprising a repeating unit-a having a structure selected from the group consisting of salts of an ammonium, a sodium, a potassium, and a silver of one or more of fluorosulfonic acid, fluorosulfonimide, and fluorosulfonamide,
wherein the repeating unit-a is a repeating unit having a structure shown by the following general formula (1)-4, or a repeating unit shown by the following general formula (2)

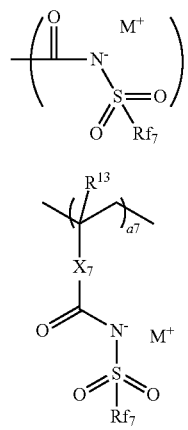

wherein $Rf_7$ represents a fluorine atom, or a linear or branched alkyl group having 1 to 4 carbon atoms, provided that one or more fluorine atoms are contained; $R^{13}$ represents a hydrogen atom or a methyl group; $X_7$ represents a single bond, an arylene group having 6 to 12 carbon atoms, or —C(=O)—O—$X_{10}$—; $X_{10}$ represents a linear, branched, or cyclic alkylene group having 1 to 12 carbon atoms, or a divalent aromatic hydrocarbon group having 6 to 10 carbon atoms, optionally having an ether group, a carbonyl group, or an ester group in $X_{10}$; a7 is a number defined in terms of mole fraction satisfying 0<a7<1.0, and $M^+$ is an ion selected from the group consisting of an ammonium ion, a sodium ion, a potassium ion, and a silver ion.

16. The bio-electrode composition according to claim 15, wherein the ionic material (A) has a repeating unit-b having silicon in addition to the repeating unit-a.

17. The bio-electrode composition according to claim 16, wherein the repeating unit-b having silicon is shown by the following general formula (2'),

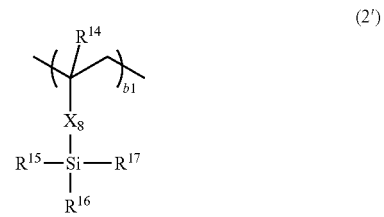

wherein $R^{14}$ represents a hydrogen atom or a methyl group; $X_8$ represents any of an arylene group having 6 to 12 carbon atoms, a —C(=O)—O—$R^{18}$- group, or a —C(=O)—NH—$R^{18}$- group; $R^{18}$ represents any of a single bond, a linear, branched, or cyclic alkylene group having 2 to 12 carbon atoms, or a phenylene group, optionally having one or more groups selected from the group consisting of an ether group, a carbonyl group, an ester group, and an amide group; $R^{15}$, $R^{16}$, and $R^{17}$ each represent a linear, branched, or cyclic alkyl group having 1 to 6 carbon atoms or an aryl group having 6 to 10 carbon atoms, with the alkyl group optionally having at least one of a siloxane bond and/or silicon atom in a chain of the alkyl group, and the alkyl group and/or the aryl group optionally having a halogen atom; $R^{15}$ and $R^{16}$, or $R^{15}$, $R^{16}$, and $R^{17}$ are optionally bonded to each other to form a ring or a three dimensional structure; and b1 is a number defined in terms of mole fraction satisfying 0<b1<1.0 and 0<a7+b1≤1.0.

18. The bio-electrode composition according to claim 15, wherein the ionic material (A) contains an ammonium ion shown by the following general formula (3) as $M^+$ in the repeating unit-a,

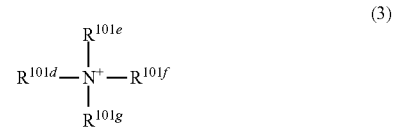

wherein $R^{101d}$, $R^{101e}$, $R^{101f}$, and $R^{101g}$ each represent a hydrogen atom, a linear, branched, or cyclic alkyl group having 1 to 12 carbon atoms, a linear, branched, or cyclic alkenyl group or alkynyl group having 2 to 12 carbon atoms, or an aromatic group having 4 to 20 carbon atoms, with each group optionally having one or more species selected from the group consisting of an ether group, a carbonyl group, an ester group, a hydroxy group, an amino group, a nitro group, a sulfonyl group, a sulfinyl group, a halogen atom, and a sulfur atom; $R^{101d}$ and $R^{101e}$, or $R^{101d}$, $R^{101e}$, and $R^{101f}$ are optionally bonded to each other together with the nitrogen atom bonded therewith to form a ring in which $R^{101d}$ and $R^{101e}$, or $R^{101d}$, $R^{101e}$, and $R^{101f}$ are each an alkylene group having 3 to 10 carbon atoms, or to form a heteroaromatic ring having the nitrogen atom in the formula within the ring.

19. The bio-electrode composition according to claim 15, further comprising an organic solvent.

20. The bio-electrode composition according to claim 15, wherein the metal powder (C) is a powder of a metal selected from the group consisting of gold, silver, platinum, copper, tin, titanium, nickel, aluminum, tungsten, molybdenum, ruthenium, chromium, and indium.

21. The bio-electrode composition according to claim 20, wherein the metal powder (C) is a silver powder, a copper powder, a tin powder, or a titanium powder.

* * * * *